US010563226B2

(12) United States Patent
Scharenberg et al.

(10) Patent No.: US 10,563,226 B2
(45) Date of Patent: Feb. 18, 2020

(54) ENHANCING ENDONUCLEASE BASED GENE EDITING IN PRIMARY CELLS

(71) Applicant: Seattle Children's Hospital, Seattle, WA (US)

(72) Inventors: Andrew Scharenberg, Seattle, WA (US); David Rawlings, Seattle, WA (US); Michael C. Jensen, Bainbridge Island, WA (US); Kamila Gwiazda, Seattle, WA (US); Alexandra Grier, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

(21) Appl. No.: 15/152,960

(22) Filed: May 12, 2016

(65) Prior Publication Data

US 2016/0333377 A1 Nov. 17, 2016

Related U.S. Application Data

(60) Provisional application No. 62/161,104, filed on May 13, 2015.

(51) Int. Cl.

| | |
|---|---|
| ***C12N 15/63*** | (2006.01) |
| ***C12N 15/90*** | (2006.01) |
| ***C12N 15/86*** | (2006.01) |
| ***A61K 38/46*** | (2006.01) |
| ***A61P 35/00*** | (2006.01) |
| ***A61K 48/00*** | (2006.01) |
| ***C12N 7/04*** | (2006.01) |
| ***C12N 15/113*** | (2010.01) |
| ***C12N 15/861*** | (2006.01) |

(52) U.S. Cl.

CPC .......... *C12N 15/907* (2013.01); *A61K 38/465* (2013.01); *A61K 48/005* (2013.01); *A61P 35/00* (2018.01); *C12N 7/045* (2013.01); *C12N 15/113* (2013.01); *C12N 15/86* (2013.01); *C12N 15/8616* (2013.01); *C12N 2310/20* (2017.05); *C12N 2750/14143* (2013.01); *C12N 2800/80* (2013.01)

(58) Field of Classification Search

None

See application file for complete search history.

(56) References Cited

U.S. PATENT DOCUMENTS 6,635,244 B2 * 10/2003 Shen .................... C07K 14/005 424/93.1
8,999,641 B2 * 4/2015 Zhang ...................... C12N 9/22 424/94.1
2004/0180352 A1 9/2004 Padgett et al.
2006/0206949 A1 9/2006 Arnould et al.
2008/0271166 A1 10/2008 Epinat et al.
2012/0244131 A1 9/2012 Delacote et al.
2014/0273226 A1 9/2014 Wu
2015/0110762 A1 4/2015 Holmes et al.
2016/0237455 A1 * 8/2016 Glucksmann ........ A61K 48/005

FOREIGN PATENT DOCUMENTS

EP 2 412 806 A1 2/2012
WO WO 2012/058458 A2 5/2012
WO WO 2013/009525 A1 1/2013
WO WO 2014/165349 A1 10/2014
WO WO 2015/031775 A1 3/2015
WO WO 2016/131009 A1 8/2016

OTHER PUBLICATIONS

Gaj et al., ZFN, TALEN, and CRISPR/Cas-Based Methods for Genome Engineering, Trends in Biotechnology, vol. 31, No. 7, pp. 397-405, Jul. 2013.

International Search Report and Written Opinion dated Aug. 19, 2016 for International Application No. PCT/US2016/032153 filed May 12, 2016; 12 pages.

Ahn, B., et al., Regulation of WRN Helicase Activity in Human Base Excision Repair, The Journal of Biological Chemistry, vol. 279, No. 51, pp. 53465-53474, 2004.

Aurnhammer, C., et al., Universal real-time PCR for the detection and quantification of adeno-associated virus serotype 2-derived inverted terminal repeat sequences, Human Gene Therapy Methods: Part B, vol. 23, pp. 18-28, 2012.

Ashworth, J., et al., Computational redesign of endonuclease DNA binding and cleavage specificity, Nature, vol. 441, pp. 656-659, 2006.

Baker, A., et al., Adenovirus E4 34k and E1b 55k oncoproteins target host DNA ligase IV for proteasomal degradation, Journal of Virology, vol. 81, No. 13, pp. 7034-7040, 2007.

Balasubramanian, N., et al., Physical Interaction between the Herpes Simplex Virus Type 1 Exonuclease, UL12, and the DNA Double-Strand Break-Sensing MRN Complex, Journal of Virology, vol. 84, No. 24, pp. 12504-12514, 2010.

Bennardo, N., et al., ATM Limits Incorrect End Utilization During Non-Homologous End Joining of Multiple Chromosome Breaks, PLoS Genetics, vol. 6, No. 11, pp. 1-11, 2010.

Bennardo, N., et al., Limiting the Persistence of a Chromosome Break Diminishes Its Mutagenic Potential, PLoS Genetics, vol. 5, No. 10, pp. 1-14, 2009.

(Continued)

*Primary Examiner* — Celine X Qian

(74) *Attorney, Agent, or Firm* — Knobbe Martens Olson & Bear LLP

(57) ABSTRACT

Disclosed herein are nuclease-based systems for genome editing and methods of using the system for genome editing. Also, disclosed are approaches to enhance Cas9-mediated gene editing efficiency in primary human cells with minimal toxicity when using adeno-associated virus vectors (AAV) to express the guide RNAs necessary for CRISPR/Cas9-based genome editing in the presence of helper proteins.

14 Claims, 72 Drawing Sheets

Specification includes a Sequence Listing.

(56) References Cited

OTHER PUBLICATIONS

Boch, J., et al., Breaking the Code of DNA Binding Specificity of TAL-Type III Effectors, Science, vol. 326, pp. 1509-1512, 2009.
Boissel, S. et al., megaTALs: a rare-cleaving nuclease architecture for therapeutic genome engineering, Nucleic Acids Research, vol. 42, No. 4, pp. 2591-2601, 2014.
Boyer, J., et al., Adenovirus E4 34k and E4 11k inhibit double strand break repair and are physically associated with the cellular DNA-dependent protein kinase, Virology, vol. 263, pp. 307-312, 1999.
Chevalier, B., et al., Design, Activity, and Structure of a Highly Specific Artificial Endonuclease, Molecular Cell, vol. 10, pp. 895-905, 2002.
Chu, V.T., et al., Increasing the efficiency of homology-directed repair for CRISPR-Cas9-induced precise gene editing in mammalian cells, Nature Biotechnology, vol. 33, No. 5, pp. 543-548, 2015.
Coates, B., et al., A Helitron-Like Transposon Superfamily from Lepidoptera Disrupts $(GAAA)_n$ Microsatellites and is Responsible for Flanking Sequence Similarity within a Microsatellite Family, Journal of Molecular Evolution, vol. 70, pp. 275-288, 2010.
Dahlroth, S., et al., Crystal structure of the shutoff and exonuclease protein from the oncogenic Kaposi's sarcoma-associated herpesvirus, FEBS Journal, vol. 276, pp. 6636-6645, 2009.
Didigu, C., et al., Simultaneous zinc-finger nuclease editing of the HIV coreceptors ccr5 and cxcr4 protects CD4+ T cells from HIV-1 infection, Blood vol. 123, No. 1, pp. 61-69, 2014.
Diner, B., et al., Blowing off steam: Virus inhibition of cGAS DNA sensing, Cell Host & Microbe, vol. 18, pp. 270-272, 2015.
EP communication received in Application No. 12751744.9, dated Mar. 18, 2015.
Epinat, J.C., et al., A novel engineered meganuclease induces homologous recombination in yeast and mammalian cells, Nucleic Acids Research, vol. 31, No. 11, pp. 2952-2962, 2003.
Farjardo-Sanchez, E., et al., Computer Design of Obligate Heterodimer Meganucleases Allows Efficient Cutting of Custom DNA Sequences, Nucleic Acids Research, vol. 36, No. 7, pp. 2163-2173, 2008.
File History of U.S. Appl. No. 13/405,183, filed Feb. 24, 2012.
File History of U.S. Appl. No. 14/173,705, filed Feb. 5, 2014.
File History of U.S. Appl. No. 14/949,744, filed Nov. 23, 2015.
File History of U.S. Appl. No. 15/215,405, filed Jul. 20, 2016.
File History of U.S. Appl. No. 15/215,428, filed Jul. 20, 2016.
File History of U.S. Appl. No. 15/215,461, filed Jul. 20, 2016.
File History of U.S. Appl. No. 15/215,396, filed Jul. 20, 2016.
Gammon, D., et al., The 3'-to-5' Exonuclease Activity of Vaccinia Virus DNA Polymerase Is Essential and Plays a Role in Promoting Virus Genetic Recombination, Journal of Virology, vol. 83, No. 9, pp. 4236-4250, 2009.
Garcia, V., et al., "Bidirectional resection of DNA double-strand breaks by Mre11 and Exo1" Nature, vol. 479, pp. 241-244, 2011.
Glaunsinger, B., et al., The Exonuclease and Host Shutoff Functions of the SOX Protein of Kaposi's Sarcoma-Associated Herpesvirus Are Genetically Separable Journal of Virology, vol. 79, No. 12, pp. 7396-7401, 2005.
Gori, J., et al., Delivery and specificity of CRISPR-Cas9 genome editing technologies for human gene therapy, Hum Gene Therapy, vol. 26, No. 7, pp. 443-451, 2015.
Gunn, A., et al., Correct End Use During End Joining of Multiple Chromosomal Double Strand Breaks Is Influenced by Repair Protein RAD50, DNA-Dependent Protein Kinase DNA-PKcs, and Transcription Context, The Journal of Biological Chemistry, vol. 286, No. 49, pp. 42470-42482, 2011.
Gwiazda, K. et al., High Efficiency CRISPR/Cas9-mediated Gene Editing in Primary Human T-cells Using Mutant Adenoviral E4orf6/E1b55k "Helper" Proteins, Molecular Therapy, vol. 24, No. 9, pp. 1570-1580, 2016.
Hendel, A. et al., Chemically modified guide RNAs enhance CRISPR-Cas genome editing in human primary cells, Nature Biotechnology, vol. 33, No. 9, pp. 985-989, 2015.
International Search Report and Written Opinion dated Jun. 7, 2012, received in connection with PCT/US 12/26653.
Ishchenko, A., et al., The 3'→5' Exonuclease of Apn1 Provides an Alternative Pathway to Repair 7,8-Dihydro-8-Oxodeoxyguanosine in *Saccharomyces cerevisiae*, Molecular and Cellular Biology, pp. 6380-6390, 2005.
Jagannathan, I., et al., Activity of FEN1 Endonuclease on Nucleosome Substrates Is Dependent upon DNA Sequence but Not Flap Orientation, The Journal of Biological Chemistry, vol. 286, No. 20, pp. 17521-17529, 2011.
Jiang, W., et al., CRISPR-Cas: New tools for genetic manipulations from bacterial immunity systems, Annual Review of Microbiology, vol. 69, pp. 209-228, 2015.
Khan, I.F., et al., AAV-mediated gene targeting methods for human cells, Nature Protocols, vol. 6, No. 4, pp. 482-501, 2011.
Kotterman, Ma et al., "Engineering adeno-associated viruses for clinical gene therapy," Nature Reviews Genetics, vol. 15, pp. 445-451, 2014.
Kratz, K., et al., Deficiency of FANCD2-Associated Nuclease KIAA1018/FAN1 Sensitizes Cells to Interstrand Crosslinking Agents, Cell, vol. 142, pp. 77-99, 2010.
Kurosawa, A., et al., Functions and Regulation of Artemis: A Goddess in the Maintenance of Genome Integrity, J. Radiat. Res., vol. 51, pp. 503-509, 2010.
Lee, B., et al., The RAD2 Domain of Human Exonuclease 1 Exhibits 5' to 3' Exonuclease and Flap Structure-specific Endonuclease Activities, The Journal of Biological Chemistry, vol. 274, No. 53, pp. 37763-37769, 1999.
Lenain, C., et al., The Apollo 5' Exonuclease Functions Together with TRF2 to Protect Telomeres from DNA Repair, Current Biology, vol. 16, pp. 1303-1310, 2006.
Lentz, T.B., et al., Insight into the mechanism of inhibition of adeno-associated virus by the Mre11/Rad50/Nbs1 complex, Journal of Virology, vol. 89, No. 1, pp. 181-194, 2015.
Lisowski, L., et al., Adeno-associated virus serotypes for gene therapeutics, Current Opinion in Pharmacology, vol. 24, pp. 59-67, 2015.
Mahajan, K.N., et al., Association of terminal deoxynucleotidyl transferase with Ku PNAS, vol. 96, No. 24, pp. 13926-13931, 1999.
Maier, D., et al., Efficient clinical scale gene modification via zinc finger nuclease-targeted disruption of the HIV co-receptor CCR5, Human Gene Therapy, vol. 24, pp. 245-258, 2013.
Marcaida, M.J., et al. Homing endonucleases: from basics to therapeutic applications, Cellular Molecular Life Science, vol. 67, pp. 727-748, 2010.
Mashimo, T. et al., Efficient gene targeting by TAL effector nucleases coinjected with exonucleases in zygotes, Scientific Reports, vol. 3, Article No. 1253, 2013.
Mazur, D., et al., Excision of 3' Termini by the Trex1 and TREX2 3'→5' Exonucleases—Characterization of the Recombinant Proteins, The Journal of Biological Chemistry, vol. 276, No. 20, pp. 17022-17029, 2001.
Mock, U., et al., mRNA transfection of a novel TAL effector nuclease (TALEN) facilitates efficient knockout of HIV co-receptor CCR5, Nucleic Acids Research, vol. 43, No. 11, pp. 5560-5571; 2015.
Monteilhet, C., et al. Purification and characterization of the in vitro activity of I-Sce I, a novel and highly specific endonuclease encoded by a group I intron, Nucleic Acids Research, vol. 18, No. 6, pp. 1407-1413, 1990.
Moscou, M.J., et al., A Simple Cipher Governs DNA Recognition by TAL Effectors, Science, vol. 326, pp. 1501, 2009.
Mussolino, C., et al., TALENs facilitate targeted genome editing in human cells with high specificity and low cytotoxicity, Nucleic Acids Research, vol. 42, No. 10, pp. 6762-6773, 2014.
Nicolette, M.L., et al., Mre11-Rad50-Xrs2 and Sae2 Promote 5' Strand Resection of DNA Double-Strand Breaks, Nature Structure Molecular Biology, vol. 17, No. 12, pp. 1478-1485, 2010.
Nimonkar, A., et al., BLM-DNA2-RPA-MRN and EXO1-BLM-RPA-MRN constitute two DNA end resection machineries for human DNA break repair Genes & Development, vol. 25, pp. 350-362, 2011.
Orans, J., et al., "Structures of Human Exonuclease 1 DNA Complexes Suggest a Unified Mechanism for Nuclease Family" Cell, vol. 145, pp. 212-223, 2011.

(56) References Cited

OTHER PUBLICATIONS

Orazio, N., et al., The adenovirus E1b55K/E4orf6 complex induces degradation of the Bloom helicase during infection, Journal of Virology, vol. 85, No. 4, pp. 1887-1892, 2011.
Paques, F., et al., Meganucleases and DNA Double-Strand Break-Induced Recombination: Perspectives for Gene Therapy, Current Gene Therapy, vol. 7, pp. 49-66, 2007.
Poirot, L., et al., Multiplex genome-edited T-cell manufacturing platform for "Off-the-shelf" adoptive T-cell immunotherapies, Cancer Research, vol. 75, No. 18, pp. 3853-3864, 2015.
Porteus, M., et al., Chimeric Nucleases Stimulate Gene Targeting in Human Cells, Science, vol., No. , 2003.
Reuven, N., et al., The Herpes Simplex Virus Type 1 Alkaline Nuclease and Single-Stranded DNA Binding Protein Mediate Strand Exchange in Vitro, Journal of Virology, vol. 77, No. 13, pp. 7245-7433, 2003.
Sanchez-Rivera, F.J., et al., Applications of the CRISPR-Cas9 system in cancer biology, Nat Rev Cancer, vol. 15, pp. 387-395, 2015.
Sanlioglu, S., et al., Two independent molecular pathways for recombinant adeno-associated virus genome conversion occur after UV-C and E4orf6 augmentation of transduction, Human Gene Therapy, vol. 10, pp. 591-602, 1999.
Sather, B.D., et al., Efficient modification of CCR5 in primary human hematopoietic cells using a megaTAL nuclease and AAV donor template, Science Translational Medicine, vol. 7, Issue: 307, pp. 1-15, 2015.
Schumann, K et al., Generation of knock-in primary human T cells using Cas9 ribonucleoproteins, PNAS USA, vol. 112, No. 33, pp. 10437-10442, 2015.
Schwartz, R.A., et al., Distinct requirements of adenovirus E1b55K protein for degradation of cellular substrates, Journal of Virology, vol. 82, No. 18, pp. 9043-9055, 2008.
Schwartz, R.A., et al., The Mre11/Rad50/Nbs1 complex limits adeno-associated virus transduction and replication, Journal of Virology, vol. 81, No. 23, pp. 12936-12945, 2007.
Shalem, O, et al., High-throughput functional genomics using CRISPR-Cas9, Nature Reviews Genetics, vol. 16, pp. 299-311, 2015.
Smith, J., et al., A Combinatorial Approach to Create Artificial Homing Endonucleases Cleaving Chosen Sequences, Nucleic Acids Research, vol. 34, No. 22, pp. 1-12, 2006.
Sparrer, K.M. et al., Intracellular detection of viral nucleic acids, Current Opinion in Microbiology, vol. 26, pp. 1-9, 2015.
Stracker, T.H., et al., Adenovirus oncoproteins inactivate the Mre11-Rad50-NBS1 DNA repair complex, Nature, vol. 418, pp. 348-352, 2002.
Tebas, P., et al., Gene editing of CCR5 in autologous CD4 T cells of persons infected with HIV, The New England Journal of Medicine, vol. 370, No. 10, pp. 901-910, 2014.
Trigg, B.J., et al., Functions of DNA damage machinery in the innate immune response to DNA virus infection, Current Opinion of Virology, vol. 15, pp. 56-62, 2015.
Tsutakawa, S.E., et al., Human Flap Endonuclease Structures, DNA Double-Base Flipping, and a Unified Understanding of the FEN1 Superfamily, Cell, vol. 145, pp. 198-211, 2011.
Vallur, et al., Complementary Roles for Exonuclease 1 and Flap Endonuclease 1 in Maintenance of Triplet Repeats, The Journal of Biological Chemistry, vol. 285, No. 37, pp. 28514-28519, 2010.
Vasileva, E.A., et al., Genome-editing tools for stem cell biology, Cell Death and Disease, vol. 6, e1831, 2015.
Wang, Q., et al., Cytosolic sensing of aberrant DNA: arming STING on the endoplasmic reticulum, Expert Opinion Therapeutic Targets, vol. 19, pp. 1397-1409, 2015.
Xu, J., et al., A toolkit of CRISPR-based genome editing systems in Drosophila, Journal of Genetics and Genomics vol. 42, pp. 141-149, 2015.
Yoon, J., et al., Characterization of the 3' → 5' Exonuclease Activity Found in Human Nucleoside Diphosphate Kinase 1 (NDK1) and Several of Its Homologues, Biochemistry vol. 44, pp. 15774-15786, 2005.
Zhang, J., et al., Crystal Structure of *E. coli* RecE Protein Reveals a Toroidal Tetramer for Processing Double-Stranded DNA Breaks, Structure, vol. 17, pp. 690-702, 2009.
Zhang, J., et al., Crystal structures of λ exonuclease in complex with DNA suggest an electrostatic ratchet mechanism for processivity, PNAS, vol. 108, No. 29, pp. 11872-11877, 2011.
Zinn, E., et al., Adeno-associated virus: fit to serve, Current Opinion in Virology, vol. 8, pp. 90-97, 2014.
He Di et al., "Recent Advancement in the Generation of Genetically Modified Mammalian Models via CRISPR-Cas9," Chinese Journal of Cell Biology (Jan. 1, 2015) pp. 1295-1301.

* cited by examiner

FIG. 1E (Con'd)
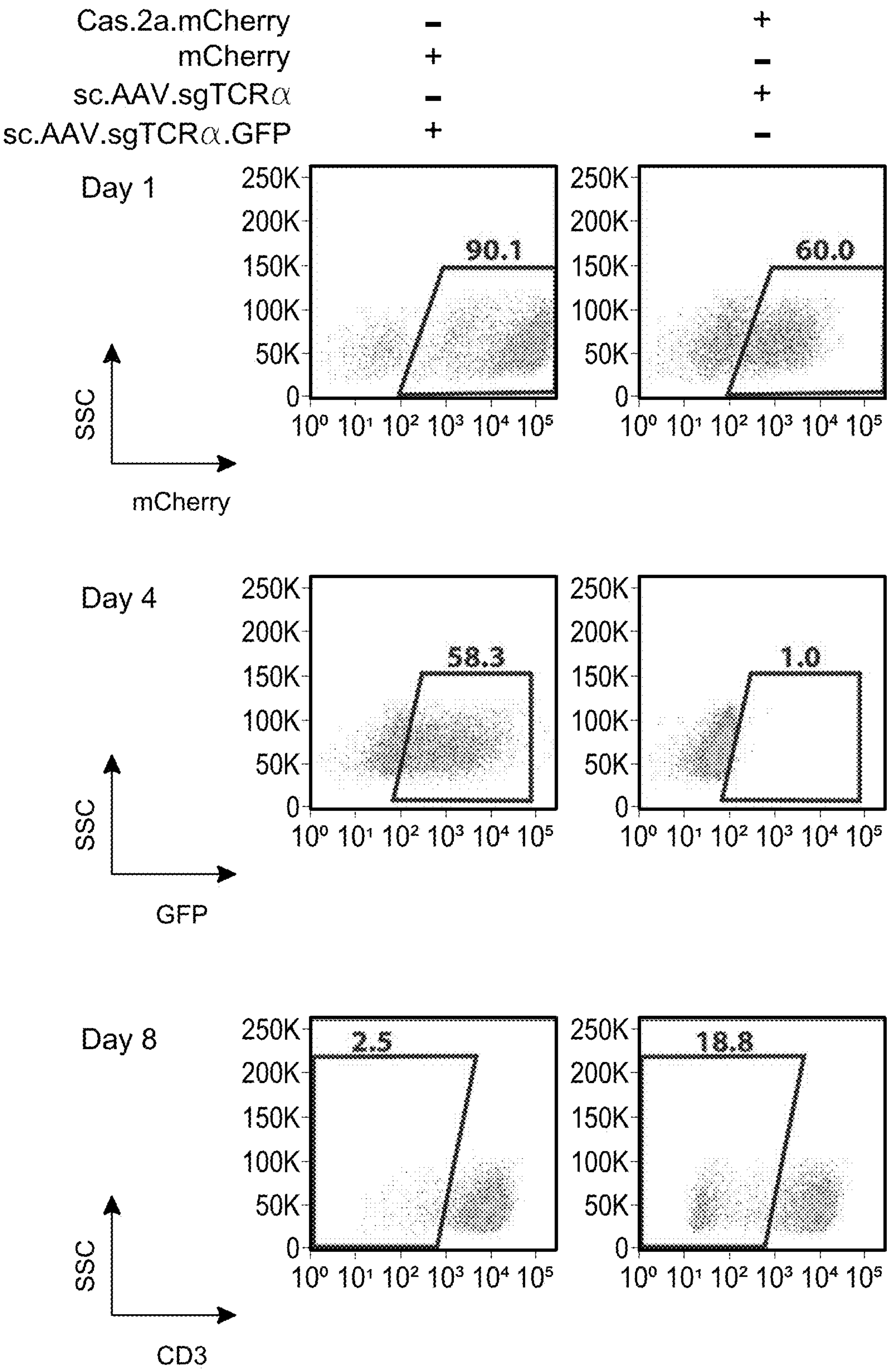

FIG. 1E (Con'd)
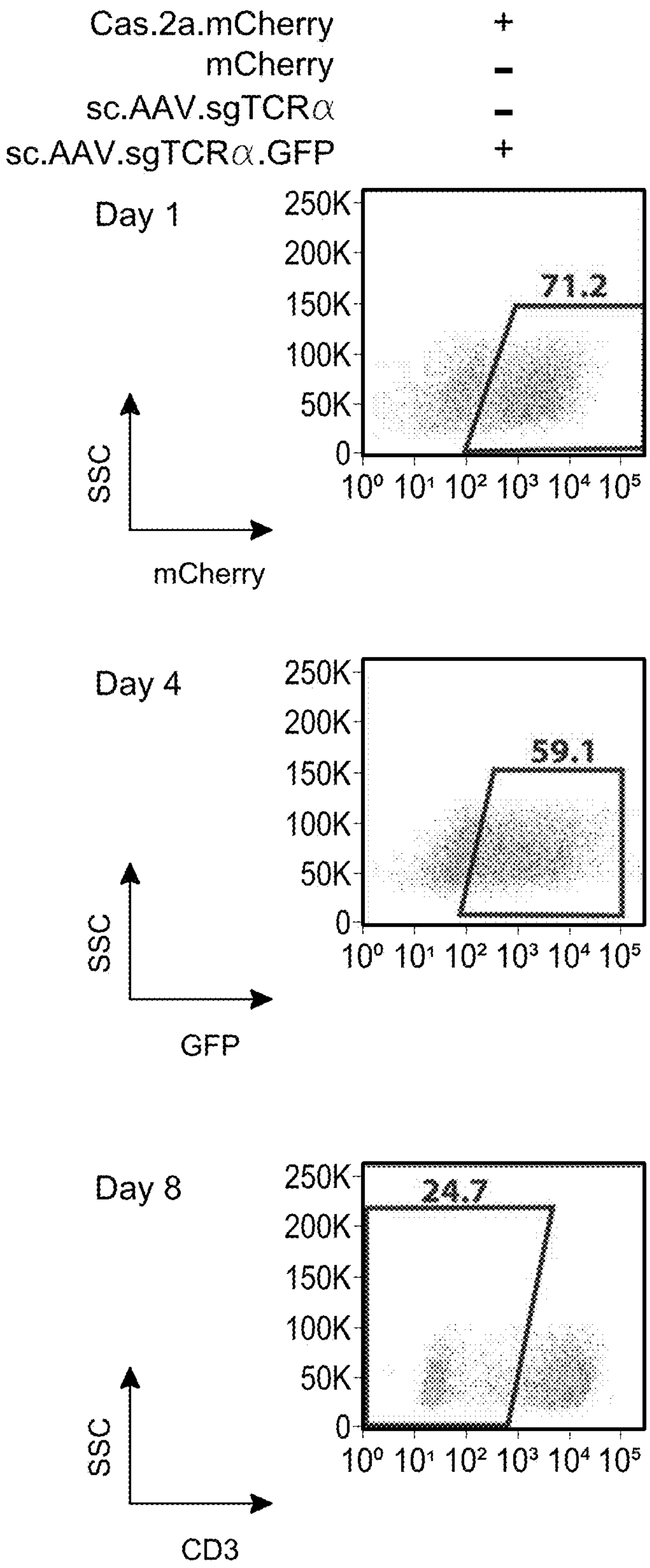

FIG. 16A

AACAAATGTGTCACAAAGTA (SEQ ID NO: 15)

ACAAAACTGTGCTAGACATG (SEQ ID NO: 16)

TGTGCTAGACATGAGGTCTA (SEQ ID NO: 17)

TCAAGAGCAACAGTGCTG (SEQ ID NO: 5)

FIG. 17

MERRNPSERGVPAGFSGHASVESGCETQESPATVVFRPPGDNTDGGAAAAAGGSQAAAAGAE
PMEPESRPGPSGMNVVQVAELYPELRRILTITEDGQGLKGVKRERGACEATEEARNLAFSLMTRH
RPECITFQQIKDNCANELDLLAQKYSIEQLTTYWLQPGDDFEEAIRVYAKVALRPDCKYKISKLVNIR
NCCYISGNGAEVEIDTEDRVAFRCSMINMWPGVLGMDGVVIMNVRFTGPNFSGTVFLANTNLI
LHGVSFYGFNNTCVEAWTDVRVRGCAFYCCWKGVVCRPKSRASIKKCLFERCTLGILSEGNSRVR
HNVASDCGCFMLVKSVAVIKHNMVCGNCEDRASQMLTCSDGNCHLLKTIHVASHSRKAWPVFE
HNILTRCSLHLGNRRGVFLPYQCNLSHTKILLEPESMSKVNLNGVFDMTMKIWKVLRYDETRTRC
RPCECGGKHIRNQPVMLDVTEELRPDHLVLACTRAEFGSSDEDTD (SEQ ID NO: 1)

FIG. 18

MERRNPSERGVPAGFSGHASVESGCETQESPATVVFRPPGDNTDGGAAAAAGGSQAAAAGAEP
MEPESRPGPSGMNVVQVAELYPELRRILTITEDGQGLKGVKRERGACEATEEARNLAFSLMTRHRP
ECITFQQIKDNCANELDLLAQKYSIEQLTTYWLQPGDDFEEAIRVYAKVALRPDCKYKISKLVNIRNC
CYISGNGAEVEIDTEDRVAFRCSMINMWPGVLGMDGVVIMNVRFTGPNFSGTVFLANTNLILHG
VSFYGFNNTCVEAWTDVRVRGCAFYCCWKGVVCRPKSRASIKKCLFERCTLGILSEGNSRVRHNVA
SDCGCFMLVKSVAVIKHNMVCGNCEDRASQMLTCSDGNCHLLKTIAVASHSRKAWPVFEHNILT
RCSLHLGNRRGVFLPYQCNLSHTKILLEPESMSKVNLNGVFDMTMKIWKVLRYDETRTRCRPCEC
GGKHIRNQPVMLDVTEELRPDHLVLACTRAEFGSSDEDTD (SEQ ID NO: 2)

FIG. 19

MTTSGVPFGMTLRPTRSRLSRRTPYSRDRLPPFETETRATILEDHPLLPECNTLTMHNVSYVRGLPC
SVGFTLIQEWVVPWDMVLTREELVILRKCMHVCLCCANIDIMTSMMIHGYESWALHCHCSSPGS
LQCIAGGQVLASWFRMVVDGAMFNQRFIWYREVVNYNMPKEVMFMSSVFMRGRHLIYLRLW
YDGHVGSVVPAMSFGYSALHCGILNNIVVLCCSYCADLSEIRVRCCARRTRRLMLRAVRIIAEETTA
MLYSCRTERRRQQFIRALLQHHRPILMHDYDSTPM (SEQ ID NO: 3)

FIG. 20

MERRNPSERGVPAGFSGHASVESGCETQESPATVVFRPPGDNTDGGAAAAAGGSQAAAAGAEP
MEPESRPGPSGMNVVQVAELYPELRRILTITEDGQGLKGVKRERGACEATEEARNLAFSLMTRHRP
ECITFQQIKDNCANELDLLAQKYSIEQLTTYWLQPGDDFEEAIRVYAKVALRPDCKYKISKLVNIRNC
CYISGNGAEVEIDTEDRVAFRCSMINMWPGVLGMDGVVIMNVRFTGPNFSGTVFLANTNLILHG
VSFYGFNNTCVEAWTDVRVRGCAFYCCWKGVVCRPKSRASIKKCLFERCTLGILSEGNSRVRHNVA
SDCGCFMLVKSVAVIKHNMVCGNCEDRAGIPASQMLTCSDGNCHLLKTIHVASHSRKAWPVFEH
NILTRCSLHLGNRRGVFLPYQCNLSHTKILLEPESMSKVNLNGVFDMTMKIWKVLRYDETRTRCRP
CECGGKHIRNQPVMLDVTEELRPDHLVLACTRAEFGSSDEDTD (SEQ ID NO: 4)

FIG. 21 (Con'd)
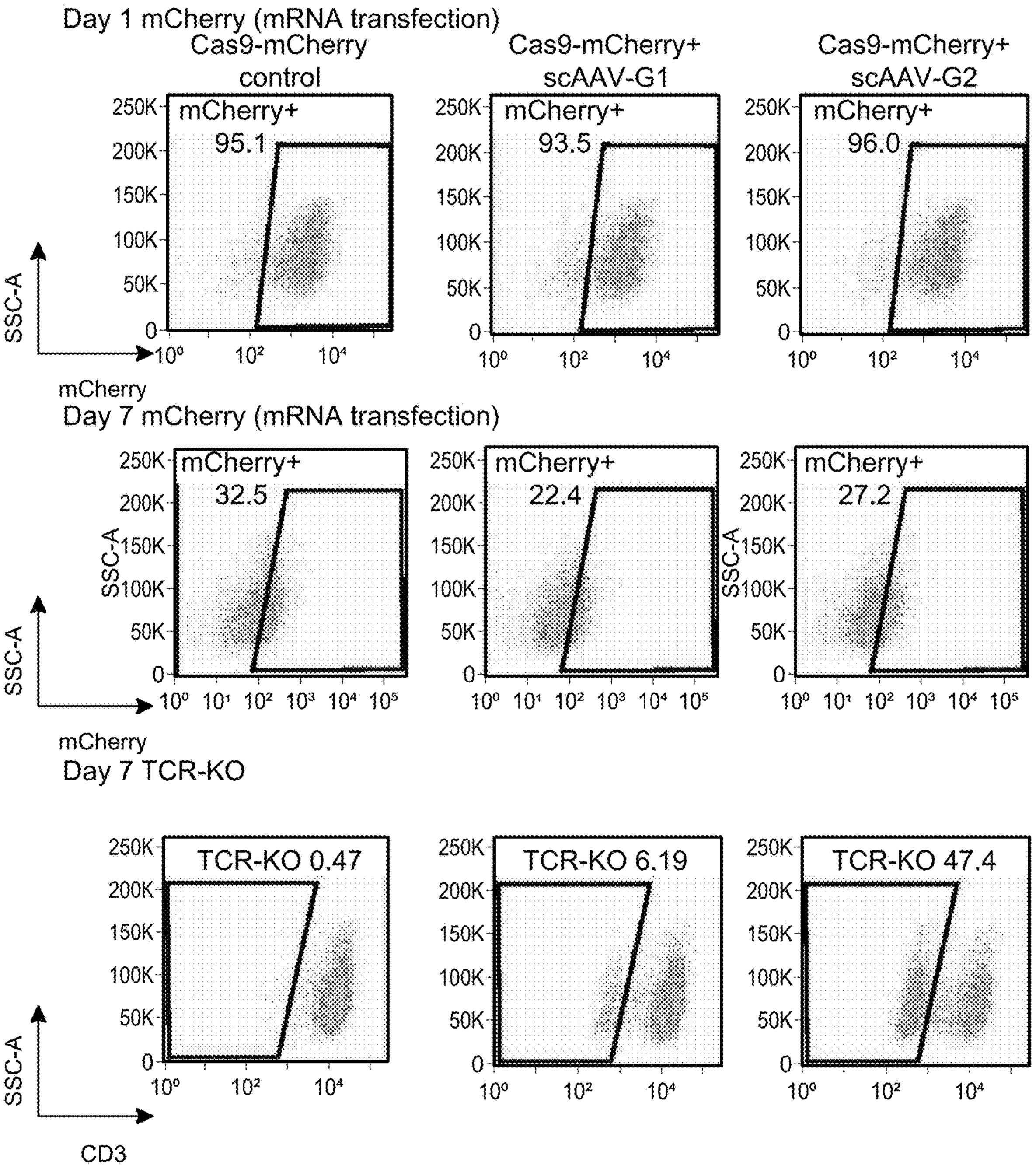

*FIG. 21 (Con'd)*
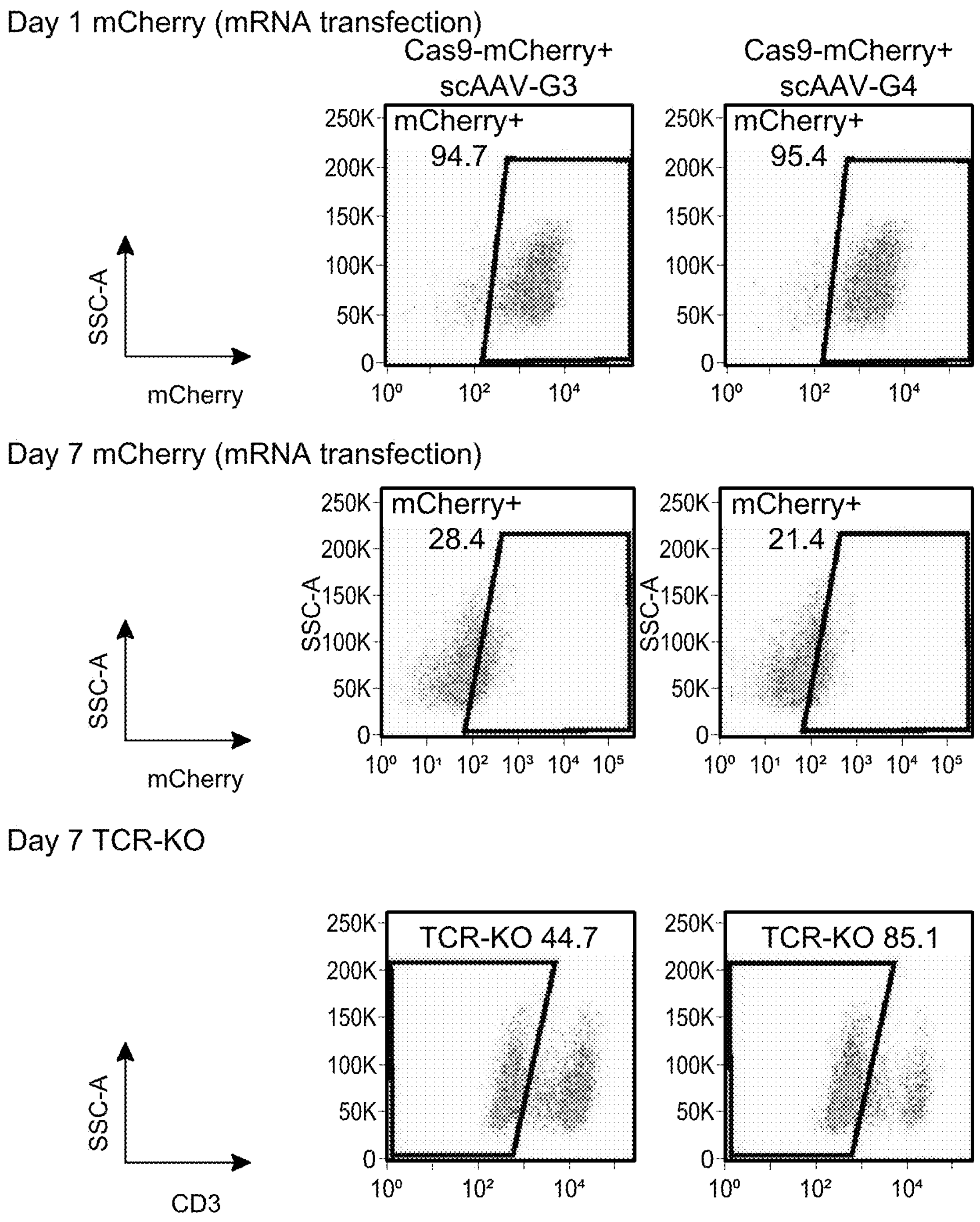

FIG. 22

MDKKYSIGLAIGTNSVGWAVITDEYKVPSKKFKVLGNTDRHSIKKNLIGALLFDSGETAEATRLKRTARRRYTRRKNRICYLQEIFSN
EMAKVDDSFFHRLEESFLVEEDKKHERHPIFGNIVDEVAYHEKYPTIYHLRKKLVDSTDKADLRLIYLALAHMIKFRGHFLIEGDLNP
DNSDVDKLFIQLVQTYNQLFEENPINASGVDAKAILSARLSKSRRLENLIAQLPGEKKNGLFGNLIALSLGLTPNFKSNFDLAEDAKL
QLSKDTYDDDLDNLLAQIGDQYADLFLAAKNLSDAILLSDILRVNTEITKAPLSASMIKRYDEHHQDLTLLKALVRQQLPEKYKEIFF
DQSKNGYAGYIDGGASQEEFYKFIKPILEKMDGTEELLVKLNREDLLRKQRTFDNGSIPHQIHLGELHAILRRQEDFYPFLKDNREK
IEKILTFRIPYYVGPLARGNSRFAWMTRKSEETITPWNFEEVVDKGASAQSFIERMTNFDKNLPNEKVLPKHSLLYEYFTVYNELTK
VKYVTEGMRKPAFLSGEQKKAIVDLLFKTNRKVTVKQLKEDYFKKIECFDSVEISGVEDRFNASLGTYHDLLKIIKDKDFLDNEENE
DILEDIVLTLTLFEDREMIEERLKTYAHLFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENIVIEMARENQTTQKGQKNSRERMKRI
EEGIKELGSQILKEHPVENTQLQNEKLYLYYLQNGRDMYVDQELDINRLSDYDVDAIVPQSFLKDDSIDNKVLTRSDKNRGKSDNV
PSEEVVKKMKNYWRQLLNAKLITQRKFDNLTKAERGGLSELDKAGFIKRQLVETRQITKHVAQILDSRMNTKYDENDKLIREVKVI
TLKSKLVSDFRKDFQFYKVREINNYHHAHDAYLNAVVGTALIKKYPKLESEFVYGDYKVYDVRKMIAKSEQEIGKATAKYFFYSNIM
NFFKTEITLANGEIRKRPLIETNGETGEIVWDKGRDFATVRKVLSMPQVNIVKKTEVQTGGFSKESILPKRNSDKLIARKKDWDPK
KYGGFDSPTVAYSVLVVAKVEKGKSKKLKSVKELLGITIMERSSFEKNPIDFLEAKGYKEVKKDLIIKLPKYSLFELENGRKRMLASAG
ELQKGNELALPSKYVNFLYLASHYEKLKGSPEDNEQKQLFVEQHKHYLDEIIEQISEFSKRVILADANLDKVLSAYNKHRDKPIREQA
ENIIHLFTLTNLGAPAAFKYFDTTIDRKRYTSTKEVLDATLIHQSITGLYETRIDLSQLGGD (SEQ ID NO: 6)

FIG. 23

ATGGATAAGAAATACTCAATAGGCTTAGATATCGGCACAAATAGCGTCGGATGGGCGGTGATCACTGATGAATATAAGGTTCCGTCTAAAAAGTTCAAGGTTCTGGGAAATACAGA
CCGCCACAGTATCAAAAAAAATCTTATAGGGGCTCTTTTATTTGACAGTGGAGAGACAGCGGAAGCGACTCGTCTCAAACGGACAGCTCGTAGAAGGTATACACGTCGGAAGAATC
GTATTTGTTATCTACAGGAGATTTTTTCAAATGAGATGGCGAAAGTAGATGATAGTTTCTTTCATCGACTTGAAGAGTCTTTTTTGGTGGAAGAAGACAAGAAGCATGAACGTCATC
CTATTTTTGGAAATATAGTAGATGAAGTTGCTTATCATGAGAAATATCCAACTATCTATCATCTGCGAAAAAAATTGGTAGATTCTACTGATAAAGCGGATTTGCGCTTAATCTATTT
GGCCTTAGCGCATATGATTAAGTTTCGTGGTCATTTTTTGATTGAGGGAGATTTAAATCCTGATAATAGTGATGTGGACAAACTATTTATCCAGTTGGTACAAACCTACAATCAATTA
TTTGAAGAAAACCCTATTAACGCAAGTGGAGTAGATGCTAAAGCGATTCTTTCTGCACGATTGAGTAAATCAAGACGATTAGAAAATCTCATTGCTCAGCTCCCCGGTGAGAAGAA
AAATGGCTTATTTGGGAATCTCATTGCTTTGTCATTGGGTTTGACCCCTAATTTTAAATCAAATTTTGATTTGGCAGAAGATGCTAAATTACAGCTTTCAAAAGATACTTACGATGATG
ATTTAGATAATTTATTGGCGCAAATTGGAGATCAATATGCTGATTTGTTTTTGGCAGCTAAGAATTTATCAGATGCTATTTTACTTTCAGATATCCTAAGAGTAAATACTGAAATAACT
AAGGCTCCCCTATCAGCTTCAATGATTAAACGCTACGATGAACATCATCAAGACTTGACTCTTTTAAAAGCTTTAGTTCGACAACAACTTCCAGAAAAGTATAAAGAAATCTTTTTTG
ATCAATCAAAAAACGGATATGCAGGTTATATTGATGGGGGAGCTAGCCAAGAAGAATTTTATAAATTTATCAAACCAATTTTAGAAAAAATGGATGGTACTGAGGAATTATTGGTG
AAACTAAATCGTGAAGATTTGCTGCGCAAGCAACGGACCTTTGACAACGGCTCTATTCCCCATCAAATTCACTTGGGTGAGCTGCATGCTATTTTGAGAAGACAAGAAGACTTTTAT
CCATTTTTAAAAGACAATCGTGAGAAGATTGAAAAAATCTTGACTTTTCGAATTCCTTATTATGTTGGTCCATTGGCGCGTGGCAATAGTCGTTTTGCATGGATGACTCGGAAGTCTG
AAGAAACAATTACCCCATGGAATTTTGAAGAAGTTGTCGATAAAGGTGCTTCAGCTCAATCATTTATTGAACGCATGACAAACTTTGATAAAAATCTTCCAAATGAAAAAGTACTAC
CAAAACATAGTTTGCTTTATGAGTATTTTACGGTTTATAACGAATTGACAAAGGTCAAATATGTTACTGAAGGAATGCGAAAACCAGCATTTCTTTCAGGTGAACAGAAGAAAGCCA
TTGTTGATTTACTCTTCAAAACAAATCGAAAAGTAACCGTTAAGCAATTAAAAGAAGATTATTTCAAAAAAATAGAATGTTTTGATAGTGTTGAAATTTCAGGAGTTGAAGATAGATT
TAATGCTTCATTAGGTACCTACCATGATTTGCTAAAAATTATTAAAGATAAAGATTTTTTGGATAATGAAGAAAATGAAGATATCTTAGAGGATATTGTTTTAACATTGACCTTATTTG
AAGATAGGGAGATGATTGAGGAAAGACTTAAAACATATGCTCACCTCTTTGATGATAAGGTGATGAAACAGCTTAAACGTCGCCGTTATACTGGTTGGGGACGTTTGTCTCGAAAA
TTGATTAATGGTATTAGGGATAAGCAATCTGGCAAAACAATATTAGATTTTTTGAAATCAGATGGTTTTGCCAATCGCAATTTTATGCAGCTGATCCATGATGATAGTTTGACATTTA
AAGAAGACATTCAAAAAGCACAAGTGTCTGGACAAGGCGATAGTTTACATGAACATATTGCAAATTTAGCTGGTAGCCCTGCTATTAAAAAAGGTATTTTACAGACTGTAAAAGTTG
TTGATGAATTGGTCAAAGTAATGGGGCGGCATAAGCCAGAAAATATCGTTATTGAAATGGCACGTGAAAATCAGACAACTCAAAAGGGCCAGAAAAATTCGCGAGAGCGTATGAA
ACGAATCGAAGAAGGTATCAAAGAATTAGGAAGTCAGATTCTTAAAGAGCATCCTGTTGAAAATACTCAATTGCAAAATGAAAAGCTCTATCTCTATTATCTCCAAAATGGAAGAGA
CATGTATGTGGACCAAGAATTAGATATTAATCGTTTAAGTGATTATGATGTCGATCACATTGTTCCACAAAGTTTCCTTAAAGACGATTCAATAGACAATAAGGTCTTAACGCGTTCT
GATAAAAATCGTGGTAAATCGGATAACGTTCCAAGTGAAGAAGTAGTCAAAAAGATGAAAAACTATTGGAGACAACTTCTAAACGCCAAGTTAATCACTCAACGTAAGTTTGATAA
TTTAACGAAAGCTGAACGTGGAGGTTTGAGTGAACTTGATAAAGCTGGTTTTATCAAACGCCAATTGGTTGAAACTCGCCAAATCACTAAGCATGTGGCACAAATTTTGGATAGTCG
CATGAATACTAAATACGATGAAAATGATAAACTTATTCGAGAGGTTAAAGTGATTACCTTAAAATCTAAATTAGTTTCTGACTTCCGAAAAGATTTCCAATTCTATAAAGTACGTGAG
ATTAACAATTACCATCATGCCCATGATGCGTATCTAAATGCCGTCGTTGGAACTGCTTTGATTAAGAAATATCCAAAACTTGAATCGGAGTTTGTCTATGGTGATTATAAAGTTTATG
ATGTTCGTAAAATGATTGCTAAGTCTGAGCAAGAAATAGGCAAAGCAACCGCAAAATATTTCTTTTACTCTAATATCATGAACTTCTTCAAAACAGAAATTACACTTGCAAATGGAGA
GATTCGCAAACGCCCTCTAATCGAAACTAATGGGGAAACTGGAGAAATTGTCTGGGATAAAGGGCGAGATTTTGCCACAGTGCGCAAAGTATTGTCCATGCCCCAAGTCAATATTG
TCAAGAAAACAGAAGTACAGACAGGCGGATTCTCCAAGGAGTCAATTTTACCAAAAAGAAATTCGGACAAGCTTATTGCTCGTAAAAAAGACTGGGATCCAAAAAAATATGGTGGT
TTTGATAGTCCAACGGTAGCTTATTCAGTCCTAGTGGTTGCTAAGGTGGAAAAAGGGAAATCGAAGAAGTTAAAATCCGTTAAAGAGTTACTAGGGATCACAATTATGGAAAGAAG
TTCCTTTGAAAAAAATCCGATTGACTTTTTAGAAGCTAAAGGATATAAGGAAGTTAAAAAAGACTTAATCATTAAACTACCTAAATATAGTCTTTTTGAGTTAGAAAACGGTCGTAAA
CGGATGCTGGCTAGTGCCGGAGAATTACAAAAAGGAAATGAGCTGGCTCTGCCAAGCAAATATGTGAATTTTTTATATTTAGCTAGTCATTATGAAAAGTTGAAGGGTAGTCCAGA
AGATAACGAACAAAAACAATTGTTTGTGGAGCAGCATAAGCATTATTTAGATGAGATTATTGAGCAAATCAGTGAATTTTCTAAGCGTGTTATTTTAGCAGATGCCAATTTAGATAA
AGTTCTTAGTGCATATAACAAACATAGAGACAAACCAATACGTGAACAAGCAGAAAATATTATTCATTTATTTACGTTGACGAATCTTGGAGCTCCCGCTGCTTTTAAATATTTTGAT
ACAACAATTGATCGTAAACGATATACGTCTACAAAAGAAGTTTTAGATGCCACTCTTATCCATCAATCCATCACTGGTCTTTATGAAACACGCATTGATTTGAGTCAGCTAGGAGGTG
ACTGA (SEQ ID NO: 7)

FIG. 24

ATGGACAAGAAGTACTCCATTGGGCTCGCTATCGGCACAAACAGCGTCGGCTGGGCCGTCATTACGGACGAGTACAAGGTGCCGAGCAAAAAATTCAAAGTTCTGGGCAATA
CCGATCGCCACAGCATAAAGAAGAACCTCATTGGCGCCCTCCTGTTCGACTCCGGGGAGACGGCCGAAGCCACGCGGCTCAAAAGAACAGCACGGCGCAGATATACCCGCAG
AAAGAATCGGATCTGCTACCTGCAGGAGATCTTTAGTAATGAGATGGCTAAGGTGGATGACTCTTTCTTCCATAGGCTGGAGGAGTCCTTTTTGGTGGAGGAGGATAAAAAGC
ACGAGCGCCACCCAATCTTTGGCAATATCGTGGACGAGGTGGCGTACCATGAAAAGTACCCAACCATATATCATCTGAGGAAGAAGCTTGTAGACAGTACTGATAAGGCTGA
CTTGCGGTTGATCTATCTCGCGCTGGCGCATATGATCAAATTTCGGGGACACTTCCTCATCGAGGGGGACCTGAACCCAGACAACAGCGATGTCGACAAACTCTTTATCCAACT
GGTTCAGACTTACAATCAGCTTTTCGAAGAGAACCCGATCAACGCATCCGGAGTTGACGCCAAAGCAATCCTGAGCGCTAGGCTGTCCAAATCCCGGCGGCTCGAAAACCTCA
TCGCACAGCTCCCTGGGGAGAAGAAGAACGGCCTGTTTGGTAATCTTATCGCCCTGTCACTCGGGCTGACCCCCAACTTTAAATCTAACTTCGACCTGGCCGAAGATGCCAAG
CTTCAACTGAGCAAAGACACCTACGATGATGATCTCGACAATCTGCTGGCCCAGATCGGCGACCAGTACGCAGACCTTTTTTTGGCGGCAAAGAACCTGTCAGACGCCATTCT
GCTGAGTGATATTCTGCGAGTGAACACGGAGATCACCAAAGCTCCGCTGAGCGCTAGTATGATCAAGCGCTATGATGAGCACCACCAAGACTTGACTTTGCTGAAGGCCCTTG
TCAGACAGCAACTGCCTGAGAAGTACAAGGAAATTTTCTTCGATCAGTCTAAAAATGGCTACGCCGGATACATTGACGGCGGAGCAAGCCAGGAGGAATTTTACAAATTTATT
AAGCCCATCTTGGAAAAAATGGACGGCACCGAGGAGCTGCTGGTAAAGCTTAACAGAGAAGATCTGTTGCGCAAACAGCGCACTTTCGACAATGGAAGCATCCCCCACCAGA
TTCACCTGGGCGAACTGCACGCTATCCTCAGGCGGCAAGAGGATTTCTACCCCTTTTTGAAAGATAACAGGGAAAAGATTGAGAAAATCCTCACATTTCGGATACCCTACTATG
TAGGCCCCCTCGCCCGGGGAAATTCCAGATTCGCGTGGATGACTCGCAAATCAGAAGAGACCATCACTCCCTGGAACTTCGAGGAAGTCGTGGATAAGGGGGCCTCTGCCCA
GTCCTTCATCGAAAGGATGACTAACTTTGATAAAAATCTGCCTAACGAAAAGGTGCTTCCTAAACACTCTCTGCTGTACGAGTACTTCACAGTTTATAACGAGCTCACCAAGGT
CAAATACGTCACAGAAGGGATGAGAAAGCCAGCATTCCTGTCTGGAGAGCAGAAGAAAGCTATCGTGGACCTCCTCTTCAAGACGAACCGGAAAGTTACCGTGAAACAGCTC
AAAGAAGACTATTTCAAAAAGATTGAATGTTTCGACTCTGTTGAAATCAGCGGAGTGGAGGATCGCTTCAACGCATCCCTGGGAACGTATCACGATCTCCTGAAAATCATTAA
AGACAAGGACTTCCTGGACAATGAGGAGAACGAGGACATTCTTGAGGACATTGTCCTCACCCTTACGTTGTTTGAAGATAGGGAGATGATTGAAGAACGCTTGAAAACTTAC
GCTCATCTCTTCGACGACAAAGTCATGAAACAGCTCAAGAGGCGCCGATATACAGGATGGGGGCGGCTGTCAAGAAAACTGATCAATGGGATCCGAGACAAGCAGAGTGGA
AAGACAATCCTGGATTTTCTTAAGTCCGATGGATTTGCCAACCGGAACTTCATGCAGTTGATCCATGATGACTCTCTCACCTTTAAGGAGGACATCCAGAAAGCACAAGTTTCT
GGCCAGGGGGACAGTCTTCACGAGCACATCGCTAATCTTGCAGGTAGCCCAGCTATCAAAAAGGGAATACTGCAGACCGTTAAGGTCGTGGATGAACTCGTCAAAGTAATGG
GAAGGCATAAGCCCGAGAATATCGTTATCGAGATGGCCCGAGAGAACCAAACTACCCAGAAGGGACAGAAGAACAGTAGGGAAAGGATGAAGAGGATTGAAGAGGGTATA
AAAGAACTGGGGTCCCAAATCCTTAAGGAACACCCAGTTGAAAACACCCAGCTTCAGAATGAGAAGCTCTACCTGTACTACCTGCAGAACGGCAGGGACATGTACGTGGATC
AGGAACTGGACATCAATCGGCTCTCCGACTACGACGTGGCTGCTATCGTGCCCCAGTCTTTTCTCAAAGATGATTCTATTGATAATAAAGTGTTGACAAGATCCGATAAAGCTA
GAGGGAAGAGTGATAACGTCCCCTCAGAAGAAGTTGTCAAGAAAATGAAAAATTATTGGCGGCAGCTGCTGAACGCCAAACTGATCACACAACGGAAGTTCGATAATCTGAC
TAAGGCTGAACGAGGTGGCCTGTCTGAGTTGGATAAAGCCGGCTTCATCAAAAGGCAGCTTGTTGAGACACGCCAGATCACCAAGCACGTGGCCCAAATTCTCGATTCACGC
ATGAACACCAAGTACGATGAAAATGACAAACTGATTCGAGAGGTGAAAGTTATTACTCTGAAGTCTAAGCTGGTCTCAGATTTCAGAAAGGACTTTCAGTTTTATAAGGTGAG
AGAGATCAACAATTACCACCATGCGCATGATGCCTACCTGAATGCAGTGGTAGGCACTGCACTTATCAAAAAATATCCCAAGCTTGAATCTGAATTTGTTTACGGAGACTATAA
AGTGTACGATGTTAGGAAAATGATCGCAAAGTCTGAGCAGGAAATAGGCAAGGCCACCGCTAAGTACTTCTTTTACAGCAATATTATGAATTTTTTCAAGACCGAGATTACACT
GGCCAATGGAGAGATTCGGAAGCGACCACTTATCGAAACAAACGGAGAAACAGGAGAAATCGTGTGGGACAAGGGTAGGGATTTCGCGACAGTCCGGAAGGTCCTGTCCAT
GCCGCAGGTGAACATCGTTAAAAAGACCGAAGTACAGACCGGAGGCTTCTCCAAGGAAAGTATCCTCCCGAAAAGGAACAGCGACAAGCTGATCGCACGCAAAAAAGATTG
GGACCCCAAGAAATACGGCGGATTCGATTCTCCTACAGTCGCTTACAGTGTACTGGTTGTGGCCAAAGTGGAGAAAGGGAAGTCTAAAAAACTCAAAAGCGTCAAGGAACTG
CTGGGCATCACAATCATGGAGCGATCAAGCTTCGAAAAAAACCCCATCGACTTTCTCGAGGCGAAAGGATATAAAGAGGTCAAAAAAGACCTCATCATTAAGCTTCCCAAGTA
CTCTCTCTTTGAGCTTGAAAACGGCCGGAAACGAATGCTCGCTAGTGCGGGCGAGCTGCAGAAAGGTAACGAGCTGGCACTGCCCTCTAAATACGTTAATTTCTTGTATCTGG
CCAGCCACTATGAAAAGCTCAAAGGGTCTCCCGAAGATAATGAGCAGAAGCAGCTGTTCGTGGAACAACACAAACACTACCTTGATGAGATCATCGAGCAAATAAGCGAATT
CTCCAAAAGAGTGATCCTCGCCGACGCTAACCTCGATAAGGTGCTTTCTGCTTACAATAAGCACAGGGATAAGCCCATCAGGGAGCAGGCAGAAAACATTATCCACTTGTTTA
CTCTGACCAACTTGGGCGCGCCTGCAGCCTTCAAGTACTTCGACACCACCATAGACAGAAAGCGGTACACCTCTACAAAGGAGGTCCTGGACGCCACACTGATTCATCAGTCA
ATTACGGGGCTCTATGAAACAAGAATCGACCTCTCTCAGCTCGGTGGAGACTAA (SEQ ID NO: 8)

FIG. 25

ATGAGCGACCTGGTGCTGGGCCTGGACATCGGCATCGGCAGCGTGGGCGTGGGCATCCTGAACAAGGTGACCGGCGAGATCATCCACAAGAACAGTCGCATCTTCCCTGCT
GCTCAGGCTGAGAACAACCTGGTGCGCCGCACCAACCGCCAGGGTCGCCGGCTTGCTCGCCGCAAGAAGCACCGGCGCGTGCGCCTGAACCGCCTGTTCGAGGAGAGCGGC
CTGATCACCGACTTCACCAAGATCAGCATCAACCTGAACCCCTACCAGCTGCGCGTGAAGGGCCTGACCGACGAGCTGAGCAACGAGGAGCTGTTCATCGCCCTGAAGAACA
TGGTGAAGCACCGCGGCATCAGCTACCTGGACGACGCCAGCGACGACGGCAACAGCAGCGTGGGCGACTACGCCCAGATCGTGAAGGAGAACAGCAAGCAGCTGGAGACC
AAGACCCCCGGCCAGATCCAGCTGGAGCGCTACCAGACCTACGGCCAGCTGCGCGGCGACTTCACCGTGGAGAAGGACGGCAAGAAGCACCGCCTGATCAACGTGTTCCCC
ACCAGCGCCTACCGCAGCGAGGCCCTGCGCATCCTGCAGACCCAGCAGGAGTTCAACCCCCAGATCACCGACGAGTTCATCAACCGCTACCTGGAGATCCTGACCGGCAAGC
GCAAGTACTACCACGGCCCCGGCAACGAGAAGAGCCGCACCGACTACGGCCGCTACCGCACCAGCGGCGAGACCCTGGACAACATCTTCGGCATCCTGATCGGCAAGTGCA
CCTTCTACCCCGACGAGTTCCGCGCCGCCAAGGCCAGCTACACCGCCCAGGAGTTCAACCTGCTGAACGACCTGAACAACCTGACCGTGCCCACCGAGACCAAGAAGCTGAG
CAAGGAGCAGAAGAACCAGATCATCAACTACGTGAAGAACGAGAAGGCCATGGGCCCCGCCAAGCTGTTCAAGTACATCGCCAAGCTGCTGAGCTGCGACGTGGCCGACAT
CAAGGGCTACCGCATCGACAAGAGCGGCAAGGCCGAGATCCACACCTTCGAGGCCTACCGCAAGATGAAGACCCTGGAGACCCTGGACATCGAGCAGATGGACCGCGAGA
CCCTGGACAAGCTGGCCTACGTGCTGACCCTGAACACCGAGCGCGAGGGCATCCAGGAGGCCCTGGAGCACGAGTTCGCCGACGGCAGCTTCAGCCAGAAGCAGGTGGAC
GAGCTGGTGCAGTTCCGCAAGGCCAACAGCAGCATCTTCGGCAAGGGCTGGCACAACTTCAGCGTGAAGCTGATGATGGAGCTGATCCCCGAGCTGTACGAGACCAGCGAG
GAGCAGATGACCATCCTGACCCGCCTGGGCAAGCAGAAGACCACCAGCAGCAGCAACAAGACCAAGTACATCGACGAGAAGCTGCTGACCGAGGAGATCTACAACCCCGTG
GTGGCCAAGAGCGTGCGCCAGGCCATCAAGATCGTGAACGCCGCCATCAAGGAGTACGGCGACTTCGACAACATCGTGATCGAGATGGCCCGCGAGACCAACGAGGACGA
CGAGAAGAAGGCCATCCAGAAGATCCAGAAGGCCAACAAGGACGAGAAGGACGCCGCCATGCTGAAGGCCGCCAACCAGTACAACGGCAAGGCCGAGCTGCCCCACAGCG
TGTTCCACGGCCACAAGCAGCTGGCCACCAAGATCCGCCTGTGGCACCAGCAGGGCGAGCGCTGCCTGTACACCGGCAAGACCATCAGCATCCACGACCTGATCAACAACAG
CAACCAGTTCGAGGTGGACCACATCCTGCCCCTGAGCATCACCTTCGACGACAGCCTGGCCAACAAGGTGCTGGTGTACGCCACCGCCAACCAGGAGAAGGGCCAGCGCAC
CCCCTACCAGGCCCTGGACAGCATGGACGACGCCTGGAGCTTCCGCGAGCTGAAGGCCTTCGTGCGCGAGAGCAAGACCCTGAGCAACAAGAAGAAGGAGTACCTGCTGAC
CGAGGAGGACATCAGCAAGTTCGACGTGCGCAAGAAGTTCATCGAGCGCAACCTGGTGGACACCCGCTACGCCAGCCGCGTGGTGCTGAACGCCCTGCAGGAGCACTTCCG
CGCCCACAAGATCGACACCAAGGTGAGCGTGGTGCGCGGCCAGTTCACCAGCCAGCTGCGCCGCCACTGGGGCATCGAGAAGACCCGCGACACCTACCACCACCACGCCGT
GGACGCCCTGATCATTGCGGCTTCTAGCCAGCTGAACCTGTGGAAGAAGCAGAAGAACACCCTGGTGAGCTACAGCGAGGACCAGCTGCTGGACATCGAGACCGGCGAGCT
GATCAGCGACGACGAGTACAAGGAGAGCGTGTTCAAGGCCCCCTACCAGCACTTCGTGGACACCCTGAAGAGCAAGGAGTTCGAGGACAGCATCCTGTTCAGCTACCAGGT
GGACAGCAAGTTCAACCGCAAGATCAGCGACGCCACCATCTACGCCACCCGCCAGGCCAAGGTGGGCAAGGACAAGGCCGACGAGACCTACGTGCTGGGCAAGATCAAGG
ACATCTACACCCAGGACGGCTACGACGCCTTCATGAAGATCTACAAGAAGGACAAGAGCAAGTTCCTGATGTACCGCCACGACCCCCAGACCTTCGAGAAGGTGATCGAGCC
CATCCTGGAGAACTACCCCAACAAGCAGATCAACGATAAAGGCAAGGAGGTGCCCTGCAACCCCTTCCTGAAGTACAAGGAGGAGCACGGCTACATCCGCAAGTACAGCAA
GAAGGGCAACGGCCCCGAGATCAAGAGCCTGAAGTACTACGACAGCAAGCTGGGCAACCACATCGACATCACCCCCAAGGACAGCAACAACAAGGTGGTGCTGCAGAGCG
TGAGCCCCTGGCGCGCCGACGTGTACTTCAACAAGACCACCGGCAAGTACGAGATCCTGGGCCTGAAGTACGCCGACCTGCAGTTTGATAAGGGCACCGGCACCTACAAGAT
CAGCCAGGAGAAGTACAACGACATCAAGAAGAAGGAGGGCGTGGACAGCGACAGCGAGTTCAAGTTCACCCTGTACAAGAACGACCTTCTGCTGGTGAAGGACACCGAGA
CCAAGGAGCAACAGCTGTTCCGCTTCCTGAGCCGCACCATGCCCAAGCAGAAGCACTACGTGGAGCTGAAGCCCTACGACAAGCAGAAGTTCGAGGGCGGCGAGGCCCTGA
TCAAGGTGCTGGGCAACGTGGCCAACAGCGGCCAGTGCAAGAAGGGCCTGGGCAAGAGCAACATCAGCATCTACAAGGTGCGCACCGACGTGCTGGGCAACCAGCACATC
ATCAAGAACGAGGGCGACAAGCCCAAGCTGGACTTCTAA (SEQ ID NO: 9)

FIG. 26

ATGAGCGACCTGGTGCTGGGCCTGGCCATCGGCATCGGCAGCGTGGGCGTGGGCATCCTGAACAAGGTGACCGGCGAGATCATCCACAAGAACAGTCGCATCTTCCCTGCTG
CTCAGGCTGAGAACAACCTGGTGCGCCGCACCAACCGCCAGGGTCGCCGGCTTGCTCGCCGCAAGAAGCACCGGCGCGTGCGCCTGAACCGCCTGTTCGAGGAGAGCGGCC
TGATCACCGACTTCACCAAGATCAGCATCAACCTGAACCCCTACCAGCTGCGCGTGAAGGGCCTGACCGACGAGCTGAGCAACGAGGAGCTGTTCATCGCCCTGAAGAACAT
GGTGAAGCACCGCGGCATCAGCTACCTGGACGACGCCAGCGACGACGGCAACAGCAGCGTGGGCGACTACGCCCAGATCGTGAAGGAGAACAGCAAGCAGCTGGAGACCA
AGACCCCCGGCCAGATCCAGCTGGAGCGCTACCAGACCTACGGCCAGCTGCGCGGCGACTTCACCGTGGAGAAGGACGGCAAGAAGCACCGCCTGATCAACGTGTTCCCCAC
CAGCGCCTACCGCAGCGAGGCCCTGCGCATCCTGCAGACCCAGCAGGAGTTCAACCCCCAGATCACCGACGAGTTCATCAACCGCTACCTGGAGATCCTGACCGGCAAGCGC
AAGTACTACCACGGCCCCGGCAACGAGAAGAGCCGCACCGACTACGGCCGCTACCGCACCAGCGGCGAGACCCTGGACAACATCTTCGGCATCCTGATCGGCAAGTGCACCT
TCTACCCCGACGAGTTCCGCGCCGCCAAGGCCAGCTACACCGCCCAGGAGTTCAACCTGCTGAACGACCTGAACAACCTGACCGTGCCCACCGAGACCAAGAAGCTGAGCAA
GGAGCAGAAGAACCAGATCATCAACTACGTGAAGAACGAGAAGGCCATGGGCCCCGCCAAGCTGTTCAAGTACATCGCCAAGCTGCTGAGCTGCGACGTGGCCGACATCAA
GGGCTACCGCATCGACAAGAGCGGCAAGGCCGAGATCCACACCTTCGAGGCCTACCGCAAGATGAAGACCCTGGAGACCCTGGACATCGAGCAGATGGACCGCGAGACCCT
GGACAAGCTGGCCTACGTGCTGACCCTGAACACCGAGCGCGAGGGCATCCAGGAGGCCCTGGAGCACGAGTTCGCCGACGGCAGCTTCAGCCAGAAGCAGGTGGACGAGC
TGGTGCAGTTCCGCAAGGCCAACAGCAGCATCTTCGGCAAGGGCTGGCACAACTTCAGCGTGAAGCTGATGATGGAGCTGATCCCCGAGCTGTACGAGACCAGCGAGGAGC
AGATGACCATCCTGACCCGCCTGGGCAAGCAGAAGACCACCAGCAGCAGCAACAAGACCAAGTACATCGACGAGAAGCTGCTGACCGAGGAGATCTACAACCCCGTGGTGG
CCAAGAGCGTGCGCCAGGCCATCAAGATCGTGAACGCCGCCATCAAGGAGTACGGCGACTTCGACAACATCGTGATCGAGATGGCCCGCGAGACCAACGAGGACGACGAGA
AGAAGGCCATCCAGAAGATCCAGAAGGCCAACAAGGACGAGAAGGACGCCGCCATGCTGAAGGCCGCCAACCAGTACAACGGCAAGGCCGAGCTGCCCCACAGCGTGTTCC
ACGGCCACAAGCAGCTGGCCACCAAGATCCGCCTGTGGCACCAGCAGGGCGAGCGCTGCCTGTACACCGGCAAGACCATCAGCATCCACGACCTGATCAACAACAGCAACCA
GTTCGAGGTGGCTGCCATCCTGCCCCTGAGCATCACCTTCGACGACAGCCTGGCCAACAAGGTGCTGGTGTACGCCACCGCCGCTCAGGAGAAGGGCCAGCGCACCCCCTAC
CAGGCCCTGGACAGCATGGACGACGCCTGGAGCTTCCGCGAGCTGAAGGCCTTCGTGCGCGAGAGCAAGACCCTGAGCAACAAGAAGAAGGAGTACCTGCTGACCGAGGA
GGACATCAGCAAGTTCGACGTGCGCAAGAAGTTCATCGAGCGCAACCTGGTGGACACCCGCTACGCCAGCCGCGTGGTGCTGAACGCCCTGCAGGAGCACTTCCGCGCCCAC
AAGATCGACACCAAGGTGAGCGTGGTGCGCGGCCAGTTCACCAGCCAGCTGCGCCGCCACTGGGGCATCGAGAAGACCCGCGACACCTACCACCACCACGCCGTGGACGCC
CTGATCATTGCGGCTTCTAGCCAGCTGAACCTGTGGAAGAAGCAGAAGAACACCCTGGTGAGCTACAGCGAGGACCAGCTGCTGGACATCGAGACCGGCGAGCTGATCAGC
GACGACGAGTACAAGGAGAGCGTGTTCAAGGCCCCCTACCAGCACTTCGTGGACACCCTGAAGAGCAAGGAGTTCGAGGACAGCATCCTGTTCAGCTACCAGGTGGACAGC
AAGTTCAACCGCAAGATCAGCGACGCCACCATCTACGCCACCCGCCAGGCCAAGGTGGGCAAGGACAAGGCCGACGAGACCTACGTGCTGGGCAAGATCAAGGACATCTAC
ACCCAGGACGGCTACGACGCCTTCATGAAGATCTACAAGAAGGACAAGAGCAAGTTCCTGATGTACCGCCACGACCCCCAGACCTTCGAGAAGGTGATCGAGCCCATCCTGG
AGAACTACCCCAACAAGCAGATCAACGATAAAGGCAAGGAGGTGCCCTGCAACCCCTTCCTGAAGTACAAGGAGGAGCACGGCTACATCCGCAAGTACAGCAAGAAGGGCA
ACGGCCCCGAGATCAAGAGCCTGAAGTACTACGACAGCAAGCTGGGCAACCACATCGACATCACCCCCAAGGACAGCAACAACAAGGTGGTGCTGCAGAGCGTGAGCCCCT
GGCGCGCCGACGTGTACTTCAACAAGACCACCGGCAAGTACGAGATCCTGGGCCTGAAGTACGCCGACCTGCAGTTTGATAAGGGCACCGGCACCTACAAGATCAGCCAGGA
GAAGTACAACGACATCAAGAAGAAGGAGGGCGTGGACAGCGACAGCGAGTTCAAGTTCACCCTGTACAAGAACGACCTTCTGCTGGTGAAGGACACCGAGACCAAGGAGCA
ACAGCTGTTCCGCTTCCTGAGCCGCACCATGCCCAAGCAGAAGCACTACGTGGAGCTGAAGCCCTACGACAAGCAGAAGTTCGAGGGCGGCGAGGCCCTGATCAAGGTGCTG
GGCAACGTGGCCAACAGCGGCCAGTGCAAGAAGGGCCTGGGCAAGAGCAACATCAGCATCTACAAGGTGCGCACCGACGTGCTGGGCAACCAGCACATCATCAAGAACGA
GGGCGACAAGCCCAAGCTGGACTTCTAA (SEQ ID NO: 10)

FIG. 27

ATGGCCGCCTTCAAGCCCAACCCCATCAACTACATCCTGGGCCTGGACATCGGCATCGCCAGCGTGGGCTGGGCCATGGTGGAGATCGACGAGGACGAGAACCCCATCTGCC
TGATCGACCTGGGTGTGCGCGTGTTCGAGCGCGCTGAGGTGCCCAAGACTGGTGACAGTCTGGCTATGGCTCGCCGGCTTGCTCGCTCTGTTCGGCGCCTTACTCGCCGGCGC
GCTCACCGCCTTCTGCGCGCTCGCCGCCTGCTGAAGCGCGAGGGTGTGCTGCAGGCTGCCGACTTCGACGAGAACGGCCTGATCAAGAGCCTGCCCAACACTCCTTGGCAGC
TGCGCGCTGCCGCTCTGGACCGCAAGCTGACTCCTCTGGAGTGGAGCGCCGTGCTGCTGCACCTGATCAAGCACCGCGGCTACCTGAGCCAGCGCAAGAACGAGGGCGAGA
CCGCCGACAAGGAGCTGGGTGCTCTGCTGAAGGGCGTGGCCGACAACGCCCACGCCCTGCAGACTGGTGACTTCCGCACTCCTGCTGAGCTGGCCCTGAACAAGTTCGAGAA
GGAGAGCGGCCACATCCGCAACCAGCGCGGCGACTACAGCCACACCTTCAGCCGCAAGGACCTGCAGGCCGAGCTGATCCTGCTGTTCGAGAAGCAGAAGGAGTTCGGCAA
CCCCCACGTGAGCGGCGGCCTGAAGGAGGGCATCGAGACCCTGCTGATGACCCAGCGCCCCGCCCTGAGCGGCGACGCCGTGCAGAAGATGCTGGGCCACTGCACCTTCGA
GCCAGCCGAGCCCAAGGCCGCCAAGAACACCTACACCGCCGAGCGCTTCATCTGGCTGACCAAGCTGAACAACCTGCGCATCCTGGAGCAGGGCAGCGAGCGCCCCCTGACC
GACACCGAGCGCGCCACCCTGATGGACGAGCCCTACCGCAAGAGCAAGCTGACCTACGCCCAGGCCCGCAAGCTGCTGGGTCTGGAGGACACCGCCTTCTTCAAGGGCCTGC
GCTACGGCAAGGACAACGCCGAGGCCAGCACCCTGATGGAGATGAAGGCCTACCACGCCATCAGCCGCGCCCTGGAGAAGGAGGGCCTGAAGGACAAGAAGAGTCCTCTG
AACCTGAGCCCCGAGCTGCAGGACGAGATCGGCACCGCCTTCAGCCTGTTCAAGACCGACGAGGACATCACCGGCCGCCTGAAGGACCGCATCCAGCCCGAGATCCTGGAG
GCCCTGCTGAAGCACATCAGCTTCGACAAGTTCGTGCAGATCAGCCTGAAGGCCCTGCGCCGCATCGTGCCCCTGATGGAGCAGGGCAAGCGCTACGACGAGGCCTGCGCCG
AGATCTACGGCGACCACTACGGCAAGAAGAACACCGAGGAGAAGATCTACCTGCCTCCTATCCCCGCCGACGAGATCCGCAACCCCGTGGTGCTGCGCGCCCTGAGCCAGGC
CCGCAAGGTGATCAACGGCGTGGTGCGCCGCTACGGCAGCCCCGCCCGCATCCACATCGAGACCGCCCGCGAGGTGGGCAAGAGCTTCAAGGACCGCAAGGAGATCGAGAA
GCGCCAGGAGGAGAACCGCAAGGACCGCGAGAAGGCCGCCGCCAAGTTCCGCGAGTACTTCCCCAACTTCGTGGGCGAGCCCAAGAGCAAGGACATCCTGAAGCTGCGCCT
GTACGAGCAGCAGCACGGCAAGTGCCTGTACAGCGGCAAGGAGATCAACCTGGGCCGCCTGAACGAGAAGGGCTACGTGGAGATCGACCACGCCCTGCCCTTCAGCCGCAC
CTGGGACGACAGCTTCAACAACAAGGTGCTGGTGCTGGGCAGCGAGAACCAGAACAAGGGCAACCAGACCCCCTACGAGTACTTCAACGGCAAGGACAACAGCCGCGAGTG
GCAGGAGTTCAAGGCCCGCGTGGAGACCAGCCGCTTCCCCCGCAGCAAGAAGCAGCGCATCCTGCTGCAGAAGTTCGACGAGGACGGCTTCAAGGAGCGCAACCTGAACGA
CACCCGCTACGTGAACCGCTTCCTGTGCCAGTTCGTGGCCGACCGCATGCGCCTGACCGGCAAGGGCAAGAAGCGCGTGTTCGCCAGCAACGGCCAGATCACCAACCTGCTG
CGCGGCTTCTGGGGCCTGCGCAAGGTGCGCGCCGAGAACGACCGCCACCACGCCCTGGACGCCGTGGTGGTGGCCTGCAGCACCGTGGCCATGCAGCAGAAGATCACCCGC
TTCGTGCGCTACAAGGAGATGAACGCCTTCGACGGTAAAACCATCGACAAGGAGACCGGCGAGGTGCTGCACCAGAAGACCCACTTCCCCCAGCCCTGGGAGTTCTTCGCCC
AGGAGGTGATGATCCGCGTGTTCGGCAAGCCCGACGGCAAGCCCGAGTTCGAGGAGGCCGACACCCCCGAGAAGCTGCGCACCCTGCTGGCCGAGAAGCTGAGCAGCCGCC
CTGAGGCCGTGCACGAGTACGTGACTCCTCTGTTCGTGAGCCGCGCCCCCAACCGCAAGATGAGCGGTCAGGGTCACATGGAGACCGTGAAGAGCGCCAAGCGCCTGGACG
AGGGCGTGAGCGTGCTGCGCGTGCCCCTGACCCAGCTGAAGCTGAAGGACCTGGAGAAGATGGTGAACCGCGAGCGCGAGCCCAAGCTGTACGAGGCCCTGAAGGCCCGC
CTGGAGGCCCACAAGGACGACCCCGCCAAGGCCTTCGCCGAGCCCTTCTACAAGTACGACAAGGCCGGCAACCGCACCCAGCAGGTGAAGGCCGTGCGCGTGGAGCAGGTG
CAGAAGACCGGCGTGTGGGTGCGCAACCACAACGGCATCGCCGACAACGCCACCATGGTGCGCGTGGACGTGTTCGAGAAGGGCGACAAGTACTACCTGGTGCCCATCTAC
AGCTGGCAGGTGGCCAAGGGCATCCTGCCCGACCGCGCCGTGGTGCAGGGCAAGGACGAGGAGGACTGGCAGCTGATCGACGACAGCTTCAACTTCAAGTTCAGCCTGCAC
CCCAACGACCTGGTGGAGGTGATCACCAAGAAGGCCCGCATGTTCGGCTACTTCGCCAGCTGCCACCGCGGCACCGGCAACATCAACATCCGCATCCACGACCTGGACCACA
AGATCGGCAAGAACGGCATCCTGGAGGGCATCGGCGTGAAGACCGCCCTGAGCTTCCAGAAGTACCAGATCGACGAGCTGGGCAAGGAGATCCGCCCCTGCCGCCTGAAGA
AGCGCCCTCCTGTGCGCTAA (SEQ ID NO: 11)

FIG. 28

ATGGCCGCCTTCAAGCCCAACCCCATCAACTACATCCTGGGCCTGGCCATCGGCATCGCCAGCGTGGGCTGGGCCATGGTGGAGATCGACGAGGACGAGAACCCCATCTGCC
TGATCGACCTGGGTGTGCGCGTGTTCGAGCGCGCTGAGGTGCCCAAGACTGGTGACAGTCTGGCTATGGCTCGCCGGCTTGCTCGCTCTGTTCGGCGCCTTACTCGCCGGCGC
GCTCACCGCCTTCTGCGCGCTCGCCGCCTGCTGAAGCGCGAGGGTGTGCTGCAGGCTGCCGACTTCGACGAGAACGGCCTGATCAAGAGCCTGCCCAACACTCCTTGGCAGC
TGCGCGCTGCCGCTCTGGACCGCAAGCTGACTCCTCTGGAGTGGAGCGCCGTGCTGCTGCACCTGATCAAGCACCGCGGCTACCTGAGCCAGCGCAAGAACGAGGGCGAGA
CCGCCGACAAGGAGCTGGGTGCTCTGCTGAAGGGCGTGGCCGACAACGCCCACGCCCTGCAGACTGGTGACTTCCGCACTCCTGCTGAGCTGGCCCTGAACAAGTTCGAGAA
GGAGAGCGGCCACATCCGCAACCAGCGCGGCGACTACAGCCACACCTTCAGCCGCAAGGACCTGCAGGCCGAGCTGATCCTGCTGTTCGAGAAGCAGAAGGAGTTCGGCAA
CCCCCACGTGAGCGGCGGCCTGAAGGAGGGCATCGAGACCCTGCTGATGACCCAGCGCCCCGCCCTGAGCGGCGACGCCGTGCAGAAGATGCTGGGCCACTGCACCTTCGA
GCCAGCCGAGCCCAAGGCCGCCAAGAACACCTACACCGCCGAGCGCTTCATCTGGCTGACCAAGCTGAACAACCTGCGCATCCTGGAGCAGGGCAGCGAGCGCCCCCTGACC
GACACCGAGCGCGCCACCCTGATGGACGAGCCCTACCGCAAGAGCAAGCTGACCTACGCCCAGGCCCGCAAGCTGCTGGGTCTGGAGGACACCGCCTTCTTCAAGGGCCTGC
GCTACGGCAAGGACAACGCCGAGGCCAGCACCCTGATGGAGATGAAGGCCTACCACGCCATCAGCCGCGCCCTGGAGAAGGAGGGCCTGAAGGACAAGAAGAGTCCTCTG
AACCTGAGCCCCGAGCTGCAGGACGAGATCGGCACCGCCTTCAGCCTGTTCAAGACCGACGAGGACATCACCGGCCGCCTGAAGGACCGCATCCAGCCCGAGATCCTGGAG
GCCCTGCTGAAGCACATCAGCTTCGACAAGTTCGTGCAGATCAGCCTGAAGGCCCTGCGCCGCATCGTGCCCCTGATGGAGCAGGGCAAGCGCTACGACGAGGCCTGCGCCG
AGATCTACGGCGACCACTACGGCAAGAAGAACACCGAGGAGAAGATCTACCTGCCTCCTATCCCCGCCGACGAGATCCGCAACCCCGTGGTGCTGCGCGCCCTGAGCCAGGC
CCGCAAGGTGATCAACGGCGTGGTGCGCCGCTACGGCAGCCCCGCCCGCATCCACATCGAGACCGCCCGCGAGGTGGGCAAGAGCTTCAAGGACCGCAAGGAGATCGAGAA
GCGCCAGGAGGAGAACCGCAAGGACCGCGAGAAGGCCGCCGCCAAGTTCCGCGAGTACTTCCCCAACTTCGTGGGCGAGCCCAAGAGCAAGGACATCCTGAAGCTGCGCCT
GTACGAGCAGCAGCACGGCAAGTGCCTGTACAGCGGCAAGGAGATCAACCTGGGCCGCCTGAACGAGAAGGGCTACGTGGAGATCGCCGCTGCCCTGCCCTTCAGCCGCAC
CTGGGACGACAGCTTCAACAACAAGGTGCTGGTGCTGGGCAGCGAGGCTCAGAACAAGGGCAACCAGACCCCCTACGAGTACTTCAACGGCAAGGACAACAGCCGCGAGTG
GCAGGAGTTCAAGGCCCGCGTGGAGACCAGCCGCTTCCCCCGCAGCAAGAAGCAGCGCATCCTGCTGCAGAAGTTCGACGAGGACGGCTTCAAGGAGCGCAACCTGAACGA
CACCCGCTACGTGAACCGCTTCCTGTGCCAGTTCGTGGCCGACCGCATGCGCCTGACCGGCAAGGGCAAGAAGCGCGTGTTCGCCAGCAACGGCCAGATCACCAACCTGCTG
CGCGGCTTCTGGGGCCTGCGCAAGGTGCGCGCCGAGAACGACCGCCACCACGCCCTGGACGCCGTGGTGGTGGCCTGCAGCACCGTGGCCATGCAGCAGAAGATCACCCGC
TTCGTGCGCTACAAGGAGATGAACGCCTTCGACGGTAAAACCATCGACAAGGAGACCGGCGAGGTGCTGCACCAGAAGACCCACTTCCCCCAGCCCTGGGAGTTCTTCGCCC
AGGAGGTGATGATCCGCGTGTTCGGCAAGCCCGACGGCAAGCCCGAGTTCGAGGAGGCCGACACCCCCGAGAAGCTGCGCACCCTGCTGGCCGAGAAGCTGAGCAGCCGCC
CTGAGGCCGTGCACGAGTACGTGACTCCTCTGTTCGTGAGCCGCGCCCCCAACCGCAAGATGAGCGGTCAGGGTCACATGGAGACCGTGAAGAGCGCCAAGCGCCTGGACG
AGGGCGTGAGCGTGCTGCGCGTGCCCCTGACCCAGCTGAAGCTGAAGGACCTGGAGAAGATGGTGAACCGCGAGCGCGAGCCCAAGCTGTACGAGGCCCTGAAGGCCCGC
CTGGAGGCCCACAAGGACGACCCCGCCAAGGCCTTCGCCGAGCCCTTCTACAAGTACGACAAGGCCGGCAACCGCACCCAGCAGGTGAAGGCCGTGCGCGTGGAGCAGGTG
CAGAAGACCGGCGTGTGGGTGCGCAACCACAACGGCATCGCCGACAACGCCACCATGGTGCGCGTGGACGTGTTCGAGAAGGGCGACAAGTACTACCTGGTGCCCATCTAC
AGCTGGCAGGTGGCCAAGGGCATCCTGCCCGACCGCGCCGTGGTGCAGGGCAAGGACGAGGAGGACTGGCAGCTGATCGACGACAGCTTCAACTTCAAGTTCAGCCTGCAC
CCCAACGACCTGGTGGAGGTGATCACCAAGAAGGCCCGCATGTTCGGCTACTTCGCCAGCTGCCACCGCGGCACCGGCAACATCAACATCCGCATCCACGACCTGGACCACA
AGATCGGCAAGAACGGCATCCTGGAGGGCATCGGCGTGAAGACCGCCCTGAGCTTCCAGAAGTACCAGATCGACGAGCTGGGCAAGGAGATCCGCCCCTGCCGCCTGAAGA
AGCGCCCTCCTGTGCGCTAA (SEQ ID NO: 12)

FIG. 29

ATGAAGAAGGAGATCAAGGACTACTTCCTGGGCCTGGACGTGGGCACCGGCAGCGTGGGCTGGGCCGTGACCGACACCGACTACAAGCTGCTGAAGGCCAACCGCAAGGAC
CTGTGGGGCATGCGCTGCTTCGAGACTGCTGAGACCGCCGAGGTGCGCCGGCTGCACCGCGGTGCTCGCCGGCGCATCGAGCGCCGCAAGAAGCGCATCAAGCTGCTGCAG
GAGCTGTTCAGCCAGGAGATCGCCAAGACCGACGAGGGCTTCTTCCAGCGCATGAAGGAGAGCCCCTTCTACGCCGAGGACAAGACCATCCTGCAGGAGAACACCCTGTTCA
ACGACAAGGACTTCGCCGACAAGACCTACCACAAGGCCTACCCCACCATCAACCACCTGATCAAGGCCTGGATCGAGAACAAGGTGAAGCCCGACCCTCGCCTGCTGTACCTG
GCCTGCCACAACATCATCAAGAAGCGCGGCCACTTCCTGTTCGAGGGCGACTTCGACAGCGAGAACCAGTTCGACACCAGCATCCAGGCCCTGTTCGAGTACCTGCGCGAGG
ACATGGAGGTGGACATCGACGCCGACAGCCAGAAGGTGAAGGAGATCCTGAAGGACAGCAGCCTGAAGAACAGCGAGAAGCAGAGCCGCCTGAACAAGATCCTGGGCCTG
AAGCCCAGCGACAAGCAGAAGAAGGCCATCACCAACCTGATCAGCGGCAACAAGATCAACTTCGCCGACCTGTACGACAACCCCGACCTGAAGGACGCCGAGAAGAACAGC
ATCAGCTTCAGCAAGGACGACTTCGACGCCCTGAGCGACGACCTGGCCAGCATCCTGGGCGACAGCTTCGAGCTGCTGCTGAAGGCCAAGGCCGTGTACAACTGCAGCGTGC
TGAGCAAGGTGATCGGCGACGAGCAGTACCTGAGCTTCGCCAAGGTGAAGATCTACGAGAAGCACAAGACCGACCTTACCAAGCTGAAGAACGTGATCAAGAAGCACTTCCC
CAAGGACTACAAGAAGGTGTTCGGCTACAACAAGAACGAGAAGAACAACAACAACTACAGCGGCTACGTGGGCGTGTGCAAGACCAAGAGCAAGAAGCTGATCATCAACAA
CAGCGTGAACCAGGAGGACTTCTACAAGTTCCTGAAGACCATCCTGAGCGCCAAGAGCGAGATCAAGGAGGTGAACGACATCCTGACCGAGATCGAGACCGGCACCTTCCTG
CCCAAGCAGATCAGCAAGAGCAACGCCGAGATCCCCTACCAGCTGCGCAAGATGGAGCTGGAGAAGATCCTGAGCAACGCCGAGAAGCACTTCAGCTTCCTGAAGCAGAAG
GACGAGAAGGGCCTGAGCCACAGCGAGAAGATCATCATGCTGCTGACCTTCAAGATCCCCTACTACATCGGCCCCATCAACGACAACCACAAGAAGTTCTTCCCCGACCGCTG
CTGGGTGGTGAAGAAGGAGAAGAGCCCCAGCGGCAAGACCACCCCCTGGAACTTCTTCGACCACATCGACAAGGAGAAGACCGCCGAGGCCTTCATCACCAGCCGCACCAA
CTTCTGCACATACCTGGTGGGCGAGAGCGTGCTGCCCAAGAGCAGCCTGCTGTACAGCGAGTACACCGTGCTGAACGAGATCAACAACCTGCAGATCATCATCGACGGCAAG
AACATCTGCGACATCAAGCTGAAGCAGAAGATCTACGAGGACCTGTTCAAGAAGTACAAGAAGATCACCCAGAAGCAGATCAGCACCTTCATCAAGCACGAGGGCATCTGCA
ACAAGACCGACGAGGTGATCATCCTGGGCATCGACAAGGAGTGCACCAGCAGCCTGAAGAGCTACATCGAGCTGAAGAACATCTTCGGCAAGCAGGTGGACGAGATCAGCA
CCAAGAACATGCTGGAGGAGATCATCCGCTGGGCCACCATCTACGACGAGGGCGAGGGCAAGACCATCCTGAAGACCAAGATCAAGGCCGAGTACGGCAAGTACTGCAGCG
ACGAGCAGATCAAGAAGATCCTGAACCTGAAGTTCAGCGGCTGGGGCCGCCTGAGCCGCAAGTTCCTGGAGACCGTGACCAGCGAGATGCCCGGCTTCAGCGAGCCCGTGA
ACATCATCACCGCCATGCGCGAGACCCAGAACAACCTGATGGAGCTGCTGAGCAGCGAGTTCACCTTCACCGAGAACATCAAGAAGATCAACAGCGGCTTCGAGGACGCCGA
GAAGCAGTTCAGCTACGACGGCCTGGTGAAGCCCCTGTTCCTGAGCCCCAGCGTGAAGAAGATGCTGTGGCAGACCCTGAAGCTGGTGAAGGAGATCAGCCACATCACCCAG
GCTCCTCCTAAGAAGATCTTCATCGAGATGGCCAAGGGCGCCGAGCTGGAGCCTGCTCGCACCAAGACCCGCCTGAAGATCCTGCAGGACCTGTACAACAACTGCAAGAACG
ACGCCGACGCATTCAGCAGCGAGATCAAGGACCTGAGCGGCAAGATCGAGAACGAGGACAACCTGCGCCTGCGCAGCGACAAGCTGTACCTGTACTACACCCAGCTGGGCA
AGTGCATGTACTGCGGCAAGCCCATCGAGATCGGCCACGTGTTCGACACCAGCAACTACGACATCGACCACATCTACCCCCAGAGCAAGATCAAGGACGACAGCATCAGCAA
CCGCGTGCTGGTGTGCAGCAGCTGCAACAAGAACAAGGAGGACAAGTACCCTCTGAAGAGCGAGATCCAGAGCAAGCAGCGCGGCTTCTGGAACTTCCTGCAGCGCAACAA
CTTCATCAGCCTGGAGAAGCTGAACCGCCTGACCCGCGCCACCCCCATCAGCGACGACGAGACCGCCAAGTTCATCGCCCGCCAGCTGGTGGAGACTCGCCAAGCTACCAAG
GTGGCCGCCAAGGTGCTGGAGAAGATGTTCCCCGAGACCAAGATCGTGTACAGCAAGGCCGAGACCGTGAGCATGTTCCGCAACAAGTTCGACATCGTGAAGTGCCGCGAG
ATCAACGACTTCCACCACGCCCACGACGCCTACCTGAACATCGTGGTGGGCAACGTGTACAACACCAAGTTCACCAACAACCCCTGGAATTTCATTAAGGAGAAGCGCGACAA
CCCCAAGATCGCCGACACCTACAACTACTACAAGGTGTTCGACTACGACGTGAAGCGCAACAACATCACCGCCTGGGAGAAGGGCAAGACCATCATCACCGTGAAGGACATG
CTGAAGCGCAACACCCCCATCTACACCCGCCAGGCCGCCTGCAAGAAGGGCGAGCTGTTCAACCAGACCATCATGAAGAAGGGCCTGGGCCAGCACCCCCTGAAGAAGGAG
GGCCCCTTCAGCAACATCAGCAAGTACGGCGGCTACAACAAGGTGAGCGCCGCCTACTACACCCTGATCGAGTACGAGGAGAAGGGCAACAAGATCCGCAGCCTGGAGACC
ATCCCCCTGTACCTGGTGAAGGACATCCAGAAGGACCAGGACGTGCTGAAGAGCTACCTGACCGACCTGCTGGGCAAGAAGGAGTTCAAGATCCTGGTGCCCAAGATCAAGA
TCAACAGCCTGCTGAAGATCAACGGCTTCCCCTGCCACATCACCGGCAAGACCAACGACAGCTTCCTGCTGCGCCCCGCCGTGCAGTTCTGCTGCAGCAACAACGAGGTGCTG
TACTTCAAGAAGATCATCCGCTTCAGCGAGATCCGCAGCCAGCGCGAGAAGATCGGCAAGACCATCAGCCCCTACGAGGACCTGAGCTTCCGCAGCTACATCAAGGAGAACC
TGTGGAAGAAGACCAAGAACGACGAGATCGGCGAGAAGGAGTTCTACGACCTGCTGCAGAAGAAGAACCTGGAGATCTACGACATGCTGCTGACCAAGCACAAGGACACCA
TCTACAAGAAGCGCCCCAACAGCGCCACCATCGACATCCTGGTGAAGGGCAAGGAGAAGTTCAAGAGCCTGATCATCGAGAACCAGTTCGAGGTGATCCTGGAGATCCTGAA
GCTGTTCAGCGCCACCCGCAACGTGAGCGACCTGCAGCACATCGGCGGCAGCAAGTACAGCGGCGTGGCCAAGATCGGCAACAAGATCAGCAGCCTGGACAACTGCATCCT
GATCTACCAGAGCATCACCGGCATCTTCGAGAAGCGCATCGACCTGCTGAAGGTGTAA (SEQ ID NO: 13)

FIG. 30

ATGAAGAAGGAGATCAAGGACTACTTCCTGGGCCTGGCCGTGGGCACCGGCAGCGTGGGCTGGGCCGTGACCGACACCGACTACAAGCTGCTGAAGGCCAACCGCAAGGAC
CTGTGGGGCATGCGCTGCTTCGAGACTGCTGAGACCGCCGAGGTGCGCCGGCTGCACCGCGGTGCTCGCCGGCGCATCGAGCGCCGCAAGAAGCGCATCAAGCTGCTGCAG
GAGCTGTTCAGCCAGGAGATCGCCAAGACCGACGAGGGCTTCTTCCAGCGCATGAAGGAGAGCCCCTTCTACGCCGAGGACAAGACCATCCTGCAGGAGAACACCCTGTTCA
ACGACAAGGACTTCGCCGACAAGACCTACCACAAGGCCTACCCCACCATCAACCACCTGATCAAGGCCTGGATCGAGAACAAGGTGAAGCCCGACCCTCGCCTGCTGTACCTG
GCCTGCCACAACATCATCAAGAAGCGCGGCCACTTCCTGTTCGAGGGCGACTTCGACAGCGAGAACCAGTTCGACACCAGCATCCAGGCCCTGTTCGAGTACCTGCGCGAGG
ACATGGAGGTGGACATCGACGCCGACAGCCAGAAGGTGAAGGAGATCCTGAAGGACAGCAGCCTGAAGAACAGCGAGAAGCAGAGCCGCCTGAACAAGATCCTGGGCCTG
AAGCCCAGCGACAAGCAGAAGAAGGCCATCACCAACCTGATCAGCGGCAACAAGATCAACTTCGCCGACCTGTACGACAACCCCGACCTGAAGGACGCCGAGAAGAACAGC
ATCAGCTTCAGCAAGGACGACTTCGACGCCCTGAGCGACGACCTGGCCAGCATCCTGGGCGACAGCTTCGAGCTGCTGCTGAAGGCCAAGGCCGTGTACAACTGCAGCGTGC
TGAGCAAGGTGATCGGCGACGAGCAGTACCTGAGCTTCGCCAAGGTGAAGATCTACGAGAAGCACAAGACCGACCTTACCAAGCTGAAGAACGTGATCAAGAAGCACTTCCC
CAAGGACTACAAGAAGGTGTTCGGCTACAACAAGAACGAGAAGAACAACAACAACTACAGCGGCTACGTGGGCGTGTGCAAGACCAAGAGCAAGAAGCTGATCATCAACAA
CAGCGTGAACCAGGAGGACTTCTACAAGTTCCTGAAGACCATCCTGAGCGCCAAGAGCGAGATCAAGGAGGTGAACGACATCCTGACCGAGATCGAGACCGGCACCTTCCTG
CCCAAGCAGATCAGCAAGAGCAACGCCGAGATCCCCTACCAGCTGCGCAAGATGGAGCTGGAGAAGATCCTGAGCAACGCCGAGAAGCACTTCAGCTTCCTGAAGCAGAAG
GACGAGAAGGGCCTGAGCCACAGCGAGAAGATCATCATGCTGCTGACCTTCAAGATCCCCTACTACATCGGCCCCATCAACGACAACCACAAGAAGTTCTTCCCCGACCGCTG
CTGGGTGGTGAAGAAGGAGAAGAGCCCCAGCGGCAAGACCACCCCCTGGAACTTCTTCGACCACATCGACAAGGAGAAGACCGCCGAGGCCTTCATCACCAGCCGCACCAA
CTTCTGCACATACCTGGTGGGCGAGAGCGTGCTGCCCAAGAGCAGCCTGCTGTACAGCGAGTACACCGTGCTGAACGAGATCAACAACCTGCAGATCATCATCGACGGCAAG
AACATCTGCGACATCAAGCTGAAGCAGAAGATCTACGAGGACCTGTTCAAGAAGTACAAGAAGATCACCCAGAAGCAGATCAGCACCTTCATCAAGCACGAGGGCATCTGCA
ACAAGACCGACGAGGTGATCATCCTGGGCATCGACAAGGAGTGCACCAGCAGCCTGAAGAGCTACATCGAGCTGAAGAACATCTTCGGCAAGCAGGTGGACGAGATCAGCA
CCAAGAACATGCTGGAGGAGATCATCCGCTGGGCCACCATCTACGACGAGGGCGAGGGCAAGACCATCCTGAAGACCAAGATCAAGGCCGAGTACGGCAAGTACTGCAGCG
ACGAGCAGATCAAGAAGATCCTGAACCTGAAGTTCAGCGGCTGGGGCCGCCTGAGCCGCAAGTTCCTGGAGACCGTGACCAGCGAGATGCCCGGCTTCAGCGAGCCCGTGA
ACATCATCACCGCCATGCGCGAGACCCAGAACAACCTGATGGAGCTGCTGAGCAGCGAGTTCACCTTCACCGAGAACATCAAGAAGATCAACAGCGGCTTCGAGGACGCCGA
GAAGCAGTTCAGCTACGACGGCCTGGTGAAGCCCCTGTTCCTGAGCCCCAGCGTGAAGAAGATGCTGTGGCAGACCCTGAAGCTGGTGAAGGAGATCAGCCACATCACCCAG
GCTCCTCCTAAGAAGATCTTCATCGAGATGGCCAAGGGCGCCGAGCTGGAGCCTGCTCGCACCAAGACCCGCCTGAAGATCCTGCAGGACCTGTACAACAACTGCAAGAACG
ACGCCGACGCATTCAGCAGCGAGATCAAGGACCTGAGCGGCAAGATCGAGAACGAGGACAACCTGCGCCTGCGCAGCGACAAGCTGTACCTGTACTACACCCAGCTGGGCA
AGTGCATGTACTGCGGCAAGCCCATCGAGATCGGCCACGTGTTCGACACCAGCAACTACGACATCGCTGCTATCTACCCCCAGAGCAAGATCAAGGACGACAGCATCAGCAA
CCGCGTGCTGGTGTGCAGCAGCTGCGCCAAGAACAAGGAGGACAAGTACCCTCTGAAGAGCGAGATCCAGAGCAAGCAGCGCGGCTTCTGGAACTTCCTGCAGCGCAACAA
CTTCATCAGCCTGGAGAAGCTGAACCGCCTGACCCGCGCCACCCCCATCAGCGACGACGAGACCGCCAAGTTCATCGCCCGCCAGCTGGTGGAGACTCGCCAAGCTACCAAG
GTGGCCGCCAAGGTGCTGGAGAAGATGTTCCCCGAGACCAAGATCGTGTACAGCAAGGCCGAGACCGTGAGCATGTTCCGCAACAAGTTCGACATCGTGAAGTGCCGCGAG
ATCAACGACTTCCACCACGCCCACGACGCCTACCTGAACATCGTGGTGGGCAACGTGTACAACACCAAGTTCACCAACAACCCCTGGAATTTCATTAAGGAGAAGCGCGACAA
CCCCAAGATCGCCGACACCTACAACTACTACAAGGTGTTCGACTACGACGTGAAGCGCAACAACATCACCGCCTGGGAGAAGGGCAAGACCATCATCACCGTGAAGGACATG
CTGAAGCGCAACACCCCCATCTACACCCGCCAGGCCGCCTGCAAGAAGGGCGAGCTGTTCAACCAGACCATCATGAAGAAGGGCCTGGGCCAGCACCCCCTGAAGAAGGAG
GGCCCCTTCAGCAACATCAGCAAGTACGGCGGCTACAACAAGGTGAGCGCCGCCTACTACACCCTGATCGAGTACGAGGAGAAGGGCAACAAGATCCGCAGCCTGGAGACC
ATCCCCCTGTACCTGGTGAAGGACATCCAGAAGGACCAGGACGTGCTGAAGAGCTACCTGACCGACCTGCTGGGCAAGAAGGAGTTCAAGATCCTGGTGCCCAAGATCAAGA
TCAACAGCCTGCTGAAGATCAACGGCTTCCCCTGCCACATCACCGGCAAGACCAACGACAGCTTCCTGCTGCGCCCCGCCGTGCAGTTCTGCTGCAGCAACAACGAGGTGCTG
TACTTCAAGAAGATCATCCGCTTCAGCGAGATCCGCAGCCAGCGCGAGAAGATCGGCAAGACCATCAGCCCCTACGAGGACCTGAGCTTCCGCAGCTACATCAAGGAGAACC
TGTGGAAGAAGACCAAGAACGACGAGATCGGCGAGAAGGAGTTCTACGACCTGCTGCAGAAGAAGAACCTGGAGATCTACGACATGCTGCTGACCAAGCACAAGGACACCA
TCTACAAGAAGCGCCCCAACAGCGCCACCATCGACATCCTGGTGAAGGGCAAGGAGAAGTTCAAGAGCCTGATCATCGAGAACCAGTTCGAGGTGATCCTGGAGATCCTGAA
GCTGTTCAGCGCCACCCGCAACGTGAGCGACCTGCAGCACATCGGCGGCAGCAAGTACAGCGGCGTGGCCAAGATCGGCAACAAGATCAGCAGCCTGGACAACTGCATCCT
GATCTACCAGAGCATCACCGGCATCTTCGAGAAGCGCATCGACCTGCTGAAGGTGTAA (SEQ ID NO: 14)

FIG. 31

GCCCACGACACCAACCACCA (SEQ ID NO: 18)

TCTTCCCTAGGAATGATGAC (SEQ ID NO: 19)

GCGGTCCCTGAGGTGCACCG (SEQ ID NO: 20)

AGAAGTGGAATACAGAGCGG (SEQ ID NO: 21)

FIG. 33

ATGGAGAGAAGGAATCCTAGTGAGAGGGGAGTGCCCGCCGGGTTTTCTGGTCACGCCTCCGTGGAATCCGGATGTGAGAC
TCAGGAGTCCCCCGCCACCGTGGTGTTCCGCCCACCAGGAGACAACACTGACGGTGGCGCGGCGGCTGCTGCAGGTGGA
AGCCAAGCCGCCGCTGCTGGGGCCGAGCCGATGGAACCCGAATCCAGACCCGGTCCCTCTGGCATGAACGTTGTGCAGGT
CGCAGAACTCTACCCCGAACTCCGCAGGATCTTGACAATCACGGAGGACGGCCAGGGCCTCAAGGGAGTGAAGAGAGAG
AGAGGGGCTTGTGAGGCCACTGAGGAAGCTCGCAATCTGGCGTTTTCATTGATGACAAGGCACAGGCCGGAATGCATTAC
ATTCCAACAGATTAAGGACAACTGCGCAAACGAGCTCGATCTCCTGGCCCAGAAGTATAGCATCGAGCAGCTGACAACCTAT
TGGCTGCAGCCCGGCGACGATTTTGAAGAGGCCATCCGCGTGTACGCAAAGGTGGCCCTGCGACCTGACTGCAAATATAAG
ATTTCCAAACTGGTTAACATCCGGAATTGTTGTTATATTAGTGGAAATGGCGCAGAAGTGGAGATTGACACAGAGGATCGAG
TCGCTTTCCGGTGCTCTATGATCAACATGTGGCCCGGTGTGCTCGGCATGGATGGCGTAGTCATTATGAATGTGGCTTTCACC
GGACCTAATTTTAGCGGAACCGTCTTCCTGGCAAACACTAATCTGATCCTGCATGGAGTTTCTTTCTATGGATTTAATAACACC
TGTGTTGAAGCTTGGACCGACGTGCGGGTTAGAGGGTGTGCTTTTTATTGCTGCTGGAAAGGCGTCGTGTGTAGACCCAAA
AGTAGAGCTTCTATCAAGAAATGCCTGTTCGAGAGGTGTACTCTGGGCATTCTCAGTGAAGGTAATAGCAGGGTCAGGCATA
ACGTGGCCTCAGATTGCGGATGTTTTATGTTGGTTAAATCCGTGGCTGTGATCAAGCACAACATGGTGTGTGGCAATTGTGA
GGACCGGGCATCTCAAATGCTGACATGTTCCGATGGCAACTGTCACCTGCTCAAAACAATTCACGTTGCGAGCCATTCTCGG
AAGGCCTGGCCAGTTTTCGAGCATAACATCCTGACGCGCTGTAGTCTCCACCTGGGTAACAGACGGGGCGTTTTCCTGCCAT
ATCAGTGTAACCTGTCACATACCAAGATACTCCTGGAACCAGAATCTATGAGTAAAGTGAACCTGAATGGTGTATTCGATATG
ACCATGAAGATATGGAAAGTCCTCCGCTATGACGAAACTAGGACTAGGTGTAGGCCCTGCGAGTGTGGCGGCAAGCATATC
CGCAACCAACCCGTGATGCTGGACGTGACCGAGGAGCTGCGCCCCGATCACCTGGTGCTGGCCTGCACCAGAGCAGAATT
CGGGAGCTCAGACGAAGACACTGATTAA (SEQ ID NO: 22)

FIG. 34

ATGGGCACTACTAGTGGGGTACCCTTTGGCATGACCCTCCGCCCCACTCGGTCAAGGCTCTCCCGGAGAACTCCTTACTCTC
GCGATAGGCTTCCTCCGTTCGAAACCGAAACACGGGCAACCATTCTGGAAGATCATCCACTGCTGCCAGAGTGTAATACCCT
GACGATGCATAACGTTTCTTACGTCCGCGGTCTGCCCTGTTCCGTGGGTTTTACTCTGATCCAGGAGTGGGTCGTGCCTTGG
GATATGGTCCTCACACGCGAGGAGCTGGTGATCCTGAGAAAGTGTATGCATGTCTGCTTGTGTTGCGCAAACATCGACATTAT
GACCAGTATGATGATTCATGGATACGAGAGCTGGGCGCTTCACTGCCACTGCTCATCCCCTGGCAGCCTGCAGTGTATTGCA
GGGGGCCAGGTGCTCGCTTCCTGGTTTAGAATGGTAGTGGATGGCGCCATGTTTAATCAGAGATTCATTTGGTATCGGGAG
GTTGTGAACTATAACATGCCAAAGGAAGTCATGTTTATGAGCAGCGTGTTCATGCGGGGGCGGCATCTGATATATCTGAGAC
TGTGGTACGACGGTCACGTGGGCTCTGTCGTGCCTGCAATGTCCTTCGGATACAGCGCCCTGCACTGTGGGATCCTCAATAAT
ATAGTCGTCTTGTGTTGCTCTTATTGCGCAGATCTCAGTGAGATAAGAGTCAGGTGCTGTGCAAGACGGACCGCAAGGGCG
ATGCTCCGCGCCGTGCGCATCATTGCCGAGGAGACAACTGCCATGCTTTACAGCTGTAGAACAGAGCGCAGACGCCAGCAG
TTTATCAGAGCCCTGCTGCAGCACCACCGCCCCATACTCATGCATGACTACGACAGTACGCCAATGTAA (SEQ ID NO: 23)

SEQUENCE LISTING

```
<160> NUMBER OF SEQ ID NOS: 23

<210> SEQ ID NO 1
<211> LENGTH: 496
<212> TYPE: PRT
<213> ORGANISM: adeno-associated virus

<400> SEQUENCE: 1

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30
```

-continued

```
Thr Val Val Phe Arg Pro Pro Gly Asp Asn Thr Asp Gly Gly Ala Ala
        35                  40                  45

Ala Ala Ala Gly Gly Ser Gln Ala Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
    290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
        355                 360                 365

Leu Lys Thr Ile His Val Ala Ser His Ser Arg Lys Ala Trp Pro Val
    370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
```

```
    450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495


<210> SEQ ID NO 2
<211> LENGTH: 496
<212> TYPE: PRT
<213> ORGANISM: adeno-associated virus

<400> SEQUENCE: 2

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
    290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335
```

-continued

```
Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
        355                 360                 365

Leu Lys Thr Ile Ala Val Ala Ser His Ser Arg Lys Ala Trp Pro Val
    370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
    450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495


<210> SEQ ID NO 3
<211> LENGTH: 294
<212> TYPE: PRT
<213> ORGANISM: adeno-associated virus

<400> SEQUENCE: 3

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
            180                 185                 190

Tyr Asp Gly His Val Gly Ser Val Val Pro Ala Met Ser Phe Gly Tyr
        195                 200                 205

Ser Ala Leu His Cys Gly Ile Leu Asn Asn Ile Val Val Leu Cys Cys
    210                 215                 220
```

```
Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
    290


<210> SEQ ID NO 4
<211> LENGTH: 500
<212> TYPE: PRT
<213> ORGANISM: adeno-associated virus

<400> SEQUENCE: 4

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
```

```
    290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Gly Ile Pro Ala Ser Gln Met Leu Thr Cys Ser Asp Gly
        355                 360                 365

Asn Cys His Leu Leu Lys Thr Ile His Val Ala Ser His Ser Arg Lys
    370                 375                 380

Ala Trp Pro Val Phe Glu His Asn Ile Leu Thr Arg Cys Ser Leu His
385                 390                 395                 400

Leu Gly Asn Arg Arg Gly Val Phe Leu Pro Tyr Gln Cys Asn Leu Ser
                405                 410                 415

His Thr Lys Ile Leu Leu Glu Pro Glu Ser Met Ser Lys Val Asn Leu
            420                 425                 430

Asn Gly Val Phe Asp Met Thr Met Lys Ile Trp Lys Val Leu Arg Tyr
        435                 440                 445

Asp Glu Thr Arg Thr Arg Cys Arg Pro Cys Glu Cys Gly Gly Lys His
    450                 455                 460

Ile Arg Asn Gln Pro Val Met Leu Asp Val Thr Glu Glu Leu Arg Pro
465                 470                 475                 480

Asp His Leu Val Leu Ala Cys Thr Arg Ala Glu Phe Gly Ser Ser Asp
                485                 490                 495

Glu Asp Thr Asp
            500


<210> SEQ ID NO 5
<211> LENGTH: 18
<212> TYPE: DNA
<213> ORGANISM: Artificial
<220> FEATURE:
<223> OTHER INFORMATION: Synthetic

<400> SEQUENCE: 5

tcaagagcaa cagtgctg                                                    18


<210> SEQ ID NO 6
<211> LENGTH: 1368
<212> TYPE: PRT
<213> ORGANISM: Streptococcus pyogenes

<400> SEQUENCE: 6

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

-continued

```
Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
```

-continued

```
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335
```

```
Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 7
<211> LENGTH: 4107
<212> TYPE: DNA
<213> ORGANISM: Streptococcus pyogenes

<400> SEQUENCE: 7

atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agatttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttgatt gagggagatt taaatcctga taatagtgat    540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatact gaaataacta aggctcccct atcagcttca    960

atgattaaac gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140

gaaaaaatgg atggtactga ggaattattg gtgaaactaa atcgtgaaga tttgctgcgc   1200

aagcaacgga cctttgacaa cggctctatt ccccatcaaa ttcacttggg tgagctgcat   1260

gctattttga gaagacaaga agacttttat ccatttttaa aagacaatcg tgagaagatt   1320

gaaaaaatct tgacttttcg aattccttat tatgttggtc cattggcgcg tggcaatagt   1380

cgttttgcat ggatgactcg gaagtctgaa gaaacaatta ccccatggaa ttttgaagaa   1440

gttgtcgata aaggtgcttc agctcaatca tttattgaac gcatgacaaa ctttgataaa   1500

aatcttccaa atgaaaaagt actaccaaaa catagtttgc tttatgagta ttttacggtt   1560

tataacgaat tgacaaaggt caaatatgtt actgaaggaa tgcgaaaacc agcatttctt   1620

tcaggtgaac agaagaaagc cattgttgat ttactcttca aaacaaatcg aaaagtaacc   1680

gttaagcaat taaaagaaga ttatttcaaa aaaatagaat gttttgatag tgttgaaatt   1740

tcaggagttg aagatagatt taatgcttca ttaggtacct accatgattt gctaaaaatt   1800

attaaagata aagatttttt ggataatgaa gaaaatgaag atatcttaga ggatattgtt   1860

ttaacattga ccttatttga agatagggag atgattgagg aaagacttaa aacatatgct   1920

cacctctttg atgataaggt gatgaaacag cttaaacgtc gccgttatac tggttgggga   1980
```

-continued

```
cgtttgtctc gaaaattgat taatggtatt agggataagc aatctggcaa aacaatatta   2040
gattttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                       4107
```

<210> SEQ ID NO 8
<211> LENGTH: 4107
<212> TYPE: DNA
<213> ORGANISM: Streptococcus pyogenes -continued

<400> SEQUENCE: 8

```
atggacaaga agtactccat tgggctcgct atcggcacaa acagcgtcgg ctgggccgtc     60
attacggacg agtacaaggt gccgagcaaa aaattcaaag ttctgggcaa taccgatcgc    120
cacagcataa agaagaacct cattggcgcc ctcctgttcg actccgggga gacggccgaa    180
gccacgcggc tcaaaagaac agcacggcgc agatataccc gcagaaagaa tcggatctgc    240
tacctgcagg agatctttag taatgagatg gctaaggtgg atgactcttt cttccatagg    300
ctggaggagt cctttttggt ggaggaggat aaaaagcacg agcgccaccc aatctttggc    360
aatatcgtgg acgaggtggc gtaccatgaa aagtacccaa ccatatatca tctgaggaag    420
aagcttgtag acagtactga taaggctgac ttgcggttga tctatctcgc gctggcgcat    480
atgatcaaat ttcggggaca cttcctcatc gaggggggacc tgaacccaga caacagcgat    540
gtcgacaaac tctttatcca actggttcag acttacaatc agcttttcga agagaacccg    600
atcaacgcat ccggagttga cgccaaagca atcctgagcg ctaggctgtc caaatcccgg    660
cggctcgaaa acctcatcgc acagctccct ggggagaaga agaacggcct gtttggtaat    720
cttatcgccc tgtcactcgg gctgaccccc aactttaaat ctaacttcga cctggccgaa    780
gatgccaagc ttcaactgag caaagacacc tacgatgatg atctcgacaa tctgctggcc    840
cagatcggcg accagtacgc agaccttttt ttggcggcaa agaacctgtc agacgccatt    900
ctgctgagtg atattctgcg agtgaacacg gagatcacca aagctccgct gagcgctagt    960
atgatcaagc gctatgatga gcaccaccaa gacttgactt tgctgaaggc ccttgtcaga   1020
cagcaactgc ctgagaagta caaggaaatt ttcttcgatc agtctaaaaa tggctacgcc   1080
ggatacattg acggcggagc aagccaggag gaattttaca aatttattaa gcccatcttg   1140
gaaaaaatgg acggcaccga ggagctgctg gtaaagctta acagagaaga tctgttgcgc   1200
aaacagcgca ctttcgacaa tggaagcatc ccccaccaga ttcacctggg cgaactgcac   1260
gctatcctca ggcggcaaga ggatttctac ccctttttga aagataacag ggaaaagatt   1320
gagaaaatcc tcacatttcg gataccctac tatgtaggcc ccctcgcccg gggaaattcc   1380
agattcgcgt ggatgactcg caaatcagaa gagaccatca ctccctggaa cttcgaggaa   1440
gtcgtggata agggggcctc tgcccagtcc ttcatcgaaa ggatgactaa ctttgataaa   1500
aatctgccta acgaaaaggt gcttcctaaa cactctctgc tgtacgagta cttcacagtt   1560
tataacgagc tcaccaaggt caaatacgtc acagaaggga tgagaaagcc agcattcctg   1620
tctggagagc agaagaaagc tatcgtggac ctcctcttca agacgaaccg gaaagttacc   1680
gtgaaacagc tcaaagaaga ctatttcaaa aagattgaat gtttcgactc tgttgaaatc   1740
agcggagtgg aggatcgctt caacgcatcc ctgggaacgt atcacgatct cctgaaaatc   1800
attaaagaca aggacttcct ggacaatgag gagaacgagg acattcttga ggacattgtc   1860
ctcaccctta cgttgtttga agatagggag atgattgaag aacgcttgaa aacttacgct   1920
catctcttcg acgacaaagt catgaaacag ctcaagaggc gccgatatac aggatggggg   1980
cggctgtcaa gaaaactgat caatgggatc cgagacaagc agagtggaaa gacaatcctg   2040
gattttctta agtccgatgg atttgccaac cggaacttca tgcagttgat ccatgatgac   2100
tctctcacct ttaaggagga catccagaaa gcacaagttt ctggccaggg ggacagtctt   2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
```

-continued

```
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggctgct   2520
atcgtgcccc agtcttttct caaagatgat tctattgata ataaagtgtt gacaagatcc   2580
gataaagcta gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaggcag   2760
cttgttgaga cacgccagat caccaagcac gtggcccaaa ttctcgattc acgcatgaac   2820
accaagtacg atgaaaatga caaactgatt cgagaggtga aagttattac tctgaagtct   2880
aagctggtct cagatttcag aaaggacttt cagttttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata aagtgtacga tgttaggaaa   3060
atgatcgcaa agtctgagca ggaaataggc aaggccaccg ctaagtactt cttttacagc   3120
aatattatga atttttcaa gaccgagatt acactggcca atggagagat tcggaagcga   3180
ccacttatcg aaacaaacgg agaaacagga gaaatcgtgt gggacaaggg tagggatttc   3240
gcgacagtcc ggaaggtcct gtccatgccg caggtgaaca tcgttaaaaa gaccgaagta   3300
cagaccggag gcttctccaa ggaaagtatc ctcccgaaaa ggaacagcga caagctgatc   3360
gcacgcaaaa aagattggga ccccaagaaa tacggcggat tcgattctcc tacagtcgct   3420
tacagtgtac tggttgtggc caaagtggag aaagggaagt ctaaaaaact caaaagcgtc   3480
aaggaactgc tgggcatcac aatcatggag cgatcaagct tcgaaaaaaa ccccatcgac   3540
tttctcgagg cgaaaggata taaagaggtc aaaaaagacc tcatcattaa gcttcccaag   3600
tactctctct ttgagcttga aaacggccgg aaacgaatgc tcgctagtgc gggcgagctg   3660
cagaaaggta acgagctggc actgccctct aaatacgtta atttcttgta tctggccagc   3720
cactatgaaa agctcaaagg gtctcccgaa gataatgagc agaagcagct gttcgtggaa   3780
caacacaaac actaccttga tgagatcatc gagcaaataa gcgaattctc caaaagagtg   3840
atcctcgccg acgctaacct cgataaggtg ctttctgctt acaataagca cagggataag   3900
cccatcaggg agcaggcaga aaacattatc cacttgttta ctctgaccaa cttgggcgcg   3960
cctgcagcct tcaagtactt cgacaccacc atagacagaa agcggtacac ctctacaaag   4020
gaggtcctgg acgccacact gattcatcag tcaattacgg ggctctatga aacaagaatc   4080
gacctctctc agctcggtgg agactaa                                       4107
```

<210> SEQ ID NO 9
<211> LENGTH: 3366
<212> TYPE: DNA
<213> ORGANISM: Streptococcus thermophilus

<400> SEQUENCE: 9

```
atgagcgacc tggtgctggg cctggacatc ggcatcggca gcgtgggcgt gggcatcctg     60
aacaaggtga ccggcgagat catccacaag aacagtcgca tcttccctgc tgctcaggct    120
gagaacaacc tggtgcgccg caccaaccgc cagggtcgcc ggcttgctcg ccgcaagaag    180
caccggcgcg tgcgcctgaa ccgcctgttc gaggagagcg gcctgatcac cgacttcacc    240
aagatcagca tcaacctgaa cccctaccag ctgcgcgtga agggcctgac cgacgagctg    300
```

-continued

```
agcaacgagg agctgttcat cgccctgaag aacatggtga agcaccgcgg catcagctac    360
ctggacgacg ccagcgacga cggcaacagc agcgtgggcg actacgccca gatcgtgaag    420
gagaacagca agcagctgga gaccaagacc cccggccaga tccagctgga gcgctaccag    480
acctacggcc agctgcgcgg cgacttcacc gtggagaagg acggcaagaa gcaccgcctg    540
atcaacgtgt tccccaccag cgcctaccgc agcgaggccc tgcgcatcct gcagacccag    600
caggagttca acccccagat caccgacgag ttcatcaacc gctacctgga gatcctgacc    660
ggcaagcgca agtactacca cggccccggc aacgagaaga gccgcaccga ctacggccgc    720
taccgcacca gcggcgagac cctggacaac atcttcggca tcctgatcgg caagtgcacc    780
ttctaccccg acgagttccg cgccgccaag gccagctaca ccgcccagga gttcaacctg    840
ctgaacgacc tgaacaacct gaccgtgccc accgagacca agaagctgag caaggagcag    900
aagaaccaga tcatcaacta cgtgaagaac gagaaggcca tgggccccgc caagctgttc    960
aagtacatcg ccaagctgct gagctgcgac gtggccgaca tcaagggcta ccgcatcgac   1020
aagagcggca aggccgagat ccacaccttc gaggcctacc gcaagatgaa gaccctggag   1080
accctggaca tcgagcagat ggaccgcgag accctggaca agctggccta cgtgctgacc   1140
ctgaacaccg agcgcgaggg catccaggag gccctggagc acgagttcgc cgacggcagc   1200
ttcagccaga agcaggtgga cgagctggtg cagttccgca aggccaacag cagcatcttc   1260
ggcaagggct ggcacaactt cagcgtgaag ctgatgatgg agctgatccc cgagctgtac   1320
gagaccagcg aggagcagat gaccatcctg acccgcctgg gcaagcagaa gaccaccagc   1380
agcagcaaca agaccaagta catcgacgag aagctgctga ccgaggagat ctacaacccc   1440
gtggtggcca agagcgtgcg ccaggccatc aagatcgtga acgccgccat caaggagtac   1500
ggcgacttcg acaacatcgt gatcgagatg gcccgcgaga ccaacgagga cgacgagaag   1560
aaggccatcc agaagatcca gaaggccaac aaggacgaga aggacgccgc catgctgaag   1620
gccgccaacc agtacaacgg caaggccgag ctgccccaca gcgtgttcca cggccacaag   1680
cagctggcca ccaagatccg cctgtggcac cagcagggcg agcgctgcct gtacaccggc   1740
aagaccatca gcatccacga cctgatcaac aacagcaacc agttcgaggt ggaccacatc   1800
ctgcccctga gcatcacctt cgacgacagc ctggccaaca aggtgctggt gtacgccacc   1860
gccaaccagg agaagggcca gcgcaccccc taccaggccc tggacagcat ggacgacgcc   1920
tggagcttcc gcgagctgaa ggccttcgtg cgcgagagca agaccctgag caacaagaag   1980
aaggagtacc tgctgaccga ggaggacatc agcaagttcg acgtgcgcaa gaagttcatc   2040
gagcgcaacc tggtggacac ccgctacgcc agccgcgtgg tgctgaacgc cctgcaggag   2100
cacttccgcg cccacaagat cgacaccaag gtgagcgtgg tgcgcggcca gttcaccagc   2160
cagctgcgcc gccactgggg catcgagaag acccgcgaca cctaccacca ccacgccgtg   2220
gacgccctga tcattgcggc ttctagccag ctgaacctgt ggaagaagca gaagaacacc   2280
ctggtgagct acagcgagga ccagctgctg gacatcgaga ccggcgagct gatcagcgac   2340
gacgagtaca aggagagcgt gttcaaggcc ccctaccagc acttcgtgga caccctgaag   2400
agcaaggagt tcgaggacag catcctgttc agctaccagg tggacagcaa gttcaaccgc   2460
aagatcagcg acgccaccat ctacgccacc cgccaggcca aggtgggcaa ggacaaggcc   2520
gacgagacct acgtgctggg caagatcaag gacatctaca cccaggacgg ctacgacgcc   2580
ttcatgaaga tctacaagaa ggacaagagc aagttcctga tgtaccgcca cgacccccag   2640
accttcgaga aggtgatcga gcccatcctg gagaactacc ccaacaagca gatcaacgat   2700
```

aaaggcaagg aggtgccctg caaccccttc ctgaagtaca aggaggagca cggctacatc 2760
cgcaagtaca gcaagaaggg caacggcccc gagatcaaga gcctgaagta ctacgacagc 2820
aagctgggca accacatcga catcaccccc aaggacagca acaacaaggt ggtgctgcag 2880
agcgtgagcc cctggcgcgc cgacgtgtac ttcaacaaga ccaccggcaa gtacgagatc 2940
ctgggcctga agtacgccga cctgcagttt gataagggca ccggcaccta caagatcagc 3000
caggagaagt acaacgacat caagaagaag gagggcgtgg acagcgacag cgagttcaag 3060
ttcaccctgt acaagaacga ccttctgctg gtgaaggaca ccgagaccaa ggagcaacag 3120
ctgttccgct tcctgagccg caccatgccc aagcagaagc actacgtgga gctgaagccc 3180
tacgacaagc agaagttcga gggcggcgag gccctgatca aggtgctggg caacgtggcc 3240
aacagcggcc agtgcaagaa gggcctgggc aagagcaaca tcagcatcta caaggtgcgc 3300
accgacgtgc tgggcaacca gcacatcatc aagaacgagg gcgacaagcc caagctggac 3360
ttctaa 3366

<210> SEQ ID NO 10
<211> LENGTH: 3366
<212> TYPE: DNA
<213> ORGANISM: Streptococcus thermophilus

<400> SEQUENCE: 10
atgagcgacc tggtgctggg cctggccatc ggcatcggca gcgtgggcgt gggcatcctg 60
aacaaggtga ccggcgagat catccacaag aacagtcgca tcttccctgc tgctcaggct 120
gagaacaacc tggtgcgccg caccaaccgc cagggtcgcc ggcttgctcg ccgcaagaag 180
caccggcgcg tgcgcctgaa ccgcctgttc gaggagagcg gcctgatcac cgacttcacc 240
aagatcagca tcaacctgaa cccctaccag ctgcgcgtga agggcctgac cgacgagctg 300
agcaacgagg agctgttcat cgccctgaag aacatggtga agcaccgcgg catcagctac 360
ctggacgacg ccagcgacga cggcaacagc agcgtgggcg actacgccca gatcgtgaag 420
gagaacagca agcagctgga gaccaagacc cccggccaga tccagctgga gcgctaccag 480
acctacggcc agctgcgcgg cgacttcacc gtggagaagg acggcaagaa gcaccgcctg 540
atcaacgtgt tccccaccag cgcctaccgc agcgaggccc tgcgcatcct gcagacccag 600
caggagttca acccccagat caccgacgag ttcatcaacc gctacctgga gatcctgacc 660
ggcaagcgca agtactacca cggccccggc aacgagaaga gccgcaccga ctacggccgc 720
taccgcacca gcggcgagac cctggacaac atcttcggca tcctgatcgg caagtgcacc 780
ttctaccccg acgagttccg cgccgccaag gccagctaca ccgcccagga gttcaacctg 840
ctgaacgacc tgaacaacct gaccgtgccc accgagacca agaagctgag caaggagcag 900
aagaaccaga tcatcaacta cgtgaagaac gagaaggcca tgggccccgc caagctgttc 960
aagtacatcg ccaagctgct gagctgcgac gtggccgaca tcaagggcta ccgcatcgac 1020
aagagcggca aggccgagat ccacaccttc gaggcctacc gcaagatgaa gaccctggag 1080
accctggaca tcgagcagat ggaccgcgag accctggaca agctggccta cgtgctgacc 1140
ctgaacaccg agcgcgaggg catccaggag gccctggagc acgagttcgc cgacggcagc 1200
ttcagccaga agcaggtgga cgagctggtg cagttccgca aggccaacag cagcatcttc 1260
ggcaagggct ggcacaactt cagcgtgaag ctgatgatgg agctgatccc cgagctgtac 1320
gagaccagcg aggagcagat gaccatcctg acccgcctgg gcaagcagaa gaccaccagc 1380
agcagcaaca agaccaagta catcgacgag aagctgctga ccgaggagat ctacaacccc 1440
gtggtggcca agagcgtgcg ccaggccatc aagatcgtga acgccgccat caaggagtac 1500
ggcgacttcg acaacatcgt gatcgagatg gcccgcgaga ccaacgagga cgacgagaag 1560
aaggccatcc agaagatcca gaaggccaac aaggacgaga aggacgccgc catgctgaag 1620
gccgccaacc agtacaacgg caaggccgag ctgccccaca gcgtgttcca cggccacaag 1680
cagctggcca ccaagatccg cctgtggcac cagcagggcg agcgctgcct gtacaccggc 1740
aagaccatca gcatccacga cctgatcaac aacagcaacc agttcgaggt ggctgccatc 1800
ctgcccctga gcatcacctt cgacgacagc ctggccaaca aggtgctggt gtacgccacc 1860
gccgctcagg agaagggcca gcgcaccccc taccaggccc tggacagcat ggacgacgcc 1920
tggagcttcc gcgagctgaa ggccttcgtg cgcgagagca agaccctgag caacaagaag 1980
aaggagtacc tgctgaccga ggaggacatc agcaagttcg acgtgcgcaa gaagttcatc 2040
gagcgcaacc tggtggacac ccgctacgcc agccgcgtgg tgctgaacgc cctgcaggag 2100
cacttccgcg cccacaagat cgacaccaag gtgagcgtgg tgcgcggcca gttcaccagc 2160
cagctgcgcc gccactgggg catcgagaag acccgcgaca cctaccacca ccacgccgtg 2220
gacgccctga tcattgcggc ttctagccag ctgaacctgt ggaagaagca gaagaacacc 2280
ctggtgagct acagcgagga ccagctgctg gacatcgaga ccggcgagct gatcagcgac 2340
gacgagtaca aggagagcgt gttcaaggcc ccctaccagc acttcgtgga caccctgaag 2400
agcaaggagt tcgaggacag catcctgttc agctaccagg tggacagcaa gttcaaccgc 2460
aagatcagcg acgccaccat ctacgccacc cgccaggcca aggtgggcaa ggacaaggcc 2520
gacgagacct acgtgctggg caagatcaag gacatctaca cccaggacgg ctacgacgcc 2580
ttcatgaaga tctacaagaa ggacaagagc aagttcctga tgtaccgcca cgacccccag 2640
accttcgaga aggtgatcga gcccatcctg gagaactacc ccaacaagca gatcaacgat 2700
aaaggcaagg aggtgccctg caacccettc ctgaagtaca aggaggagca cggctacatc 2760
cgcaagtaca gcaagaaggg caacggcccc gagatcaaga gcctgaagta ctacgacagc 2820
aagctgggca accacatcga catcaccccc aaggacagca acaacaaggt ggtgctgcag 2880
agcgtgagcc cctggcgcgc cgacgtgtac ttcaacaaga ccaccggcaa gtacgagatc 2940
ctgggcctga agtacgccga cctgcagttt gataagggca ccggcaccta caagatcagc 3000
caggagaagt acaacgacat caagaagaag gagggcgtgg acagcgacag cgagttcaag 3060
ttcaccctgt acaagaacga ccttctgctg gtgaaggaca ccgagaccaa ggagcaacag 3120
ctgttccgct tcctgagccg caccatgccc aagcagaagc actacgtgga gctgaagccc 3180
tacgacaagc agaagttcga gggcggcgag gccctgatca aggtgctggg caacgtggcc 3240
aacagcggcc agtgcaagaa gggcctgggc aagagcaaca tcagcatcta caaggtgcgc 3300
accgacgtgc tgggcaacca gcacatcatc aagaacgagg gcgacaagcc caagctggac 3360
ttctaa 3366

<210> SEQ ID NO 11
<211> LENGTH: 3249
<212> TYPE: DNA
<213> ORGANISM: Neisseria meningitidis

<400> SEQUENCE: 11
atggccgcct tcaagcccaa ccccatcaac tacatcctgg gcctggacat cggcatcgcc 60
agcgtgggct gggccatggt ggagatcgac gaggacgaga accccatctg cctgatcgac 120

-continued

```
ctgggtgtgc gcgtgttcga gcgcgctgag gtgcccaaga ctggtgacag tctggctatg    180
gctcgccggc ttgctcgctc tgttcggcgc cttactcgcc ggcgcgctca ccgccttctg    240
cgcgctcgcc gcctgctgaa gcgcgagggt gtgctgcagg ctgccgactt cgacgagaac    300
ggcctgatca agagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact tccgcactcc tgctgagctg    540
gccctgaaca agttcgagaa ggagagcggc cacatccgca accagcgcgg cgactacagc    600
cacaccttca gccgcaagga cctgcaggcc gagctgatcc tgctgttcga gaagcagaag    660
gagttcggca acccccacgt gagcggcggc ctgaaggagg gcatcgagac cctgctgatg    720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
accaagctga acaacctgcg catcctggag cagggcagcg agcgccccct gaccgacacc    900
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagg ccagcaccct gatggagatg aaggcctacc acgccatcag ccgcgccctg   1080
gagaaggagg gcctgaagga caagaagagt cctctgaacc tgagccccga gctgcaggac   1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg gcaagaagaa caccgaggag   1380
aagatctacc tgcctcctat ccccgccgac gagatccgca accccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgcct gtacagcggc aaggagatca acctgggccg cctgaacgag   1740
aagggctacg tggagatcga ccacgccctg cccttcagcc gcacctggga cgacagcttc   1800
aacaacaagg tgctggtgct gggcagcgag aaccagaaca agggcaacca gaccccctac   1860
gagtacttca acggcaagga caacagccgc gagtggcagg agttcaaggc ccgcgtggag   1920
accagccgct tcccccgcag caagaagcag cgcatcctgc tgcagaagtt cgacgaggac   1980
ggcttcaagg agcgcaacct gaacgacacc cgctacgtga accgcttcct gtgccagttc   2040
gtggccgacc gcatgcgcct gaccggcaag ggcaagaagc gcgtgttcgc cagcaacggc   2100
cagatcacca acctgctgcg cggcttctgg ggcctgcgca aggtgcgcgc cgagaacgac   2160
cgccaccacg ccctggacgc cgtggtggtg gcctgcagca ccgtggccat gcagcagaag   2220
atcacccgct tcgtgcgcta caaggagatg aacgccttcg acggtaaaac catcgacaag   2280
gagaccggcg aggtgctgca ccagaagacc cacttccccc agccctggga gttcttcgcc   2340
caggaggtga tgatccgcgt gttcggcaag cccgacggca agcccgagtt cgaggaggcc   2400
gacacccccg agaagctgcg caccctgctg gccgagaagc tgagcagccg ccctgaggcc   2460
```

-continued gtgcacgagt acgtgactcc tctgttcgtg agccgcgccc ccaaccgcaa gatgagcggt 2520
cagggtcaca tggagaccgt gaagagcgcc aagcgcctgg acgagggcgt gagcgtgctg 2580
cgcgtgcccc tgacccagct gaagctgaag gacctggaga agatggtgaa ccgcgagcgc 2640
gagcccaagc tgtacgaggc cctgaaggcc cgcctggagg cccacaagga cgacccccgcc 2700 aaggccttcg ccgagccctt ctacaagtac gacaaggccg gcaaccgcac ccagcaggtg 2760
aaggccgtgc gcgtggagca ggtgcagaag accggcgtgt gggtgcgcaa ccacaacggc 2820
atcgccgaca acgccaccat ggtgcgcgtg gacgtgttcg agaagggcga caagtactac 2880
ctggtgccca tctacagctg gcaggtggcc aagggcatcc tgcccgaccg cgccgtggtg 2940
cagggcaagg acgaggagga ctggcagctg atcgacgaca gcttcaactt caagttcagc 3000
ctgcacccca acgacctggt ggaggtgatc accaagaagg cccgcatgtt cggctacttc 3060
gccagctgcc accgcggcac cggcaacatc aacatccgca tccacgacct ggaccacaag 3120
atcggcaaga acggcatcct ggagggcatc ggcgtgaaga ccgccctgag cttccagaag 3180
taccagatcg acgagctggg caaggagatc cgcccctgcc gcctgaagaa gcgccctcct 3240
gtgcgctaa 3249

<210> SEQ ID NO 12
<211> LENGTH: 3249
<212> TYPE: DNA
<213> ORGANISM: Neisseria meningitidis

<400> SEQUENCE: 12
atggccgcct tcaagcccaa ccccatcaac tacatcctgg gcctggccat cggcatcgcc 60
agcgtgggct gggccatggt ggagatcgac gaggacgaga accccatctg cctgatcgac 120
ctgggtgtgc gcgtgttcga gcgcgctgag gtgcccaaga ctggtgacag tctggctatg 180
gctcgccggc ttgctcgctc tgttcggcgc cttactcgcc ggcgcgctca ccgccttctg 240
cgcgctcgcc gcctgctgaa gcgcgagggt gtgctgcagg ctgccgactt cgacgagaac 300
ggcctgatca agagcctgcc caacactcct tggcagctgc gcgctgccgc tctggaccgc 360
aagctgactc ctctggagtg gagcgccgtg ctgctgcacc tgatcaagca ccgcggctac 420
ctgagccagc gcaagaacga gggcgagacc gccgacaagg agctgggtgc tctgctgaag 480
ggcgtggccg acaacgccca cgccctgcag actggtgact tccgcactcc tgctgagctg 540
gccctgaaca agttcgagaa ggagagcggc cacatccgca accagcgcgg cgactacagc 600
cacaccttca gccgcaagga cctgcaggcc gagctgatcc tgctgttcga gaagcagaag 660
gagttcggca acccccacgt gagcggcggc ctgaaggagg gcatcgagac cctgctgatg 720
acccagcgcc ccgccctgag cggcgacgcc gtgcagaaga tgctgggcca ctgcaccttc 780
gagccagccg agcccaaggc cgccaagaac acctacaccg ccgagcgctt catctggctg 840
accaagctga acaacctgcg catcctggag cagggcagcg agcgccccct gaccgacacc 900
gagcgcgcca ccctgatgga cgagccctac cgcaagagca agctgaccta cgcccaggcc 960
cgcaagctgc tgggtctgga ggacaccgcc ttcttcaagg gcctgcgcta cggcaaggac 1020
aacgccgagg ccagcaccct gatggagatg aaggcctacc acgccatcag ccgcgccctg 1080
gagaaggagg gcctgaagga caagaagagt cctctgaacc tgagccccga gctgcaggac 1140
gagatcggca ccgccttcag cctgttcaag accgacgagg acatcaccgg ccgcctgaag 1200
gaccgcatcc agcccgagat cctggaggcc ctgctgaagc acatcagctt cgacaagttc 1260
gtgcagatca gcctgaaggc cctgcgccgc atcgtgcccc tgatggagca gggcaagcgc 1320

```
tacgacgagg cctgcgccga gatctacggc gaccactacg gcaagaagaa caccgaggag   1380
aagatctacc tgcctcctat ccccgccgac gagatccgca accccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgcct gtacagcggc aaggagatca acctgggccg cctgaacgag   1740
aagggctacg tggagatcgc cgctgccctg cccttcagcc gcacctggga cgacagcttc   1800
aacaacaagg tgctggtgct gggcagcgag gctcagaaca agggcaacca gaccccctac   1860
gagtacttca acggcaagga caacagccgc gagtggcagg agttcaaggc ccgcgtggag   1920
accagccgct tcccccgcag caagaagcag cgcatcctgc tgcagaagtt cgacgaggac   1980
ggcttcaagg agcgcaacct gaacgacacc cgctacgtga accgcttcct gtgccagttc   2040
gtggccgacc gcatgcgcct gaccggcaag ggcaagaagc gcgtgttcgc cagcaacggc   2100
cagatcacca acctgctgcg cggcttctgg ggcctgcgca aggtgcgcgc cgagaacgac   2160
cgccaccacg ccctggacgc cgtggtggtg gcctgcagca ccgtggccat gcagcagaag   2220
atcacccgct tcgtgcgcta caaggagatg aacgccttcg acggtaaaac catcgacaag   2280
gagaccggcg aggtgctgca ccagaagacc cacttccccc agccctggga gttcttcgcc   2340
caggaggtga tgatccgcgt gttcggcaag cccgacggca agcccgagtt cgaggaggcc   2400
gacacccccg agaagctgcg caccctgctg gccgagaagc tgagcagccg ccctgaggcc   2460
gtgcacgagt acgtgactcc tctgttcgtg agccgcgccc ccaaccgcaa gatgagcggt   2520
cagggtcaca tggagaccgt gaagagcgcc aagcgcctgg acgagggcgt gagcgtgctg   2580
cgcgtgcccc tgacccagct gaagctgaag gacctggaga agatggtgaa ccgcgagcgc   2640
gagcccaagc tgtacgaggc cctgaaggcc cgcctggagg cccacaagga cgaccccgcc   2700
aaggccttcg ccgagccctt ctacaagtac gacaaggccg gcaaccgcac ccagcaggtg   2760
aaggccgtgc gcgtggagca ggtgcagaag accggcgtgt gggtgcgcaa ccacaacggc   2820
atcgccgaca acgccaccat ggtgcgcgtg gacgtgttcg agaagggcga caagtactac   2880
ctggtgccca tctacagctg gcaggtggcc aagggcatcc tgcccgaccg cgccgtggtg   2940
cagggcaagg acgaggagga ctggcagctg atcgacgaca gcttcaactt caagttcagc   3000
ctgcacccca acgacctggt ggaggtgatc accaagaagg cccgcatgtt cggctacttc   3060
gccagctgcc accgcggcac cggcaacatc aacatccgca tccacgacct ggaccacaag   3120
atcggcaaga acggcatcct ggagggcatc ggcgtgaaga ccgccctgag cttccagaag   3180
taccagatcg acgagctggg caaggagatc cgcccctgcc gcctgaagaa gcgccctcct   3240
gtgcgctaa                                                           3249
```

<210> SEQ ID NO 13
<211> LENGTH: 4188
<212> TYPE: DNA
<213> ORGANISM: Treponema denticola

<400> SEQUENCE: 13

```
atgaagaagg agatcaagga ctacttcctg ggcctggacg tgggcaccgg cagcgtgggc     60
tgggccgtga ccgacaccga ctacaagctg ctgaaggcca accgcaagga cctgtggggc    120
```

-continued

```
atgcgctgct tcgagactgc tgagaccgcc gaggtgcgcc ggctgcaccg cggtgctcgc    180
cggcgcatcg agcgccgcaa gaagcgcatc aagctgctgc aggagctgtt cagccaggag    240
atcgccaaga ccgacgaggg cttcttccag cgcatgaagg agagcccctt ctacgccgag    300
gacaagacca tcctgcagga gaacaccctg ttcaacgaca aggacttcgc cgacaagacc    360
taccacaagg cctaccccac catcaaccac ctgatcaagg cctggatcga gaacaaggtg    420
aagcccgacc ctcgcctgct gtacctggcc tgccacaaca tcatcaagaa gcgcggccac    480
ttcctgttcg agggcgactt cgacagcgag aaccagttcg acaccagcat ccaggccctg    540
ttcgagtacc tgcgcgagga catggaggtg gacatcgacg ccgacagcca gaaggtgaag    600
gagatcctga aggacagcag cctgaagaac agcgagaagc agagccgcct gaacaagatc    660
ctgggcctga agcccagcga caagcagaag aaggccatca ccaacctgat cagcggcaac    720
aagatcaact tcgccgacct gtacgacaac cccgacctga aggacgccga gaagaacagc    780
atcagcttca gcaaggacga cttcgacgcc ctgagcgacg acctggccag catcctgggc    840
gacagcttcg agctgctgct gaaggccaag gccgtgtaca actgcagcgt gctgagcaag    900
gtgatcggcg acgagcagta cctgagcttc gccaaggtga agatctacga gaagcacaag    960
accgacctta ccaagctgaa gaacgtgatc aagaagcact tccccaagga ctacaagaag   1020
gtgttcggct acaacaagaa cgagaagaac aacaacaact acagcggcta cgtgggcgtg   1080
tgcaagacca agagcaagaa gctgatcatc aacaacagcg tgaaccagga ggacttctac   1140
aagttcctga agaccatcct gagcgccaag agcgagatca aggaggtgaa cgacatcctg   1200
accgagatcg agaccggcac cttcctgccc aagcagatca gcaagagcaa cgccgagatc   1260
ccctaccagc tgcgcaagat ggagctggag aagatcctga gcaacgccga gaagcacttc   1320
agcttcctga agcagaagga cgagaagggc ctgagccaca gcgagaagat catcatgctg   1380
ctgaccttca agatccccta ctacatcggc cccatcaacg acaaccacaa gaagttcttc   1440
cccgaccgct gctgggtggt gaagaaggag aagagcccca gcggcaagac caccccctgg   1500
aacttcttcg accacatcga caaggagaag accgccgagg ccttcatcac cagccgcacc   1560
aacttctgca catacctggt gggcgagagc gtgctgccca agagcagcct gctgtacagc   1620
gagtacaccg tgctgaacga gatcaacaac ctgcagatca tcatcgacgg caagaacatc   1680
tgcgacatca agctgaagca gaagatctac gaggacctgt tcaagaagta caagaagatc   1740
acccagaagc agatcagcac cttcatcaag cacgagggca tctgcaacaa gaccgacgag   1800
gtgatcatcc tgggcatcga caaggagtgc accagcagcc tgaagagcta catcgagctg   1860
aagaacatct tcggcaagca ggtggacgag atcagcacca agaacatgct ggaggagatc   1920
atccgctggg ccaccatcta cgacgagggc gagggcaaga ccatcctgaa gaccaagatc   1980
aaggccgagt acggcaagta ctgcagcgac gagcagatca agaagatcct gaacctgaag   2040
ttcagcggct ggggccgcct gagccgcaag ttcctggaga ccgtgaccag cgagatgccc   2100
ggcttcagcg agcccgtgaa catcatcacc gccatgcgcg agacccagaa caacctgatg   2160
gagctgctga gcagcgagtt caccttcacc gagaacatca agaagatcaa cagcggcttc   2220
gaggacgccg agaagcagtt cagctacgac ggcctggtga agcccctgtt cctgagcccc   2280
agcgtgaaga agatgctgtg gcagaccctg aagctggtga aggagatcag ccacatcacc   2340
caggctcctc ctaagaagat cttcatcgag atggccaagg gcgccgagct ggagcctgct   2400
cgcaccaaga cccgcctgaa gatcctgcag gacctgtaca acaactgcaa gaacgacgcc   2460
gacgcattca gcagcgagat caaggacctg agcggcaaga tcgagaacga ggacaacctg   2520
```

cgcctgcgca gcgacaagct gtacctgtac tacacccagc tgggcaagtg catgtactgc 2580
ggcaagccca tcgagatcgg ccacgtgttc gacaccagca actacgacat cgaccacatc 2640
tacccccaga gcaagatcaa ggacgacagc atcagcaacc gcgtgctggt gtgcagcagc 2700
tgcaacaaga acaaggagga caagtaccct ctgaagagcg agatccagag caagcagcgc 2760
ggcttctgga acttcctgca gcgcaacaac ttcatcagcc tggagaagct gaaccgcctg 2820
acccgcgcca cccccatcag cgacgacgag accgccaagt tcatcgcccg ccagctggtg 2880
gagactcgcc aagctaccaa ggtggccgcc aaggtgctgg agaagatgtt ccccgagacc 2940
aagatcgtgt acagcaaggc cgagaccgtg agcatgttcc gcaacaagtt cgacatcgtg 3000
aagtgccgcg agatcaacga cttccaccac gcccacgacg cctacctgaa catcgtggtg 3060
ggcaacgtgt acaacaccaa gttcaccaac aacccctgga atttcattaa ggagaagcgc 3120
gacaacccca agatcgccga cacctacaac tactacaagg tgttcgacta cgacgtgaag 3180
cgcaacaaca tcaccgcctg ggagaagggc aagaccatca tcaccgtgaa ggacatgctg 3240
aagcgcaaca cccccatcta cacccgccag gccgcctgca agaagggcga gctgttcaac 3300
cagaccatca tgaagaaggg cctgggccag cacccccctga agaaggaggg cccccttcagc 3360 aacatcagca agtacggcgg ctacaacaag gtgagcgccg cctactacac cctgatcgag 3420
tacgaggaga agggcaacaa gatccgcagc ctggagacca tcccccctgta cctggtgaag 3480 gacatccaga aggaccagga cgtgctgaag agctacctga ccgacctgct gggcaagaag 3540
gagttcaaga tcctggtgcc caagatcaag atcaacagcc tgctgaagat caacggcttc 3600
ccctgccaca tcaccggcaa gaccaacgac agcttcctgc tgcgccccgc cgtgcagttc 3660
tgctgcagca acaacgaggt gctgtacttc aagaagatca tccgcttcag cgagatccgc 3720
agccagcgcg agaagatcgg caagaccatc agcccctacg aggacctgag cttccgcagc 3780
tacatcaagg agaacctgtg gaagaagacc aagaacgacg agatcggcga gaaggagttc 3840
tacgacctgc tgcagaagaa gaacctggag atctacgaca tgctgctgac caagcacaag 3900
gacaccatct acaagaagcg ccccaacagc gccaccatcg acatcctggt gaagggcaag 3960
gagaagttca agagcctgat catcgagaac cagttcgagg tgatcctgga gatcctgaag 4020
ctgttcagcg ccacccgcaa cgtgagcgac ctgcagcaca tcggcggcag caagtacagc 4080
ggcgtggcca agatcggcaa caagatcagc agcctggaca actgcatcct gatctaccag 4140
agcatcaccg gcatcttcga gaagcgcatc gacctgctga aggtgtaa 4188

<210> SEQ ID NO 14
<211> LENGTH: 4188
<212> TYPE: DNA
<213> ORGANISM: Treponema denticola

<400> SEQUENCE: 14
atgaagaagg agatcaagga ctacttcctg ggcctggccg tgggcaccgg cagcgtgggc 60
tgggccgtga ccgacaccga ctacaagctg ctgaaggcca accgcaagga cctgtggggc 120
atgcgctgct tcgagactgc tgagaccgcc gaggtgcgcc ggctgcaccg cggtgctcgc 180
cggcgcatcg agcgccgcaa gaagcgcatc aagctgctgc aggagctgtt cagccaggag 240
atcgccaaga ccgacgaggg cttcttccag cgcatgaagg agagcccctt ctacgccgag 300
gacaagacca tcctgcagga gaacaccctg ttcaacgaca aggacttcgc cgacaagacc 360
taccacaagg cctaccccac catcaaccac ctgatcaagg cctggatcga gaacaaggtg 420

-continued

```
aagcccgacc ctcgcctgct gtacctggcc tgccacaaca tcatcaagaa gcgcggccac    480
ttcctgttcg agggcgactt cgacagcgag aaccagttcg acaccagcat ccaggccctg    540
ttcgagtacc tgcgcgagga catggaggtg gacatcgacg ccgacagcca gaaggtgaag    600
gagatcctga aggacagcag cctgaagaac agcgagaagc agagccgcct gaacaagatc    660
ctgggcctga agcccagcga caagcagaag aaggccatca ccaacctgat cagcggcaac    720
aagatcaact tcgccgacct gtacgacaac cccgacctga aggacgccga gaagaacagc    780
atcagcttca gcaaggacga cttcgacgcc ctgagcgacg acctggccag catcctgggc    840
gacagcttcg agctgctgct gaaggccaag gccgtgtaca actgcagcgt gctgagcaag    900
gtgatcggcg acgagcagta cctgagcttc gccaaggtga agatctacga gaagcacaag    960
accgacctta ccaagctgaa gaacgtgatc aagaagcact tccccaagga ctacaagaag   1020
gtgttcggct acaacaagaa cgagaagaac aacaacaact acagcggcta cgtgggcgtg   1080
tgcaagacca agagcaagaa gctgatcatc aacaacagcg tgaaccagga ggacttctac   1140
aagttcctga agaccatcct gagcgccaag agcgagatca aggaggtgaa cgacatcctg   1200
accgagatcg agaccggcac cttcctgccc aagcagatca gcaagagcaa cgccgagatc   1260
ccctaccagc tgcgcaagat ggagctggag aagatcctga gcaacgccga gaagcacttc   1320
agcttcctga agcagaagga cgagaagggc ctgagccaca gcgagaagat catcatgctg   1380
ctgaccttca agatccccta ctacatcggc cccatcaacg acaaccacaa gaagttcttc   1440
cccgaccgct gctgggtggt gaagaaggag aagagcccca gcggcaagac caccccctgg   1500
aacttcttcg accacatcga caaggagaag accgccgagg ccttcatcac cagccgcacc   1560
aacttctgca catacctggt gggcgagagc gtgctgccca agagcagcct gctgtacagc   1620
gagtacaccg tgctgaacga gatcaacaac ctgcagatca tcatcgacgg caagaacatc   1680
tgcgacatca agctgaagca gaagatctac gaggacctgt tcaagaagta caagaagatc   1740
acccagaagc agatcagcac cttcatcaag cacgagggca tctgcaacaa gaccgacgag   1800
gtgatcatcc tgggcatcga caaggagtgc accagcagcc tgaagagcta catcgagctg   1860
aagaacatct tcggcaagca ggtggacgag atcagcacca agaacatgct ggaggagatc   1920
atccgctggg ccaccatcta cgacgagggc gagggcaaga ccatcctgaa gaccaagatc   1980
aaggccgagt acggcaagta ctgcagcgac gagcagatca agaagatcct gaacctgaag   2040
ttcagcggct ggggccgcct gagccgcaag ttcctggaga ccgtgaccag cgagatgccc   2100
ggcttcagcg agcccgtgaa catcatcacc gccatgcgcg agacccagaa caacctgatg   2160
gagctgctga gcagcgagtt caccttcacc gagaacatca agaagatcaa cagcggcttc   2220
gaggacgccg agaagcagtt cagctacgac ggcctggtga agcccctgtt cctgagcccc   2280
agcgtgaaga agatgctgtg gcagaccctg aagctggtga aggagatcag ccacatcacc   2340
caggctcctc ctaagaagat cttcatcgag atggccaagg gcgccgagct ggagcctgct   2400
cgcaccaaga cccgcctgaa gatcctgcag gacctgtaca acaactgcaa gaacgacgcc   2460
gacgcattca gcagcgagat caaggacctg agcggcaaga tcgagaacga ggacaacctg   2520
cgcctgcgca gcgacaagct gtacctgtac tacacccagc tgggcaagtg catgtactgc   2580
ggcaagccca tcgagatcgg ccacgtgttc gacaccagca actacgacat cgctgctatc   2640
tacccccaga gcaagatcaa ggacgacagc atcagcaacc gcgtgctggt gtgcagcagc   2700
tgcgccaaga acaaggagga caagtaccct ctgaagagcg agatccagag caagcagcgc   2760
ggcttctgga acttcctgca gcgcaacaac ttcatcagcc tggagaagct gaaccgcctg   2820
```

```
acccgcgcca cccccatcag cgacgacgag accgccaagt tcatcgcccg ccagctggtg   2880

gagactcgcc aagctaccaa ggtggccgcc aaggtgctgg agaagatgtt ccccgagacc   2940

aagatcgtgt acagcaaggc cgagaccgtg agcatgttcc gcaacaagtt cgacatcgtg   3000

aagtgccgcg agatcaacga cttccaccac gcccacgacg cctacctgaa catcgtggtg   3060

ggcaacgtgt acaacaccaa gttcaccaac aacccctgga atttcattaa ggagaagcgc   3120

gacaacccca agatcgccga cacctacaac tactacaagg tgttcgacta cgacgtgaag   3180

cgcaacaaca tcaccgcctg ggagaagggc aagaccatca tcaccgtgaa ggacatgctg   3240

aagcgcaaca cccccatcta cacccgccag gccgcctgca agaagggcga gctgttcaac   3300

cagaccatca tgaagaaggg cctgggccag cacccccctga agaaggaggg ccccttcagc   3360

aacatcagca agtacggcgg ctacaacaag gtgagcgccg cctactacac cctgatcgag   3420

tacgaggaga agggcaacaa gatccgcagc ctggagacca tccccctgta cctggtgaag   3480

gacatccaga aggaccagga cgtgctgaag agctacctga ccgacctgct gggcaagaag   3540

gagttcaaga tcctggtgcc caagatcaag atcaacagcc tgctgaagat caacggcttc   3600

ccctgccaca tcaccggcaa gaccaacgac agcttcctgc tgcgccccgc cgtgcagttc   3660

tgctgcagca acaacgaggt gctgtacttc aagaagatca tccgcttcag cgagatccgc   3720

agccagcgcg agaagatcgg caagaccatc agcccctacg aggacctgag cttccgcagc   3780

tacatcaagg agaacctgtg gaagaagacc aagaacgacg agatcggcga gaaggagttc   3840

tacgacctgc tgcagaagaa gaacctggag atctacgaca tgctgctgac caagcacaag   3900

gacaccatct acaagaagcg ccccaacagc gccaccatcg acatcctggt gaagggcaag   3960

gagaagttca agagcctgat catcgagaac cagttcgagg tgatcctgga gatcctgaag   4020

ctgttcagcg ccacccgcaa cgtgagcgac ctgcagcaca tcggcggcag caagtacagc   4080

ggcgtggcca agatcggcaa caagatcagc agcctggaca actgcatcct gatctaccag   4140

agcatcaccg gcatcttcga gaagcgcatc gacctgctga aggtgtaa               4188
```

```
<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15

aacaaatgtg tcacaaagta                                              20


<210> SEQ ID NO 16
<211> LENGTH: 20
<212> TYPE: DNA
<213> ORGANISM: Artificial
<220> FEATURE:
<223> OTHER INFORMATION: Synthetic

<400> SEQUENCE: 16

acaaaactgt gctagacatg                                              20


<210> SEQ ID NO 17
<211> LENGTH: 20
<212> TYPE: DNA
<213> ORGANISM: Artificial
<220> FEATURE:
<223> OTHER INFORMATION: Synthetic
```

<400> SEQUENCE: 17
tgtgctagac atgaggtcta 20

<210> SEQ ID NO 18
<211> LENGTH: 20
<212> TYPE: DNA
<213> ORGANISM: Artificial
<220> FEATURE:
<223> OTHER INFORMATION: Synthetic

<400> SEQUENCE: 18
gcccacgaca ccaaccacca 20

<210> SEQ ID NO 19
<211> LENGTH: 20
<212> TYPE: DNA
<213> ORGANISM: Artificial
<220> FEATURE:
<223> OTHER INFORMATION: Synthetic

<400> SEQUENCE: 19
tcttccctag gaatgatgac 20

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
gcggtccctg aggtgcaccg 20

<210> SEQ ID NO 21
<211> LENGTH: 20
<212> TYPE: DNA
<213> ORGANISM: Artificial
<220> FEATURE:
<223> OTHER INFORMATION: Synthetic

<400> SEQUENCE: 21
agaagtggaa tacagagcgg 20

<210> SEQ ID NO 22
<211> LENGTH: 1491
<212> TYPE: DNA
<213> ORGANISM: adeno-associated virus

<400> SEQUENCE: 22
atggagagaa ggaatcctag tgagagggga gtgcccgccg ggttttctgg tcacgcctcc 60
gtggaatccg gatgtgagac tcaggagtcc cccgccaccg tggtgttccg cccaccagga 120
gacaacactg acggtggcgc ggcggctgct gcaggtggaa gccaagccgc cgctgctggg 180
gccgagccga tggaacccga atccagaccc ggtccctctg gcatgaacgt tgtgcaggtc 240
gcagaactct accccgaact ccgcaggatc ttgacaatca cggaggacgg ccagggcctc 300
aagggagtga agagagagag aggggcttgt gaggccactg aggaagctcg caatctggcg 360
ttttcattga tgacaaggca caggccggaa tgcattacat tccaacagat taaggacaac 420

-continued

```
tgcgcaaacg agctcgatct cctggcccag aagtatagca tcgagcagct gacaacctat    480

tggctgcagc ccggcgacga ttttgaagag gccatccgcg tgtacgcaaa ggtggccctg    540

cgacctgact gcaaatataa gatttccaaa ctggttaaca tccggaattg ttgttatatt    600

agtggaaatg gcgcagaagt ggagattgac acagaggatc gagtcgcttt ccggtgctct    660

atgatcaaca tgtggcccgg tgtgctcggc atggatggcg tagtcattat gaatgtggct    720

ttcaccggac ctaattttag cggaaccgtc ttcctggcaa acactaatct gatcctgcat    780

ggagtttctt tctatggatt taataacacc tgtgttgaag cttggaccga cgtgcgggtt    840

agagggtgtg ctttttattg ctgctggaaa ggcgtcgtgt gtagacccaa aagtagagct    900

tctatcaaga aatgcctgtt cgagaggtgt actctgggca ttctcagtga aggtaatagc    960

agggtcaggc ataacgtggc ctcagattgc ggatgtttta tgttggttaa atccgtggct   1020

gtgatcaagc acaacatggt gtgtggcaat tgtgaggacc gggcatctca aatgctgaca   1080

tgttccgatg gcaactgtca cctgctcaaa acaattcacg ttgcgagcca ttctcggaag   1140

gcctggccag ttttcgagca taacatcctg acgcgctgta gtctccacct gggtaacaga   1200

cggggcgttt tcctgccata tcagtgtaac ctgtcacata ccaagatact cctggaacca   1260

gaatctatga gtaaagtgaa cctgaatggt gtattcgata tgaccatgaa gatatggaaa   1320

gtcctccgct atgacgaaac taggactagg tgtaggccct gcgagtgtgg cggcaagcat   1380

atccgcaacc aacccgtgat gctggacgtg accgaggagc tgcgccccga tcacctggtg   1440

ctggcctgca ccagagcaga attcgggagc tcagacgaag acactgatta a             1491
```

<210> SEQ ID NO 23
<211> LENGTH: 888
<212> TYPE: DNA
<213> ORGANISM: adeno-associated virus

<400> SEQUENCE: 23

```
atgggcacta ctagtggggt accctttggc atgaccctcc gccccactcg gtcaaggctc     60

tcccggagaa ctccttactc tcgcgatagg cttcctccgt tcgaaaccga aacacgggca    120

accattctgg aagatcatcc actgctgcca gagtgtaata ccctgacgat gcataacgtt    180

tcttacgtcc gcggtctgcc ctgttccgtg ggttttactc tgatccagga gtgggtcgtg    240

ccttgggata tggtcctcac acgcgaggag ctggtgatcc tgagaaagtg tatgcatgtc    300

tgcttgtgtt gcgcaaacat cgacattatg accagtatga tgattcatgg atacgagagc    360

tgggcgcttc actgccactg ctcatcccct ggcagcctgc agtgtattgc agggggccag    420

gtgctcgctt cctggtttag aatggtagtg gatggcgcca tgtttaatca gagattcatt    480

tggtatcggg aggttgtgaa ctataacatg ccaaaggaag tcatgtttat gagcagcgtg    540

ttcatgcggg ggcggcatct gatatatctg agactgtggt acgacggtca cgtgggctct    600

gtcgtgcctg caatgtcctt cggatacagc gccctgcact gtgggatcct caataatata    660

gtcgtcttgt gttgctctta ttgcgcagat ctcagtgaga taagagtcag gtgctgtgca    720

agacggaccg caagggcgat gctccgcgcc gtgcgcatca ttgccgagga gacaactgcc    780

atgctttaca gctgtagaac agagcgcaga cgccagcagt ttatcagagc cctgctgcag    840

caccaccgcc ccatactcat gcatgactac gacagtacgc caatgtaa                 888
```

ENHANCING ENDONUCLEASE BASED GENE EDITING IN PRIMARY CELLS

PRIORITY AND CROSS-REFERENCE TO RELATED APPLICATIONS

This application claims the benefit of priority to U.S. Provisional Application 62/161,104, filed on May 13, 2015, which is hereby expressly incorporated by reference in its entirety.

REFERENCE TO SEQUENCE LISTING

The present application is being filed along with a Sequence Listing in electronic format. The Sequence Listing is provided as a file entitled SCRI_094A_SEQLIST.txt which is 72,183 bytes in size, created on May 11, 2016 and last modified on May 11, 2016.

FIELD

Aspects of the disclosure provided herein are generally related to endonuclease-based gene editing systems and methods. Some aspects of the disclosure provided herein are related to the CRISPR/Cas9 gene editing system.

BACKGROUND

Endonuclease-based systems have rapidly become significant gene editing tools in biomedical research, with their application for gene disruption and/or gene targeting demonstrated in a variety of cultured cell and model organism systems.

Endonuclease-based systems for gene editing allow scientists to edit genomes with unprecedented precision, efficiency, and flexibility. Examples of endonuclease-based approaches for gene editing include systems comprising, without limitations, zinc finger nucleases (ZFNs), TAL effector nucleases (TALENs), meganucleases (such as MegaTALs), and CRISPR/Cas9.

SUMMARY

The present disclosure provides several methods for applying CRISPR/Cas9 in primary cells in which an mRNA is used to express Cas9, and simultaneously, mRNA is used to transiently express two adenoviral proteins, E4ORF6 and an H373A or H354 mutant version of E1B55K. The wild type E4ORF6 and E1B55K proteins relieve post-entry defects for expression from AAV vectors; however, if the wild type E1B55K or E4ORF6 proteins are used, they disable an important protein complex involved in DNA repair (known as the MRN complex), which leads to cell cycle arrest and high toxicity due to lack of repair of DNA breaks. Instead of using the wild type proteins mutants of E1B55K, which do not disable the MRN complex are utilized. Co-expression of Cas9 with E4ORF6/E1B55K mutants results in sufficient relief of the post-entry restriction on AAV expression while maintaining intact DNA repair. This allows for a substantial improvement in Cas9-mediated gene editing efficiency with minimal toxicity when an AAV vector is used to express the guide RNA's necessary for Cas9 targeting.

Some alternatives of the system provided herein, comprise endonucleases so as to provide additional tools useful in gene disruption. Several alternatives, for example, relate to systems utilizing CRISPR/Cas9 systems and methods for enhancing the efficiency of inactivation of a target gene concurrently with endonucleases. More alternatives relate to the inactivation of a target gene for therapeutic, agricultural and/or other commercially useful purposes utilizing one or more of the systems described herein. Still more alternatives relate to the production of autologous and/or non-autologous primary cells having an inactivated target gene and the use of these cells for therapeutic and/or other commercial applications.

In some alternatives, a system for editing at least one target gene in a cell is provided, the system comprising a first nucleic acid sequence encoding a CRISPR guide RNA, wherein the CRISPR guide RNA is complimentary to at least one target gene in a cell and, wherein said first nucleic acid sequence is present in a vector; a second nucleic acid sequence encoding a Cas9 protein, a derivative or fragment thereof; a third nucleic acid sequence encoding a first adenoviral protein; and a fourth nucleic acid sequence encoding a second adenoviral protein. In some alternatives of the system, the cell is a eukaryotic cell. In some alternatives of the system, the cell is a mammalian cell. In some alternatives of the system, the cell is a human cell. In some alternatives of the system, the cell is a primary cell. In some alternatives of the system, the cell is not a transformed cell. In some alternatives of the system, the cell is a primary lymphocyte, a CD34+ stem cell, a hepatocyte, a cardiomyocyte, a neuron, a glial cell, a muscle cell or an intestinal cell.

In some alternatives of the system, the vector is a viral vector. In some alternatives of the system, the viral vector is an Adeno-associated virus (AAV) vector. In some alternatives of the system, the second nucleic acid encoding the Cas9 protein, a derivative or fragment thereof is an mRNA. In some alternatives of the system, the second nucleic acid sequence encoding the Cas9 protein is codon optimized for expression in a eukaryotic cell, such as a human cell. In some alternatives of the system, the Cas9 protein, a derivative or fragment thereof is from *S. pyogenes*. In some alternatives of the system, the third nucleic acid encoding the first adenoviral protein is an mRNA. In some alternatives of the system, the mRNA is codon optimized for expression in a eukaryotic cell, such as a human cell. In some alternatives of the system, the first adenoviral protein is E4ORF6. In some alternatives of the system, the fourth nucleic acid encoding the second adenoviral protein is an mRNA. In some alternatives of the system, the fourth nucleic acid encoding the second adenoviral protein is codon optimized for expression in a eukaryotic cell, such as a human cell. In some alternatives of the system, the second adenoviral protein is an E1B55K mutant. In some alternatives of the system, the first, second, third and fourth nucleic acid sequences are joined to regulatory elements that are operable in a eukaryotic cell, such as a human cell. In some alternatives of the system, the first nucleic acid sequence encoding the CRISPR guide RNA is operably linked to a regulatory element. In some alternatives of the system, the nucleic acid sequence encoding the CRISPR guide RNA is operably linked to a promoter, for example, a U6 promoter. In some alternatives of the system, the first nucleic acid sequence encoding the CRISPR guide RNA is constitutively expressed.

In some alternatives, a method of editing at least one target gene in a cell is provided, the method comprising introducing into a cell a first vector that comprises a first nucleic acid sequence encoding a CRISPR guide RNA, wherein the CRISPR guide RNA is complimentary to at least one target gene in said cell; introducing into said cell a second nucleic acid sequence encoding a Cas9 protein, a derivative or fragment thereof; introducing into said cell a third nucleic acid sequence encoding a first adenoviral protein; and introducing into said cell a fourth nucleic acid sequence encoding a second adenoviral protein. In some alternatives of the method, the cell is a eukaroytic cell. In some alternatives of the method, the cell is a mammalian cell. In some alternatives of the method, the cell is a human cell. In some alternatives of the method, the cell is a primary cell. In some alternatives of the method, the cell is not a transformed cell. In some alternatives of the method, the cell is a primary lymphocyte, a CD34+ stem cell, a hepatocyte, a cardiomyocyte, a neuron, a glial cell, a muscle cell or an intestinal cell.

In some alternatives of the method, the first vector comprising the first nucleic acid sequence encoding the CRISPR guide RNA is a viral vector. In some alternatives of the method, the viral vector is an Adeno-associated virus (AAV) vector. In some alternatives of the method, the second, third and fourth nucleic acid sequences are mRNA. In some alternatives of the method, the mRNAs are codon optimized for expression in a eukaryotic cell, such as a human. In some alternatives of the method, the Cas9 protein, a derivative or fragment thereof is from *S. pyogenes*. In some alternatives of the method, the first adenoviral protein is E4ORF6. In some alternatives of the method, the second adenoviral protein is a E1B55K mutant. In some alternatives of the method, the CRISPR guide RNA is complimentary to a target gene of interest. In some alternatives of the method, the CRISPR guide RNA is complimentary to a target gene of interest. In some alternatives of the method, the first, second, third and fourth nucleic acid sequences are transiently introduced into the cell. In some alternatives of the method, the first, second, third and fourth nucleic acid sequences are not permanently introduced into the cell. In some alternatives of the method, the introducing of the first, second, third and fourth nucleic acid sequences into the cell does not transform the cell. In some alternatives of the method, the target gene is a selected or identified gene of interest. In some alternatives of the method and/or the system, the second, third, or fourth nucleic acid sequence is provided on a vector. In some alternatives, a method of editing at least one target gene in a cell is practiced by introducing into a cell any of the alternatives of the system described herein.

In some alternatives, a method of treating, ameliorating, or inhibiting a disease and/or a condition in a subject is practiced by providing to a subject having a disease and/or a condition any of the alternatives of the system described herein.

BRIEF DESCRIPTION OF THE DRAWINGS

FIG. 10A-FIG. 10C show data related the effect of using E1B55K mutants (E4ORF6/E1B55K) enhance targeted CRISPR knock-in.

FIG. 16A shows alternatives of polynucleotide sequences of guide RNAs guide1 (SEQ ID NO: 15), guide2 (SEQ ID NO: 16), guide3 (SEQ ID NO: 17), and guide4 (SEQ ID NO: 5) used for generating TCR knockout using the CRISPR/Cas9 system.

FIG. 17 shows the protein sequence of an alternative of a wild type adenoviral protein E1B55K (SEQ ID NO: 1).

FIG. 18 shows the protein sequence of an alternative of a mutant adenoviral protein E1B55K with an H373A polymorphism (SEQ ID NO: 2). The mutation is shown in bold and underlined.

FIG. 19 shows the protein sequence of an alternative of a wild type adenoviral protein E4ORF6 (SEQ ID NO: 3).

FIG. 20 shows the protein sequence of an alternative of a mutant adenoviral protein E1B55K with an H354 (SEQ ID NO: 4). The mutation/insertion is shown in bold and underlined.

FIG. 22 shows the protein sequence of an alternative dCas9 variant of Cas9 protein of *Streptococcus pyogenes* (SEQ ID NO: 6).

FIG. 23 shows the nucleotide sequence of an alternative Cas9-SP variant from *Streptococcus pyogenes* (SEQ ID NO: 7).

FIG. 24 shows the nucleotide sequence of an alternative Cas9-SPm4 variant from *Streptococcus pyogenes* (SEQ ID NO: 8).

FIG. 25 shows the nucleotide sequence of an alternative Cas9-ST1 variant from *Streptococcus thermophilus* (SEQ ID NO: 9).

FIG. 26 shows the nucleotide sequence of an alternative Cas9-ST1m4 variant from *Streptococcus thermophilus* (SEQ ID NO: 10).

FIG. 27 shows the nucleotide sequence of an alternative Cas9-NM variant from *Neisseria meningitidis* (SEQ ID NO: 11).

FIG. 28 shows the nucleotide sequence of an alternative Cas9-NMm4 variant from *Neisseria meningitidis* (SEQ ID NO: 12).

FIG. 29 shows the nucleotide sequence of an alternative Cas9-TD variant from *Treponema denticola* (SEQ ID NO: 13).

FIG. 30 shows the nucleotide sequence of an alternative Cas9-TDm4 variant from *Treponema denticola* (SEQ ID NO: 14).

FIG. 31 shows alternatives of polynucleotide sequences of PD1 guide RNA (SEQ ID NO: 18), TIGIT guide RNA (SEQ ID NO: 19), Lag3 guide RNA (SEQ ID NO: 20) and Tim3 guide RNA (SEQ ID NO: 21).

FIG. 33 shows the nucleotide sequence of an alternative of an R240A mutant of the adenoviral protein E1B55K (SEQ ID NO: 22).

FIG. 34 shows the nucleotide sequence of an alternative of an AXA mutant of the adenoviral protein E4ORF6 (SEQ ID NO: 23).

DETAILED DESCRIPTION

Figure 1A:
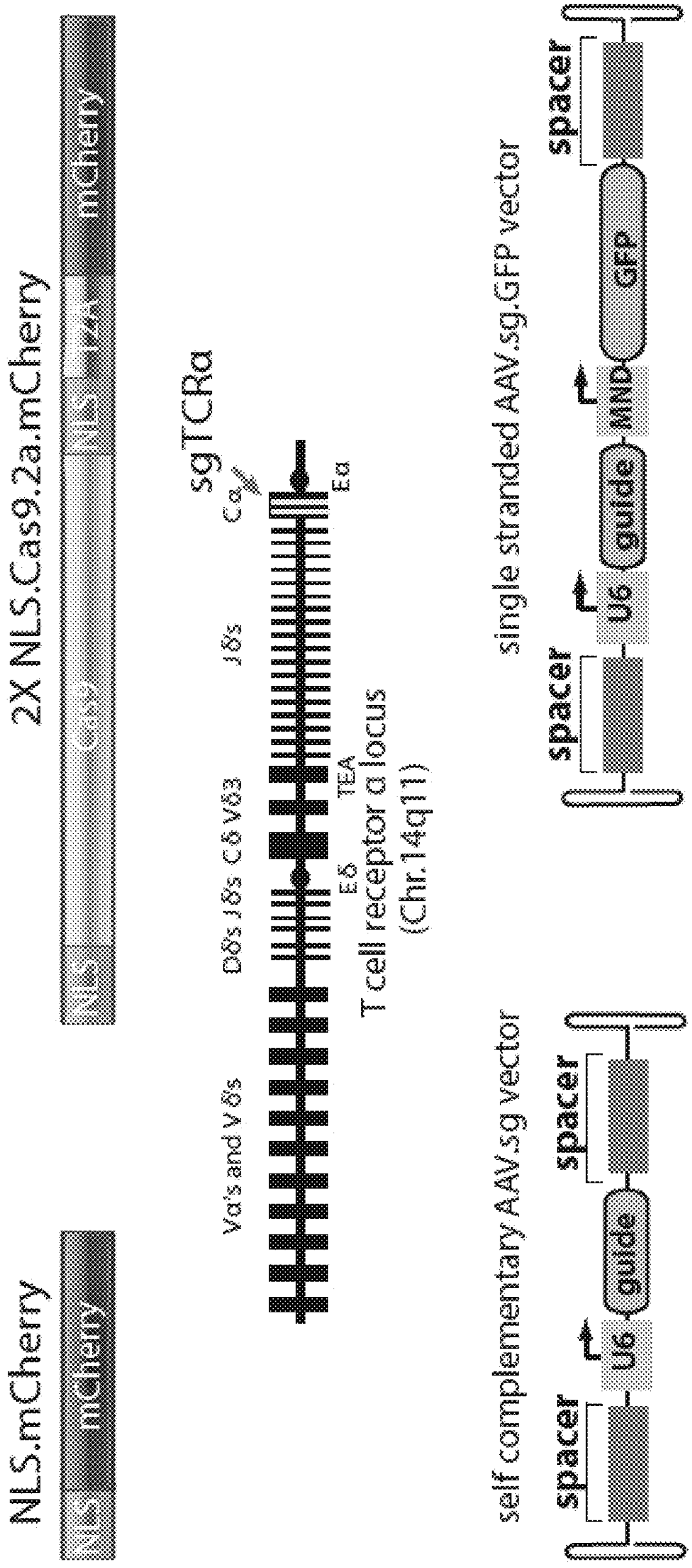
FIG. 1A shows a schematic of mRNA and AAV vector constructs used for TCR locus targeting.

In some alternatives, nuclease-based gene editing systems and methods are provided. Examples of nuclease-based approaches for gene editing include systems comprising nucleases such as, without limitations, ZFNs, TALENs, meganucleases (e.g., MegaTALs) and CRISPR/Cas9.

The gene-editing systems and methods provided herein can be applied to any nuclease-based gene editing approach comprising, without limitations, gene disruption and/or gene targeting. For example, aspects of the present disclosure are related to CRISPR/Cas9-based gene editing. In some alternatives, Cas9 nuclease-mediated enhancement of gene editing is provided.

An important aspect of applying CRISPR/Cas9 for gene editing is the need for a system to express the guide RNA's efficiently in a wide variety of cell types. An important system for expressing guide RNAs is based on the use of adeno-associated virus vectors (AAV). AAV vectors are able to transduce a wide range of primary cells.

However, in many cell types, there is a post-entry restriction on AAV vectors that renders AAV-mediated expression of transgenes, including guide RNAs, very inefficient, thus substantially compromising the utility of AAV vectors for this purpose. Therefore, an approach to substantially improve and expand the potential applications of the CRISPR/Cas9 system in primary cells is contemplated.

In some alternatives, Cas9-based approach enhances gene editing efficiency with minimal toxicity when adeno-associated virus vectors (AAV) are used to express the guide RNA's necessary for Cas9 targeting.

CRISPR/Cas9 and related programmable endonuclease systems have rapidly become significant gene editing tools of the biomedical research laboratory, with their application for gene disruption and/or gene targeting demonstrated in a variety of cultured cell and model organism systems. Although the flexibility with which the Cas9 nuclease can be re-programmed to target new sites is a major advantage for genome engineering in the research setting, several practical barriers limit the direct extension of research-based gene editing methods to editing of primary human cells for therapeutic purposes.

Examples of some of these practical barriers include limited opportunities to identify and enrich for cells that have incurred a desired editing event; the requirement for transient (e.g. a few days) nuclease delivery due to safety and immunogenicity issues associated with longer term and/or in vivo nuclease expression; and limitations in vector systems for nuclease or recombination template delivery posed by primary cells' robust capacity to detect the presence of cytosolic DNA and consequent generation of anti-viral or pro-apoptotic signals.

Driven by the practical barriers delineated herein, therapeutic gene editing strategies utilizing zinc finger nucleases (ZFNs), TAL effector nucleases (TALENs), and meganucleases, have gravitated towards delivery approaches that ensure transient nuclease expression, most notably mRNA transfection, and the use of viral vectors for recombination template delivery. For these same reasons, mRNA-based CRISPR component expression has recently been extended to human primary cells for the purpose of gene disruption through the use of electroporation to deliver Cas9 mRNA or protein in conjunction with either native or degradation-resistant guide RNAs.

While RNA or protein/RNA-based nuclease delivery are straightforward methods for disrupting individual genes, applications of CRISPR-based gene editing that involve gene targeting require efficient delivery of three components: Cas9, guide RNA, and a recombination template.

In some alternatives, an electroporation/transduction co-delivery method for CRISPR/Cas9 gene editing that utilizes mRNA electroporation-mediated expression of Cas9 in conjunction with variants of two adenoviral serotype 5 proteins, E4ORF6 and E1B55K is provided, that transiently enhance both primary cells' capacity for transduction by AAV and gene editing efficiency.

In some alternatives, using a cell culture/manufacturing protocol compatible with clinical translation, the application of this method for efficient gene disruption and homology-directed gene targeting in primary human T-cells is provided.

DEFINITIONS

In the description that follows, a number of terms are used extensively. The following definitions are provided to facilitate understanding of the present alternatives.

As used herein, "a" or "an" may mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. The basic components of CRISPR/Cas9 system comprise a target gene, a guide RNA, and a Cas9 endonuclease, derivative, or fragment thereof. An important aspect of applying CRISPR/Cas9 for gene editing is the need for a system to deliver the guide RNAs efficiently to a wide variety of cell types. This could for example involve delivery of an in vitro generated guide RNA as a nucleic acid (the guide RNA generated by in vitro transcription or chemical synthesis). In some alternatives the nucleic acid encoding the guide RNA is rendered nuclease resistant by incorporation of modified bases, such as 2'O-methyl bases. In some alternatives, the CRISPR/Cas9 system described herein, whereby the polynucleotide encoding the Cas9 nuclease or a derivative or functional fragment thereof (e.g., SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 or SEQ ID NO: 14) is provided with a poly(T) or poly(A) tail of a desired length and prepared in accordance with the teachings described herein, for example, is provided with a guide RNA that comprises one or more modified bases, such as any one or more of the modified bases described herein.

Exemplary guide RNAs useful with the alternatives described herein, which may contain one or more of the modified bases set forth herein are provided in SEQ ID NO: 5, SEQ ID NO: 15, SEQ ID NO: 16, SEQ ID NO: 17, SEQ ID NO: 18, SEQ ID NO: 19, SEQ ID NO: 20 and SEQ ID NO: 21. Furthermore, an important system for expressing guide RNAs in this context is based on the use of adeno-associated virus (AAV) vectors because AAV vectors are able to transduce a wide range of primary cells. AAV vectors do not cause infection and are not known to integrate into the genome. Therefore, the use of AAV vectors has the benefits of being both safe and efficacious.

The term "complementary to" means that the complementary sequence is homologous to all or one or more portions of a reference polynucleotide sequence. For illustration, the nucleotide sequence "CATTAG" corresponds to a reference sequence "CATTAG" and is complementary to a reference sequence "GTAATC."

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993); incorporated by reference in its entirety herein), cyclic AMP response elements (CREs), serum response elements (SREs; Treisman, Seminars in Cancer Biol. 1:47 (1990); incorporated by reference in its entirety herein), glucocorticoid response elements (GREs), and binding sites for other transcription factors, such as CRE/ATF (O'Reilly et al., J. Biol. Chem. 267:19938 (1992)), AP2 (Ye et al., J. Biol. Chem. 269:25728 (1994)), SP1, cAMP response element binding protein (CREB; Loeken, Gene Expr. 3:253 (1993)) and octamer factors (see, in general, Watson et al., eds., Molecular Biology of the Gene, 4th ed. (The Benjamin/Cummings Publishing Company, Inc. 1987), and Lemaigre and Rousseau, Biochem. J. 303:1 (1994); all references incorporated by reference in their entireties herein). As used herein, a promoter may be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives, a regulatory element can be an untranslated region. In some alternatives, an untranslated region is a 5' untranslated region. In some alternatives, an untranslated region is a 3' untranslated region. In some alternatives, either 5' or 3' untranslated region is used. In some alternatives, both 5' and 3' untranslated regions are used. One skilled in the art will understand the meaning of an untranslated region as used in the alternatives here.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. In some alternatives, a system for editing at least one target gene in a cell is provided, wherein the system comprises a first nucleic acid sequence encoding a CRISPR guide RNA, wherein the CRISPR guide RNA is complimentary to at least one target gene in a cell and, wherein said first nucleic acid sequence is present in a vector; said system also comprising a second nucleic acid sequence encoding a Cas9 protein, a third nucleic acid sequence encoding a first adenoviral protein, and a fourth nucleic acid sequence encoding a second adenoviral protein. In some alternatives, the first, second, third and fourth nucleic acid sequences are joined to regulatory elements that are operable in a eukaryotic cell, such as a human cell.

A "polypeptide" is a polymer of amino acid residues joined by peptide bonds, whether produced naturally or synthetically. Polypeptides of less than about 10 amino acid residues are commonly referred to as "peptides." A polypeptide can be considered as a protein.

A "protein" is a macromolecule comprising one or more polypeptide chains. A protein may also comprise non-peptide components, such as carbohydrate groups. Carbohydrates and other non-peptide substituents may be added to a protein by the cell in which the protein is produced, and will vary with the type of cell. Proteins are defined herein in terms of their amino acid backbone structures; substituents such as carbohydrate groups are generally not specified, but may be present nonetheless. In some embodiments, a system for editing at least one target gene in a cell is provided, wherein the method comprises a first nucleic acid sequence encoding a CRISPR guide RNA, wherein the CRISPR guide RNA is complimentary to at least one target gene in a cell and, wherein said first nucleic acid sequence is present in a vector; said system also comprising a second nucleic acid sequence encoding a Cas9 protein, a third nucleic acid sequence encoding a first adenoviral protein and a fourth nucleic acid sequence encoding a second adenoviral protein.

As used herein, "transient transfection" refers to the introduction of exogenous nucleic acid(s) into a host cell by a method that does not generally result in the integration of the exogenous nucleic into the genome of the transiently transfected host cell. In some alternatives, the nucleic acid is RNA. In some alternatives, the nucleic acid is DNA. In some alternatives, when the nucleic acid is RNA, the nucleic acid does not generally integrate in the genome of the transiently transfected cell. In some alternatives, when the nucleic acid is DNA, the nucleic acid can integrate in the genome of the transiently transfected cell.

By the term "host cell" is meant a cell that is introduced with Cas9-mRNA/AAV-guide RNA according to the present alternatives, as well as, cells that are provided with the systems herein. Host cells can be prokaryotic cells or eukaryotic cells. Examples of prokaryotic host cells include, but are not limited to *E. coli*, nitrogen fixing bacteria, *Staphylococcus aureus, Staphylococcus albus, Lactobacillus acidophilus, Bacillus anthracis, Bacillus subtilis, Bacillus thuringiensis, Clostridium tetani, Clostridium botulinum, Streptococcus mutans, Streptococcus pneumoniae*, mycoplasmas, and cyanobacteria. Examples of eukaryotic host cells include, but are not limited to, protozoa, fungi, algae, plant, insect, amphibian, avian and mammalian cells. In some alternatives, a system for editing at least one target gene in a cell is provided, wherein the cell is a eukaryotic cell. In some alternatives, the cell is a mammalian cell. In some alternatives, the cell is a human cell. In some alternatives, the cell is a primary cell. In some alternatives, the cell is not a transformed cell. In some alternatives, the cell is a primary lymphocyte. In some alternatives, the cell is a primary lymphocyte, a CD34+ stem cell, a hepatocyte, a cardiomyocyte, a neuron, a glial cell, a muscle cell or an intestinal cell.

The term "gene expression" refers to the biosynthesis of a gene product. For example, in the case of a structural gene, gene expression involves transcription of the structural gene into mRNA and the translation of mRNA into one or more polypeptides.

The term "endonuclease" refers to enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases. In some alternatives of the system, the system can further provide nucleic acids that encode an endonuclease, such as Cas9, TALEN, or MegaTAL, or a fusion protein comprising a domain of an endonuclease, for example, Cas9, TALEN, or MegaTAL, or one or more portion thereof. These examples are not meant to be limiting and other endonucleases and alternatives of the system and methods comprising other endonucleases and variants and modifications of these exemplary alternatives are possible without undue experimentation. All such variations and modifications are within the scope of the current teachings.

The term "TAL Effector Nuclease" (TALEN) refers to a nuclease comprising a TAL-effector domain fused to a nuclease domain. TAL-effector DNA binding domains, isolated from the plant pathogen *Xanthomonas* have been described (see Boch et al., (2009) Science 29 Oct. 2009 (10.1126/science.117881) and Moscou and Bogdanove, (2009) Science 29 Oct. 2009 (10.1126/science. 1178817); both references incorporated by reference in their entireties herein). These DNA binding domains may be engineered to bind to a desired target and fused to a nuclease domain, such as the Fok1 nuclease domain, to derive a TAL effector domain-nuclease fusion protein. The methods and systems described herein may be applied to cleavage sites generated by TAL effector nucleases. In some alternatives of the systems provided herein, the systems can further comprise a TALEN nuclease or a vector or nucleic acid encoding a TALEN nuclease. In some alternatives of the methods provided herein, the method can further comprise providing a nuclease, such as a TALEN nuclease.

MegaTALs are derived from the combination of two distinct classes of DNA targeting enzymes. Meganucleases (also referred to as homing endonucleases) are single peptide chains that have the advantage of both DNA recognition and nuclease functions in the same domain. In some alternatives of the systems provided herein, the systems can further comprise a MegaTAL nuclease or a vector or nucleic acid encoding a MegaTAL nuclease. In some alternatives of the methods provided herein, the methods can further comprise providing MegaTAL nuclease or a vector or nucleic acid encoding a MegaTAL nuclease.

Cas9 (CRISPR associated protein 9) is an RNA-guided DNA endonuclease enzyme associated with the CRISPR (Clustered Regularly Interspersed Palindromic Repeats) adaptive immunity system in *Streptococcus pyogenes*, among other bacteria. *S. pyogenes* utilizes Cas9 to memorize and later interrogate and cleave foreign DNA, such as invading bacteriophage DNA or plasmid DNA. Cas9 performs this interrogation by unwinding foreign DNA and checking for if it is complementary to the 20 base pair spacer region of the guide RNA. If the DNA substrate is complementary to the guide RNA, Cas9 cleaves the invading DNA.

CRISPRs (clustered regularly interspaced short palindromic repeats) are segments of prokaryotic DNA containing short repetitions of base sequences. Each repetition is followed by short segments of "spacer DNA" from previous exposures to a bacterial virus or plasmid. CRISPR/Cas system has been used for gene editing (adding, disrupting or changing the sequence of specific genes) and gene regulation in species throughout the tree of life. By delivering the Cas9 protein, a derivative, or fragment thereof and appropriate guide RNAs into a cell, the organism's genome can be cut at any desired location. It can be possible to use CRISPR to build RNA-guided gene drives capable of altering the genomes of entire populations. In some alternatives, a system for editing at least one target gene in a cell is provided, wherein the method comprises a first nucleic acid sequence encoding a CRISPR guide RNA, wherein the CRISPR guide RNA is complimentary to at least one target gene in a cell and, wherein said first nucleic acid sequence is present in a vector, a second nucleic acid sequence encoding a Cas9 protein, a derivative, or fragment thereof, a third nucleic acid sequence encoding a first adenoviral protein and a fourth nucleic acid sequence encoding a second adenoviral protein. Exemplary guide RNAs useful with the alternatives described herein, which may contain one or more modified bases, are provided in SEQ ID NO: 5, SEQ ID NO: 15, SEQ ID NO: 16, SEQ ID NO: 17, SEQ ID NO: 18, SEQ ID NO: 19, SEQ ID NO: 20 and/or SEQ ID NO: 21.

In some alternatives, the use of chemically modified guide RNAs is contemplated. Chemically-modified guide RNAs have been used in CRISPR-Cas genome editing in human primary cells (Hendel, A. et al., Nat Biotechnol. 2015 September; 33(9):985-9), expressly incorporated by reference. Chemical modifications of guide RNAs can include modifications that confer nuclease resistance. Nucleases can be endonucleases, or exonucleases, or both. Some chemical modification, without limitations, include 2'-fluoro, 2'O-methyl, phosphorothioate dithiol 3'-3' end linkage, 2-amino-dA, 5-mehtyl-dC, C-5 propynyl-C, C-5 propynyl-U, morpholino, etc. These examples are not meant to be limiting and other chemical modifications and variants and modifications of these exemplary alternatives are also contemplated.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolosis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8 (Yoon J-H, et al., Characterization of the 3' to 5' exonuclease activity found in human nucleoside diphosphate kinase 1 (NDK1) and several of its homologues. (Biochemistry 2005: 44(48):15774-15786.), WRN (Ahn, B., et al., Regulation of WRN helicase activity in human base excision repair. J. Biol. Chem. 2004, 279:53465-53474) and Three prime repair exonuclease 2 (Trex2) (Mazur, D. J., Perrino, F. W., Excision of 3' termini by the Trex1 and TREX2 3'→5' exonucleases. Characterization of the recombinant proteins. J. Biol. Chem. 2001, 276:17022-17029; both references incorporated by reference in their entireties herein). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases. In some alternatives of the systems provided herein, the systems can further comprise an exonuclease or a vector or nucleic acid encoding an exonuclease. In some alternatives, the exonuclease is Trex2. In some alternatives of the methods provided herein, the methods can further comprise providing exonuclease or a vector or nucleic acid encoding an exonuclease, such as Trex2.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"Prokaryotic" cells lack a true nuclease. Examples of prokaryotic cells are bacteria (e.g., cyanobacteria, *Lactobacillus acidophilus*, Nitrogen-Fixing Bacteria, *Helicobacter pylori, Bifidobacterium, Staphylococcus aureus, Bacillus anthrax, Clostridium tetani, Streptococcus pyogenes, Staphylococcus pneumoniae, Klebsiella pneumoniae* and *Escherichia coli*) and archaea (e.g., Crenarchaeota, Euryarchaeota, and Korarchaeota). The Cas9 protein described herein is a protein from a prokaryotic cell.

"Eukaryotic" cells include, but are not limited to, algae cells, fungal cells (such as yeast), plant cells, animal cells, mammalian cells, and human cells (e.g., T-cells).

The term "subject" as used herein includes all members of the animal kingdom including non-human primates and humans. In some alternatives, a system for editing at least one target gene in a cell is provided, wherein the method comprises a first nucleic acid sequence encoding a CRISPR guide RNA, wherein the CRISPR guide RNA is complimentary to at least one target gene in a cell and, wherein said first nucleic acid sequence is present in a vector, a second nucleic acid sequence encoding a Cas9 protein, a derivative, or fragment thereof, a third nucleic acid sequence encoding a first adenoviral protein and a fourth nucleic acid sequence encoding a second adenoviral protein. In some alternatives, the cell that comprises an edited gene is delivered to a subject in need.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low. In some alternatives of the systems provided herein, the systems can further comprise a meganuclease or a vector or nucleic acid encoding a meganuclease. In some alternatives of the methods provided herein, the methods can further comprise providing a meganuclease or a vector or nucleic acid encoding a meganuclease.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease. In some alternatives of the systems provided herein, the systems can further comprise an engineered meganuclease or a vector or nucleic acid encoding an engineered meganuclease.

Targeted DNA double-strand breaks introduced by rare-cleaving endonucleases can be harnessed for gene disruption applications in diverse cell types by engaging non-homologous end joining DNA repair pathways. However, endonucleases create chemically clean breaks that are often subject to precise repair, limiting the efficiency of targeted gene disruption. Several alternatives described herein relate to a method of improving the rate of targeted gene disruptions caused by imprecise repair of endonuclease-induced site-specific DNA double-strand breaks. In some alternatives, systems can further comprise site specific endonucleases that are coupled with end-processing enzymes to enhance the rate of targeted gene disruption. Coupling may be, for example, physical, spatial, and/or temporal.

Not to be bound by any particular theory, the resolution of a double-strand DNA breaks by "error-prone" non-homologous end-joining (NHEJ) can be harnessed to create targeted disruptions and genetic knockouts, as the NHEJ process can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, and ligates ends back together with minimal processing. As the DNA breaks created by designer endonuclease platforms (zinc-finger nucleases (ZFNs), TAL effector nucleases (TALENs), and homing endonucleases (HEs)) all leave chemically clean, compatible overhang breaks that do not require processing prior to ligation, they are excellent substrates for precise repair by the cNHEJ pathway. In the absence or failure of the classical NHEJ pathway to resolve a break, alternative NHEJ pathways (altNHEJ) can substitute: however, these pathways are considerably more mutagenic.

Not to be bound by any particular theory, modification of DNA double-strand breaks by end-processing enzymes may bias repair towards an altNHEJ pathway. Further, different subsets of end-processing enzymes may enhance disruption by different mechanisms. For example, Trex2, an exonuclease that specifically hydrolyzes the phosphodiester bonds which are exposed at 3' overhangs, biases repair at break sites toward mutagenic deletion. By contrast, terminal deoxynucleotidyl transferase (TdT), a non-templative polymerase, is expected to bias repair at break sites toward mutagenic insertions by promoting the addition of nucleotide bases to alter DNA ends prior to ligation. Accordingly, one of skill in the art can use end-processing enzymes with different activities to provide for a desired engineering outcome with any of the systems or methods provided herein. Further one of skill in the art may use the synergy between different end-processing enzymes so as to achieve maximal or unique types of effects.

Several alternatives described herein couple DNA breaks created by endonucleases with end-processing enzymes, which can improve the rates of targeted disruption in a variety of cell types and species, without associated toxicity to the host. This is an important advance at least because: 1) Double-strand breaks (DSBs) trigger cell cycle checkpoints to arrest division until the break has been resolved; in the case of a "persistent break" (a repetitive cycle of cleaving and precise repair), cells may arrest indefinitely, leading to apoptosis. 2) Engineering applications often utilize transient delivery of an endonuclease, providing only a short window in which enzyme concentration is sufficient to achieve breaks. 3) Persistent breaks can be a source of translocations. Coupling endonucleases to end-processing enzymes prevents the establishment of a persistent break and reduces the incidence of gross chromosomal rearrangements, thereby improving the safety of endonuclease-induced targeted disruption. 4) Multiple changes in a single round of mutagenesis can be achieved, for use for example, in multi-allelic knockouts and multiplexing, as data described herein provides evidence that coupling endonucleases to end-processing enzymes improves the mutagenic rate of two given endonucleases 5-fold at their respective targets, a 25-fold improvement can be realized in disrupting both targets simultaneously.

The system can further comprise endonucleases, end-processing enzymes, and/or fusion proteins having endonuclease and end-processing activity, for delivery to host cells. In some alternative of the system described herein, the system can further comprise a protein such as one or more polypeptides having endonuclease and/or end-processing activity may be provided directly to cells. In some alternatives, expression of endonucleases, end-processing enzymes and/or fusion proteins having endonuclease and end-processing activity in a host cell can result from delivery of one or more polynucleotides encoding one or more endonucleases, end-processing enzymes, and/or fusion proteins having endonuclease and end-processing activity to the host cell. In some alternatives, one or more polynucleotides is a DNA expression vector. In some alternatives, one or more polynucleotides is an RNA expression vector. In some alternatives, trans-splicing, polypeptide cleavage and/or polypeptide ligation can be involved in expression of one or more proteins in a cell.

The systems and methods described herein are useful for generating targeted disruptions of the coding sequences of genes and in some alternatives, creating gene knockouts. Targeted cleavage by the compositions and methods described herein can also be used to alter non-coding sequences (e.g., regulatory sequences such as promoters, enhancers, initiators, terminators, splice sites) to alter the levels of expression of a gene product. Such methods can be used, for example, for biological research, for biotechnology applications such as crop modification, for therapeutic purposes, functional genomics, and/or target validation studies.

Some alternatives of the system are coupled to the activity of one or more site-specific endonucleases with one or more end-processing enzymes. In some alternatives, the endonucleases and end-processing enzymes are provided as separate proteins with the system. In some alternatives, the endonucleases and end-processing enzymes are co-expressed in a cell. If expression of the separate endonucleases and end-processing enzymes is by polynucleotide delivery, each of the endonucleases and end-processing enzymes can be encoded by separate polynucleotides, or by a single polynucleotide. In some alternatives, the endonucleases and end-processing enzymes are encoded by a single polynucleotide and expressed by a single promoter. In some alternatives, an endonuclease and end-processing enzymes are linked by a T2A sequence, which allows for two separate proteins to be produced from a single translation. In some alternatives, a different linker sequence can be used. In other alternatives a single polynucleotide encodes the endonucleases and end-processing enzymes separated by an Internal Ribosome Entry Sequence (IRES).

Several alternatives of the system comprises coupling the system with endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII with one or more DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some alternatives, the homing endonucleases and DNA end-processing enzymes are provided as a fusion protein. In some alternatives, the endonucleases and DNA end-processing enzymes are provided as separate proteins. In some alternatives, the endonucleases and DNA end-processing enzymes are co-expressed in a host cell.

Several alternatives relate to coupling the system described herein, with DNA end-processing enzymes selected from the group consisting of: Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some alternatives of the system, the end-processing enzymes are provided as separate proteins. In some alternatives of the system, the end-processing enzymes are co-expressed in a host cell.

In several alternatives, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Artemis, Trex1, Flap endonuclease, terminal deoxynucleotide transferase, Trex2, Vaccinia DNA polymerase, Mre11, exonuclease I, exonuclease III, NDK1, NDK5, NDK7, NDK8, and WRN. In some alternatives, the homing endonucleases and DNA end-processing enzymes are provided as a fusion protein. In some alternatives, the endonucleases and DNA end-processing enzymes are provided as separate proteins. In some alternatives, the endonucleases and DNA end-processing enzymes are co-expressed in a host cell.

Several alternatives of the system further comprise a heterologous fusion protein, which comprises an endonuclease domain and an end-processing domain or one or more portions thereof. Several alternatives relate to a heterologous fusion construct, which encodes a fusion protein having endonuclease and end-processing activity. The present alternatives also relate to systems and methods that further comprise the heterologous fusion construct, as well as, methods for producing a fusion protein having endonuclease and end-processing activity and compositions thereof. In one alternative, the endonuclease domain is coupled to the end-processing domain by recombinant means (e.g., the fusion protein is generated by translation of a nucleic acid in which a polynucleotide encoding all or one or more portions of a endonuclease is joined in-frame with a polynucleotide encoding all or one or more portions of an end-processing enzyme). In other alternatives, the endonuclease domain and end-processing domain of a fusion protein are linked chemically. This chemical linkage can be carried out, for example, by using bifunctional linker molecules, such as, BS3 (Bis [sulfosuccinimidyl] suberate).

Some alternatives of the system further comprise a protein comprising an endonuclease domain and exonuclease domain in which it is provided as a protein or a vector or nucleic acid encoding the protein comprising an endonuclease domain and exonuclease domain as a fusion protein. In some alternatives, the fusion protein comprises at least a fragment or variant of a homing endonuclease and at least a fragment or variant of an exonuclease, for example a 3' exonuclease, which are associated with one another by genetic or chemical conjugation to one another. In several alternatives, the 3' exonuclease is a Trex2 monomer, dimer, or a variant thereof. In other alternatives, the fusion protein comprises at least a fragment or variant of a zinc finger endonuclease and at least a fragment or variant of a 5' exonuclease, which are associated with one another, by genetic fusion or chemical conjugation to one another. The endonuclease and exonuclease, once part of the fusion protein, may be referred to as a “portion”, “region,” “domain” or “moiety” of the endo/exonuclease fusion protein. In some alternatives, the exonuclease domain comprises Trex or one or more portions thereof.

An endonuclease/end-processing enzyme fusion protein may optionally include a linker peptide between the endonuclease and end-processing enzyme domains to provide greater physical separation between the moieties and thus maximize the accessibility of the endonuclease portion, for instance, for binding to its target sequence. The linker peptide may consist of amino acids selected to make it more flexible or more rigid depending on the relevant function. The linker sequence can be cleavable by a protease or cleavable chemically to yield separate endonuclease and end-processing enzyme moieties. Examples of enzymatic cleavage sites in the linker include sites for cleavage by a proteolytic enzyme, such as enterokinase, Factor Xa, trypsin, collagenase, and thrombin. In some alternatives, the protease is one, which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the endonuclease moiety with respect to the end-processing enzyme moiety so that the endonuclease domain can recognize and cleave its target sequence and the end-processing domain can modify the DNA ends exposed at the cleavage site. The linker may also be a simple amino acid sequence of a sufficient length to prevent any steric hindrance between the endonuclease domain and the end-processing domain. In addition, the linker sequence may provide for post-translational modification including, but not limited to, e.g., phosphorylation sites, biotinylation sites, sulfation sites, γ-carboxylation sites, and the like. In some alternatives, the system can further comprise a fusion with an endonuclease/end-processing protein.

In some alternatives, the linker sequence comprises from 4 to 30 amino acids, more preferably from 8 to 22 amino acids. That is, the linker sequence can be any number of amino acids from 4 to 30, such as at least or equal to 4, 5, 6, 7, 8, 9, 10, 11, 12, 13, 14, 15, 16, 17, 18, 19, 20, 21, 22, 23, 24, 25, 26, 27, 28, 29, or 30 amino acids or a length that is within a range defined by any two of the aforementioned lengths. In some alternatives, the linker sequence is flexible so as not hold the biologically active peptide in a single undesired conformation. The linker may be predominantly comprised of amino acids with small side chains, such as glycine, alanine, and serine, so as to provide for flexibility. In some alternatives about 80 or 90 percent or greater of the linker sequence comprises glycine, alanine, or serine residues, particularly glycine and serine residues. In several alternatives, a G4S linker peptide separates the end-processing and endonuclease domains of the fusion protein. In other alternatives, a T2A linker sequence allows for two separate proteins to be produced from a single translation. Suitable linker sequences can be readily identified empirically. Additionally, suitable size and sequences of linker sequences also can be determined by conventional computer modeling techniques.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are well known in the art.

A variety of DNA molecules encoding the endonucleases described herein, end-processing enzymes and fusion proteins may be constructed for providing the selected proteins or peptides to a cell. The DNA molecules encoding the endonucleases, end-processing enzyme, and fusion proteins may be modified to contain different codons to optimize expression in a selected host cell, as is known in the art.

A variety of RNA molecules encoding the endonucleases described herein, end-processing enzymes and fusion proteins may be constructed for providing the selected proteins or peptides to a cell. The RNA molecules encoding the endonucleases, end-processing enzyme, and fusion proteins may be modified to contain different codons to optimize expression in a selected host cell, as is known in the art. In some alternatives, the RNA can comprise a poly(A) tail of 50, 100, 150, 200, 250, 300, 350, 400, 450, 500 covalently linked adenosine residues, or an amount of residues within a range defined by any two of the aforementioned values.

Several alternatives of the system further comprise a vector or nucleic acid for the simultaneous expression of a site-specific endonuclease and an end-processing enzyme to improve the efficiency of targeted gene disruption by up to ~70 fold, essentially fixing a mutagenic outcome in 100% of a population of cells containing the target site in less than 72 hours.

In some alternatives of the system, an additional vector or nucleic acid is provided for effective amounts of endonucleases and end-processing enzymes or an effective amount of a fusion protein for delivery to a cell either directly by contacting the cell will the protein(s) or by transient expression from an expression construct. In such alternatives of the system, in which the system is delivered to a cell, cell division reduces the concentration of the nucleases to sub-active levels within a few cell divisions.

Several alternatives of the systems and methods provided herein, further provide a fusion protein for conferring site specificity on a DNA end-processing enzyme by physically tethering an end-processing enzyme domain to a site specific DNA binding domain. In some alternatives, the end-processing enzyme domain is tethered to a DNA binding domain through a linker peptide. The composition and structure of the linker peptide is not especially limited and in some alternatives the linker may be chemically or enzymatically cleavable. The linker peptide may be flexible or rigid and may comprise from about 4 to 30 amino acids. In other alternatives, the end-processing enzyme domain is chemically fused to a DNA binding domain. Not wishing to be bound by a particular theory, imparting site specificity to an end-processing enzyme through tethering the end-processing enzyme to a site specific DNA binding domain decreases toxicity associated with indiscriminate end-processing activity, such as exonuclease activity, and reduces the effective amount of end-processing enzyme required for efficient modification of the exposed double stranded DNA break caused by endonuclease activity compared to untethered end-processing enzyme. In some alternatives, the end-processing enzyme is tethered to a homing endonuclease. In other alternatives, the end-processing enzyme is tethered to zinc finger endonuclease. In some alternatives, an end-processing enzyme domain is tethered to a zinc finger DNA binding domain which binds to a DNA sequence adjacent to the cleavage site of a homing endonuclease or zinc finger endonuclease.

Several alternatives of the system and methods relate to coupling the activity of the CRISPR/Cas9 system with one or more site-specific endonucleases with Trex2, in order to promote gene knockout efficiently when coupled with the systems provided herein. Trex2 may be provided as a monomer or dimer. The Trex2 enzyme specifically hydrolyzes the phosphodiester bonds, which are exposed at 3' overhangs. While homing endonucleases can generate 3' overhangs, which are susceptible to Trex2 exonuclease activity, the zinc finger nucleases, which utilize the Fok1 cleavage domain, generate double strand DNA breaks with 5' overhangs. The homing endonucleases and zinc finger nucleases generate mutations at their cleavage sites at a baseline rate. Co-expression of Trex2 with homing endonucleases increased the mutation rate ~70 fold. Co-expression of Trex2 with zinc finger endonucleases was also observed to effect on the rate of mutation. Some alternatives of the methods relate to providing the system described herein, with co-expression of a exonuclease, Trex2.

As used herein, an Ad5 adenoviral protein, and Ad5 viral protein or an Ad5 protein refers to a protein that is encoded by adenovirus serotype 5. Non-limiting examples include E4ORF6 and E1B55K. The protein sequence of an alternative of the wild type E1B55K protein is shown in FIG. 17 (SEQ ID NO: 1). The protein sequence of an alternative of the wild type E4ORF6 protein is shown in FIG. 19 (SEQ ID NO: 3). In some alternatives, a mutant form of an Ad5 protein is used. Non-limiting examples include the H373A mutant of E1B55K and the H354 mutant of E1B55K. In some alternatives, Ad5 refers to a combination of two or more Ad5 viral proteins. In some alternatives, Ad5 refers to a combination two or more wild type Ad5 viral proteins. In some alternatives, Ad5 refers to a combination two or more Ad5 viral proteins at least one of which is a wild type form. In some alternatives, Ad5 refers to a combination two or more Ad5 viral proteins at least one of which is a mutant form. In some alternatives, $Ad5^{wt}$ refers to one or more wild type Ad5 viral proteins. In some alternatives, $Ad5^{MRN-}$ refers to one or more mutant Ad5 viral proteins that do not disable the MRN complex. In some alternatives, at least one Ad5 viral protein is used in combination with or not in combination with a nuclease. In some alternatives, the nuclease is an endonuclease. In some alternatives, the endonuclease is Cas9, a derivative, or fragment thereof. In some alternatives, the nuclease is an exonuclease. In some alternatives, the exonuclease is Trex2. In some alternatives, at least one Ad5 viral protein is used in combination with more than one a nuclease. In some alternatives, at least one Ad5 viral protein is used in combination with Cas9, a derivative, or fragment thereof and Trex2.

Expression Vectors

Expression constructs can be readily designed using methods known in the art. Examples of nucleic acid expression vectors include, but are not limited to: recombinant viruses, lentiviruses, adenoviruses, plasmids, bacterial artificial chromosomes, yeast artificial chromosomes, human artificial chromosomes, minicircle DNA, episomes, cDNA, RNA, and PCR products. In some alternatives, nucleic acid expression vectors encode a single peptide (e.g., an endonuclease, an end-processing enzyme, or a fusion protein having endonuclease and end-processing activity). In some alternatives, nucleic acid expression vectors encode one or more endonucleases and one or more end-processing enzymes in a single, polycistronic expression cassette. In some alternatives of the system, one or more endonucleases and one or more end-processing enzymes are provided, wherein they are linked to each other by a 2A peptide sequence or an "autocleavage" or self-cleavage sequence. In some alternatives, the nucleic acid expression vectors are DNA expression vectors. In some alternatives, the nucleic acid expression vectors are RNA expression vectors. In some alternatives, the expression vectors are viral vectors. In some alternatives of the systems provided herein, the viral vector is an Adeno-associated virus (AAV) vector.

In some alternatives, a nucleic acid expression vector further comprises one or more selection markers that facilitate identification or selection of host cells that have received and express the endonuclease(s), end-processing enzyme(s), and/or fusion protein(s) having endonuclease and end-processing activity along with the selection marker. Examples of selection markers include, but are not limited to, genes encoding fluorescent proteins, e.g., EGFP, DS-Red, YFP, and CFP; genes encoding proteins conferring resistance to a selection agent, e.g., PuroR gene, ZeoR gene, HygroR gene, neoR gene, and the blasticidin resistance gene. In some cases, the selection marker comprises a fluorescent reporter and a selection marker.

In some alternatives, a DNA expression vector comprises a promoter capable of driving expression of one or more endonuclease(s), end-processing enzyme(s), and/or fusion protein(s) having endonuclease and end-processing activity. Examples of promoters include, but are not limited to, retroviral LTR elements; constitutive promoters such as CMV, HSV1-TK, SV40, EF-1α, β-actin; inducible promoters, such as those containing Tet-operator elements; and tissue specific promoters. Suitable bacterial and eukaryotic promoters are well known in the art and described, e.g., in Sambrook et al., Molecular Cloning, A Laboratory Manual (2nd ed. 2001); Kriegler, Gene Transfer and Expression: A Laboratory Manual (1990); and Current Protocols in Molecular Biology (2010), the references are incorporated by reference in their entireties herein. Non-limiting examples of plant promoters include promoter sequences derived from *A. thaliana* ubiquitin-3 (ubi-3).

In some alternatives, a nucleic acid encoding one or more endonucleases, end-processing enzymes, and/or fusion proteins having endonuclease and end-processing activity or exonuclease activity are cloned into a vector for transformation into eukaryotic cells along with the vectors and nucleic acid of the systems provided herein. In some alternatives, nucleic acids encoding different endonucleases and end-processing enzymes are cloned into the same vector. In such cases, the nucleic acids encoding different endonucleases and end-processing enzymes may optionally be separated by T2A, self-cleavage sequences, protease cleavage sites, or IRES sequences. Vectors can be prokaryotic vectors, e.g., plasmids, or shuttle vectors, insect vectors, or eukaryotic vectors, including plant vectors described herein. Expression of the nucleases and fusion proteins may be under the control of a constitutive promoter or an inducible promoter. In some alternatives, the vector comprises a nucleic acid sequence that encodes Cas9, a derivative, or fragment thereof. In some alternatives, the vector comprises a nucleic acid sequence that encodes Trex. In some alternatives, the genes and/or nucleic acids in the vector are codon optimized for expression in a mammalian cell, such as a human cell. In some alternatives, the vector is an mRNA. In some alternatives, the vector is an mRNA encoding a Cas9 protein, a derivative, or fragment thereof. In some alternatives, the nucleic acid encoding Cas9 protein, a derivative, or fragment thereof is codon optimized for expression in a eukaryotic cell, such as a human cell. In some alternatives, the Cas9 protein, a derivative, or fragment thereof is from *S. pyogenes* or is a consensus sequence made from other Cas9 proteins from other organisms.

Introduction of polypeptides having endonuclease and/or end-processing activity and/or polynucleotides encoding polypeptides having endonuclease and/or end-processing activity into host cells may use any suitable methods for nucleic acid or protein delivery as described herein or as would be known to one of ordinary skill in the art. The polypeptides and polynucleotides described herein can be delivered into cultured cells in vitro, as well as in situ into tissues and whole organisms. Introduction of the polypeptides and polynucleotides of the present alternatives into a host cell can be accomplished chemically, biologically, or mechanically. This may include, but is not limited to, electroporation, sonoporation, use of a gene gun, lipotransfection, calcium phosphate transfection, use of dendrimers, microinjection, polybrene, protoplast fusion, the use of viral vectors including adenoviral, AAV, and retroviral vectors, and group II ribozymes.

Immune Response against AAV Vectors

Adeno-associated viral (AAV) vectors are widely used for gene therapy-based treatment genetic diseases. However, generation of immune responses against the AAV vector can undermine the therapeutic efficacy of the vector. Similarly, generation of immune responses against the AAV vector used in CRISPR/Cas9-based (or one or more other nucleases-based) genome editing can undermine the efficacy of gene targeting.

In some alternatives, it is contemplated that the AAV vectors used for CRISPR/Cas9-based (and/or one or more other nucleases-based) genome editing will possess reduced immunogenicity. In some alternatives, it is contemplated that the AAV vectors used for CRISPR/Cas9-based (and/or one or more other nucleases-based) genome editing will possess no immunogenicity. In some alternatives, because of the reduced immunogenicity, the likelihood of development of resistance against the AAV vector will be minimal. In some alternatives, because of the lack of immunogenicity, the likelihood of development of resistance against the AAV vector will be non-existent.

Organisms

The alternatives described herein are applicable to any eukaryotic organism in which it is desired to edit a gene. Examples of eukaryotic organisms include, but are not limited to, algae, plants, animals (e.g., mammals such as mice, rats, primates, pigs, cows, sheep, rabbits, dogs, cats, or horses etc.), fish, and insects. In some alternatives, isolated cells from the organism are genetically modified as described herein. In some alternatives, the modified cells develop into reproductively mature organisms. Eukaryotic (e.g., algae, yeast, plant, fungal, piscine, avian, and mammalian cells) cells can be used. Cells from organisms containing one or more additional genetic modifications can also be used.

Examples of mammalian cells include any cell or cell line of the organism of interest, for example oocytes, somatic cells, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells and myeloma cells like SP2 or NS0. Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, muscle stem cells, skin stem cells, adipose derived stem cells, and neuronal stem cells. In some alternatives, a system for editing at least one target gene in a cell is provided, wherein the system comprises a first nucleic acid sequence encoding a CRISPR guide RNA, wherein the CRISPR guide RNA is complimentary to at least one target gene in a cell and, wherein said first nucleic acid sequence is present in a vector, wherein said system further comprises a second nucleic acid sequence encoding a Cas9 protein, a derivative, or fragment thereof, a third nucleic acid sequence encoding a first adenoviral protein and a fourth nucleic acid sequence encoding a second adenoviral protein. In some alternatives, the cell is a eukaryotic cell. In some alternatives, the cell is a mammalian cell, such as a human cell. In some alternatives, the cell is a primary cell. In some alternatives the cell is not a transformed cell. In some alternatives, the cell is a primary lymphocyte, a CD34+ stem cell, a hepatocyte, a cardiomyocyte, a neuron, a glial cell, a muscle cell or an intestinal cell.

Examples of target plants and plant cells include, but are not limited to, monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, *Avena, Brassica*, Citrus, *Citrullus, Capsicum, Cucurbita, Daucus*, Erigeron, Glycine, *Gossypium, Hordeum, Lactuca, Lolium, Lycopersicon*, Malus, *Manihot, Nicotiana*, Orychophragmus, *Oryza, Persea, Phaseolus, Pisum, Pyrus, Prunus, Raphanus, Secale, Solanum*, Sorghum, *Triticum, Vitis, Vigna*, and *Zea*. The term plant cells include isolated plant cells as well as whole plants or one or more portions of whole plants such as seeds, callus, leaves, roots, etc. The present disclosure also encompasses seeds of the plants described herein. The present disclosure further encompasses the progeny, clones, cell lines, or cells of the plants described.

Generating Homozygously Modified Organisms

Cells in which systems are provided with one or more vectors or nucleic acids encoding endonucleases for co-expression with one or more fusion proteins comprising endonuclease and end-processing activity are expressed and are assayed for site specific cleavage. Such modified cells can be identified using any suitable method known to the skilled artisan, including sequencing, PCR analysis, southern blotting, and the like. In some alternatives, an amplicon spanning the endonuclease target site is generated by PCR.

Pharmaceutical Compositions and Administration

Cells manufactured by the systems or methods provided herein can be administered directly to a patient for targeted cleavage of a DNA sequence and for therapeutic or prophylactic applications, for example, for treating, inhibiting, or ameliorating cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, or hemophilia. In some alternatives, cells are manufactured by the systems provided herein. In some alternatives, a method of editing at least one target gene in a cell is provided, wherein the method comprises introducing into a cell a first vector that comprises a first nucleic acid sequence encoding a CRISPR guide RNA, wherein the CRISPR guide RNA is complimentary to at least one target gene in said cell, introducing into said cell a second nucleic acid sequence encoding a Cas9 protein, a derivative, or fragment thereof; introducing into said cell a third nucleic acid sequence encoding a first adenoviral protein; and introducing into said cell a fourth nucleic acid sequence encoding a second adenoviral protein. In some alternatives, a cell is provided, wherein the cell is manufactured by the said methods. In some alternatives, a composition is provided, wherein the composition comprises the cell. In some alternatives, the compositions described herein, can be used in methods of treating, preventing, ameliorating, or inhibiting a disease (e.g., cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia) or ameliorating a disease condition or symptom associated with a disease, such as, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, or hemophilia. In some alternatives, the cells or compositions are administered to treat, prevent, ameliorate, or inhibit an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis or ameliorate a disease condition or symptom associated with an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and/or neurofibromatosis. In some alternatives, the cells or compositions provided herein, are administered to treat, prevent, ameliorate, or inhibit a disease caused by misregulation of genes. In some alternatives, the cells or compositions provided herein, are administered to treat, prevent, ameliorate, or inhibit a cancer, such as BCL-2, Bcl-XI, and FLIP, or ameliorate a disease condition or symptom associated with a cancer, such as BCL-2, Bcl-XI, and FLIP.

The compositions comprising the cells are administered in any suitable manner, and in some alternatives with pharmaceutically acceptable carriers. Suitable methods of administering such proteins or polynucleotides are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences).

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

In some alternatives, one or more of parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal routes of administration are contemplated. In some embodiments, the composition to be administered can be formulated for delivery via one or more of the above noted routes.

Additional Alternatives

RNA-guided endonuclease (RGEN) technology has great promise for enabling efficient editing of a target genomic locus. In some alternatives, the application of *S. pyogenes* Cas9 for gene editing in primary human cells such as primary human T-cells using mRNA-mediated delivery of a first generation spCas9 and adeno-associated virus (AAV) to drive guide RNA expression has been evaluated. In some alternatives, spCas9-mediated editing using mRNA-mediated delivery of a first generation spCas9 and adeno-associated virus (AAV) to drive guide RNA expression achieves targeted gene disruption rates at the TCRα locus of up to 30%. In some alternatives, the evaluation of the dose response of editing efficiency at different Cas9 mRNA doses and over a range of AAV MOI provided evidence that editing efficiency is limited primarily by AAV-driven guide RNA expression. In some alternatives, the evaluation of several approaches to achieve higher editing efficiencies led to the development of approaches that achieve up to 90% TCRα disruption at reduced AAV MOI in selected cell populations. In some alternatives, the results provide evidence that a Cas9-mRNA/AAV-guide approach can be applied to effectively disrupt multiple individual genes in primary human T-cells, and resulted in an innovative method through which CRISPR/Cas9 technology has enhanced efficiency.

The basic components of CRISPR/Cas9 system comprise a target gene, a protospacer adjacent motif (PAM), a guide RNA, Cas9 endonuclease. An important aspect of applying CRISPR/Cas9 for gene editing is the need for a system to deliver the guide RNAs efficiently to a wide variety of cell types. This could, for example, involve delivery of an in vitro generated guide RNA as a nucleic acid (the guide RNA generated by in vitro transcription or chemical synthesis). In some alternatives the nucleic acid could be rendered nuclease resistant by incorporation of modified bases. An important system for expressing guide RNAs is based on the use of adeno-associated virus (AAV) vectors because AAV vectors are able to transduce a wide range of primary cells. AAV vectors do not cause infection and are not known to integrate into the genome. Therefore, the use of AAV vectors has the benefits of being both safe and efficacious.

In some alternatives, an AAV vector is used to deliver one or more components of the CRISPR/Cas9 system for gene editing. In some alternatives, an AAV vector is used to deliver one or more components of CRISPR/Cas9 system for gene editing in primary cells. In some alternatives, an AAV vector is used to deliver a CRISPR guide RNA for gene editing. In some alternatives, an AAV vector is used to deliver a CRISPR guide RNA for gene editing in primary cells. In some alternatives, a primary cell, is a cell directly derived from a host donor, which is not transformed or cancerous and which cannot be propagated indefinitely outside the host.

In many cell types, there is a post-entry or post-delivery restriction on AAV vectors. This renders AAV-mediated expression of transgenes, including guide RNAs, very inefficient, thus substantially compromising the utility of AAV vectors for this purpose. Certain adenoviral proteins facilitate expression and replication of AAV and AAV vectors. In particular, in some alternatives, E4ORF6 and E1B55K are used as helper proteins in AAV vector production and/or as helper proteins in replication of AAV vector encoding guide RNA.

Previous work has shown that wild type E1B55K or wild type E4ORF6 proteins can disable an important protein complex involved in DNA repair (known as the MRN complex). This leads to cell cycle arrest and high toxicity due to lack of repair of DNA breaks. On the other hand, it has been realized that neither the H373A mutant of E1B55K nor the H354 mutant of E1B55K disable the MRN complex. This leaves the DNA repair machinery intact and provides increased safety and efficacy when using the mutant form of ad proteins for AAV replication in cells. Thus, in some alternatives, the wild type E1B55K is used in combination with the H373A mutant of E1B55K protein. In some alternatives, the wild type E4ORF6 is used in combination with the H354 mutant of E1B55K protein. In some alternatives, the use of wild type E4ORF6 in combination with the H373A mutant of E1B55K protein does not disable the MRN complex. In some alternatives, the use of wild type E4ORF6 in combination with the H354 mutant of E1B55K protein does not disable the MRN complex. In some alternatives, the use of wild type E4ORF6 in combination with the H373A mutant of E1B55K protein does not lead to cell cycle arrest. In some alternatives, the use of wild type E4ORF6 in combination with the H354 mutant of E1B55K protein does not lead to cell cycle arrest. In some alternatives, the use of wild type E4ORF6 in combination with the H373A mutant of E1B55K protein does not lead to toxicity due to lack of repair of DNA breaks. In some alternatives, the use of wild type E4ORF6 in combination with the H354 mutant of E1B55K protein does not lead to toxicity due to lack of repair of DNA breaks.

In some alternatives, the use of mutant adenoviral proteins for AAV transduction resulted in lower transduction efficiency of primary cells, as compared to wild type adenoviral proteins. However, the use of mutant adenoviral proteins resulted in dramatic enhancement of CRISPR/Cas9-based gene editing. In some alternatives, this is likely due to enhancing gRNA expression from the AAV vector. In some alternatives, this is likely due to modulation of the DNA repair environment of the cell to promote mutagenic repair of double strand breaks created by CRISPR. In some alternatives, this is likely due to both enhancing gRNA expression from the AAV vector as well as modulation of the DNA repair environment of the cell to promote mutagenic repair of double strand breaks created by CRISPR.

In some alternatives, expression of E4ORF6 and mutant E1B55K-H373A results in sufficient relief of the post-entry restriction on AAV expression while maintaining intact DNA repair. In some alternatives, expression of E4ORF6 and mutant E1B55K-H354 results in sufficient relief of the post-entry restriction on AAV expression while maintaining intact DNA repair. In some alternatives, expression of E4ORF6 and E1B55K-H373A allows for a substantial improvement in gene editing efficiency. In some alternatives, expression of E4ORF6 and E1B55K-H354 allows for a substantial improvement in gene editing efficiency. In some alternatives, expression of E4ORF6 and E1B55K-H373A allows for a substantial improvement in CRISPR/Cas9-mediated gene editing efficiency. In some alternatives, expression of E4ORF6 and E1B55K-H354 allows for a substantial improvement in CRISPR/Cas9-mediated gene editing efficiency. In some alternatives, expression of E4ORF6 and E1B55K-H373A allows a substantial improvement in gene editing efficiency in primary cells. In some alternatives, expression of E4ORF6 and E1B55K-H354 allows a substantial improvement in gene editing efficiency in primary cells. In some alternatives, expression of E4ORF6 and E1B55K-H373A allows for a substantial improvement in CRISPR/Cas9-mediated gene editing efficiency in primary cells. In some alternatives, expression of E4ORF6 and E1B55K-H354 allows for a substantial improvement in CRISPR/Cas9-mediated gene editing efficiency in primary cells.

In some alternatives, a system of introducing CRISPR/Cas9 in primary cells using an AAV-mRNA split system approach is provided. In some alternatives of the split system, Cas9, a derivative, or fragment thereof and adenoviral proteins are expressed from mRNA and expressed transiently, and gRNA is expressed constantly and expressed from AAV. In some alternatives, the split system increased the efficiency of gene editing in primary human cells.

Some alternatives relate to a method of introducing CRISPR guide RNA in primary cells using an AAV vector. More alternatives relate to a method of introducing Cas9, a derivative, or fragment thereof in primary cells encoded by an mRNA. In some alternatives, a method of introducing Cas9, a derivative, or fragment thereof in primary cells encoded as a fusion protein by an mRNA is provided. In some alternatives, Cas9 is fused with a fluorophore at the C terminus. In some alternatives, Cas9, a derivative, or fragment thereof is fused with a fluorophore at the N terminus. In some alternatives, Cas9, a derivative, or fragment thereof is fused with a fluorophore and the Cas9, a derivative, or fragment thereof and fluorophore are separated by a self-cleavage sequence, such as a T2A sequence. In some alternatives, Cas9, a derivative, or fragment thereof is fused to an NLS. In some alternatives, the NLS is fused at the N terminus of Cas9, a derivative, or fragment thereof. In some alternatives, the NLS is fused at the C terminus of Cas9, a derivative, or fragment thereof. In some alternatives, the NLS is fused at both the N and the C terminus of Cas9, a derivative, or fragment thereof. In some alternatives, Cas9, a derivative, or fragment thereof is tagged with an mCherry fluorophore.

In some alternatives, the mRNA comprises a poly A tail. In some alternatives, the poly A tail confers stability to the mRNA. In some alternatives, the length of the poly A tail is greater than or equal to 100, 125, 150, 175, 200, 225, 250, 275, 300, 325, 350, 375, 400, 425, 450, 475, or 500 base pairs or a length that is within a range defined by any two of the aforementioned lengths. In some alternatives, the mRNA is encoded by a vector. In some alternatives, the mRNA is expressed from the vector by in vitro transcription. In some alternatives, the mRNA encodes a nuclease, helicase and/or an adenoviral protein. In some alternatives, the mRNA encodes Cas9, a derivative, or fragment thereof. In some alternatives, the mRNA encodes MegaTAL or TALEN. In some alternatives, the mRNA encodes E4ORF6. In some alternatives, the mRNA encodes E1B55K. In some alternatives, the mRNA encodes H373A E1B55K. In some alternatives, the mRNA encodes H354 E1B55K. In some alternatives, the mRNA encodes Trex2.

In some alternatives, the expression of adenoviral proteins is desired along with the Cas9 protein. mRNAs with poly A tails that are greater than or equal to 100, 125, 150, 175, 200, 225, 250, 275, 300, 325, 350, 375, 400, 425, 450, 475, or 500 base pairs or a length that is within a range defined by any two of the aforementioned lengths, wherein said mRNAs encode Cas9, a derivative, or fragment thereof, TALEN, or MegaTAL, can be efficiently co-expressed in primary human cells. In some alternatives, said mRNA is used to express Cas9, a derivative, or fragment thereof. In some alternatives, said mRNA is used to express wild type adenoviral proteins. In some alternatives, said mRNA is used to express mutant adenoviral proteins. In some alternatives, AAV is used to express guide RNA. Some alternatives relate to methods of introducing adenoviral proteins in primary cells encoded by an mRNA. In some alternatives, mRNA is used to introduce the wild type adenoviral protein E4ORF6. In some alternatives, mRNA is used to introduce the mutant adenoviral protein H373A E1B55K. In some alternatives, mRNA is used to introduce the mutant adenoviral protein H354 E1B55K. In some alternatives, separate mRNAs are used to introduce both wild type E4ORF6 and the mutant H373A E1B55K. In some alternatives, separate mRNAs are used to introduce both wild type E4ORF6 and the mutant H354 E1B55K. In some alternatives, the mRNAs are on a vector. In some alternatives, AAV with guide RNA and mRNA encoding Cas9, a derivative, or fragment thereof, and E4ORF6 and mutant H373A E1B55K or AAV with guide RNA and mRNA encoding Cas9, E4ORF6 and mutant H354 E1B55K are simultaneously introduced. In some alternatives, AAV with guide RNA and mRNA encoding Cas9, a derivative, or fragment thereof, and E4ORF6 and mutant H373A E1B55K or AAV with guide RNA and mRNA encoding Cas9, E4ORF6 and mutant H354 E1B55K are sequentially introduced. In some alternatives, AAV with guide RNA and mRNA encoding Cas9, a derivative, or fragment thereof, and E4ORF6 and mutant H373A E1B55K or AAV with guide RNA and mRNA encoding Cas9, E4ORF6 and H354 E1B55K are present in a cell at the same time. In some alternatives, mRNA is used to transiently express wild type adenoviral proteins. In some alternatives, mRNA is used to transiently express mutant adenoviral proteins. In some alternatives, mRNA is used to simultaneously albeit transiently to express Cas9, a derivative, or fragment thereof, wild type adenoviral proteins and mutant adenoviral protein. In some alternatives, guide RNA is prone to degradation. In some alternatives, therefore AAV is used to constantly express guide RNA. In some alternatives, AAV with guide RNA and mRNA encoding Cas9, a derivative, or fragment thereof, and E4ORF6 and mutant H373A E1B55K or AAV with guide RNA and mRNA encoding Cas9, and E4ORF6 and H354 E1B55K are present transiently. In some alternatives, AAV with guide RNA and mRNA encoding Cas9, a derivative, or fragment thereof, E4ORF6 and mutant H373A E1B55K or AAV with guide RNA and mRNA encoding Cas9, E4ORF6 and H354 E1B55K are not present permanently.

In some alternatives, co-expressing Cas9, a derivative, or fragment thereof with E4ORF6/E1B55K-H373A results in sufficient relief of post-entry restriction on AAV expression while maintaining intact DNA repair. This allows substantial improvement in Cas9-mediated gene editing efficiency with minimal toxicity when an AAV vector is simultaneously used to express the guide RNAs necessary for Cas9 targeting, thus yielding results counterintuitive to what one might have expected from the use of AAV vectors and substantially improving and expanding the potential applications of the CRISPR/Cas9 system in primary cells.

In some alternatives, the use of adenoviral proteins to enhance CRISPR-mediated gene knockout in primary cells is provided. In some alternatives, the use of adenoviral proteins to enhance CRISPR-mediated gene knockout in primary T-cells is provided. In some alternatives, the use of adenoviral proteins to enhance CRISPR-mediated gene knockout in Jurkat T-cells is provided. In some alternatives, the use of adenoviral proteins to enhance CRISPR-mediated gene knockout in primary cells using a combined mRNA/AAV approach is provided. In some alternatives, the use of adenoviral proteins to enhance CRISPR-mediated gene knockout in primary T-cells using a combined mRNA/AAV approach is provided. In some alternatives, the use of adenoviral proteins to enhance CRISPR-mediated gene knockout in Jurkat T-cells using a combined mRNA/AAV approach is provided. In some alternatives, the use of mutant adenoviral proteins to enhance CRISPR-mediated gene knockout is provided. In some alternatives, the use of mutant adenoviral proteins to enhance CRISPR-mediated gene knockout in primary cells is provided. In some alternatives, the use of mutant adenoviral proteins to enhance CRISPR-mediated gene knockout in primary T-cells is provided. In some alternatives, the use of mutant adenoviral proteins to enhance CRISPR-mediated gene knockout in Jurkat T-cells is provided.

In some alternatives, the use of adenoviral proteins to enhance CRISPR-mediated gene knockout and enhanced homologous recombination in primary T-cells is described. In some alternatives, the use of adenoviral proteins to enhance CRISPR-mediated gene knockout and enhanced homologous recombination in primary T-cells using a combined mRNA/AAV approach is described. In some alternatives, the use of mutant adenoviral proteins to enhance CRISPR-mediated gene knockout and enhanced homologous recombination is provided. In some alternatives, the mutant adenoviral proteins enhance CRISPR-mediated gene knockout and enhance homologous recombination in primary T-cells.

The application of this technology is not limited to primary human cells. In some alternatives, a system for targeting of non-human sequences, for example pathogenic organisms, is provided. In some alternatives, a method for targeting of non-human sequences, for example pathogenic organisms, is provided. In some alternatives, a system for targeting diseases is provided. In some alternatives, a method for targeting diseases is provided. In some alternatives, the disease can be an infectious disease caused by a pathogenic organism. In some alternatives, the disease can be a non-infectious disease.

Double strand DNA break repair through the NHEJ pathway is often not mutagenic. The majority of endonuclease-induced breaks repaired by the NHEJ pathway involve precise re-ligation, resulting in the restoration of the original DNA sequence. HDR, in contrast to NHEJ, requires a repair template and imprecise repair through this pathway can result in mutations at the break site, such as DNA base deletions and insertions, as well as, translocations and telomere fusion.

In some alternatives, the use of Cas9-mRNA/AAV-guide system results in increased NHEJ rates. Thus, in some alternatives of the Cas9-mRNA/AAV-guide system, a repair template is introduced into the cell. In some alternatives the repair template is RNA. In some alternatives, the repair template is DNA. In some alternatives, the Cas9-mRNA/AAV-guide system is driven towards HDR to achieve greater mutation rate. In some alternatives, the mRNA-AAV system is implemented with another nuclease without providing a repair template. In some alternatives, the mRNA-AAV system implemented with another nuclease without providing a repair template allows for NHEJ. In some alternatives, the system further comprises a nuclease, wherein the nuclease is MegaTAL.

Additional Preferred Alternatives

In some alternatives, a system for editing at least one target gene in a cell, comprising a first nucleic acid sequence encoding a CRISPR guide RNA, wherein the CRISPR guide RNA is complimentary to at least one target gene in a cell and, wherein said first nucleic acid sequence is present in a vector, wherein said system further comprises a second nucleic acid sequence encoding a Cas9 protein, a derivative, or fragment thereof; a third nucleic acid sequence encoding a first adenoviral protein, and a fourth nucleic acid sequence encoding a second adenoviral protein. In some alternatives of the system, the cell is a eukaryotic cell. In some alternatives of the system, the cell is a mammalian cell. In some alternatives, the cell is a human cell. In some alternatives of the system, the cell is a primary cell. In some alternatives, the cell is not a transformed cell. In some alternatives of the system, the cell is a primary lymphocyte, a CD34+ stem cell, a hepatocyte, a cardiomyocyte, a neuron, a glial cell, a muscle cell or an intestinal cell. In some alternatives of the system, the vector is a viral vector. In some alternatives of the system, the viral vector is an Adeno-associated virus (AAV) vector. In some alternatives of the system, the second nucleic acid encoding the Cas9 protein, a derivative, or fragment thereof is an mRNA. In some alternatives of the system, the second nucleic acid sequence encoding the Cas9 protein, a derivative, or fragment thereof is codon optimized for expression in a eukaryotic cell, such as a human cell. In some alternatives of the system, the Cas9 protein, a derivative, or fragment thereof is from *S. pyogenes*. In some alternatives of the system, the third nucleic acid encoding the first adenoviral protein is an mRNA. In some alternatives of the system, the mRNA is codon optimized for expression in a eukaryotic cell, such as a human cell. In some alternatives of the system, the first adenoviral protein is E4ORF6. In some alternatives of the system, the fourth nucleic acid encoding the second adenoviral protein is an mRNA. In some alternatives of the system, the fourth nucleic acid encoding the second adenoviral protein is codon optimized for expression in a eukaryotic cell, such as a human cell. In some alternatives of the system, the second adenoviral protein is an E1B55K mutant. In some alternatives of the system, the second adenoviral protein comprises the amino acid sequence set forth in SEQ ID NO: 2. In some alternatives of the system, the second adenoviral protein comprises the amino acid sequence set forth in SEQ ID NO: 4. In some alternatives of the system, the first, second, third and fourth nucleic acid sequences are joined to regulatory elements that are operable in a eukaryotic cell, such as a human cell. In some alternatives of the system, the first nucleic acid sequence encoding the CRISPR guide RNA is operably linked to a regulatory element. In some alternatives of the system, the nucleic acid sequence encoding the CRISPR guide RNA is operably linked to a U6 promoter. In some alternatives of the system, the nucleic acid sequence encoding the CRISPR guide RNA is constitutively expressed.

In some alternatives, a method of editing at least one target gene in a cell, comprises introducing into a cell a first vector that comprises a first nucleic acid sequence encoding a CRISPR guide RNA, wherein the CRISPR guide RNA is complimentary to at least one target gene in said cell; introducing into said cell a second nucleic acid sequence encoding a Cas9 protein, a derivative, or fragment thereof; introducing into said cell a third nucleic acid sequence encoding a first adenoviral protein; and introducing into said cell a fourth nucleic acid sequence encoding a second adenoviral protein.

In some alternatives of the method, the cell is a eukaroytic cell. In some alternatives of the method, the cell is a mammalian cell. In some alternatives of the method, the cell is a human cell. In some alternatives of the method, the cell is a primary cell. In some alternatives of the method, the cell is not a transformed cell. In some alternatives of the method, the cell is a primary lymphocyte, a CD34+ stem cell, a hepatocyte, a cardiomyocyte, a neuron, a glial cell, a muscle cell or an intestinal cell. In some alternatives of the method, the first vector comprising the first nucleic acid sequence encoding the CRISPR guide RNA is a viral vector. In some alternatives of the method, the viral vector is an Adeno-associated virus (AAV) vector. In some alternatives of the method, the second, third and fourth nucleic acid sequences are mRNA. In some alternatives of the method, the mRNAs are codon optimized for expression in a eukaryotic cell, such as a human. In some alternatives of the method, the Cas9 protein, a derivative, or fragment thereof is from *S. pyogenes*. In some alternatives of the method, the first adenoviral protein is E4ORF6. In some alternatives of the method, the second adenoviral protein is an E1B55K mutant. In some alternatives of the method, the second adenoviral protein comprises the amino acid sequence set forth in SEQ ID NO: 2. In some alternatives of the method, the second adenoviral protein comprises the amino acid sequence set forth in SEQ ID NO: 4.

In some alternatives of the system, the CRISPR guide RNA is any and all guide RNAs that are complimentary to a gene of interest. In some alternatives of the system, the CRISPR guide RNA is complimentary to a target gene on interest. Some non-limiting examples of target genes of interest include TCRα, TCRβ, PD-1, Tim3, Lag3, TIGIT or HBB.

In some alternatives of the system, the CRISPR guide RNA sequence targeting TCR comprises a sequence set forth in SEQ ID NO: 15, SEQ ID NO: 16, SEQ ID NO: 17, or SEQ ID NO: 5. These sequences are described in FIG. 16A. In some alternatives of the system, polynucleotide sequence alternatives of PD1 guide target comprises a sequence set forth in SEQ ID NO: 18, TIGIT guide target comprises a sequence set forth in SEQ ID NO: 19, Lag3 guide target comprises a sequence set forth in SEQ ID NO: 20 and Tim3 guide target comprises a sequence set forth in SEQ ID NO: 21. These sequences are provided in FIG. 31.

In some alternatives of the method, the first, second, third and fourth nucleic acid sequences are not permanently introduced into the cell. In some alternatives of the method, introducing the first, second, third and fourth nucleic acid sequences into the cell does not transform the cell. In some alternatives of the method and/or the system, the second, third, or fourth nucleic acid sequence is provided on a vector. In some alternatives, a method of editing at least one target gene in a cell, the method comprising introducing into the cell any of the alternatives of the system described herein.

In some alternatives, a method of treating, ameliorating, or inhibiting a disease and/or a condition in a subject, the method comprising providing to the subject having a disease and/or a condition and in need thereof, any of the alternatives of the system described herein. Some non-limiting examples of diseases and/or conditions can be sickle cell disease, hypercholesterolemia, cancer, autoimmune disease, inherited disorder of metabolism, immunodeficiency or genetic disease such as any disease due to a functional deficit in a gene product due to an alteration in the genome of the cell relative to a reference human genome.

More Alternatives

In more alternatives, a system for editing at least one target gene in a cell is provided, the system comprising a nucleic acid encoding Cas9 protein, at least one nucleic acid encoding at least protein, which alone or together with other proteins modifies the substrate specificity of at least one ubiquitin ligase enzyme or enzyme complex in the cell, and a vector that comprises at least one nucleic acid sequence encoding a CRISPR guide RNA, wherein the one or more CRISPR guide RNAs is/are complimentary to at least one target gene in a cell and in some alternatives of the system a vector that comprises a nucleic acid template for homologous gene targeting.

In some alternatives of the system, the Cas9 protein, a derivative, or fragment thereof and the ubiquitin ligase substrate specificity modifying proteins are encoded on the same nucleic acid. In some alternatives of the system, the Cas9 protein, a derivative, or fragment thereof and the ubiquitin ligase substrate specificity modifying proteins are encoded on two or more nucleic acids. In some alternatives of the system, the cell is a eukaryotic cell. In some alternatives of the system, the cell is a mammalian cell. In some alternatives of the system, the cell is a human cell. In some alternatives of the system, the cell is a primary cell. In some alternatives of the system, the cell is not a transformed cell. In some alternatives of the system, the cell is a primary lymphocyte, a CD34+ stem cell, a hepatocyte, a cardiomyocyte, a neuron, a glial cell, a muscle cell or an intestinal cell. In some alternatives of the system, the vector encoding the guide RNA(s) is a viral vector. In some alternatives of the system, the viral vector is an Adeno-associated virus (AAV) vector. In some alternatives, the viral vector is a lentiviral vector.

In some alternatives of the system, the nucleic acid encoding the Cas9 protein, a derivative, or fragment thereof is an mRNA the second nucleic acid encoding the Cas9 protein, a derivative, or fragment thereof is an mRNA. In some alternatives of the system, the nucleic acid sequence encoding the Cas9 protein is codon optimized for expression in a eukaryotic cell, such as a human cell. In some alternatives of the system, the Cas9 protein, a derivative, or fragment thereof is from *S. pyogenes*.

In some alternatives of the system, the nucleic acid or nucleic acids encoding any of the ubiquitin ligase enzyme/enzyme complex substrate specificity modifying proteins are mRNA. In some alternatives of the system, the one or more mRNA's encoding ubiquitin ligase enzyme/enzyme complex substrate specificity modifying proteins are codon optimized for expression in a eukaryotic cell, such as a human cell. In some alternatives of the system, one of the ubiquitin ligase enzyme/enzyme complex substrate specificity modifying proteins is the adenoviral protein E4ORF6 of any adenoviral serotype. In some alternatives of the system, one of the ubiquitin ligase enzyme/enzyme complex substrate specificity modifying proteins is E1B55K of any adenovirus serotype.

In some alternatives of the system, one of the ubiquitin ligase enzyme/enzyme complex substrate specificity modifying proteins is an E1B55K mutant, said mutant having an one or more amino acid changes or additions relative to the wild type E1B55K protein, which cause an alteration in the mutant protein's ability to modify cellular ubiquitin ligase substrate specificity relative the wild type E1B55K protein.

In some alternatives of the system, one of the ubiquitin ligase enzyme/enzyme complex substrate specificity modifying proteins comprises the amino acid sequence set forth in SEQ ID NO: 2.

In some alternatives of the system, one of the ubiquitin ligase enzyme/enzyme complex substrate specificity modifying proteins comprises the amino acid sequence set forth in SEQ ID NO: 4.

In some alternatives of the system, the nucleic acid sequences are joined to regulatory elements that are operable in a eukaryotic cell, such as a human cell. In some alternatives of the system, the nucleic acid sequence encoding the CRISPR guide RNA is operably linked to a regulatory element. In some alternatives of the system, the nucleic acid sequence encoding the CRISPR guide RNA is operably linked to a U6 promoter. In some alternatives of the system, the nucleic acid sequence encoding the CRISPR guide RNA is constitutively expressed. In some alternatives, the nucleic acid sequence encoding the CRISPR guide RNA is operably linked to the U6 promoter and constitutively expressed.

In some alternatives, a method of editing at least one target gene in a cell is provided, the method comprising introducing into the cell a nucleic acid sequence encoding a Cas9 protein, a derivative, or fragment thereof; introducing into said cell at least one nucleic acid sequence encoding a ubiquitin ligase enzyme/enzyme complex substrate specificity modifying protein; introducing into said cell a vector that comprises at least one nucleic acid sequence encoding a CRISPR guide RNA, wherein the CRISPR guide RNA is complimentary to at least one target gene in said cell; and in some alternative of the method, introducing into said cell a vector that comprises a nucleic acid template for homologous gene targeting.

In some alternatives of the method, the cell is a eukaryotic cell. In some alternatives of the method, the cell is a mammalian cell. In some alternatives of the method, the cell is a human cell. In some alternatives of the method, the cell is a primary cell. In some alternatives of the method, the cell is not a transformed cell. In some alternatives of the method, the cell is a primary lymphocyte, a CD34+ stem cell, a hepatocyte, a cardiomyocyte, a neuron, a glial cell, a muscle cell or an intestinal cell. In some alternatives of the method, the vector comprising the first nucleic acid sequence encoding the endonuclease is a viral vector. In some alternatives, Cas9 is encoded in a viral vector. In some alternatives, a guide RNA is encoded in a viral vector. In some alternatives, a Cas9 and a guide RNA are encoded together in a viral vector. In some alternatives, a Cas9 and a guide RNA encoded together in a viral vector is used in combination with one or more Ad5 protein encoded by mRNA.

In some alternatives of the method, the vector comprising the nucleic acid sequence encoding the one or more CRISPR guide RNAs is a viral vector. In some alternatives of the method, the viral vector is an Adeno-associated virus (AAV) vector. In some alternatives of the method, the viral vector is a lentiviral vector. In some alternatives of the method, the nucleic acids encoding Cas9, a derivative, or fragment thereof and/or the ubiquitin ligase substrate specificity modifying proteins are mRNA. In some alternatives of the method, the mRNAs are codon optimized for expression in a eukaryotic cell, such as a human.

In some alternatives of the method, the Cas9 protein, a derivative, or fragment thereof is from *S. pyogenes*. In some alternatives of the method, the ubiquitin ligase substrate specificity modifying proteins is E4ORF6 of any adenoviral serotype. In some alternatives of the method, the ubiquitin ligase substrate specificity modifying proteins is E1B55K of any adenoviral serotype. In some alternatives of the method, the second adenoviral protein comprises the amino acid sequence set forth in SEQ ID NO: 2. In some alternatives of the method, the second adenoviral protein comprises the amino acid sequence set forth in SEQ ID NO: 4.

In some alternatives of the system, the CRISPR guide RNA is any and all guide RNAs that are complimentary to a gene of interest. In some alternatives of the system, the CRISPR guide RNA is complimentary to a target gene on interest. Some non-limiting examples of target genes of interest include TCRα, TCRβ, PD-1, Tim3, Lag3, TIGIT or HBB.

In some alternatives of the system, alternatives of the CRISPR guide RNA sequence targeting TCR comprise a sequence set forth in SEQ ID NO: 15, SEQ ID NO: 16, SEQ ID NO: 17, or SEQ ID NO: 5. These sequences are shown in FIG. 16A. In some alternatives of the system, a polynucleotide sequence comprises alternatives of PD1 guide target (SEQ ID NO: 18), TIGIT guide target (SEQ ID NO: 19), Lag3 guide target (SEQ ID NO: 20) or Tim3 guide target (SEQ ID NO: 21). These sequences are provided in FIG. 31.

In some alternatives of the method, the nucleic acid sequences are transiently introduced into the cell. In some alternatives of the method, the nucleic acid sequences are not permanently introduced into the cell. In some alternatives of the method, introducing the nucleic acid sequences into the cell does not permanently transform the cell.

Any of the alternatives of the system or the method described herein, wherein said second, third, or fourth nucleic acid sequence is provided on a vector.

In some alternatives, a method of editing at least one target gene in a cell, the method comprising introducing into the cell any of the alternatives of the system described herein.

In some alternatives, a method of treating, ameliorating, or inhibiting a disease and/or a condition in a subject, the method comprising providing to the subject having a disease and/or a condition and in need thereof, any of the alternatives of the system described herein. Some non-limiting examples of diseases and/or conditions can be sickle cell disease, hypercholesterolemia, cancer, autoimmune disease, inherited disorder of metabolism, immunodeficiency or genetic disease such as any disease due to a functional deficit in a gene product due to an alteration in the genome of the cell relative to a reference human genome.

In some alternatives, a system for editing at least one target gene in a cell is provided, the system comprising a nucleic acid encoding an endonuclease protein that targets at least one sequence in a cell, and at least one nucleic acid encoding at least one protein, which alone or together with other proteins modifies the substrate specificity of at least one ubiquitin ligase enzyme or enzyme complex in the cell, and, optionally, a vector that comprises a nucleic template for homologous gene targeting. In some alternatives of the system, the nuclease protein and the ubiquitin ligase substrate specificity modifying proteins are encoded on the same nucleic acid. In some alternatives of the system, the nuclease protein and the ubiquitin ligase substrate specificity modifying proteins are encoded on two or more nucleic acids. In some alternatives of the system, the nucleic template for homologous gene targeting is a DNA. In some alternatives of the system, the nucleic template for homologous gene targeting is an RNA. In some alternatives of the system, the cell is a eukaryotic cell. In some alternatives of the system, the cell is a mammalian cell. In some alternatives of the system, the cell is a human cell. In some alternatives of the system, the cell is a primary cell. In some alternatives of the system, the cell is not a transformed cell. In some alternatives of the system, the cell is a primary lymphocyte, a CD34+ stem cell, a hepatocyte, a cardiomyocyte, a neuron, a glial cell, a muscle cell or an intestinal cell. In some alternatives of the system, the vector is a viral vector. In some alternatives of the system, the viral vector is an Adeno-associated virus (AAV) vector. In some alternatives of the system, the viral vector is a lentiviral vector.

In some alternatives of the system, the nucleic acid encoding the Cas9 nuclease, a derivative, or fragment thereof is an mRNA. In some alternatives of the system, the nucleic acid sequence encoding the nuclease is codon optimized for expression in a eukaryotic cell, such as a human cell. In some alternatives of the system, the nucleic acid or nucleic acids encoding any of the ubiquitin ligase enzyme/enzyme complex substrate specificity modifying proteins are mRNA. In some alternatives of the system, the one or more mRNAs encoding ubiquitin ligase enzyme/enzyme complex substrate specificity modifying proteins are codon optimized for expression in a eukaryotic cell, such as a human cell.

In some alternatives of the system, the ubiquitin ligase enzyme/enzyme complex substrate specificity modifying proteins is the adenoviral protein E4ORF6 of any adenoviral serotype. In some alternatives of the system, the ubiquitin ligase enzyme/enzyme complex substrate specificity modifying proteins is E1B55K of any adenovirus serotype. In some alternatives of the system, the ubiquitin ligase enzyme/enzyme complex substrate specificity modifying proteins is an E1B55K mutant, said mutant having an one or more amino acid changes relative to the wild type E1B55K protein which cause an alteration in the mutant protein's ability to modify cellular ubiquitin ligase substrate specificity relative the wild type E1B55K protein. In some alternatives of the system, the ubiquitin ligase enzyme/enzyme complex substrate specificity modifying proteins comprises the amino acid sequence set forth in SEQ ID NO: 2. In some alternatives of the system, the ubiquitin ligase enzyme/enzyme complex substrate specificity modifying proteins comprises the amino acid sequence set forth in SEQ ID NO: 4. In some alternatives of the system, the ubiquitin ligase substrate specificity modifying proteins are one or more viral proteins.

In some alternatives of the system, the nucleic acid sequence encoding the endonuclease RNA is operably linked to a regulatory element. In some alternatives of the system, the nucleic acid sequence encoding the endonuclease RNA is operably linked to a U6 promoter. In some alternatives of the system, the nucleic acid sequence encoding the endonuclease RNA is constitutively expressed. In some alternatives, the nucleic acid sequence encoding the endonuclease RNA is operably linked to the U6 promoter and constitutively expressed.

In some alternatives, a method of editing at least one target gene in a cell is provided, the method comprising introducing into a cell a nucleic acid sequence encoding an endonuclease, introducing into said cell at least one nucleic acid sequence encoding a ubiquitin ligase enzyme/enzyme complex substrate specificity modifying protein; and optionally introducing into said cell a vector that comprises a nucleic acid template capable of homologous gene targeting of at least one genomic sequence in the cell. In some alternatives of the method, the nucleic template for homologous gene targeting is a DNA. In some alternatives of the method, the nucleic template for homologous gene targeting is an RNA.

In some alternatives of the method, the cell is a eukaroytic cell. In some alternatives, a method the cell is a mammalian cell. In some alternatives of the method, the cell is a human cell. In some alternatives of the method, the cell is a primary cell. In some alternatives of the method, the cell is not a transformed cell. In some alternatives of the method, the cell is a primary lymphocyte, a CD34+ stem cell, a hepatocyte, a cardiomyocyte, a neuron, a glial cell, a muscle cell or an intestinal cell. In some alternatives of the method, the vector comprising the first nucleic acid sequence encoding the endonuclease is a viral vector. In some alternatives, Cas9, a derivative, or fragment thereof is encoded in a viral vector. In some alternatives, a guide RNA is encoded in a viral vector. In some alternatives, a Cas9, a derivative, or fragment thereof and a guide RNA are encoded together in a viral vector. In some alternatives, a Cas9, a derivative, or fragment thereof and a guide RNA encoded together in a viral vector is used in combination with one or more Ad5 protein encoded by mRNA. In some alternatives of the method, the viral vector is an Adeno-associated virus (AAV) vector. In some alternatives of the method, the viral vector is a lentiviral vector. In some alternatives of the method, the nucleic acids encoding the nuclease and/or the ubiquitin ligase substrate specificity modifying proteins are mRNA. In some alternatives of the method, the mRNAs are codon optimized for expression in a eukaryotic cell, such as a human. In some alternatives of the method, the endonuclease protein is a meganuclease, a TALEN, a zinc finger nuclease, or a MegaTAL. In some alternatives of the method, one of the ubiquitin ligase substrate specificity modifying proteins is E4ORF6 of any adenoviral serotype. In some alternatives of the method, one of the ubiquitin ligase substrate specificity modifying proteins is E1B55K of any adenoviral serotype. In some alternatives of the method, one of the ubiquitin ligase substrate specificity modifying proteins comprises the amino acid sequence set forth in SEQ ID NO: 2. In some alternatives of the method, one of the ubiquitin ligase substrate specificity modifying proteins comprises the amino acid sequence set forth in SEQ ID NO: 4. In some alternatives of the system, the nuclease targets a gene of interest. Some non-limiting examples of target genes of interest include TCRα, TCRβ, PD-1, Tim3, Lag3, TIGIT or HBB.

In some alternatives of the method, the nucleic acid sequences are transiently introduced into the cell. In some alternatives of the method, the nucleic acid sequences are not permanently introduced into the cell. In some alternatives of the method, introducing the nucleic acid sequences into the cell does not transform the cell. In some alternatives of the system, the target gene intended for homologous gene targeting is a gene of interest. Some non-limiting examples of target genes of interest include TCRα, TCRβ, PD-1, Tim3, Lag3, TIGIT or HBB. In some alternatives of any of the system or any of the method described herein, the nucleic acid sequences are provided on a vector. In some alternatives, a method of editing at least one target gene in a cell is provided, the method comprising introducing into the cell any of the alternatives of the system described herein.

In some alternatives, a method of treating, ameliorating, or inhibiting a disease and/or a condition in a subject, the method comprises providing to the subject having a disease and/or a condition and in need thereof, any of the alternatives of the system described herein. Some non-limiting examples of diseases and/or conditions can be sickle cell disease, hypercholesterolemia, cancer, autoimmune disease, inherited disorder of metabolism, immunodeficiency or genetic disease such as any disease due to a functional deficit in a gene product due to an alteration in the genome of the cell relative to a reference human genome.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The present alternatives should therefore not be limited by the herein described embodiment, method, and examples, but by all alternatives and methods within the scope and spirit of the present alternatives. The following examples are presented for illustrative purposes and should not be construed as being limiting.

Further Alternatives

Alternative of Cas9 described herein can be used in any and all of the alternatives of the system and/or method described herein. Some alternatives of Cas9 are disclosed in the following references which are hereby incorporated by reference in their entirety (Gilbert et al, Cell, July 18, 154(2): 442-451, 2013; Hilton et al, Nat Biotechnol. April 6. doi: 10.1038/nbt.3199, 2015; Qi et al, Cell, February 28; 152(5): 1173-1183, 2013; Esvelt et al, Nature Methods 10, 1116-1121, 2013; Zetsche et al, Nature Biotechnology, 33, 139-142, 2015; all references incorporated by reference in their entireties herein). The ability of Cas9 to co-localizing RNA, DNA and protein to a target region of a genome offers unprecedented control over cellular organization, regulation and behavior using the Cas9 system (Mali et al).

The CRISPR-associated catalytically inactive variant of *S. pyogenes* Cas9 (dCas9 or nuclease null Cas9) can be used for RNA-guided DNA targeting (Gilbert et al; incorporated by reference in its entirety herein). Fusion of dCas9 to effector domains of regulatory proteins (for example, a transcriptional activator (hereinafter, activator domain) or a transcriptional repressor (hereinafter, repressor domain) enables stable and efficient transcriptional regulation in human and yeast cells (Gilbert et al; incorporated by reference in its entirety herein). The site-specific delivery of dCas9 is determined solely by a guide RNA (Gilbert et al). CRISPR interference (CRISPRi)-mediated transcriptional repression, which entails coupling dCas9 to a transcriptional repressor domain, can robustly and specifically silence gene expression in eukaryotic cells (Gilbert et al; incorporated by reference in its entirety herein) and *Escherichia coli* (Qi et al; incorporated by reference in its entirety herein).

Thus, in some alternatives, a catalytically inactive Cas9 (dCas9) is used which does not cause a double stranded DNA break. In some alternatives, a dCas9 is fused to an activator domain. In some alternatives, a dCas9 is fused to a repressor domain. In some alternatives, a dCas9-activator domain is encoded by an mRNA. In some alternatives, a dCas9-repressor domain is encoded by an mRNA. In some alternatives, an mRNA encoding dCas9-activator domain is used in combination an AAV vector encoding a guide RNA. In some alternatives, an mRNA encoding dCas9-repressor domain is used in combination an AAV vector encoding a guide RNA. In some alternatives, an mRNA encoding dCas9-activator domain is used in combination an mRNA encoding an Ad5 protein and an AAV vector encoding a guide RNA. In some alternatives, an mRNA encoding dCas9-repressor domain is used in combination an mRNA encoding an Ad5 protein and an AAV vector encoding a guide RNA. In some alternatives, a dCas9-activator domain activates transcription. In some alternatives, a dCas9-repressor domain represses transcription. In some alternatives, one or more Ad5 proteins further increases activation of transcription by a dCas9-activator domain fusion. In some alternatives, one or more Ad5 proteins further increases repression of transcription by dCas9-repressor domain fusion.

Creating a fusion of dCas9 with a catalytic core of a human acetyltransferase led to acetylation of histone H3, resulting in robust transcriptional activation of target genes from promoters and both proximal and distal enhancers (Hilton et al; incorporated by reference in its entirety herein). Thus, in some alternatives, dCas9 is fused to a functional catalytic domain of a histone modifying enzyme. In some alternatives, dCas9 is fused to a functional catalytic domain, for example, a catalytic core of a histone acetyltransferase. In some alternatives, dCas9 is fused to a functional catalytic domain of a histone deacetylase. In some alternatives, dCas9 is fused to a functional catalytic domain of a histone methyl transferase. In some alternatives, dCas9 fused to a functional catalytic domain of a histone modifying enzyme can activate transcription. In some alternatives, dCas9 fused to a functional catalytic domain of a histone modifying enzyme can repress transcription.

A set of fully orthogonal Cas9 proteins mediated simultaneous and independently targeted gene regulation and editing in bacteria and in human cells (Esvelt et al). In some alternatives, the Cas9 variants recognize different variants of PAM (Kleinstiver et al). A PAM is a DNA sequence immediately following a DNA sequence targeted by Cas9. Thus, in some alternatives, Cas9 is from *S. pyogenes*. In some alternatives, an *S. pyogenes* Cas9 variant can recognize an NGG protospacer PAM. In some alternatives, an *S. pyogenes* Cas9 variant can recognize a PAM that is not NGG. In some alternatives, Cas9 variants can be from *Staphylococcus aureus*. In some alternatives, Cas9 variants can be from *Streptococcus thermophiles*. In some alternatives, Cas9 variants can be from *Neisseria meningitidis*. In some alternatives, Cas9 variants can be is from *Treponema denticola*. In some alternatives, the sequence of Cas9 can be a Cas9 consensus sequence derived from two or more of the organisms provided herein, for example, *Staphylococcus aureus* and *Streptococcus thermophiles*. In some alternatives, the sequence of Cas9 can be from any of the organisms provided herein and codon optimized for expression in any of the other organisms provided herein.

Examples of desirable alternatives of Cas9 include Cas9 from *S. pyogenes* and variants thereof. In some alternatives, Cas9 can be from *S. pyogenes*. In some alternatives, Cas9 can be a variant of Cas9 from *S. pyogenes*. In some alternatives, Cas9 can be an ortholog of Cas9 from *S. pyogenes*. In some alternatives, Cas9 can be a variant of an ortholog of Cas9 from *S. pyogenes*. In some alternatives, Cas9 is catalytically inactive. In some alternatives, a dCas9 is inactive because of mutations. In some alternatives, a dCas9 is inactive because of mutations D10A and H841A in the protein sequence.

A modular Cas9 architecture for inducible genome editing and transcription modulation was reported in which Cas9 was split into an N terminal piece and a C terminal piece, each catalytically active and fused to a dimerization domain. The two dimerization domains of each of the two Cas9 pieces were brought together by a small molecule (for example, a drug) to generate a functional Cas9 capable of generating a double strand break (Zetsche et al; incorporated by reference in its entirety herein). Thus, in some alternatives, an N terminal fragment of Cas9 is used. In some alternatives, a C terminal fragment of Cas9 is used. In some alternatives, an N terminal fragment of Cas9 is used in combination a C terminal fragment of Cas9. In some alternatives, an N terminal fragment of Cas9 is fused to a dimerization domain. In some alternatives, a C terminal fragment of Cas9 is fused to a dimerization domain. In some alternatives, the dimerization domains dimerize. In some alternatives, the dimerization domains do not dimerize. In some alternatives, the dimerization domains dimerize in the presence of a small molecule, for example, a drug. In some alternatives, the dimerization domains do not dimerize in the presence of a small molecule, for example, a drug. In some alternatives, the dimerization domains dimerize in the absence of a small molecule, for example, a drug. In some alternatives, the dimerization domains do not dimerize in the absence of a small molecule, for example, a drug. In some alternatives, dimerization of the dimerization domains brings the N and C terminal fragments of Cas9 into close proximity. In some alternatives, a double stranded DNA break is created at a target genomic locus when the two Cas9 fragments are brought into close proximity. Examples of desirable alternatives of N terminal fragments of Cas9 can be Cas9 fragments extending from amino acids 1-203, 1-256, 1-311, 1-535, 1-573, 1-714, 1-1004, 1-1055, 1-1115, 1-1153 or 1-1246. Examples of desirable alternatives of C terminal fragments of Cas9 can be Cas9 fragments extending from amino acids 204-1368, 257-1368, 312-1368, 536-1368, 574-1368, 715-1368, 1005-1368, 1056-1368, 1116-1368, 1154-1368 or 1247-1368.

Endonuclease-based Gene Editing in Primary Human T-cells

Many future therapeutic applications of RNA-guided endonucleases are likely to require their use to promote gene targeting, thus necessitating development of methods that provide for delivery of three components—endonuclease, guide RNAs and recombination templates—to primary cells rendered proficient for homology-directed repair to achieve gene disruption and/or gene targeting for recombination.

For example, many future therapeutic applications of CRISPR/Cas9 and related RNA-guided endonucleases are likely to require their use to promote gene targeting, thus necessitating development of methods that provide for delivery of three components—Cas9, guide RNAs and recombination templates—to primary cells rendered proficient for homology-directed repair. Thus, in some alternatives, a CRISPR gene editing in primary human T-cells using mRNA/AAV co-delivery is contemplated.

In some alternatives, a high efficiency CRISPR/Cas9-mediated gene editing in primary human T-cells using mutant adenoviral E4ORF6/E1B55K "helper" proteins are provided.

In some alternatives, an electroporation/transduction co-delivery method that utilizes mRNA to express Cas9 in conjunction with mutant adenoviral E4ORF6 and E1B55K helper proteins is provided. In some alternatives, the mutant adenoviral E4ORF6 and E1B55K helper proteins serve to transiently enhance both the target cells' permissiveness to AAV transduction and its gene editing efficiency.

In some alternatives, the system and/or method provided herein can be applied for efficient gene disruption at one or more loci and/or simultaneously at multiple loci in cells in general is contemplated. In some alternatives, the system and/or method provided herein can be applied for efficient homologous gene targeting at one or more loci and/or simultaneously at multiple loci in cells in general is contemplated. In some alternatives, the system and/or method provided herein can be applied for efficient gene disruption and homologous gene targeting at one or more loci and/or simultaneously at multiple loci in cells in general is contemplated.

In some alternatives, the system and/or method provided herein can be applied for efficient gene disruption at one or more loci and/or simultaneously at multiple loci in primary cells is contemplated. In some alternatives, the system and/or method provided herein can be applied for efficient homologous gene targeting at one or more loci and/or simultaneously at multiple loci in primary cells is contemplated. In some alternatives, the system and/or method provided herein can be applied for efficient gene disruption and homologous gene targeting at one or more loci and/or simultaneously at multiple loci in primary cells is contemplated.

In some alternatives, the system and/or method provided herein can be applied for efficient gene disruption at one or more loci and/or simultaneously at multiple loci in primary T-cells is contemplated. In some alternatives, the system and/or method provided herein can be applied for efficient homologous gene targeting at one or more loci and/or simultaneously at multiple loci in primary T-cells is contemplated. In some alternatives, the system and/or method provided herein can be applied for efficient gene disruption and homologous gene targeting at one or more loci and/or simultaneously at multiple loci in primary T-cells is contemplated.

In some alternatives, the system and/or method provided herein can be applied for both efficient gene disruption and/or homologous gene targeting at one or more loci and/or simultaneously at multiple loci in human cells in general, illustrating its broad potential for application in translational gene editing. For example, in some alternatives, this method can be applied for both efficient gene disruption and/or homologous gene targeting at multiple loci in primary human T-cells, illustrating its broad potential for application in translational gene editing.

Preferred Alternatives

In some alternatives, a system for editing at least one target gene in a cell, the system comprising a first nucleic acid sequence, or a set of nucleic acid sequences, encoding one or more CRISPR guide RNA, wherein the one or more CRISPR guide RNA is complimentary to the at least one target gene in a cell and, wherein the first nucleic acid sequence, or the set of nucleic acid sequences, may be comprised in one or more vectors, but not required to be comprised in one or more vectors; a Cas9 protein or a second nucleic acid sequence encoding a Cas9 protein; a third nucleic acid sequence encoding a first adenoviral protein; and a fourth nucleic acid sequence encoding a second adenoviral protein.

In some alternatives of the system, the cell is a eukaryotic cell. In some alternatives of the system, the cell is a mammalian cell. In some alternatives of the system, the cell is a human cell. In some alternatives of the system, the cell is a primary cell. In some alternatives of the system, the cell is not a transformed cell. In some alternatives of the system, the cell is a primary lymphocyte, a CD34+ stem cell, a hepatocyte, a cardiomyocyte, a neuron, a glial cell, a muscle cell or an intestinal cell.

In some alternatives of the system, the vector is a viral vector. In some alternatives of the system, the viral vector is an Adeno-associated virus (AAV) vector. In some alternatives of the system, the AAV vector is a self-complementary vector. In some alternatives of the system, the AAV vector is a single stranded vector. In some alternatives of the system, the AAV vector is a combination of a self-complementary vector and a single stranded vector.

In some alternatives of the system, the second nucleic acid encoding the Cas9 protein is an mRNA. In some alternatives of the system, the second nucleic acid sequence encoding the Cas9 protein is codon optimized for expression in a eukaryotic cell, such as a human cell.

In some alternatives of the system, the Cas9 protein is from *S. pyogenes*.

In some alternatives of the system, the third nucleic acid encoding the first adenoviral protein is an mRNA. In some alternatives of the system, the third nucleic acid encoding the first adenoviral protein is codon optimized for expression in a eukaryotic cell, such as a human cell. In some alternatives of the system, the first adenoviral protein is from an AAV of serotype 5.

In some alternatives of the system, the first adenoviral protein is a wild type E4ORF6. In some alternatives of the system, the sequence of the wild type E4ORF6 is set forth in SEQ ID NO: 3. In some alternatives of the system, the first adenoviral protein is a mutant E4ORF6. In some alternatives of the system, the mutant E4ORF6 protein is an AXA mutant. In some alternatives of the system, the AXA mutant is set forth in SEQ ID NO: 23.

In some alternatives of the system, the fourth nucleic acid encoding the second adenoviral protein is an mRNA. In some alternatives of the system, the fourth nucleic acid encoding the second adenoviral protein is codon optimized for expression in a eukaryotic cell, such as a human cell. In some alternatives of the system, the second adenoviral protein is from an AAV of serotype 5.

In some alternatives of the system, the second adenoviral protein is a wild type E1B55K. In some alternatives of the system, the sequence of the wild type E1B55K is set forth in SEQ ID NO: 1. In some alternatives of the system, the second adenoviral protein is a mutant E1B55K. In some alternatives of the system, the mutant E1B55K is an H373A mutant. In some alternatives of the system, the sequence of the H373A mutant is set forth in SEQ ID NO: 2. In some alternatives of the system, the mutant E1B55K is an H354 mutant. In some alternatives of the system, the sequence of the H354 mutant is set forth in SEQ ID NO: 4. In some alternatives of the system, the mutant E1B55K is an R240A mutant. In some alternatives of the system, the sequence of R240A mutant is set forth in SEQ ID NO: 22.

In some alternatives of the system, the first, second, third and fourth nucleic acid sequences are operably linked to regulatory elements that are operable in a eukaryotic cell, such as a human cell.

In some alternatives of the system, the first nucleic acid sequence encoding one or more CRISPR guide RNA is operably linked to a regulatory element. In some alternatives of the system, the first nucleic acid sequence encoding one or more CRISPR guide RNA is operably linked to a U6 promoter. In some alternatives of the system, when the first nucleic acid sequence encodes more than one CRISPR guide RNA, each guide RNA is operably linked to a separate regulatory element.

In some alternatives of the system, the first nucleic acid sequence encoding the CRISPR guide RNA is constitutively expressed. In some alternatives of the system, the first nucleic acid sequence encoding the CRISPR guide RNA is transiently expressed.

In some alternatives of the system, the CRISPR guide RNA sequences for the TCRα gene are set forth in SEQ ID NO: 5, SEQ ID NO: 15, SEQ ID NO: 16 and/or SEQ ID NO: 17.

In some alternatives of the system, the CRISPR guide RNA sequence for the PD1 gene is set forth in SEQ ID NO: 18, for the TIGIT gene is set forth in SEQ ID NO: 19, for the Lag3 gene is set forth in SEQ ID NO: 20, and for the Tim3 gene is set forth in SEQ ID NO: 21.

In some alternatives of the system, the system can be used for gene knockout, gene knock-in, or both.

In some alternatives of the system, the first nucleic acid sequence, or the set of nucleic acid sequences, and the Cas9 protein or the second nucleic acid sequence encoding the Cas9 protein, are collectively replaced by a fifth nucleic sequence and a sixth nucleic acid sequence, wherein the fifth and sixth nucleic acid sequences comprise mRNAs encoding a left component and a right component of a TALEN nuclease, respectively.

In some alternatives, a method for editing at least one target gene in a cell, the method comprising introducing into a cell a first nucleic acid sequence, or a set of nucleic acid sequences, encoding one or more CRISPR guide RNA, wherein the one or more CRISPR guide RNA is complimentary to at least one target gene in the cell; introducing into the cell a Cas9 protein or a second nucleic acid sequence encoding a Cas9 protein; introducing into the cell a third nucleic acid sequence encoding a first adenoviral protein; and introducing into the cell a fourth nucleic acid sequence encoding a second adenoviral protein.

In some alternatives of the method, the cell is a eukaroytic cell. In some alternatives of the method, the cell is a mammalian cell. In some alternatives of the method, the cell is a human cell. In some alternatives of the method, the cell is a primary cell. In some alternatives of the method, the cell is not a transformed cell. In some alternatives of the method, the cell is a primary lymphocyte, a CD34+ stem cell, a hepatocyte, a cardiomyocyte, a neuron, a glial cell, a muscle cell or an intestinal cell.

In some alternatives of the method, the vector comprising the first nucleic acid sequence, or a set of nucleic acid sequences, encoding the one or more CRISPR guide RNAs, may be comprised in one or more vectors, but not required to be comprised in one or more vectors. In some alternatives of the method, the viral vector is an Adeno-associated virus (AAV) vector. In some alternatives of the method, the AAV vector is a self-complementary vector. In some alternatives of the method, the AAV vector is a single stranded vector. In some alternatives of the method, the AAV vector is a combination of a self-complementary vector and a single stranded vector.

In some alternatives of the method, the second, third and fourth nucleic acid sequences are mRNA. In some alternatives of the method, the mRNAs are codon optimized for expression in a eukaryotic cell, such as a human.

In some alternatives of the method, the Cas9 protein is from *S. pyogenes*.

In some alternatives of the method, the first adenoviral protein is from an AAV of serotype 5. In some alternatives of the method, the first adenoviral protein is a wild type E4ORF6. In some alternatives of the method, the sequence of the wild type E4ORF6 is set forth in SEQ ID NO: 3.

In some alternatives of the method, the first adenoviral protein is a mutant E4ORF6. In some alternatives of the method, the mutant E4ORF6 protein is an AXA mutant. In some alternatives of the method, the sequence of the AXA mutant is set forth in SEQ ID NO: 23.

In some alternatives of the method, the second adenoviral protein is from an AAV of serotype 5. In some alternatives of the method, the second adenoviral protein is a wild type E1B55K. In some alternatives of the method, the sequence of the wild type E1B55K is set forth in SEQ ID NO: 1. In some alternatives of the method, the second adenoviral protein is a mutant E1B55K. In some alternatives of the method, the mutant E1B55K is an H373A mutant. In some alternatives of the method, the sequence of the H373A mutant is set forth in SEQ ID NO: 2. In some alternatives of the method, the mutant E1B55K is an H354 mutant. In some alternatives of the method, the sequence of the H354 mutant is set forth in SEQ ID NO: 4. In some alternatives of the method, the mutant E1B55K is an R240A mutant. In some alternatives of the method, the sequence of R240A mutant is set forth in SEQ ID NO: 22. In some alternatives of the method, wherein any one of the E4ORF6 variants can be used in combination with any one the E1B55K variants.

In some alternatives of the method, the number of genes that are simultaneously knocked out is 2-10. In some alternatives of the method, the number of genes that are simultaneously knocked out is 2-5. In some alternatives of the method, the dose of mRNA is 0.01 μg to 1 μg. In some alternatives of the method, there is a 1.5 fold to 9 fold increase in the rate of mutations.

In some alternatives of the method, the CRISPR guide RNA sequences for the TCRα gene are set forth in SEQ ID NO: 5, SEQ ID NO: 15, SEQ ID NO: 16 and/or SEQ ID NO: 17.

In some alternatives of the method, the CRISPR guide RNA sequence for the PD1 gene is set forth in SEQ ID NO: 18, for the TIGIT gene is set forth in SEQ ID NO: 19, for the Lag3 gene is set forth in SEQ ID NO: 20, and for the Tim3 gene is set forth in SEQ ID NO: 21.

In some alternatives of the method, the first, second, third and fourth nucleic acid sequences are transiently introduced into the cell. In some alternatives of the method, the first, second, third and fourth nucleic acid sequences are not permanently introduced into the cell. In some alternatives of the method, introducing the first, second, third and fourth nucleic acid sequences into the cell do not transform the cell.

In some alternatives of the system, the target gene is a gene of interest. In some alternatives of the method, the target gene is a gene of interest.

In some alternatives of the system and/or method provided herein, the third nucleic acid sequence and fourth nucleic acid sequence are comprised in the AAV vector.

In some alternatives of the method, the second nucleic acid sequence is introduced into the cell first followed by the AAV vector comprising the first nucleic acid sequence, the second nucleic acid sequence, and the third nucleic acid sequence.

In some alternatives of the method, the AAV vector comprising the first nucleic acid sequence, the second nucleic acid sequence, and the third nucleic acid sequence is introduced into the cell first followed by second nucleic acid sequence.

In some alternatives of the method, the second nucleic acid sequence and the AAV vector comprising the first nucleic acid sequence, the second nucleic acid sequence, and the third nucleic acid sequence are co-delivered and introduced into the cell at the same time.

In some alternatives of the method, the system can be used for gene knockout, gene knock-in, or both.

In some alternatives of the method, the first nucleic acid sequence, or the set of nucleic acid sequences, and the Cas9 protein or the second nucleic acid sequence encoding the Cas9 protein, are collectively replaced by a fifth nucleic sequence and a sixth nucleic acid sequence, wherein the fifth and sixth nucleic acid sequences comprise mRNAs encoding a left component and a right component of a TALEN nuclease, respectively.

In some alternatives, a method for editing at least one target gene in a cell, comprising introducing into a cell any of the alternatives of the system provided herein.

In some alternatives, a method for treating, ameliorating, and/or inhibiting a disease and/or a condition in a subject, the method comprising providing to a subject having a disease and/or a condition any of the alternatives of the system provided herein.

In some alternatives, a system for editing at least one target gene in a cell and a method of using the system for genome editing are contemplated. In some alternatives, the target gene is a gene of interest, which is edited by can be either gene disruption. In some alternatives, the cell is a primary T-cell.

In some alternatives, the system comprises a first nucleic acid sequence encoding one or more guide RNA and a second nucleic acid sequence encoding an endonuclease protein. In some alternatives, the endonuclease can be any of the endonucleases disclosed herein and/or alternative variants and modifications of that are within the scope of the current disclosure. In some alternatives, the second nucleic acid is an mRNA and encodes any of the endonuclease protein. In some alternatives, the second nucleic acid sequence encoding the endonuclease protein is codon optimized for expression in a eukaryotic cell. In some alternatives, the one or more guide RNA is complimentary to the at least one target gene in a cell. In some alternatives, the one or more guide RNA is provided in a vector. In some alternatives, the vector can be a viral vector. In some alternatives, the viral vector is an Adeno-associated virus (AAV) vector. In some alternatives, the AAV vector can be a self-complementary vector, or a single stranded vector, or a combination of a self-complementary vector and a single stranded vector.

As many cell types possess a post-entry restriction on AAV vectors that renders AAV-mediated expression of transgenes, including guide RNAs, very inefficient, proteins that suppress the post-entry restriction on AAV vectors are provided on additional nucleic acid sequences. Thus, in some alternatives, the system comprises a third nucleic acid sequence encoding a first adenoviral protein and a fourth nucleic acid sequence encoding a second adenoviral protein. In some alternatives, the third nucleic acid and the fourth nucleic acid are mRNAs, which are codon optimized for expression in a eukaryotic cell. In some alternatives, the nucleic acid sequences can either be introduced into the cell sequentially and in any order or be introduced into the cell simultaneously.

In some alternatives, the first and second adenoviral proteins are from an AAV of serotype 5. In some alternatives, the first adenoviral protein is a wild type E4ORF6, or an AXA mutant of E4ORF6. In some alternatives, the second adenoviral protein is a wild type E1B55K, or an H373A mutant of E1B55K, or an H354 mutant of E1B55K, or an R240A mutant of E1B55K. While the mutant proteins are not as efficient as wild type proteins at suppressing at post-entry restriction on AAV vectors, they are relatively more efficient at enhancing gene targeting.

In some alternatives, the first, second, third and fourth nucleic acid sequences are operably linked to regulatory elements that are operable in a eukaryotic cell. In some alternatives, the first nucleic acid sequence can encode one or more guide RNA and each guide RNA is operably linked to a separate regulatory element. In some alternatives, the first nucleic acid sequence encoding the guide RNA is transiently expressed in the cell. In some alternatives, the one or more guide RNA sequences are complementary to the TCRα gene, the PD1 gene, the TIGIT gene, the Lag3 gene, and/or the Tim3 gene. In some alternatives, the system also comprises nucleic acid sequences regions that bear homology to the gene of interest.

In some alternatives, the system comprising the above-mentioned components is introduced into the primary T cell. These nucleic acid sequence regions that bear homology to the gene of interest direct the endonuclease-based system to be targeted to a specific gene. Targeting to the specific gene can result in a gene knockout, a gene knock-in, or both.

Depending on the nature of gene targeting approach (knockout or knock-in) the result can be determined by flow cytometry, or sequencing or both. For example, if the system is used for knocking out a gene of interest that encodes a cell surface-expressed protein, flow cytometry can be used to check for suppressed and/or lack of cell surface expression of the protein. Or, if the system is used for knocking out a gene of interest that encodes an intracellularly-expressed protein, flow cytometry can be used to check for suppressed and/or lack of intracellular expression of the protein. Or, if the system is used for knock-in, for example, knock-in of a dominant epitope of an antigen into a gene of interest that encodes a cell surface-expressed protein, flow cytometry can be used to check for cell surface expression of the dominant epitope. Or, if the system is used for knock-in, for example, knock-in of a dominant epitope of an antigen into a gene of interest that encodes an intracellularly-expressed protein, flow cytometry can be used to check for intracellular expression of the dominant epitope. In any of the above cases, the DNA sequencing of genomic DNA can also be used to confirm the desired gene targeting event. In some alternatives, the number of genes that can be simultaneously targeted for knockout, knock-in or both can be 2-5.

In some alternatives, the T-cells in which the gene of interest has been targeted are enriched by cell sorting or other cell enrichments methods. If the enriched cells are intended to be used for treating, ameliorating, and/or inhibiting a disease and/or a condition in a subject, the enriched cells are administered to the subject. For example, in some alternatives, the subject may have a disease and/or a condition because the T-cells in the subject are "exhausted," and therefore, are not effective at clearing one or more antigens from the disease and/or condition.

By targeting one or more "exhaustion" markers (e.g., PD1, TIGIT, Lag3 and Tim3), the "exhausted" condition of T-cells can be reversed. In some alternatives, the targeted T-cells are administered to the subject (e.g., via the intravenous route). Follow-up testing is performed on the subject to assess the status of the targeted T-cells and their effect on the disease and/or condition. For example, in some alternatives, blood is drawn from the subject at various intervals following administration of the targeted T-cells. In some alternatives, testing is performed to determine whether the administered T-cells are activated, for example, by assessing their secretion of the cytokine (e.g., IL-2, TNFα). In some alternatives, testing is also performed to determine the effect of administration of the targeted T-cells on the disease and/or condition.

Any of the systems and/or methods provided herein in regard to humans can also be provided to one or more companion animals or animals domesticated for commercial interest. A companion animal, without limitations, can be dog, cat, guinea pig, mouse, rat, rabbit or hamster. An animal domesticated for commercial interest, without limitations, can be goat, sheep, cow, pig, monkey or elephant.

Detailed below are some non-limiting examples with references to figures illustrating how CRISPR gene editing can be implemented. These examples are not meant to be limiting and other endonucleases and alternatives of the system and methods comprising other endonucleases and variants and modifications of these exemplary alternatives are possible without undue experimentation. All such variations and modifications are within the scope of the current teachings.

EXAMPLE 1

An mRNA/AAV Delivery Method Effects Cas9-mediated Gene Disruption in Primary Human T-Cells In some alternatives, CRISPR gene editing in primary human T-cells using mRNA/AAV co-delivery is provided.

AAV6 capsid-based AAV vectors are able to achieve sufficient transduction efficiencies of human primary T-cells and CD34+ cells to serve as templates for TALEN and other nuclease-catalyzed homologous recombination. Thus, it was hypothesized that AAV vectors might serve as safe and effective vectors for transient expression of guide RNAs as well as delivery of recombination templates for Cas9-induced gene targeting.

In some alternatives, cell used can be, without limitations, a primary lymphocyte, a CD34+ stem cell, a hepatocyte, a cardiomyocyte, a neuron, a glial cell, a muscle cell or an intestinal cell.

In some alternatives, the duration of transient expression of guide RNAs can be 1 min to 1 week or within a range defined by any two of the aforementioned values.

In some alternatives, the size of the recombination template can range from 0.05 kb to 1 kb. In some alternatives, the length of the homology arm can be 0.05, 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 or 1 kb or within a range defined by any two of the aforementioned values.

Through this series of experiments and our previous experience with other nuclease platforms, it was observed that performing the mRNA electroporation step first appeared to work most reliably. Thus, in some alternatives, mRNA electroporation followed by AAV transduction was adopted as our standard approach. In some preferred alternatives, mRNA electroporation is performed before AAV transduction.

In some alternatives, to evaluate the potential of an mRNA/AAV delivery method in which spCas9 was expressed through mRNA electroporation, and an AAV vector was used to provide guide RNA expression, an AAV construct was generated which included both a U6 promoter driven guide RNA cassette and an MND promoter driven GFP cassette—the latter provides for tracking of AAV transduction efficiency.

FIG. 1A, top panel, shows a schematic of mCherry and Cas9-T2A-mCherry constructs that were cloned in different in-house backbones to generate mRNA. FIG. 1A, middle and bottom panels, show schematic of guide position(s) within the TCR genomic locus. Self-complementary and single-stranded AAV vector backbones were used for expression of guides.

In some alternatives, one or more nucleases can be delivered using a single or a plurality of mRNAs. In some alternatives, 1 to 5 nucleases can be delivered using a single mRNA or a plurality of mRNAs. In some alternatives, 1, 2, 3, 4 or 5 nucleases can be delivered using a single mRNA or a plurality of mRNAs.

In some alternatives, delivery of nuclease(s), guide RNA (s), helper protein(s), template with homologous region(s), and any additional component(s) as may be required by AAV is contemplated. In some alternatives, delivery of any one of nuclease(s), guide RNA(s), helper protein(s), template with homologous region(s), and any additional component(s) as may be required by mRNA and the rest by AAV is contemplated. In some alternatives, delivery of any two of nuclease (s), guide RNA(s), helper protein(s), template with homologous region(s), and any additional component(s) as may be required by mRNA and the rest by AAV is contemplated. In some alternatives, delivery of any three of nuclease(s), guide RNA(s), helper protein(s), template with homologous region (s), and any additional component(s) as may be required by mRNA and the rest by AAV is contemplated. In some alternatives, delivery of any four of nuclease(s), guide RNA(s), helper protein(s), template with homologous region (s), and any additional component(s) as may be required by mRNA and the rest by AAV is contemplated. In some alternatives, delivery of nuclease(s), guide RNA(s), helper protein(s) and template with homologous region(s) by mRNA is contemplated.

In some alternatives, one or more reporters can be delivered using a single mRNA or a plurality of mRNAs. In some alternatives, 1 to 5 reporters can be delivered using a single mRNA or a plurality of mRNAs. In some alternatives, 1, 2, 3, 4 or 5 reporters can be delivered using a single mRNA or a plurality of mRNAs.

In some alternatives, one or more reporters can be delivered using AAV transduction. In some alternatives, 1 to 5 reporters can be delivered using AAV transduction. In some alternatives, 1, 2, 3, 4 or 5 reporters can be delivered AAV transduction.

In some alternatives, one or more nucleases and one or more reporters can be delivered using a single mRNA or a plurality of mRNAs. In some alternatives, 1 to 5 nucleases and 1 to 5 reporters can be delivered using a single mRNA or a plurality of mRNAs. In some alternatives, 1, 2, 3, 4 or 5 nucleases and 1, 2, 3, 4 or 5 reporters can be delivered using a single mRNA or a plurality of mRNAs.

In some alternatives, mRNA electroporation of Cas9 (as a Cas9-T2A-mCherry fusion) was tested both before and after AAV transduction for guide delivery, and moderately efficient Cas9 cleavage was achieved within the constant region of the TCRα gene using several protocols with two different guides.

In some alternatives, one or more guide RNAs can be delivered using AAV transduction. In some alternatives, 1 to 5 guide RNAs can be delivered using AAV transduction. In some alternatives, 1, 2, 3, 4 or 5 guide RNAs can be delivered AAV transduction.

In some alternatives, the use of chemically modified guide RNAs is contemplated. In some alternatives, chemically modified guide RNAs can be provided as separate RNAs. Thus, in some alternatives when one or more guide RNAs are designed against one or more target genes of interest, each guide RNA is provided as a separate chemically-modified guide RNA. For example, when the use of 10 guide RNAs is contemplated against 10 separate target genes of interest, each guide RNA is a chemically-modified guide RNA and each guide RNA is separate and distinct RNA molecule from the other guide RNAs. In some alternatives, the 10 different guide RNAs can be introduced into a cell either sequentially in any order or simultaneously.

In some alternatives, when the use of Cas9 protein pre-complexed with guide RNAs in conjunction with adenoviral proteins is contemplated, the guide RNAs are provided as chemically modified guide RNAs, wherein when one or more guide RNAs are designed against one or more target genes of interest, each guide RNA is provided as a separate chemically-modified guide RNA.

Thus, in some alternatives, mRNA electroporation can be performed before AAV transduction. In some alternatives, mRNA electroporation can be performed after AAV transduction. In some alternatives, mRNA and AAV can be co-delivered.

Figure 1B:
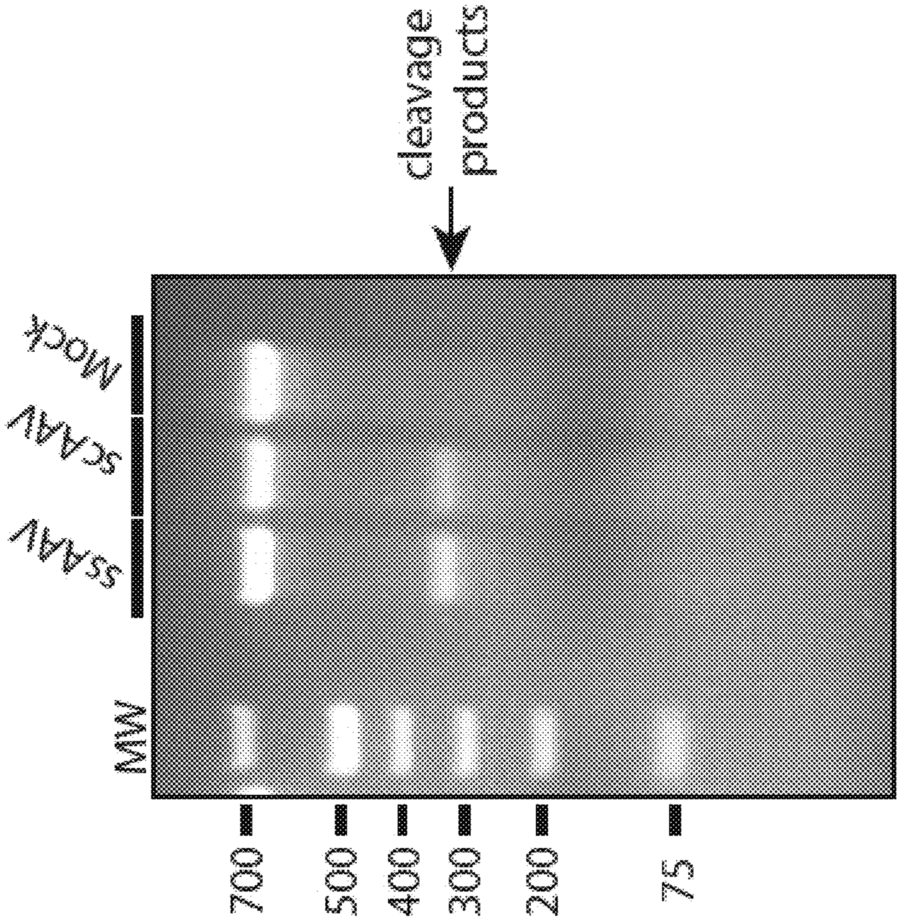
FIG. 1B shows T7 assay of editing-induced insertions-deletions (indels) at TCRα locus.
Figure 1C:
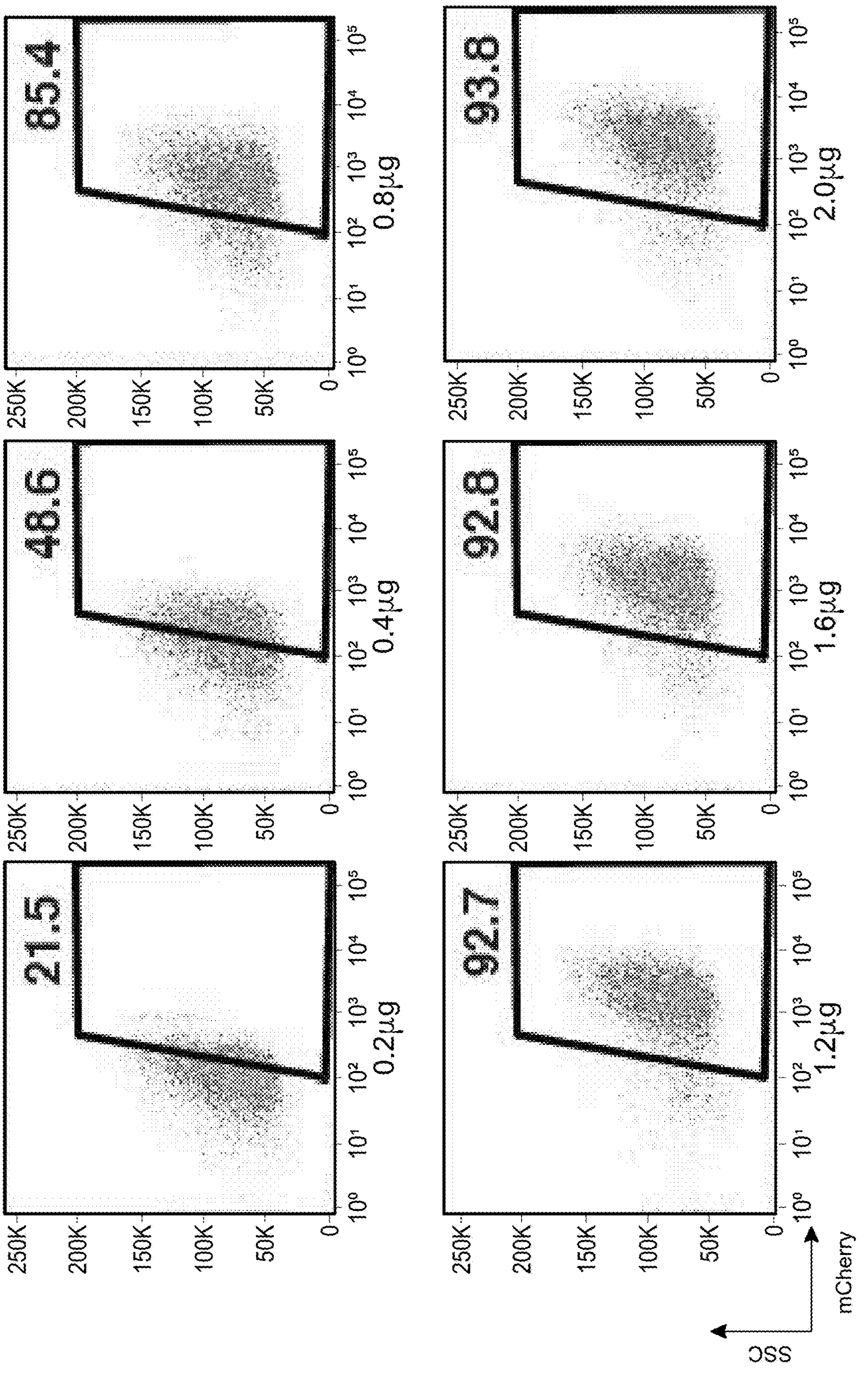
FIG. 1C shows the effect of Cas9-T2A-mCherry mRNA dose on expression at 24 h post transfection.

In some alternatives, for optimization of Cas9 mRNA transfection in primary human T-cells, CD4+ T-cells were transfected with varying concentrations of Cas9-T2A-mcherry mRNA using the Neon electroporation system and cultured at 30° C. for the initial 24 hrs, after which they were transferred to 37° C. Flow cytometry analysis of T-cells 24 hrs after electroporation with the indicated amounts of Cas9-T2A-mCherry mRNA (FIG. 1C). Percentages of mCherry positive cells are indicated in FIG. 1C.

Figure 1D:
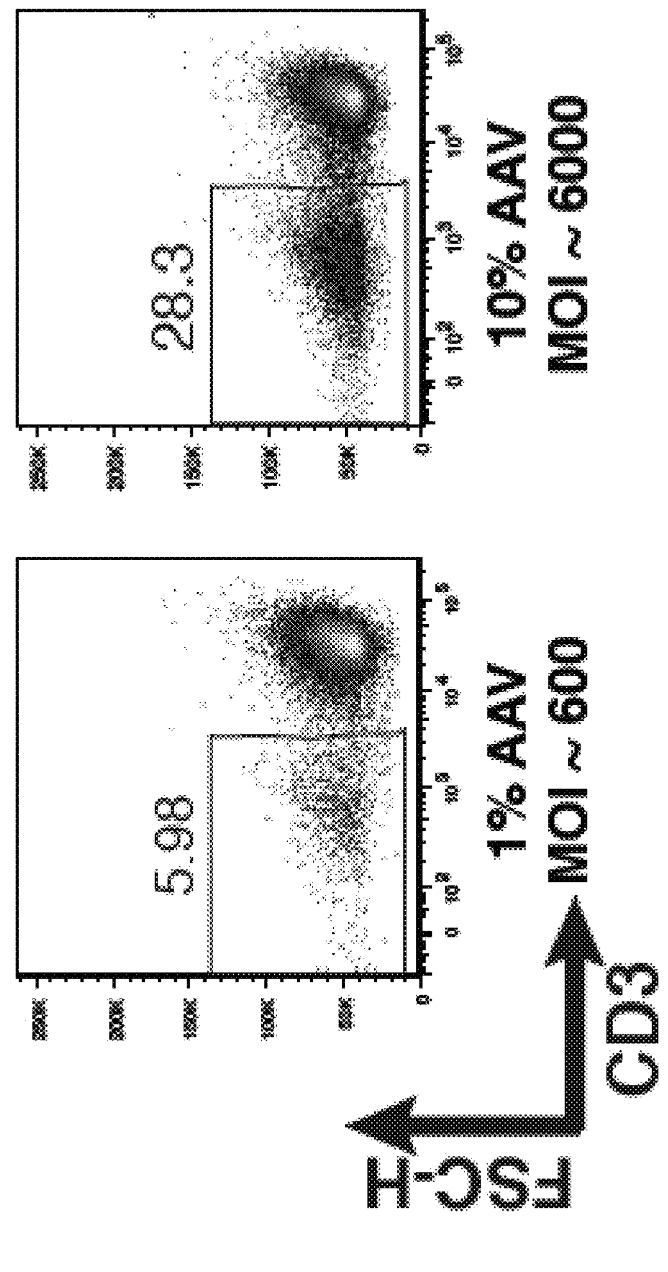
FIG. 1D shows the effect of increasing AAV dose on TCRα knockout.

In some alternatives, analysis of AAV-guide doses in primary human T-cells was performed by transfecting CD4+ T-cells with 1 μg of Cas9-T2A-mcherry mRNA. Two hours post-electroporation, cells were transduced with AAV expressing TCRα guide at MOI 600 and 6000 (corresponding to culture volume of 1% and 10%, respectively). Cells were cultured at 30° C. for the initial 24 hrs, after which cells were transferred to 37° C. and kept there for the duration of the experiment. Cells were analyzed by flow cytometry for loss of surface CD3 expression as an index of TCRα gene knockout on day 7 post EP/transduction (FIG. 1D).

In some alternatives, using the mRNA/AAV transduction protocol, a range of Cas9 mRNA and AAV-guide doses were evaluated (FIG. 1C and FIG. 1D) to determine ranges that maximize Cas9 cleavage efficiency and minimize toxicity. In some alternatives, while mRNA dose appeared to saturate (1 μg in our standard electroporation conditions). In some alternatives, the mRNA dose can range from 0.05 to 3 μg. In some alternatives, the mRNA dose can be 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75 or 3 μg or within a range defined by any two of the aforementioned doses.

In some alternatives, a dose-dependent increase in knockout with AAV up to the maximum tolerated MOI was observed. In some alternatives, the AAV dose can range from 60 to 60,000. In some alternatives, the AAV dose can range from 60, 125, 250, 500, 1,000, 2,000, 4,000, 8,000, 16,000, 30,000 or 60,000 or within a range defined by any two of the aforementioned doses.

In some alternatives, for T7 endonuclease I assay (T7EI) for cleavage following Cas9/AAV.sgRNA delivery into primary human T-cells, primary CD4+ T-cells were electroporated with Cas9 mRNA followed by AAV.sgRNA transduction 2 hours later. Ten days following electroporation/transduction, genomic DNA was isolated from the cells, and T7 endonuclease assay was performed (FIG. 1B). Arrow indicates the expected position of DNA bands cleaved by T7EI (FIG. 1B).

In some alternatives, Cas9 cleavage was detected as indel formation demonstrated by T7 assay of amplicons surrounding the predicted target site in TCRα (FIG. 1B). In some alternatives, loss of surface TCR/CD3 complex expression by flow cytometry (TCR/CD3 complex expression requires expression of a functional TCRα chain (FIG. 1D).

In some alternatives, T7 Endonuclease I assay yielded similar levels of cutting efficiency for both TCRα and CCR5 loci.

Figure 1E:
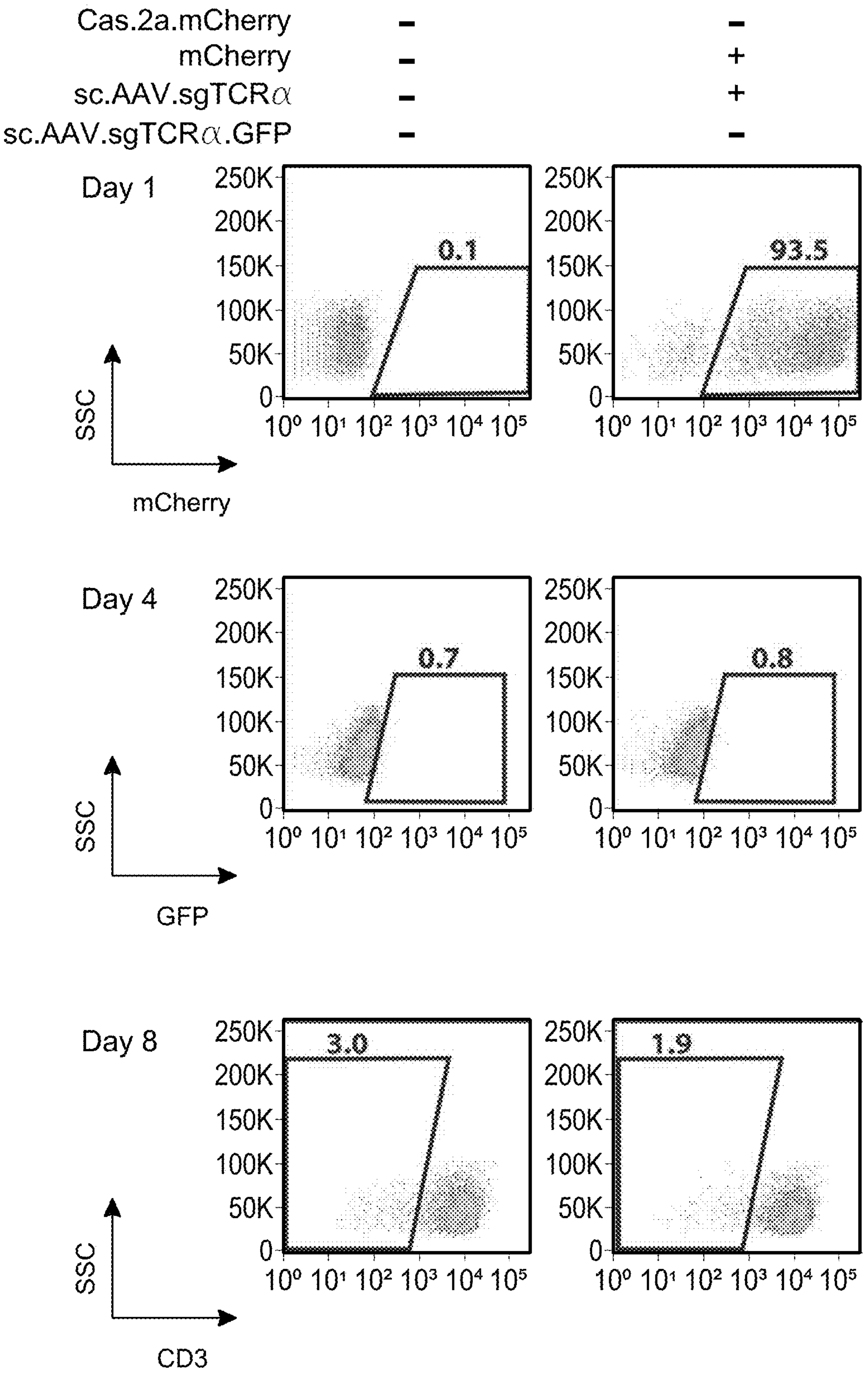
FIG. 1E shows flow cytometry data related to comparison of TCRα knockout with single stranded (ss) versus self-complementary (sc) AAV for guide expression in T-cells.

In some alternatives, both single stranded and self-complementary AAV vectors were compared (FIG. 1E). sgTCRα in FIG. 1E indicates single guide TCRα. In some alternatives, flow cytometric comparison was performed of TCRα knockout with scAAV and ssAAV-GFP by electroporating primary T-cells with mRNA encoding for control mCherry or Cas9-T2A-mCherry proteins, rested for 3 hours, and transduced with AAV driving guide RNA expression. Cells were cultured at 30° C. for the initial 24 hours, after which cells were transferred to 37° C. Cells were analyzed using flow cytometry for mCherry and GFP expression 24 and 96 hours following electroporation/transduction, and surface CD3 expression was analyzed at 7 days post electroporation/transduction.

In some alternatives, no significant differences was observed between self-complementary and single stranded AAV in the efficiency of Cas9 target cleavage as assessed by loss of surface CD3 (FIG. 1E). Thus, in some alternatives, Cas9-mRNA and guide-AAV mediated efficient TCR knockout in primary cells and both self-complementary and singe stranded guide RNA yielded similar levels of CD3 knockout.

Thus, in some alternatives the AAV vector can be single stranded. In some alternatives the AAV vector can be self-complementary. In some alternatives the AAV vector can be both single stranded and self-complementary.

EXAMPLE 2

Adenoviral Serotype 5 E4ORF6 and E1B55K Helper Proteins Enhance Permissiveness of Primary Human T-Cells to AAV Transduction In some alternatives, enhanced AAV-mediated gene expression in primary human T-cells using adenoviral E4ORF6/E1B55K proteins to relieve post-entry AAV restriction mechanisms is provided.

The dependence of Cas9 cleavage efficiency on AAV dose observed in our initial analyses suggested to us that efficiency of AAV transduction is a key limiting factor for application of the mRNA/AAV method in T-cells. AAV transduction in many human cell types is known to be subject to restriction at the cell entry stage by surface receptor expression binding properties of the capsid, and post-entry based on multiple mechanisms. In cultured transformed cells, plasmid-based expression of E4ORF6 and E1B55K proteins from multiple adenoviral serotypes is effective at relieving post-entry restrictions on AAV expression, among them genome concatamerization by DNA damage response proteins, activation of cell cycle DNA damage checkpoints, and pro-apoptotic DNA damage signaling.

Thus, in some alternatives, E4ORF6 and E1B55K proteins can be from multiple adenoviral serotypes. In some alternatives, the adenoviral serotypes can be Ad1, Ad2, Ad3, Ad4, Ad5, Ad6 or Ad7. Additional alternative serotypes are also contemplated and are within the scope of the current disclosure. In some alternatives, E4ORF6 and E1B55K proteins can be from the same adenoviral serotype. In some alternatives, E4ORF6 can be from one adenoviral serotype and E1B55K from a different serotype.

As DNA plasmid-based expression is toxic to primary T-cells, in some alternatives, it was evaluated whether electroporation of adenoviral serotype 5 E4ORF6/E1B55K mRNAs could achieve a transient relief of post-entry restriction of AAV-based expression in primary T-cells (FIG. 2).

Figure 2A:
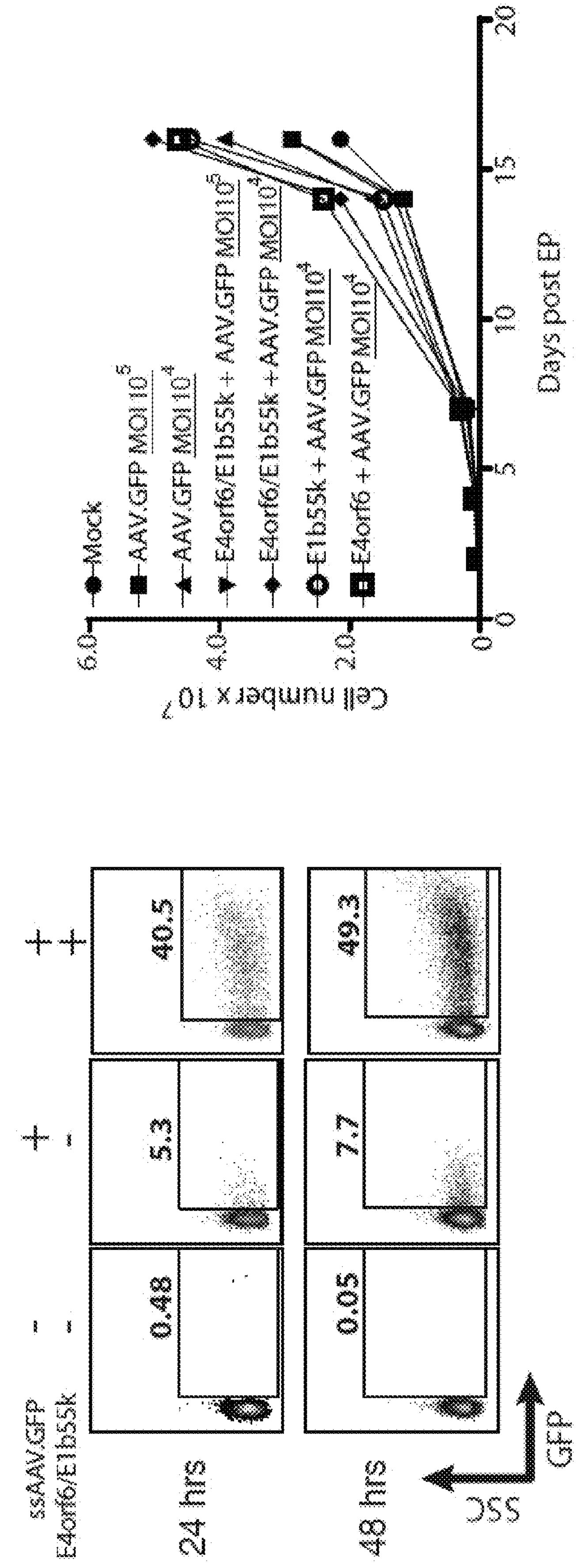
FIG. 2A shows data related to relief of post-entry restriction of AAV-mediated gene expression.

In some alternatives, for assessing AAV-mediated GFP expression following relief of post-entry AAV restriction by E4ORF6/E1B55K, primary CD4+ T-cells were electroporated with mRNA encoding adenoviral serotype 5 E4ORF6/E1B55K (0.33 μg each), rested for 2-4 hours, then transduced with AAV driving GFP expression. Cells were placed in culture for the indicated periods of time (FIG. 2A, left panel), following which the cells were collected and analyzed for GFP expression by flow cytometry. Expansion of cell populations following the indicated exposure to E4ORF6/E1B55K mRNA transfection and AAV transduction, following the same protocol as described in the left panel (FIG. 2A, right panel).

In some alternatives, following mRNA-based co-expression of E4ORF6/E1B55K in primary T-cells (but not either protein alone; data not shown), a 4 log increase in GFP mean fluorescence intensity (MFI), and an 8 fold increase in GFP expression, driven from an AAV vector encoding a promoter/GFP cassette (FIG. 2A, left panel), without compromising the rate of cell expansion (FIG. 2A, right panel) was obtained.

In some alternatives, the increase in MFI of GFP (or one or more other reporters) can range from 2 log to 8 log. In some alternatives, the increase in MFI of GFP (or one or more other reporters) can be 2 log, 3 log, 4 log, 5 log, 6 log, 7 log or 8 log or within a range defined by any two of the aforementioned values.

In some alternative, the increased GFP (or one or more other reporters) expression can range from 2 fold to 16 fold. In some alternative, the increased GFP (or one or more other reporters) expression can be 2 fold, 3 fold, 4 fold, 5 fold, 6 fold, 7 fold, 8 fold, 9 fold, 10 fold, 11 fold, 12 fold, 13 fold, 14 fold, 15 fold or 16 fold or within a range defined by any two of the aforementioned values.

Figure 2B:
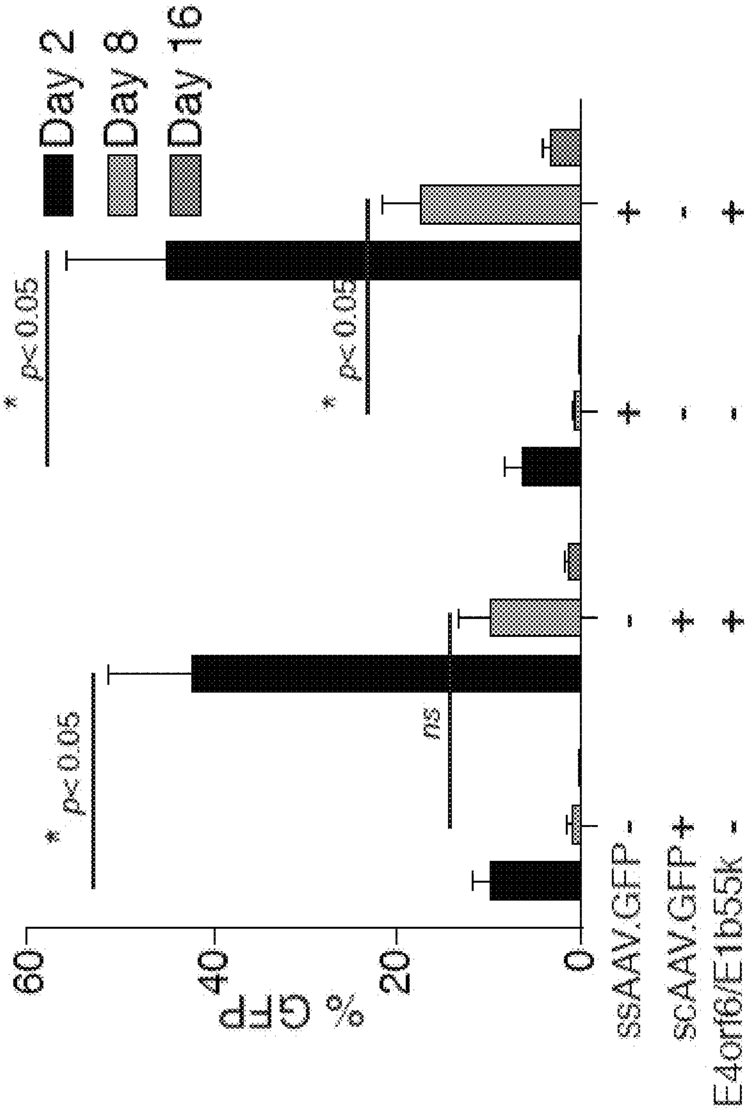
FIG. 2B shows data related to comparison of effect of E4ORF6/E1B55K proteins on self-complementary and single-stranded AAV6-mediated gene expression

In some alternatives, comparison of effect of E4ORF6/E1B55K proteins on self-complementary and single-stranded AAV6-mediated gene expression was performed by electroporating primary CD4+ T-cells with mRNA encoding E4ORF6/E1B55K proteins (0.33 μg each), rested for 2-4 hours, and transduced with either single-stranded or self-complementary AAV6 driving GFP expression (MOI of both viruses: $2\times10^4$) (FIG. 2B). Cells were placed in culture for the indicated periods of time, following which the cells were collected and analyzed for GFP expression by flow cytometry (FIG. 2B).

In some alternatives, the same enhancing effect was observed irrespective of whether a self-complementary or single stranded AAV was used (FIG. 2B), suggesting that E4ORF6/E1B55K complexes possess a robust capacity to relieve post-entry restrictions on AAV expression in primary human T-cells that is unrelated to initiation of second strand DNA synthesis. Thus, in some alternatives, the AAV vector can be single stranded. In some alternatives, the AAV vector can be self-complementary. In some alternatives, the AAV vector can be both single stranded and self-complementary.

EXAMPLE 3

MRN Complex is a Dominant Post-Entry Restriction Mechanism on AAV Transduction of Primary Human T-Cells In some alternatives, the effect of E4ORF6/E1b55K mutants on AAV-driven GFP expression was evaluated.

The ability of E4ORF6/E1B55K proteins to enhance AAV expression in cultured cell models has been reported to depend on their capacity to target the Mre11/Rad51/NBS1 DNA repair complex (MRN) for degradation, thus allowing incoming AAV genomes to escape intra-nuclear detection and silencing.

In some alternatives, to determine if this same mechanism applied to primary human T-cells, a comparison of AAV-driven gene expression alone or following transient expression of wild type E4ORF6/E1B55K proteins or E4ORF6/E1B55K-H373A and E4ORF6/E1B55K-H354 mutants (FIG. 2C) was performed. Both of these mutants have largely lost the capacity for inducing degradation of MRN, whilst fully preserving other functions of wild type E4ORF6/E1B55K.

Figure 2C:
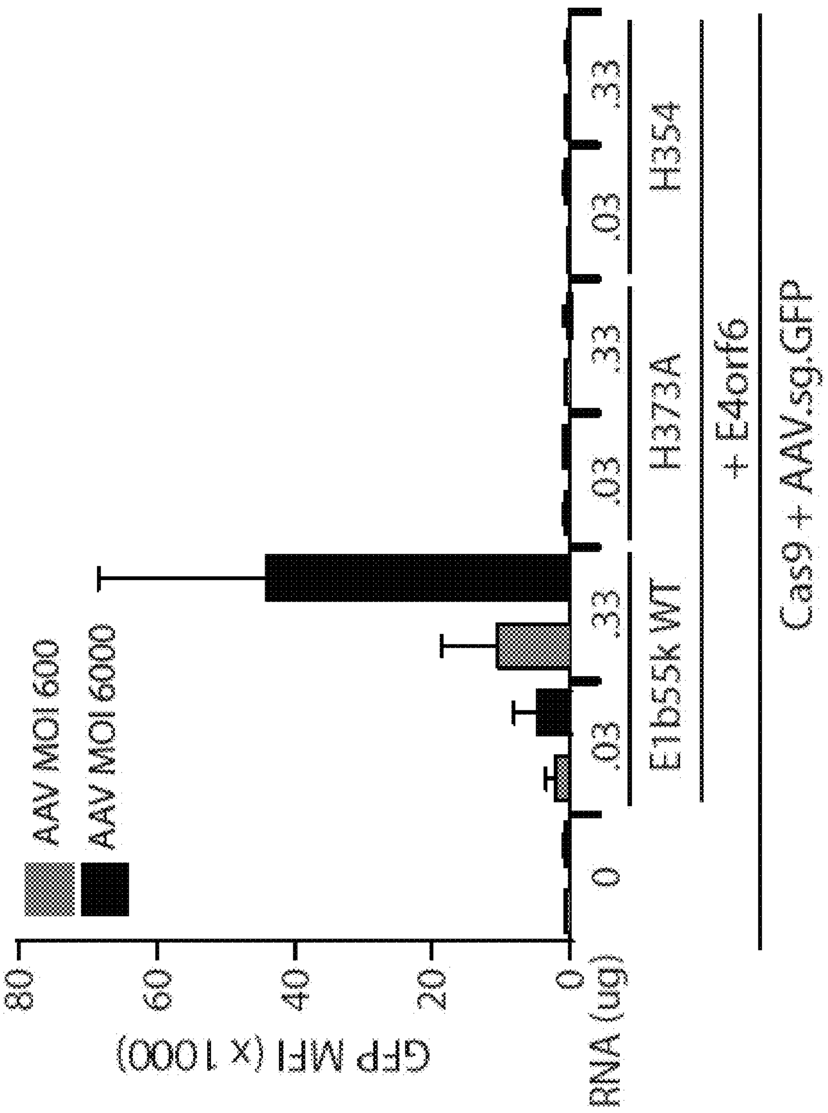
FIG. 2C shows data related to MRN inactivation and its effect of relief of post-entry restriction on AAV-mediated expression.

In some alternatives, primary CD4+ T-cells were electroporated with mRNA encoding Cas9-2A-mCherry (1 μg) along with E4ORF6/E1B55K (wild type) proteins or the indicated E1B55K mutants at the indicated RNA doses, rested for 2-4 hours, and transduced with ssAAV driving both TCRα guide and GFP expression (FIG. 2C). E4ORF6 mRNA dose was the same as each E1B55K RNA dose for each indicated point (FIG. 2C). Cells were placed in culture for 2 days, following which the cells were collected and analyzed for GFP MFI by flow cytometry. See also FIG. 3 demonstrating a 2-3 fold increase in GFP expression catalyzed by the E4ORF6/E1B55K H373A mutant complex that is not visible on the same scale as GFP expression catalyzed by the wild type E4ORF6/E1B55K complex.

In some alternatives, as assessed by GFP MFI, E1B55K mutants were markedly less efficient at relieving post-entry restrictions on AAV expression than wild type E4ORF6/E1B55K, in a dose-dependent manner. Thus, in some alternatives, E1B55K MRN degradation mutants demonstrate requirement for MRN inactivation for complete relief of post-entry restriction on AAV-mediated expression (FIG. 2C).

Figure 3A:
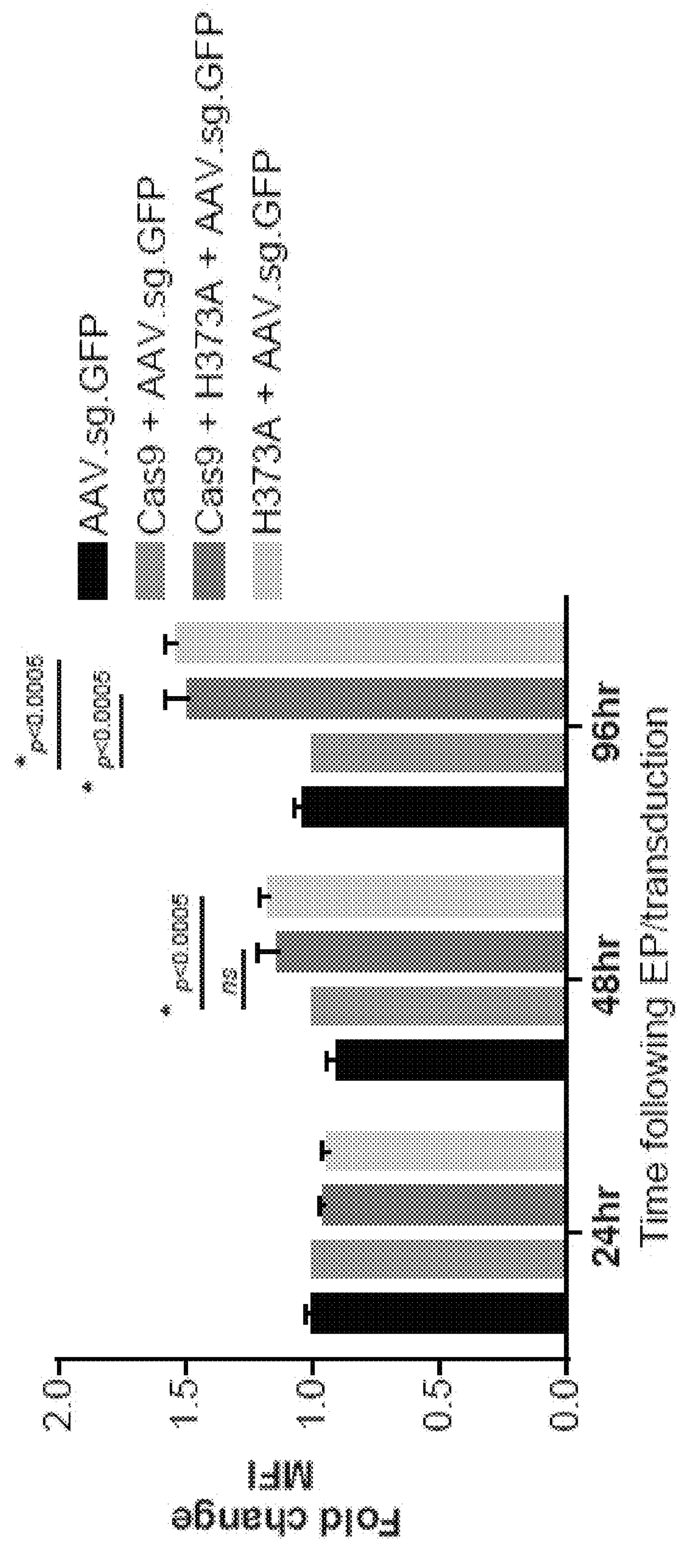
FIG. 3A shows the effect of E4ORF6/E1B55K mutants on AAV-driven GFP expression.
Figure 3B:
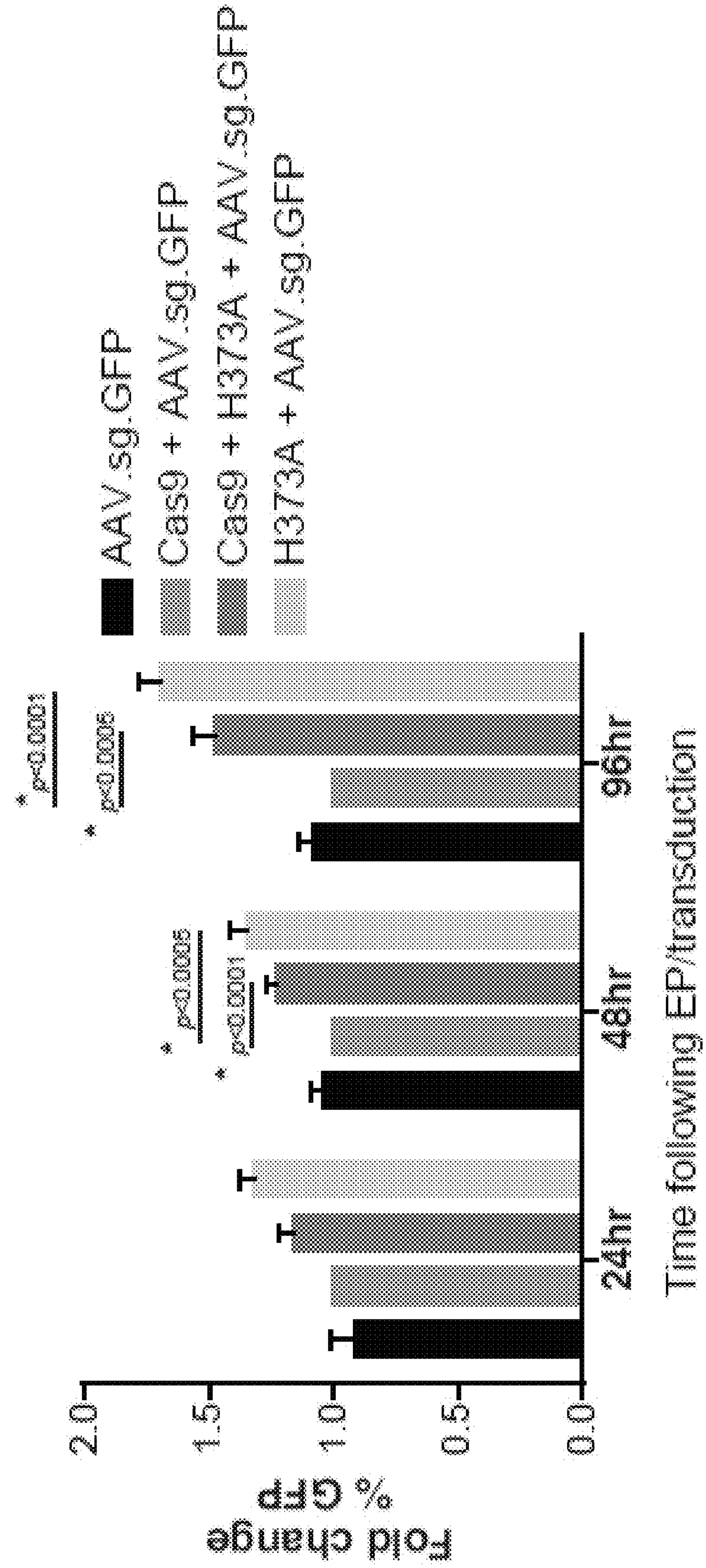
FIG. 3B shows the effect of E4ORF6/E1B55K-H373 expression on AAV transduction.

In some alternatives, replicate experiments were performed in which primary CD4+ or CD3+ human T-cells were electroporated with mRNA encoding Cas9-2A-mCherry proteins (1 μg) and either wild type or the indicated E4ORF6/E1B55K mutants (0.03 μg each), rested for 2-4 hours, and transduced with AAV driving guide expression and GFP. Cells were placed in culture for the indicated periods of time, following which the cells were collected and analyzed for GFP expression and mean fluorescence intensity (MFI) by flow cytometry and quantified. FIG. 3A and FIG. 3B represent n=5-6 independent experiments.

In some alternatives, replicate experiments using the E1B55K-H373A mutant, analyzed at a smaller scale, demonstrated that E4ORF6/E1B55K-H373A expression was able to support a level of GFP expression significantly greater (1.58±0.09-fold at 96 hours) than that observed in the absence of E4ORF6/E1B55K expression, consistent with its possessing a residual capacity to relieve post-entry transduction or expression restrictions (FIG. 3A and FIG. 3B).

In some alternatives, the role of other known E4ORF6/E1B55K functional capabilities in relieving post-entry restriction of AAV transduction in T-cells was evaluated using two additional mutants—E1B55K R240A (SEQ ID NO: 22; FIG. 33), which disrupts the ability of E1B55K to catalyze degradation of p53, and E4ORF6 AXA (SEQ ID NO: 23; FIG. 34), which binds inefficiently to E1B55K and results in generally hypofunctional E4ORF6/E1B55K complexes. In some alternatives, the E4ORF6 AXA mutant has two polymorphisms—R243A and L245A (SEQ ID NO: 23; FIG. 34).

Figure 3C:
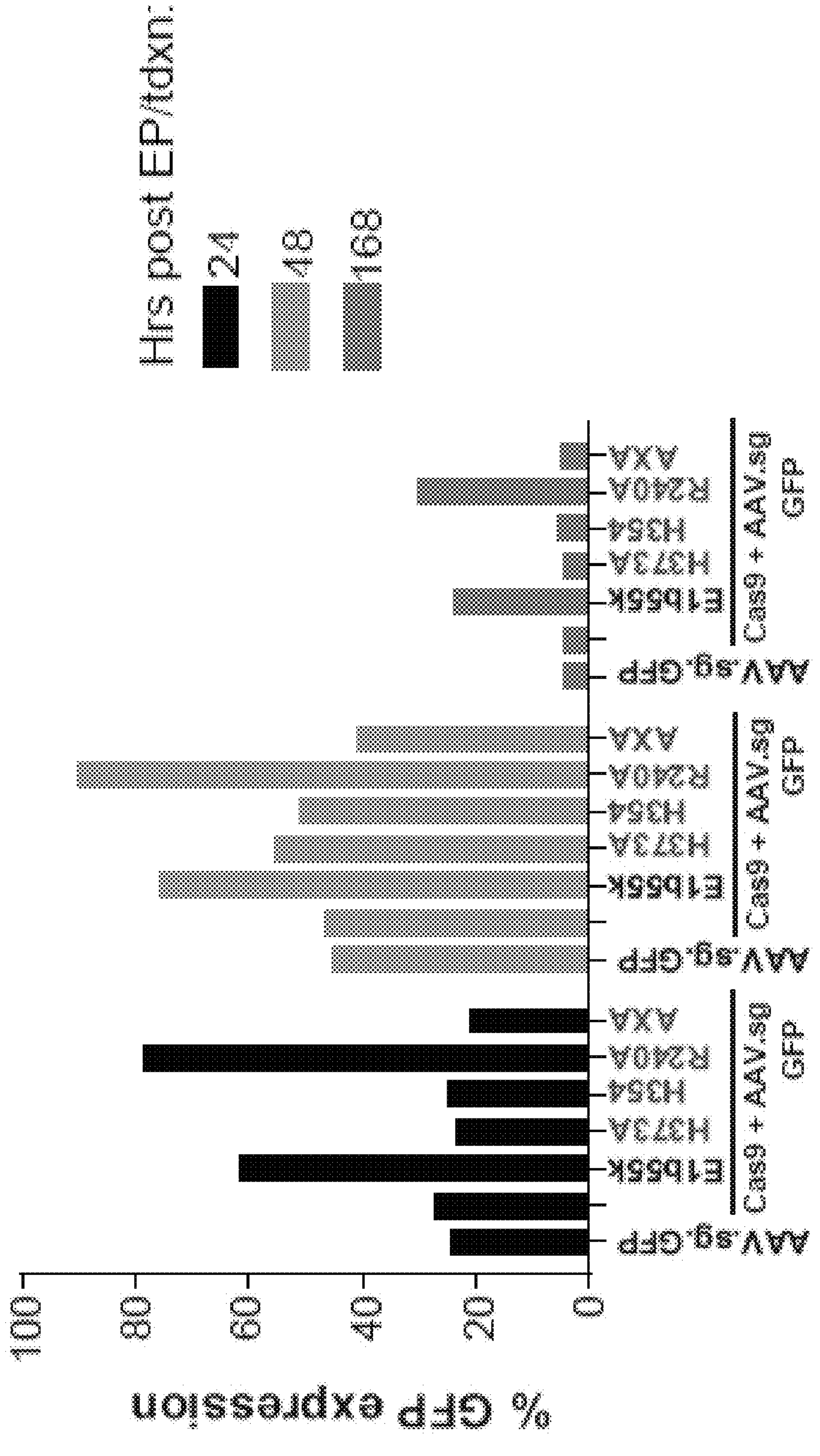
FIG. 3C shows a comparison of E1B55K, E4ORF6 mutants effects on AAV transduction.
Figure 3D:
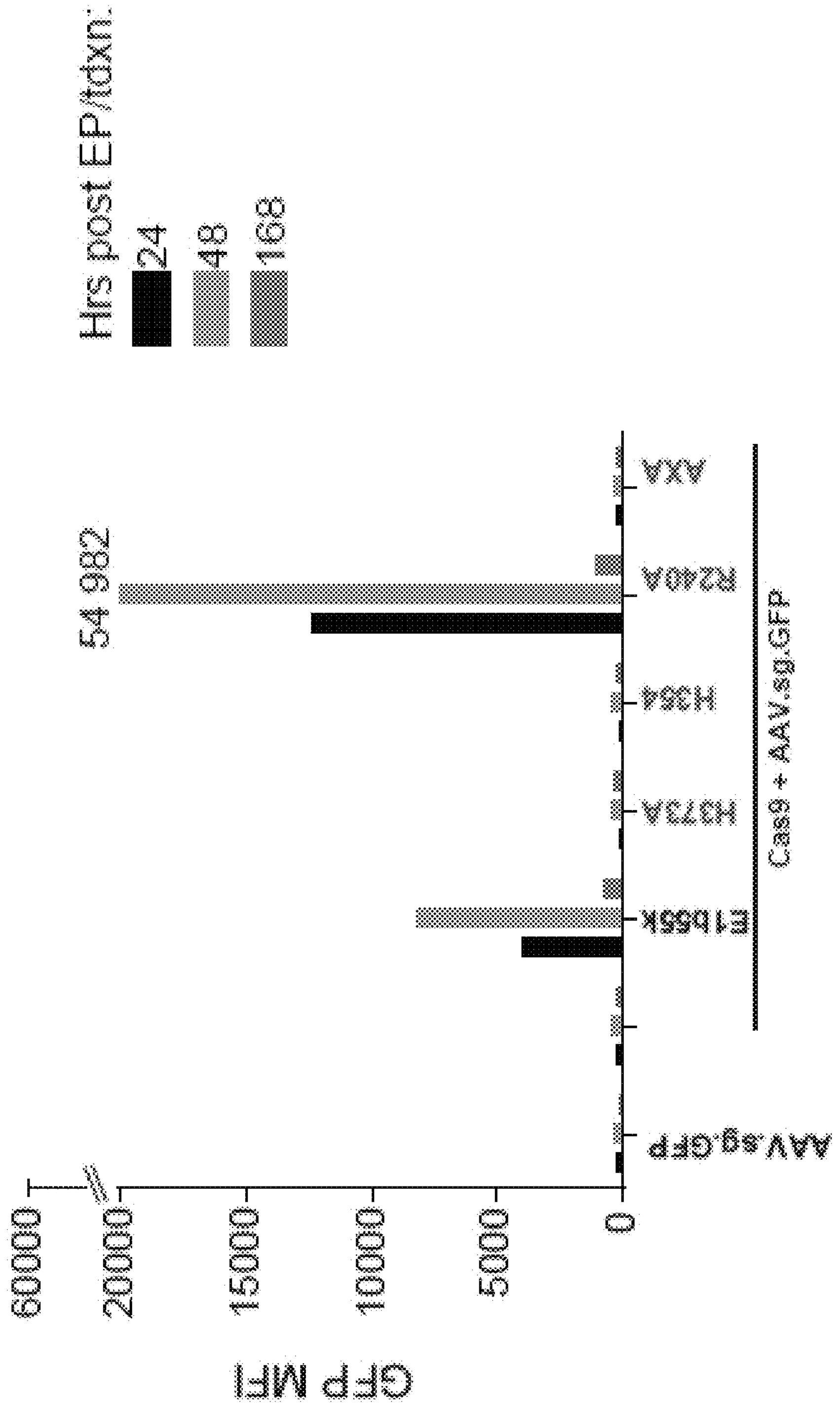
FIG. 3D shows a comparison of E1B55K, E4ORF6 mutants effects on AAV-driven GFP expression.

These mutants exhibit full (R240A) or partial (AXA) capacities to degrade the MRN complex, and consistent with a key role for MRN in post-entry restriction of AAV expression in T-cells, these mutants retained full (R240A) or partial (AXA; data not shown) capacities to enhance GFP expression following AAV transduction of T-cells (FIG. 3C and FIG. 3D). In some alternatives, expression of AXA/E1B55K was only able to enhance GFP expression from AAV vectors at high doses of mRNA electroporation (0.33 μg), and not 10-fold lower, as shown in FIG. 3.

Thus, in some alternatives, the use of various combinations of wild type and mutant forms of E4ORF6 and E1B55K proteins are contemplated. For example, in some alternatives, any one of the different forms of the E4ORF6 protein (e.g., wild type or AXA mutant) can be used in combination with any one of the different forms of E1B55K protein (e.g., wild type, H373A mutant, H354 mutant, R240A mutant). In some alternatives, the various combinations of wild type and mutant forms of E4ORF6 and E1B55K can be delivered as separate mRNAs. In some alternatives, the various combinations of wild type and mutant forms of E4ORF6 and E1B55K can be delivered as a single mRNAs.

EXAMPLE 4

H373A and H354 Mutant E4ORF6/E1B55K Expression Enhance CRISPR-Mediated Knockout in Primary Human T-Cells In some alternatives, enhancement of CRISPR-mediated gene knockout in primary human T-cells through use of adenoviral E4ORF6/E1B55K proteins was assessed.

Based on the capacity of E4ORF6/E1B55K proteins to enhance AAV-driven GFP expression in the analyses herein, it was hypothesized that their transient expression would similarly enhance the level and/or duration of guide RNA expression from a polIII-driven U6 promoter/guide RNA cassette incorporated into an AAV genome, and thus potentially enhance Cas9-mediated gene disruption efficiency by the mRNA/AAV system.

In some alternatives, this hypothesis was tested by expressing wild type E4ORF6/E1B55K proteins using the mRNA/AAV co-delivery protocol by including their respective mRNAs with Cas9 in the electroporation step, followed by transduction of the cells with an AAV vector encoding both a TCRα guide RNA and a promoter/GFP expression cassette. Thus, the effect of E4ORF6/E1B55K mutants on AAV-driven GFP expression was assessed.

In some alternatives, the expression of wild type E4ORF6/E1B55K proteins markedly increased GFP expression from the TCRα guide/GFP AAV, as expected from the analyses in FIG. 2.

Figure 4A:
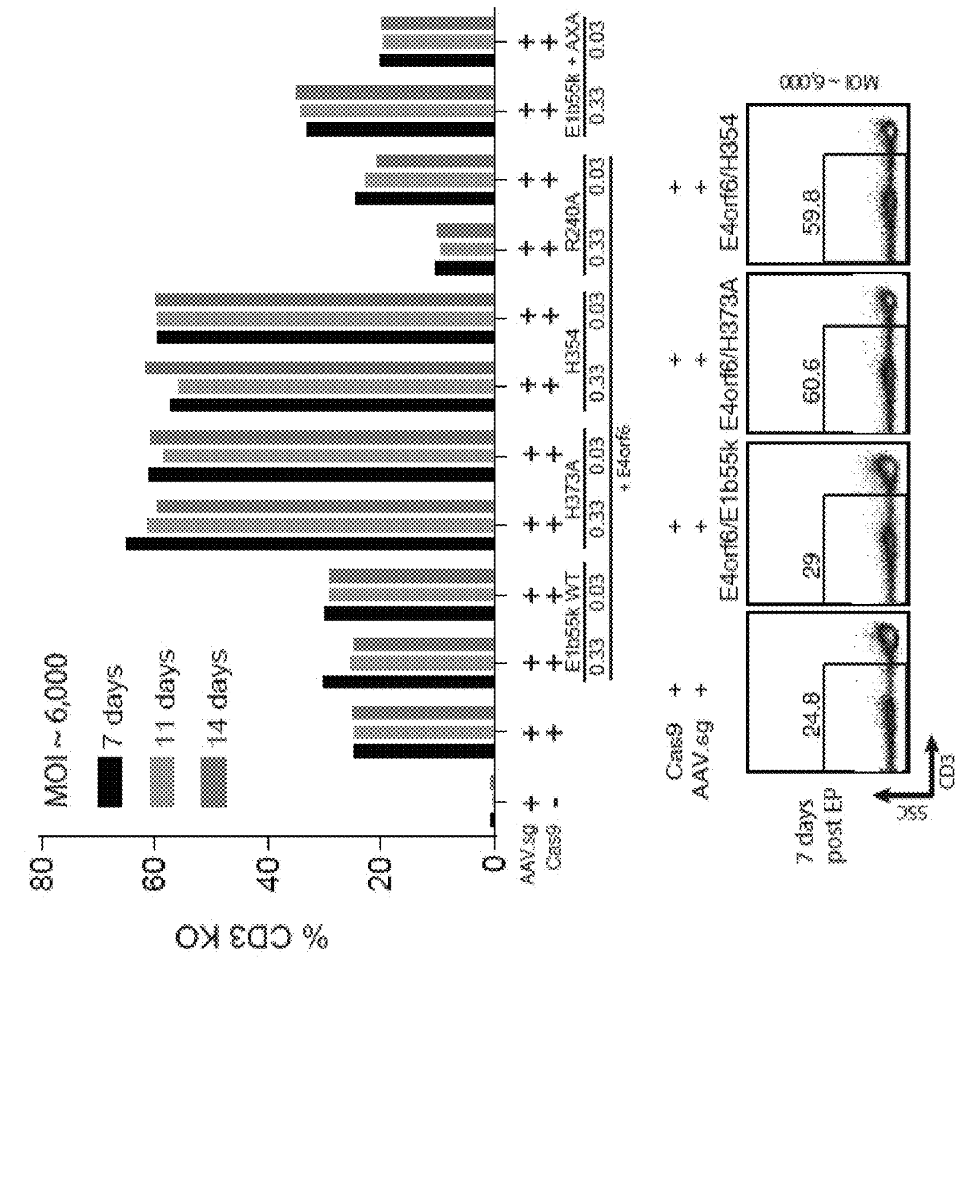
FIG. 4A-FIG. 4C show data related to CRISPR-mediated gene knockout in primary human T-cells through use of adenoviral E4ORF6/E1B55K proteins.
Figure 4B:
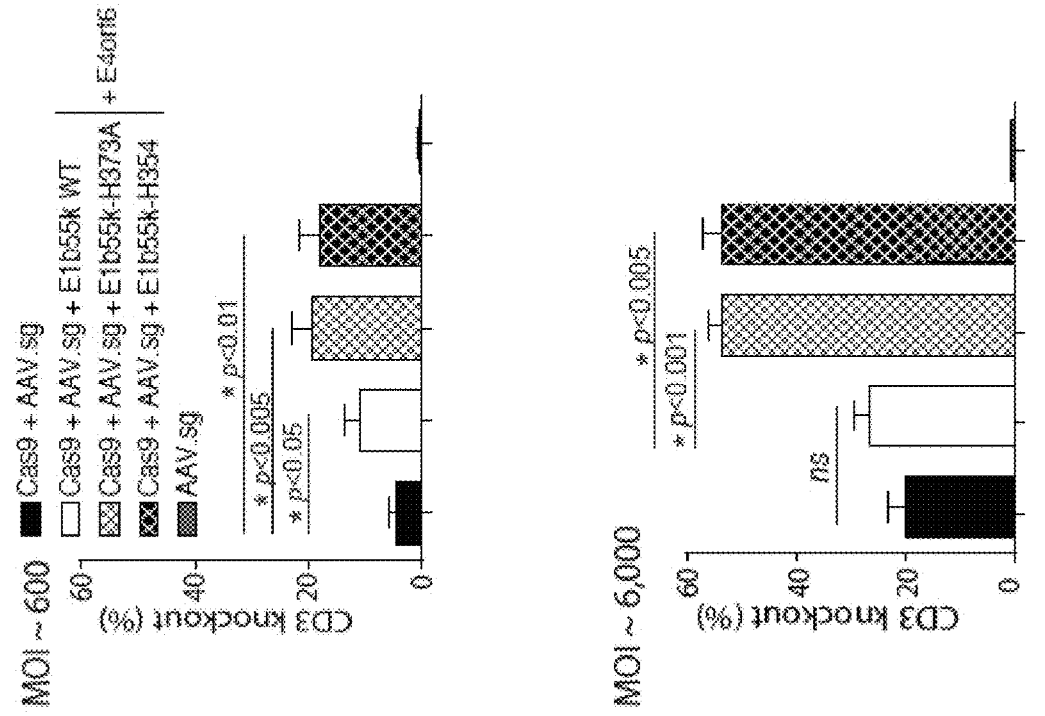

In some alternatives, despite the marked increase in AAV-based expression, only a moderately increased level of TCRα knock-out (FIG. 4A) was observed, and only at lower AAV vector doses (FIG. 4B, top panel).

Figure 5A:
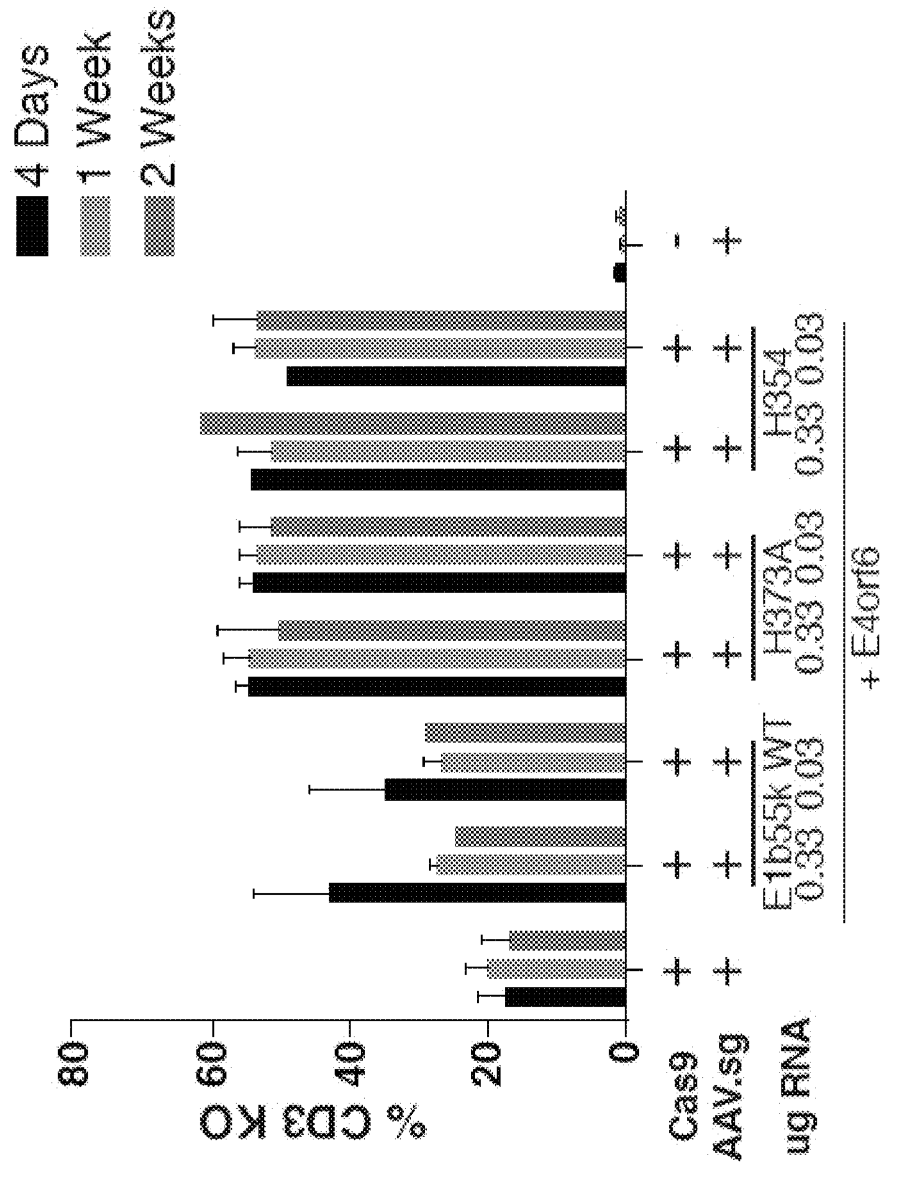
FIG. 5A-FIG. 5C show data related to the effect of E4ORF6/E1B55K MRN mutants on indel spectra.

In some alternatives, an apparent toxicity was observed that had not been observed in the absence of Cas9 expression (manifesting as a loss, rather than stable level, of $CD3^-$ cells over time. In some alternatives, primary CD4+ or CD3+ human T-cells were electroporated with mRNA encoding Cas9-T2A-mCherry proteins (1 μg) and E4ORF6/E1B55K wildtype proteins or the indicated mutants, at high or low doses, as indicated (0.33 μg or 0.03 μg), rested for 2-4 hours, and transduced with AAV driving TCRα guide expression. Cells were placed in culture, and analyzed for TCRα/CD3 expression by flow cytometry at the indicated time-points (FIG. 5A).

In some alternatives, in order to gain information on the influence of specific biochemical activities attributed to E4ORF6/E1B55K complexes on gene editing outcome, H373A, H354, R240A, and AXA mutants were also expressed, and TCRα knockout efficiency among the various contexts was compared (FIG. 4).

In some alternatives, data related to a representative experiment indicating primary CD4+ T-cells electroporated with mRNA encoding Cas9-T2A-mCherry, (1 μg), E4ORF6/E1B55K (wild type), or the indicated mutants (at 0.33 μg or 0.03 μg each), rested for 2-4 hours, and transduced with AAV driving TCRα guide expression are shown (FIG. 4A). Cells were placed in culture, following which the cells were collected and analyzed for CD3 expression by flow cytometry at the indicated time-points following EP/transduction. FIG. 4A, top panel, shows quantification of CD3 knockout. FIG. 4A, bottom panel, shows representative flow plots from a subset of the experiment at seven days post EP/transduction.

In some alternatives, E1B55K mutants enhance gene knockout achieved using mRNA/AAV delivery of CRISPR components. While expression of E4ORF6 with E1B55K-H373A and H354 mutants produced the expected much smaller effects on GFP expression (i.e., FIG. 2C), unexpectedly, substantial increases in TCRα knockout efficiency were also observed that were not accompanied by toxicity or loss of $CD3^-$ cells (FIG. 4A and FIG. 5A).

Figure 4C:
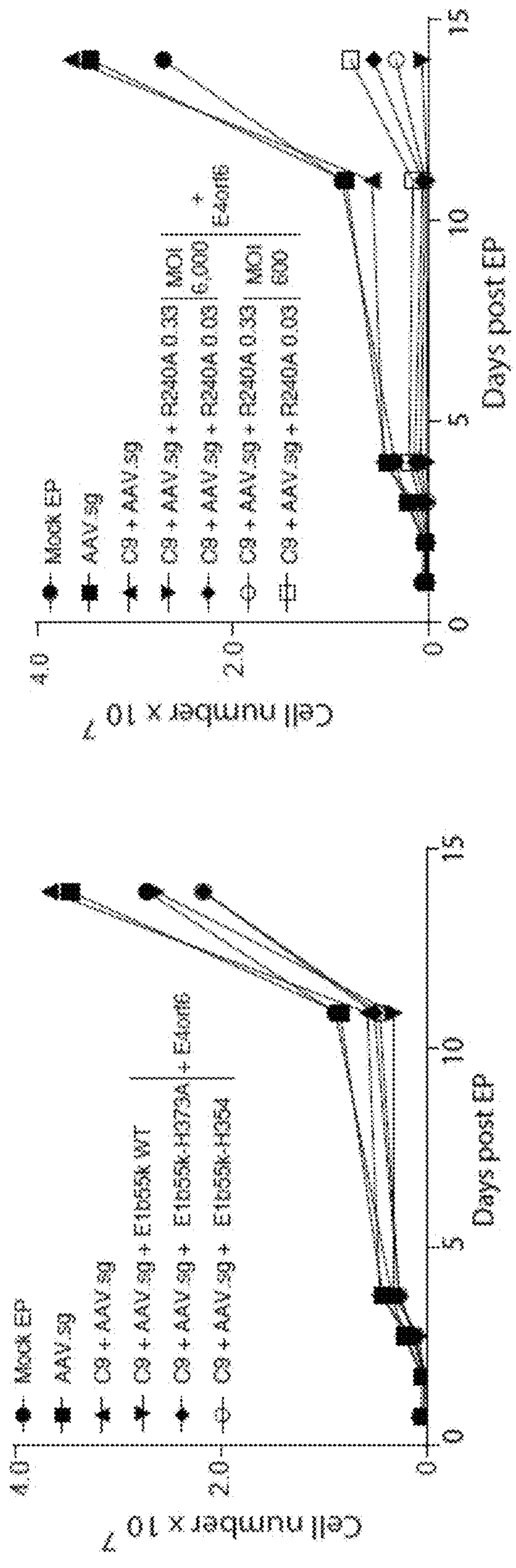

In some alternatives, despite their inability to fully relieve post-transduction restrictions on AAV gene expression, these E1B55K mutants retained residual activities that were sufficient to markedly enhance the overall efficiency of gene knockout achievable with the mRNA/AAV delivery approach. In some alternatives, this is supported by the results obtained when the E4ORF6/E1B55K R240A mutant was expressed. In some alternatives, potentiated toxicity was obtained relative to what was obtained with the wild type E4ORF6/E1B55K, along with marked reductions in efficiency of CD3 knockout (FIG. 4A and FIG. 4C). In some alternatives, p53 inactivation, for which R240A is deficient but which is preserved in the H373A and H354 mutants, contributed to the knockout potentiating properties of H373A and H354.

In some alternatives, T-cells edited using mRNA/AAV delivery exhibit normal expansion kinetics as determined by electroporating primary CD4+ T- with mRNA encoding Cas9-T2A-mCherry (1 μg) proteins along with wild type E4ORF6/E1B55K proteins or the indicated E1B55K mutants, resting for 2-4 hours, and transducing with AAV driving TCRα guide expression. Cells were placed in culture for the indicated periods of time, during which aliquots of the cells were collected and counted for quantification of cell expansion. FIG. 4C, left panel, shows low dose (0.03 μg) of E4ORF6/E1B55K mutants electroporated with high dose of AAV (MOI~6000). FIG. 4C, right panel shows electroporation and transduction of both low and high dose (0.33 μg) E4ORF6/E1B55K-R240A RNA, and low and high dose AAV.

Figure 5B:
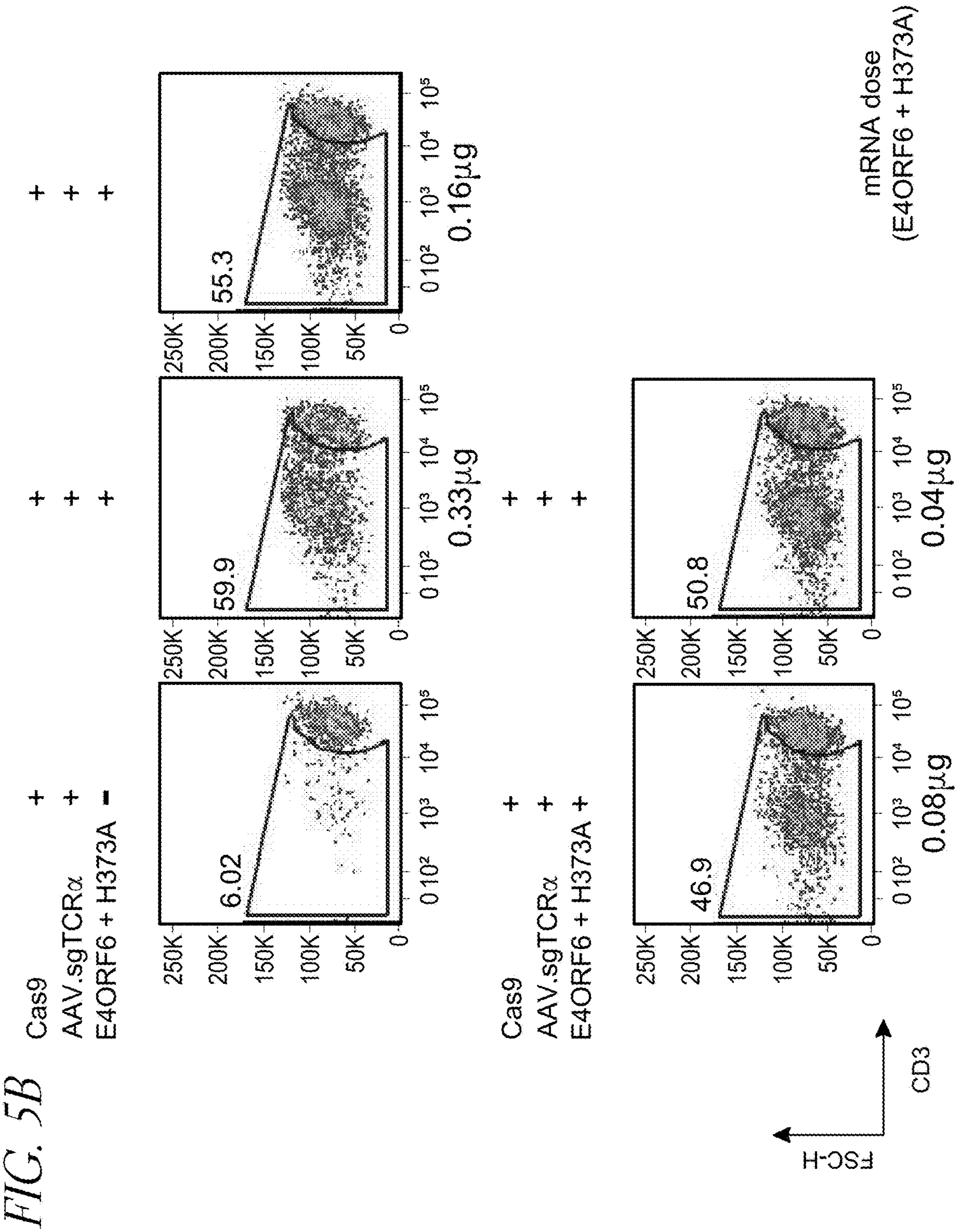

In some alternatives, the H373A and H354 mutants exhibited considerable potency in their effects on Cas9-mediated gene disruption, with dose/response testing of the H373A mutant demonstrating that it maintained a nearly full effect at enhancing TCRα knockout at mRNA doses down to <0.04

μg (FIG. 5B). In some alternatives, the mRNA dose can be 0.01 μg to 1 μg. In some alternatives, the mRNA dose can be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or 1 μg or within a range defined by any two of the aforementioned doses.

In some alternatives, representative flow plots of primary CD4+ human T-cells that were electroporated with mRNA encoding Cas9-T2A-mCherry proteins (1 μg) and E4ORF6/E1B55K H373A, at the indicated doses, rested for 2-4 hours, and transduced with AAV driving TCRα guide expression are shown in FIG. 5B. Cells were placed in culture for one week, following which the cells were collected and analyzed for TCRα/CD3 expression by flow cytometry (FIG. 5B).

In some alternatives, the effect of E4ORF6/E1B55K MRN-inactivation deficient mutants on CRISPR-mediated knockout was assessed (FIG. 4B). In some alternatives, quantification of n=3-4 independent experiments at two different AAV MOIs was performed. In some alternatives, data using primary human CD4+ or CD3+ T-cells indicating that both E1B55K H373A and H354 mutants significantly increase CRISPR-mediated TCRα knockout, quantified by CD3 staining at seven days post EP/transduction (FIG. 4B). Thus, in some alternatives, E4Orf6/E1B55K mutants enhance TCR knockout.

In some alternatives, the effect of E4ORF6/E1B55K MRN mutants on indel spectra was assessed. Primary CD4+ human T-cells were electroporated with mRNA encoding Cas9-T2A-mCherry proteins (1 μg) and E4ORF6/E1B55K H373A or H354 (0.03 μg), rested for 2-4 hours, and transduced with AAV driving TCRα guide expression. Cells were placed in culture for one week, following which cells were collected, genomic DNA was isolated, the region surrounding TCRα was amplified using PCR, cloned into a vector, and analyzed using Sanger sequencing (FIG. 5C).

Figure 5C:
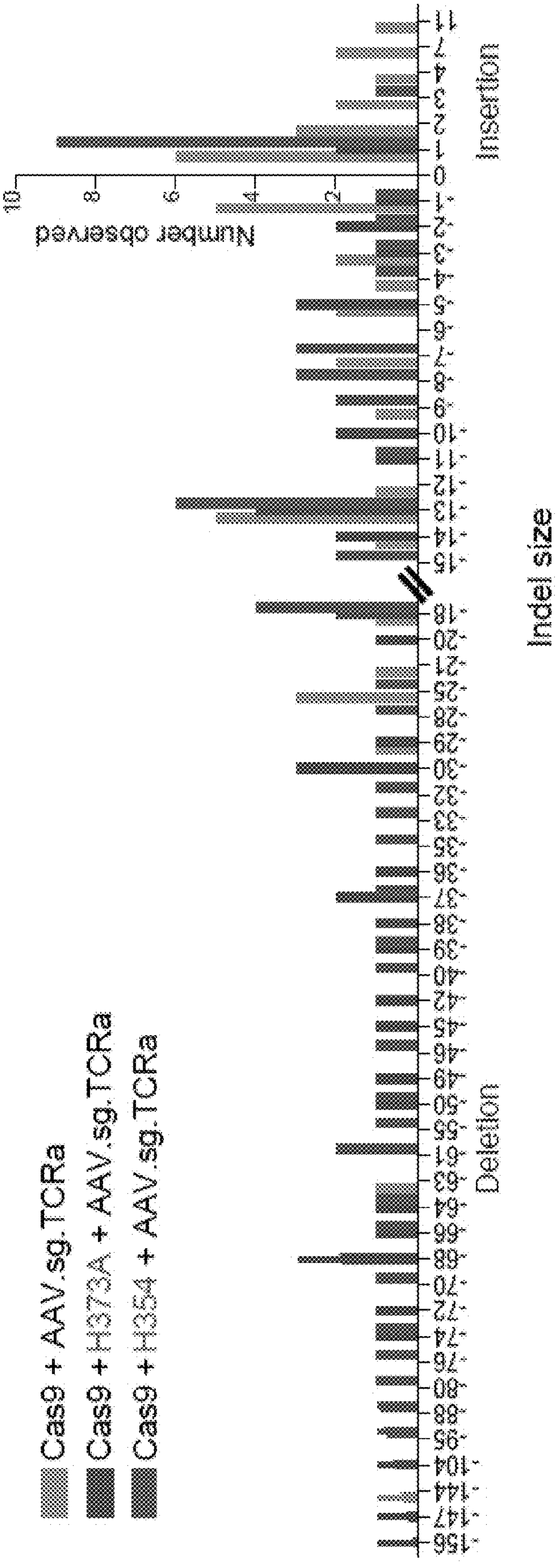

In some alternatives, amplicon sequencing of the indel spectra generated by Cas9-mediated gene disruption in the context of both H373A and H354 mutant E4ORF6/E1B55K complexes demonstrated the expected higher rate of mutations as well as an increased proportion of larger deletions, up to 150 bp, spanning the predicted Cas9 cleavage site (FIG. 5C). In some alternatives, the rate of mutations increased 1.5 fold to 10 fold. In some alternatives, the rate of mutations increased 1.5, 2, 2.5, 3, 3.5, 4, 4.5, 5, 5.5, 6, 6.5, 7, 7.5, 8, 8.5, 9, 9.5 or 10 fold or within a range defined by any two of the aforementioned values.

EXAMPLE 5

E4ORF6/E1B55K H373A and H354 Mutants Enhance CRISPR/Cas9-Mediated Homologous Recombination in Primary Human T-Cells Given their biochemical activities and capacity to enhance gene disruption efficiency achievable with the mRNA/AAV co-delivery method, it was hypothesized that the E4ORF6/E1B55K H373A and H354 mutants would have similarly enhancing effects on homology-directed gene targeting rates. To test this hypothesis, Cas9 mRNA was electroporated along with E4ORF6 and wild type E1B55K, H373A or H354 mutant mRNAs into primary human T-cells, followed by transduction of the cells with separate AAV vectors to provide guide RNA expression and recombination template delivery, respectively (FIG. 10).

In some alternatives, one or more guide RNAs can be provided in separate AAV vectors. In some alternatives, one or more templates for homologous recombination can be provided in separate AAV vectors. In some alternatives, one or more guide RNAs and one or more templates for homologous recombination can be provided in the same AAV vector. In some alternatives, one or more guide RNAs and template for homologous recombination for a particular target gene can be provided in separate AAV vectors. In some alternatives, one or more guide RNAs and template for homologous recombination for a particular target gene can be provided in the same AAV vector.

Figure 10A:
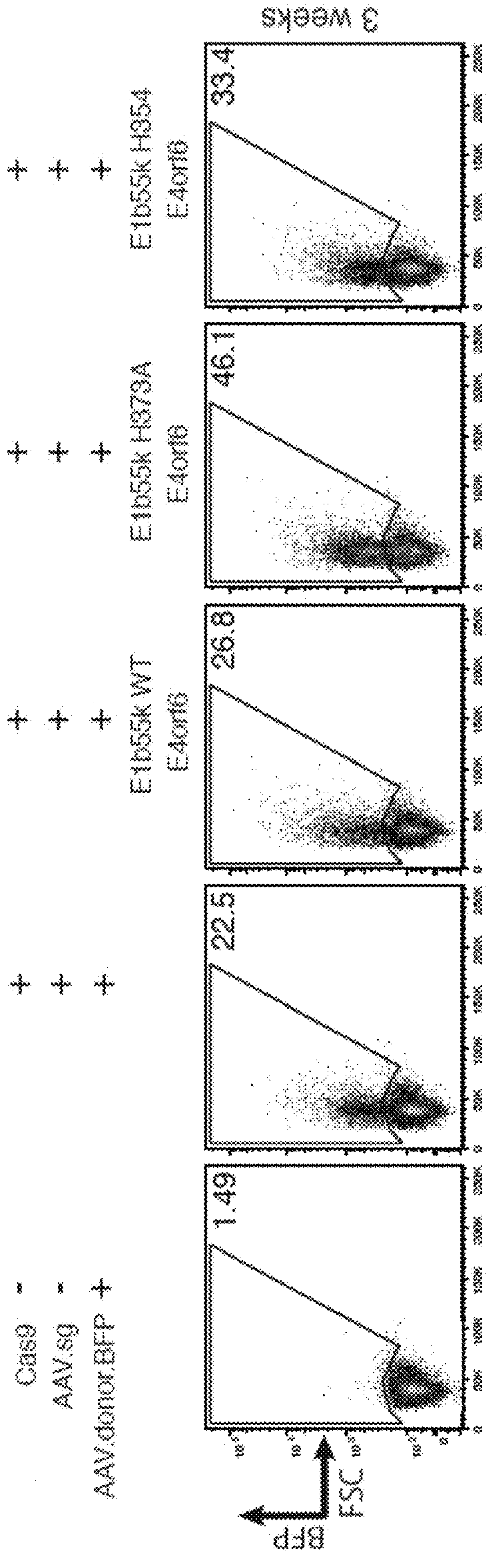
Figure 15A:
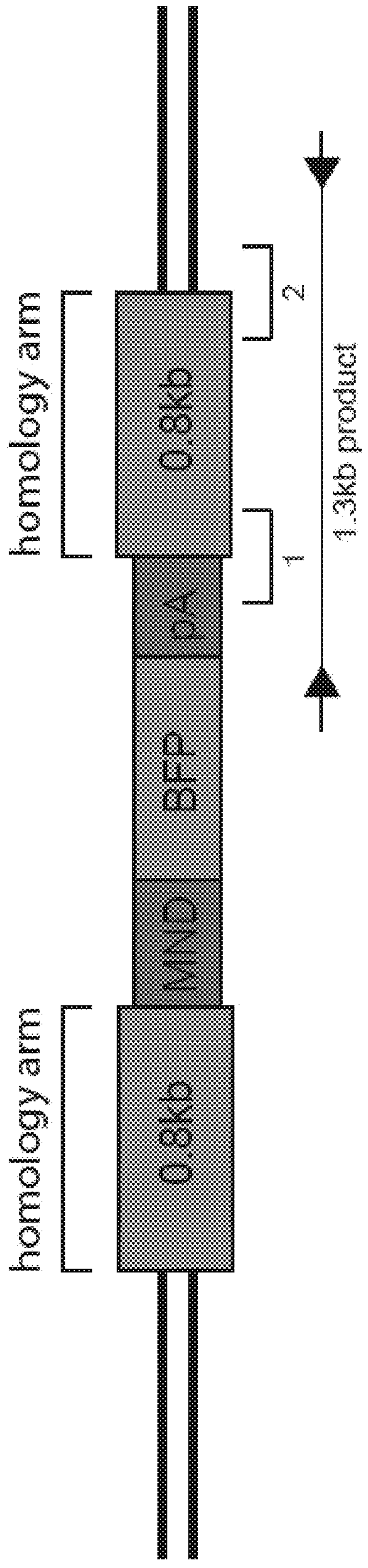
FIG. 15A-FIG. 15C show data related to molecular confirmation of HDR events following CRISPR-Cas9 breaks with E4ORF6/E1B55K H373A or H354.
Figure 15B:
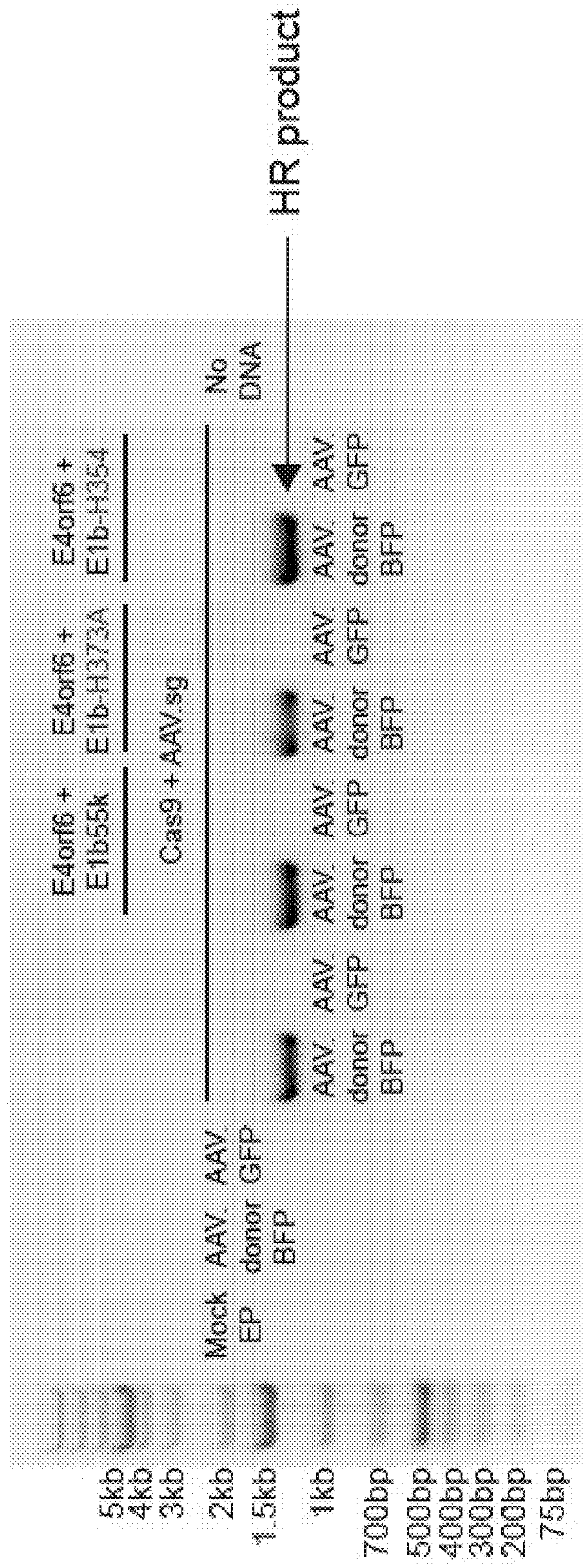
Figure 15C:
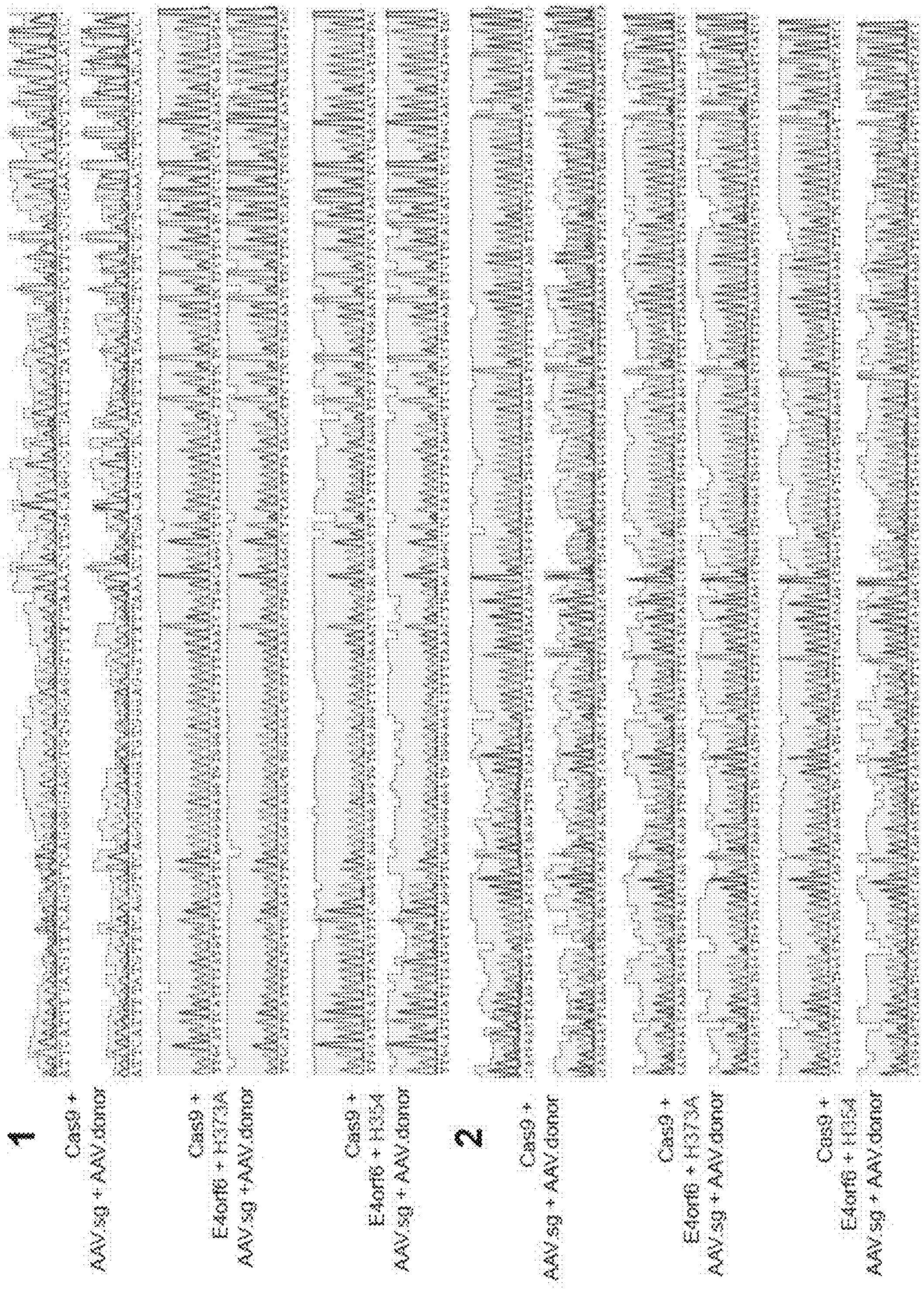

Primary CD4+ or CD3+ T-cells were electroporated using the MaxCyte GT or the Neon systems with mRNA encoding Cas9-2A-mCherry proteins (1 μg) along with wild type E4ORF6/E1B55K proteins or the indicated E1B55K mutants (0.03 μg each), rested for 2-4 hours, and transduced with separate AAVs driving CCR5 guide expression and a targeting template for the CCR5 locus (FIG. 15). Cells were placed in culture, following which the cells were collected and analyzed for BFP expression by flow cytometry. Shown are representative flow plots from the indicated manipulations at three weeks post EP/transduction, from n=5-6 independent experiments (FIG. 10A).

Figure 10B:
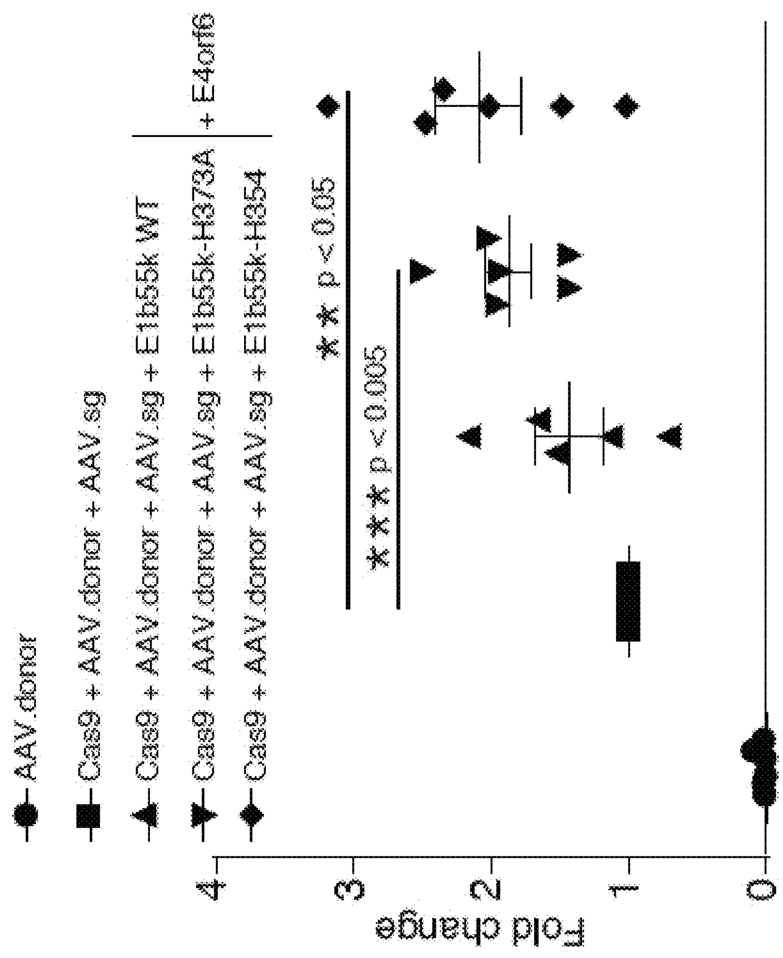

In some alternatives, quantification of n=5-6 independent experiments of the fold change in knock-in frequency (BFP+ cells) over baseline (Cas9+guide+donor) at three weeks post EP/transduction were performed (FIG. 10B).

Figure 6:
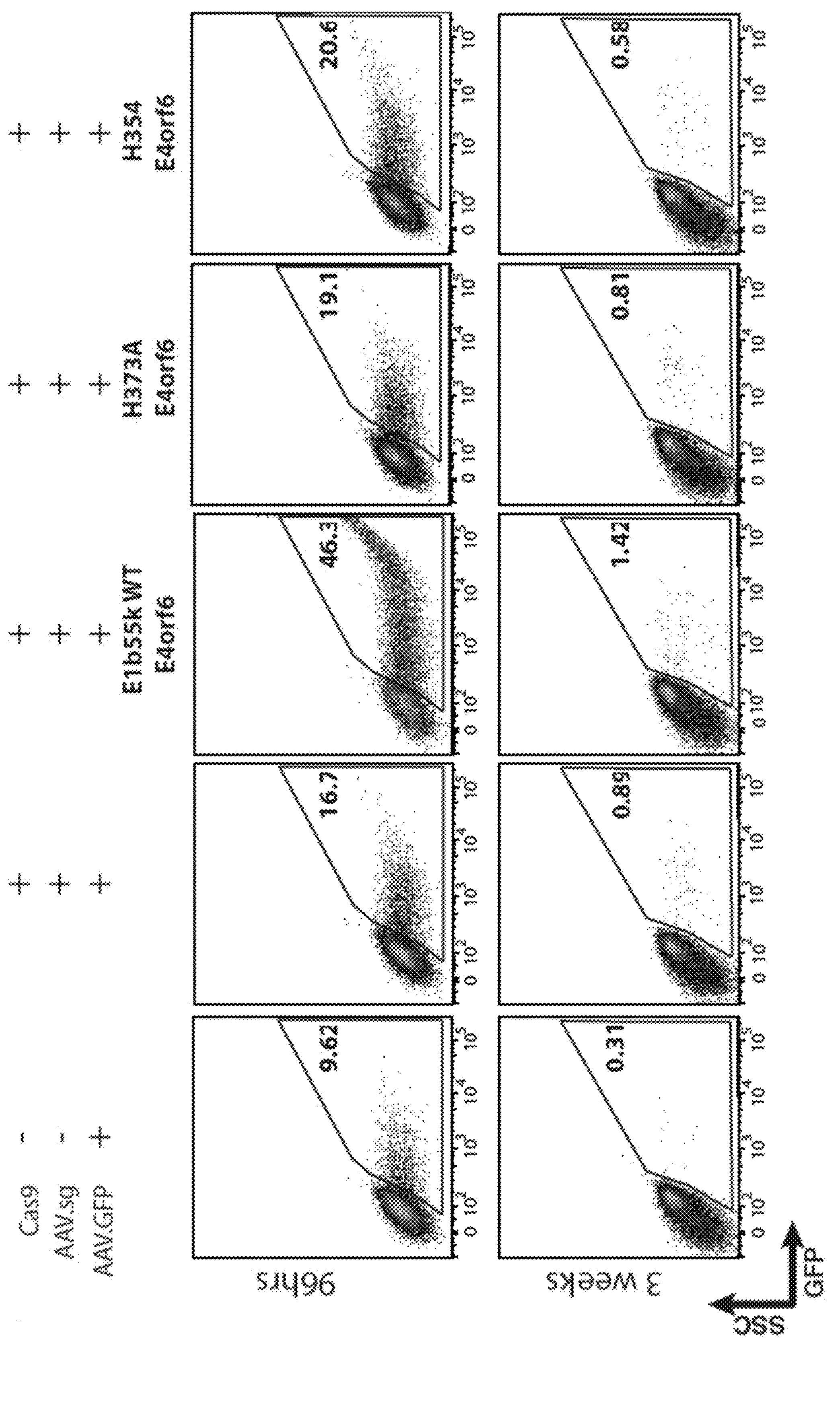
FIG. 6 shows the effect of E4ORF6/E1B55K proteins on non-homologous AAV insertion.

In these experiments, Cas9 alone plus the two AAVs allowed for integration of a promoter-BFP cassette into the CCR5 locus at an efficiency of 17.6±4.0%. In some alternatives, consistent with the results observed herein with the various E4ORF6/E1B55K complexes, substantial potentiation of early BFP expression by the wild type E4ORF6/E1B55K complexes relative to either the H373A or H354 mutants or without any Ad5 protein was observed (FIG. 6, top panel).

In some alternatives, the fold change in HDR was significantly increased using either E4ORF6/E1B55K-H354 or H373A with CRISPR/Cas9 (FIG. 10B). In some alternatives, similar to the effects of each of these mutant complexes on gene knockout, expression of either mutant complex generated significantly higher efficiency of recombination-based genome editing (FIG. 10A and FIG. 10B), increasing HDR by 1.8-fold (31.2±5.7% BFP+ with H373A, and 30.8±1.8 with H354).

In some alternatives, the rate of HDR can be increased using either E4ORF6/E1B55K-H354 or H373A with CRISPR/Cas9 by 1.5 to 3.5 fold as compared to when using wild type E4ORF6/E1B55K proteins. In some alternatives, the rate of HDR can be increased by 1.5, 1.75, 2, 2.25, 2.5, 2.75, 3, 3.25 or 3.5 fold or within a range defined by any two of the aforementioned values.

Thus, in some alternatives, enhanced targeted knock-in can be achieved using E1B55K mutant proteins. In some alternatives, E4ORF6/E1B55K mutants can enhance targeted CRISPR knock-in. In some alternatives, E4ORF6/E1B55K H373A and H354 mutants enhance CRISPR-mediated recombination achieved with mRNA/AAV co-delivery In order to determine whether T-cells edited via mRNA/AAV CRISPR-mediated recombination exhibited normal expansion kinetics, primary T-cells were electroporated with mRNA encoding control or Cas9-2A-mCherry proteins (1 μg) along with wild type E4ORF6/E1B55K and the E1B55K mutants (0.03 μg each), rested for 2-4 hours, and transduced with AAV driving CCR5 guide expression as well as AAV CCR5 BFP template. Cells were placed in culture for the indicated periods of time, following which the cells were collected and counted for quantification of cell expansion (FIG. 10C)

Figure 10C:
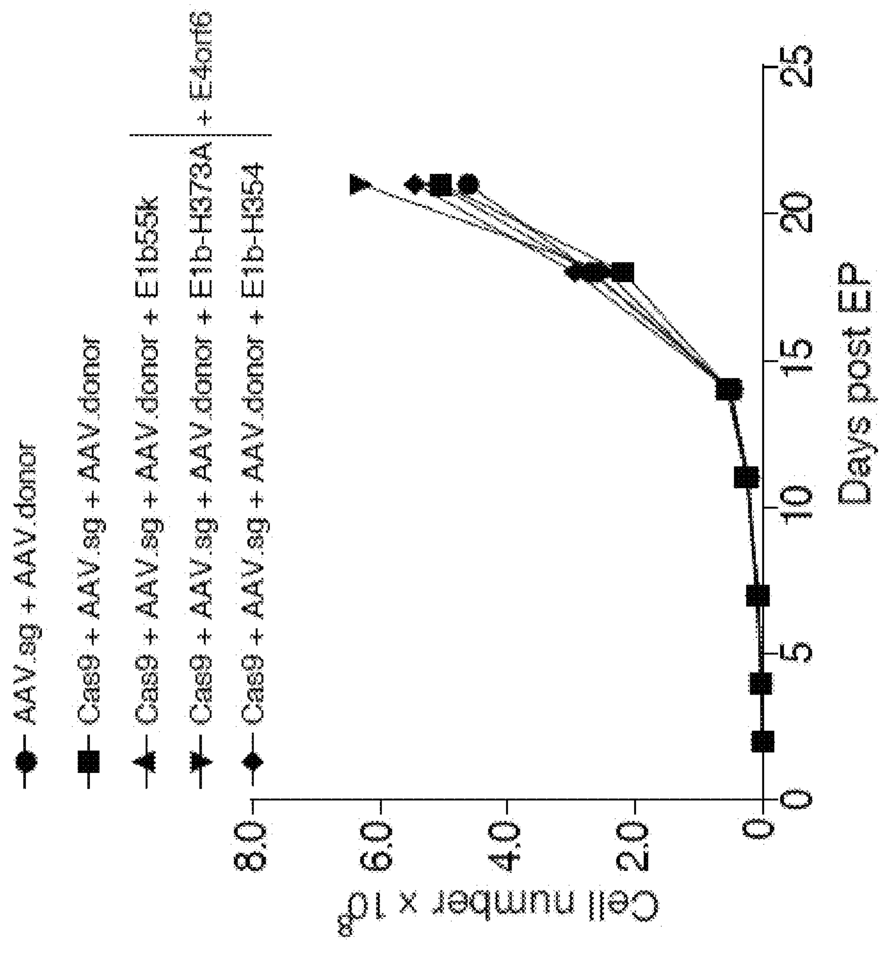

Importantly, expression of E4ORF6/E1B55K complexes (whether wild type or mutant) did not affect the rates of expansion of T-cells that had undergone homology-directed gene targeting (FIG. 10C).

EXAMPLE 6

E4ORF6/E1B55K Mutant Proteins do not Enhance Non-Homologous AAV Insertion

In some alternatives, primary CD3+ or CD4+ T-cells were electroporated with mRNA encoding Cas9-2A-mCherry proteins (1 μg) along with wild type E4ORF6/E1B55K proteins or the indicated E1B55K mutants (0.03 μg each), rested for 2-4 hours, and transduced with AAV driving CCR5 guide expression and AAV containing a promoter-GFP cassette without flanking homology arms. Cells were placed in culture for the indicated periods of time, following which the cells were collected and analyzed for GFP expression by flow cytometry. GFP fluorescence detected at 96 hours reflects expression primarily from episomal AAV genomes. GFP fluorescence detected at three weeks represents expression from both residual episomal or integrated AAV genomes. n=5-6 independent experiments (FIG. 6).

In some alternatives, representative flow plots of primary T-cells demonstrating low rate of insertion events at Cas9-induced double strand break by AAV lacking homology arms are shown in FIG. 6.

Importantly, expression of E4ORF6/E1B55K complexes (whether wild type or mutant) did not affect the rates of non-homologous AAV integration, as assessed by the rate of long term fluorophore expression following co-delivery of Cas9 with AAVs expressing the same guide and a promoter/fluorophore cassette lacking CCR5 homology arms (FIG. 6, top panel).

Thus, in some alternatives, E4ORF6/E1B55K wild type proteins mildly increase non-specific AAV integration at target site for CRISPR knockout whereas mutant proteins do not.

EXAMPLE 7

E4OrF6/E1B55K Mutants Enhance CRISP Single Knockouts for other Loci than TCR In some alternatives, the influence of E4ORF6/E1B55K H373A and H354 mutant complexes on the efficiency of CRISPR/Cas9 gene disruption at other genomic targets was evaluated. In some alternatives, guide RNAs were generated and validated targeting four translationally relevant human surface protein targets: the T-cell inhibitory checkpoint proteins PD-1, TIGIT, LAG-3, and Tim3. The guide RNAs targeting these proteins are represented by SEQ ID NO: 18 (FIG. 31) for PD1, SEQ ID NO: 19 (FIG. 31) for TIGIT, SEQ ID NO: 20 (FIG. 31) for LAG-3, and SEQ ID NO: 21 (FIG. 31) for Tim3. In some alternatives, one or more of these guide RNAs were incorporated into U6-guide expression cassettes in AAV vector backbones upstream of the MND-GFP cassette to provide for tracking of transduction/expression, and packaged into AAV vectors.

Figure 7A:
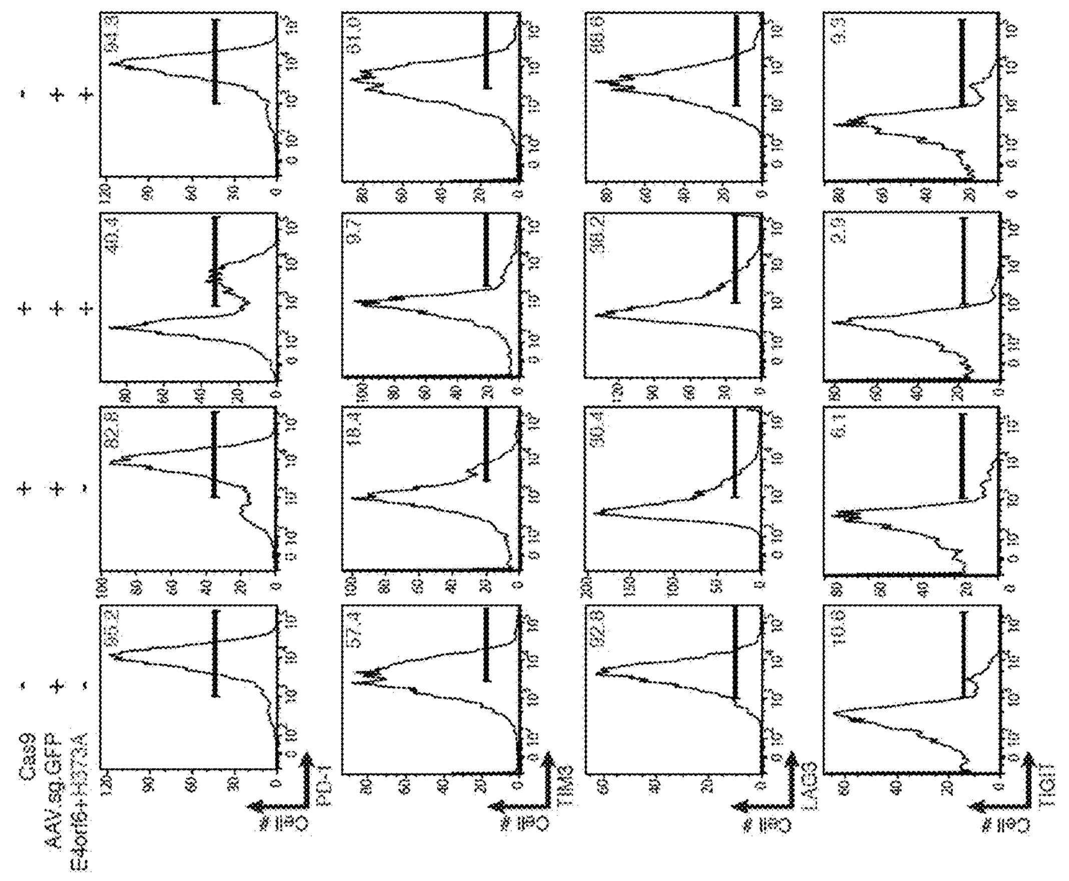
FIG. 7A-FIG. 7B show data related to implementation of CRISPR/Cas9 with mRNA/AAV delivery to achieve knock-out at multiple genomic sites.

Primary human CD3+ T-cells were electroporated using the MaxCyte GT system with mRNA encoding Cas9-2A-mCherry proteins (1 μg) along with E4ORF6/E1B55K-H373A proteins (0.03 μg each), rested for 2-4 hours, and transduced with AAV driving guide expression against the indicated surface proteins. Cells were placed in culture and allowed to expand; 9-12 days following initial stimulation, cells were re-stimulated using Dynal CD3/CD28 beads for 48 hours, following which the cells were collected and analyzed for expression of the indicated surface proteins by flow cytometry and assessed for knockout by amplicon sequencing. Representative flow cytometry plots indicating that T-cells edited using mRNA/AAV co-delivery exhibit loss of targeted surface checkpoint proteins. Data represent n=3-5 independent editing experiments. The representative flow cytometry data are presented in FIG. 7A.

Figure 7B:
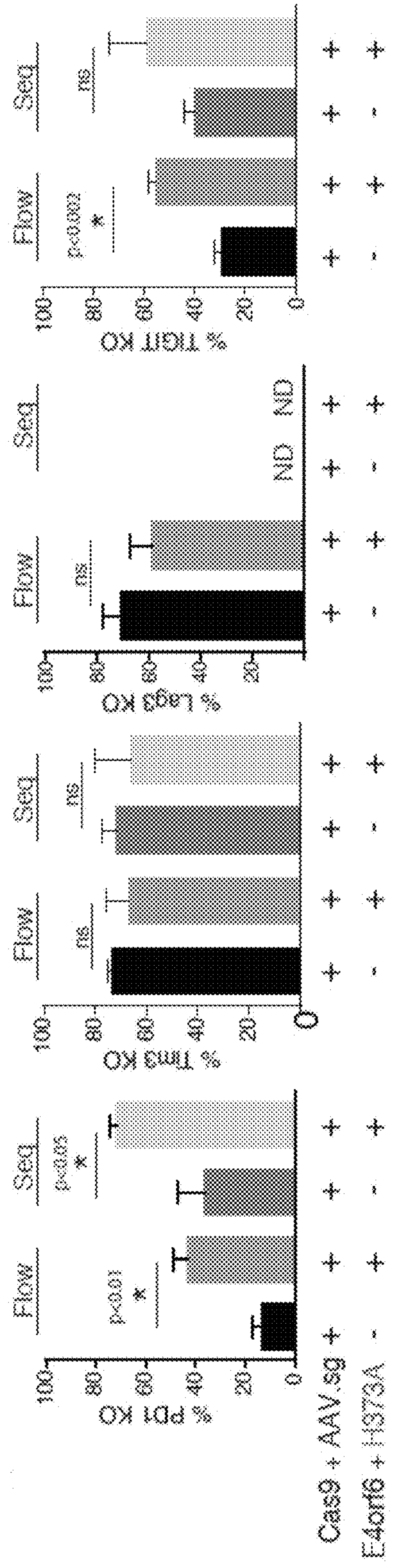

In some alternatives, analysis of knockout by flow cytometry is assessed by percent loss of induction of surface protein expression. Data represent n=3-5 independent editing experiments (FIG. 7B). Quantification and summary data from flow cytometry analysis of gene knockout and sequencing analysis of amplicons from genomic target sites are shown in FIG. 7B.

Thus, in some alternatives, knockout efficiency can be assessed by sequencing analysis of amplicons from genomic target sites. In some alternatives, knockout efficiency can be assessed by flow cytometry (if the protein encoded by the targeted gene is expressed on the surface). Thus, in some alternatives, knockout efficiency can be assessed by sequencing analysis of amplicons from genomic target sites as well as surface expression by flow cytometry (if the protein encoded by the targeted gene is expressed on the surface).

In some alternatives, the use of these AAV vectors with the E4ORF6/E1B55K H373A mutant in a scaled up expansion/manufacturing protocol based on the MaxCyte GT electroporation system resulted in generation of human T-cell populations with approximate respective targeted gene disruption efficiencies of 71.6±2.7%, 59.1±14.8%, 59.2±8.5%, and 66.1±14.3% of indels at the intended cleavage site of PD-1, TIGIT, LAG-3, and Tim3, respectively, as derived from sequence analysis (PD-1, TIGIT, Tim3) or flow cytometry (LAG-3).

Thus, in some alternatives, implementation of CRISPR/Cas9 with mRNA/AAV delivery is able to achieve efficient knockout at multiple genomic sites.

An important secondary observation that emerged from these experiments was that the influence of E4ORF6/E1B55K H373A mutant complexes on gene disruption efficiency was particularly prominent when the activity of a particular guide RNA was relatively low. For example, the knockout rates at the PD-1 and TIGIT loci doubled with the chosen guide RNAs in the presence of E4ORF6/E1B55K H373A as compared to the knockout rates in the absence of E4ORF6/E1B55K expression, which were only 36.4±10.9% and 40.4±3.6%, respectively. In some alternatives, the rates were assessed by sequencing.

Thus, in some alternatives a particularly salient feature of E4ORF6/E1B55K H373A expression is that it can 'rescue' poor guide RNA activity. In other words, in some alternatives, E4ORF6/E1B55K H373A expression can potentiate the activity of poor guide RNAs. In some alternatives, the effect of highly active guide RNAs is not as effectively potentiated by E4ORF6/E1B55K protein expression.

In some alternatives, a poor guide RNA is only 5% to 30% efficient. In some alternatives, a poor guide RNA is only 5, 10, 15, 20, 25 or 30% efficient or within a range defined by any two of the aforementioned values. In some alternatives, E4ORF6/E1B55K H373A expression potentiates the activity of a poor guide RNA by 5% to 150%. In some alternatives, E4ORF6/E1B55K H373A expression potentiates the activity of a poor guide RNA by 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150% or within a range defined by any two of the aforementioned values.

EXAMPLE 8

H373A Mutant E4ORF6/E1B55K Expression Enhance CRISPR-Mediated Multiplex Knockout of Two Genes in Primary Human T-Cells Based on our analyses herein, it was hypothesized that efficient levels of multiplex knockout could be successfully achieved, using a single AAV vector to deliver multiple guides. In some alternatives, a single AAV vector can be used to deliver one or more guides. In some alternatives, a single AAV vector can be used to deliver 1 to 5 guides. In some alternatives, a single AAV vector can be used to deliver 1, 2, 3, 4 or 5 guides. In some alternatives, one AAV vector is used to deliver a single guide. In some alternatives, separate AAV vectors are used to deliver separate guides.

In some alternatives, primary human CD3+ T-cells were electroporated using the MaxCyte GT system with mRNA encoding Cas9-2A-mCherry proteins (1 μg) along with E4ORF6/E1B55K-H373A proteins (0.03 μg each), rested for 2-4 hours, and transduced with AAVs driving guide expression against Tim3 and TCRα, as well as GFP expression to track transduction efficiency. Cells were placed in culture and allowed to expand; 7 days following EP/transduction, cells were assessed for TCRα knockout by CD3 stain. Three weeks following initial stimulation, cells were re-stimulated using PMA/ionomycin for 3-4 hours and allowed to recover for 48 hours, following which the cells were collected and analyzed for expression of Tim3 by flow cytometry (FIG. 8).

Figure 8A:
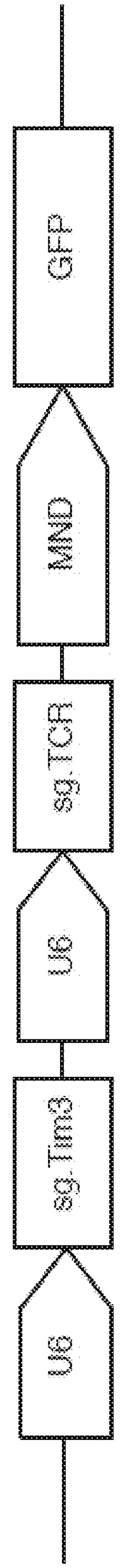
FIG. 8A-FIG. 8D show data related to implementation of Cas9 mRNA/AAV guide delivery to generate CRISPR-mediated double knockout in primary human T-cells with E4ORF6/E1B55K H373A expression.

In some alternatives, using the same architecture as the single AAV guide vectors, a dual-guide Tim3/TCRα vector was constructed, with both guides driven by individual U6 promoters. A schematic of the multiplex AAV vector expressing guide RNAs against Tim3 and TCRα, with individual U6 promoters is shown in FIG. 8A. In some alternatives, TCRα and Tim3 knockout was analyzed following MaxCyte electroporation with Cas9 or E4ORF6/E1B55K-H373A and AAV transduction with either the single Tim3 guide AAV or the AAV containing dual Tim3/TCRα guides.

Figure 8B:
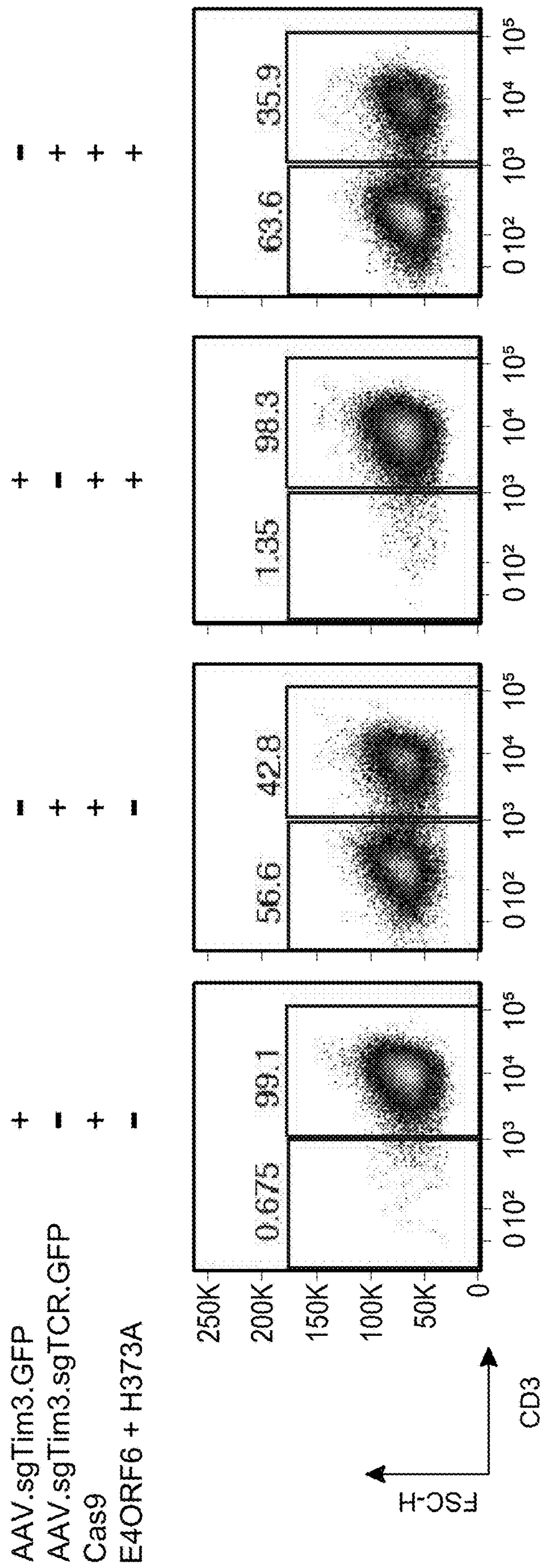
Figure 8C:
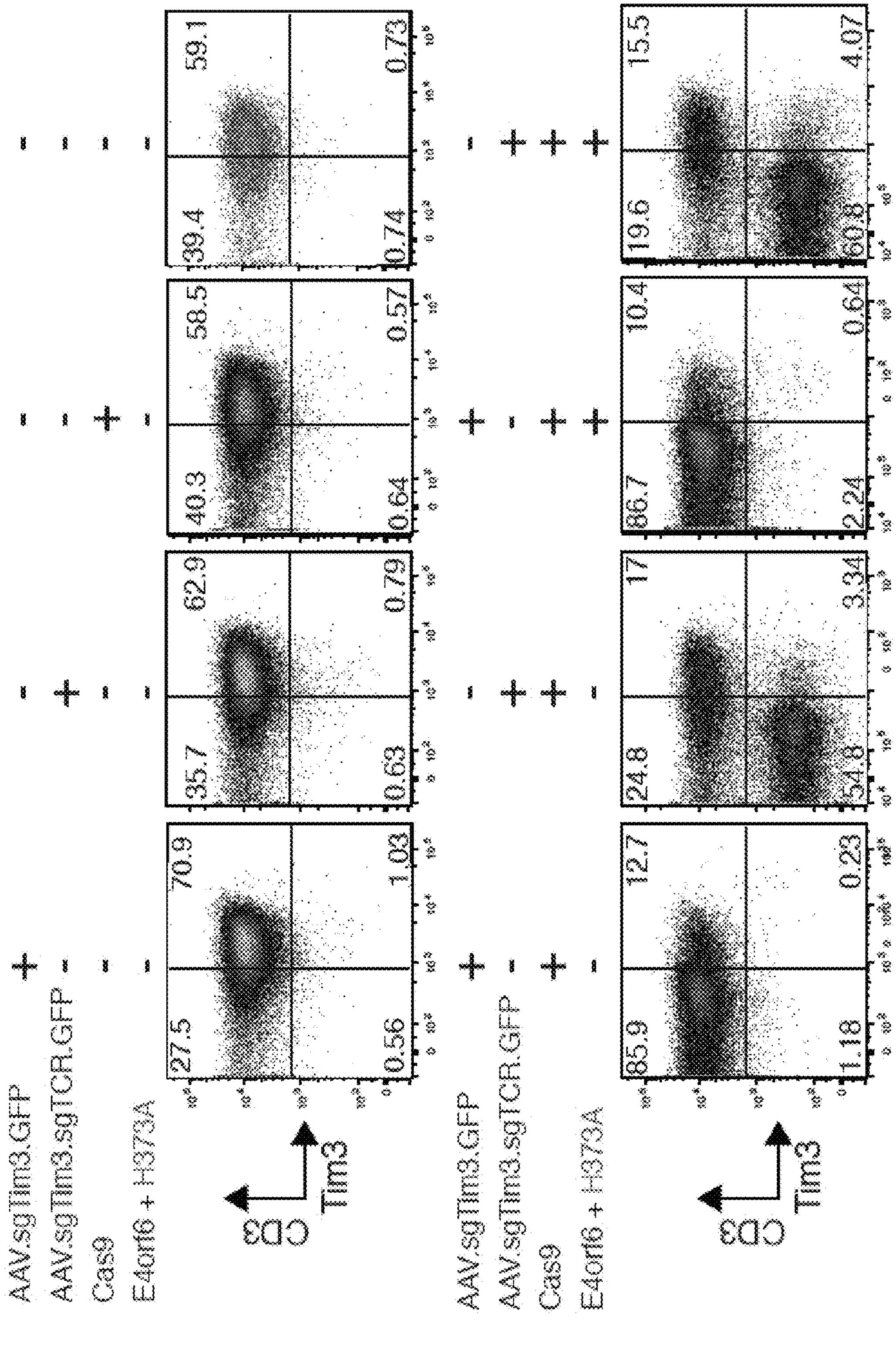

A representative flow cytometry analysis of TCRα knockout by CD3 staining, seven days after EP/transduction, is shown in FIG. 8B. A representative flow cytometry analysis of TCRα knockout and Tim3 knockout, three weeks after initial stimulation, is shown in FIG. 8C. In some alternatives, to upregulate Tim3 surface expression independently of TCR, cells were stimulated using PMA/ionomycin (10 ng/mL and 1 μg/mL, respectively), for 3-4 hours and rested for 48 hours.

Figure 8D:
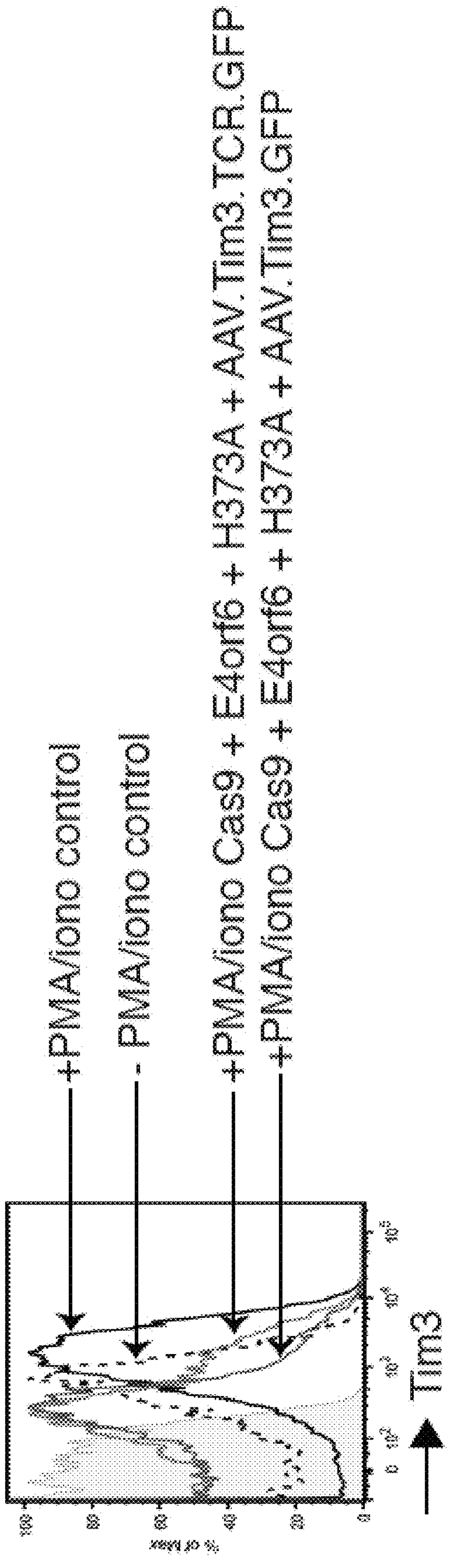

In some alternatives, upregulation of Tim3 with and without PMA/ionomycin stimulation was assessed by comparing control cells (AAV treatment only) with and without PMA/ionomycin treatment, and stimulated cells with Tim3 knockout compared to stimulated cells missing both Tim3 and TCRα. There were no differences between cells proficient and deficient in TCRα signaling, suggesting that PMA/ionomycinn stimulation is independent of this pathway. In shaded grey are unstained cells is shown in FIG. 8D.

In some alternatives, successful knockout of both targeted genes using a single AAV, along with an increased efficiency of knockout when E4ORF6/E1B55K-H373A were co-transfected with Cas9 was obtained.

In some alternatives, on significant differences in knockout efficiency between the single Tim3 guide AAV and the dual Tim3 guide/TCRa guide AAV were observed. In addition, in some alternatives, the majority of $Tim3^-$ cells were also $CD3^-$ cells (thus $TCR\alpha^-$), consistent with the expected outcome that any cell sufficiently well-transduced to drive guide expression to cleave one target gene also experienced a high level of guide expression for the other target gene.

Thus, in some alternatives, Cas9 mRNA/AAV guide delivery is able to achieve efficient CRISPR-mediated multiplex knockout in primary human T-cells with E4ORF6/E1B55K H373A expression. In some alternatives, E4OrF6/E1B55K mutants enhance CRISPR-mediated multiplex knockout of more than one gene. In some alternatives, E4OrF6/E1B55K mutants enhance CRISPR-mediated multiplex knockout of two genes.

EXAMPLE 9

H373A Mutant E4ORF6/E1B55K Expression Enhance CRISPR-Mediated Multiplex Knockout of Five Genes in Primary Human T-Cells In some alternatives, a multiplex knockout of five genes was performed. In some alternatives, cells were cultured for 3 weeks and allowed to expand prior to analysis. Unstimulated cells did not have significant expression of cell surface proteins. One million cells per condition were stimulated with PMA (10 ng/mL) and ionomycin (1 μg/mL) to upregulate surface checkpoint protein expression. PMA/ionomycin was left in the media for three hours, following which the cells were washed 4 times with PBS, and left to recover in full media for 48 hours and stained, for the indicated cell surface proteins (CD3, PD1, Tim3, Lag3, and TIGIT) as a measure of gene knockout.

Figure 9:
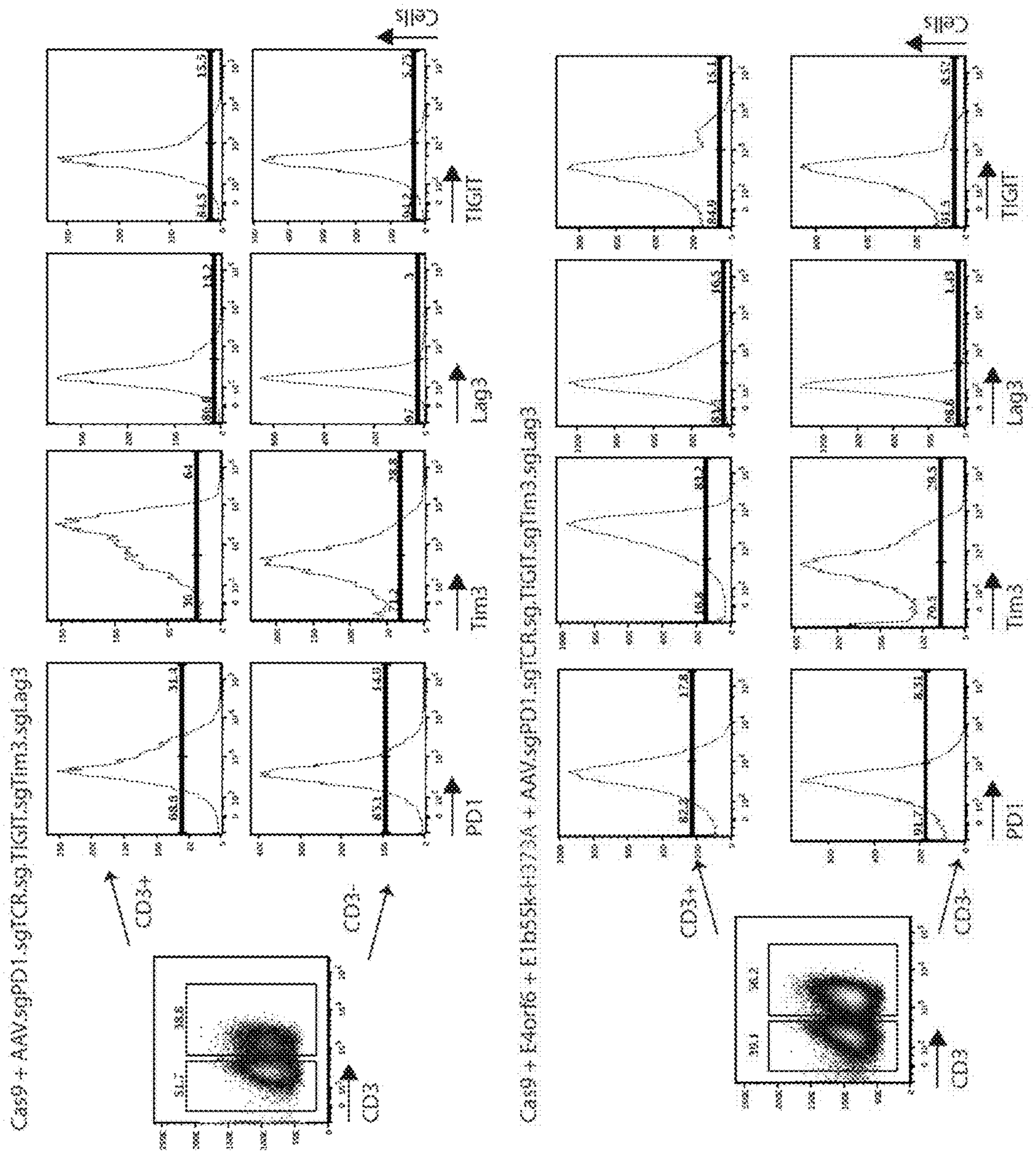
FIG. 9 shows data related to implementation of Cas9 mRNA/AAV guide delivery to generate CRISPR-mediated knockout of more than two genes in primary human T-cells with E4ORF6/E1B55K H373A expression.

Data are presented in FIG. 9. Top panel shows data for cells that received Cas9 RNA and AAV guide construct only. Bottom panel shows data for cells that received Cas9 RNA, AAV guide construct, and E4ORF6/E1B55K-H373A RNA during the electroporation.

In some alternatives, simultaneous multiplex deletion of five genes was achieved. Thus, in some alternatives, the method of the present disclosure can be used to delete at least two genes. In some alternatives, the method of the present disclosure can be used to delete at least five genes. In some alternatives, the method of the present disclosure can be used to delete 1 to 10 genes. In some alternatives, the method of the present disclosure can be used to delete 1, 2, 3, 4, 5, 6, 7, 8, 9 or 10 genes. In some alternatives, the method of the present disclosure can be used to delete at least two, at least three, at least four, at least five, at least six, at least seven, at least eight, at least nine, or at least ten genes.

In some alternatives, one or more guide RNAs targeting one or more genes can be delivered using AAV transduction. In some alternatives, 1 to 5 guide RNAs targeting 1 to 10 genes can be delivered using AAV transduction. In some alternatives, 1, 2, 3, 4 or 5 guide RNAs can be delivered targeting 1, 2, 3, 4, 5, 6, 7, 8, 9 or 10 genes using AAV transduction.

EXAMPLE 10

Addition of E4ORF6/E1B55K H373A Rescues HDR when Shorter Homology Arms are Used for Gene Knock-in with CRISPR-Cas9 at the CCR5 Locus In some alternatives, the effect of addition of the Ad5 proteins (the two E1B55K mutants, H373A or H354, both with E4ORF6) on the lower levels of HDR knock-in that are caused by using templates with shorter homology arms with CRISPR/Cas9 was evaluated.

Figure 11:
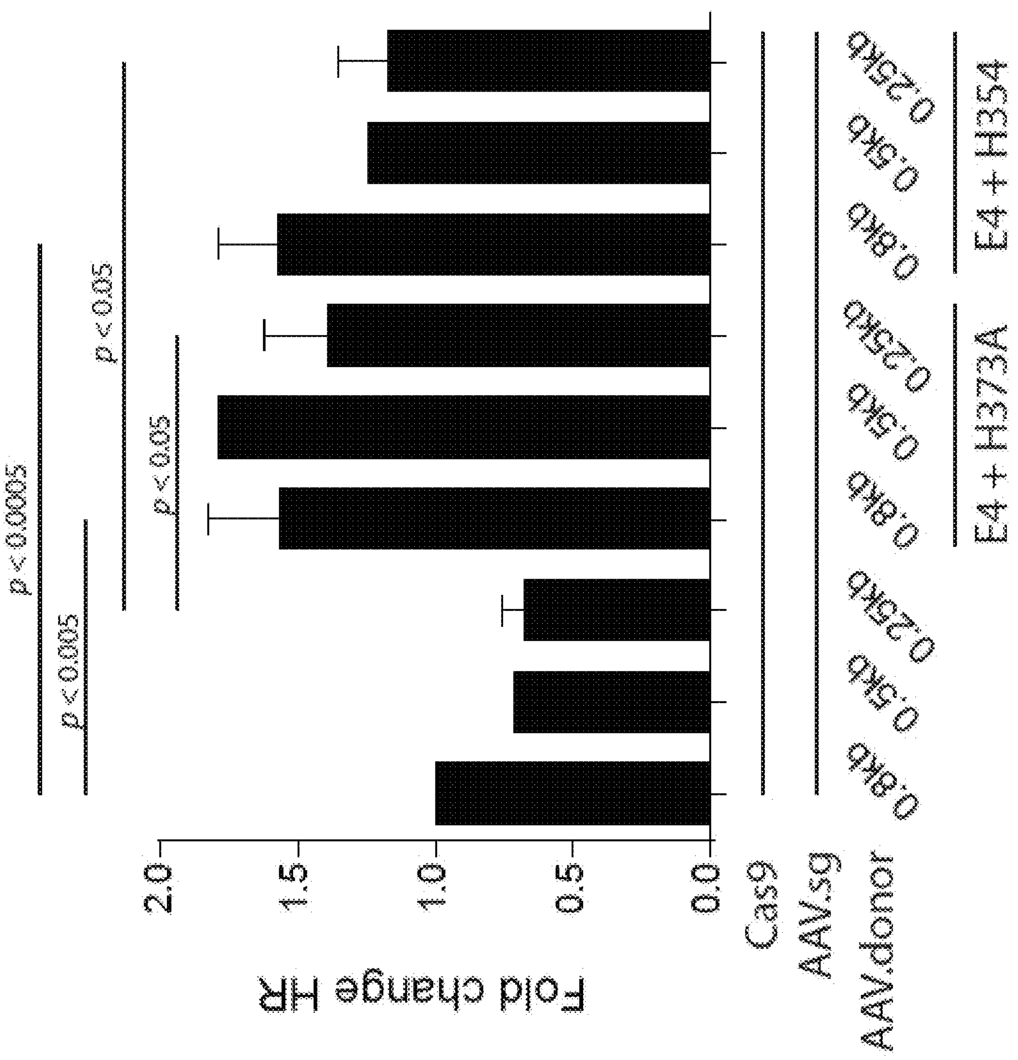
FIG. 11 shows data related to the effect of addition of E4ORF6/E1B55K H373A or H354 on homology directed repair (HDR) when using shorter homology arms for gene knock-in with CRISPR-Cas9 at the CCR5 locus.

In some alternatives, quantification of n=2-5 experiments of primary human T-cells treated with Cas9 RNA, AAV expressing a guide against the CCR5 gene, AAV donors containing a GFP knock-in construct with different homology arm lengths (0.8 kb, 0.5 kb, and 0.25 kb), and RNA expressing the E4ORF6/E1B55K H354 or H373A mutant proteins are shown in FIG. 11. Fold change in HR is calculated based on change from baseline, defined here as CRISPR-Cas9 with AAV donor containing the 0.8 kb homology arm, at three weeks following electroporation and transduction.

In some alternatives, the length of the homology arm can range from 0.05 kb to 1 kb. In some alternatives, the length of the homology arm can be 0.05, 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 or 1 kb or within a range defined by any two of the aforementioned lengths.

In some alternatives, as shown in FIG. 11, the addition of E4ORF6/E1B55K H373A proteins significantly rescues the low rate of HDR due to the use of shorter homology arms. Data are presented for the CCR5 locus.

In some alternatives, the addition of the Ad5 proteins (the two E1B55K mutants, H373A or H354, both with E4ORF6), can rescue lower levels of HDR knock-in that are caused by using templates with shorter homology arms with CRISPR/Cas9. In some alternatives, the fold change in HDR can range from 50% to 150%. In some alternatives, the fold change in HDR can be 50, 55, 60, 65, 70, 75, 80, 85, 90, 95, 100, 105, 110, 115, 120, 125, 130, 135, 140, 145 or 150% or within a range defined by any two of the aforementioned values.

EXAMPLE 11

Addition of E4ORF6/E1B55K H373A Rescues HDR when Shorter Homology Arms are Used for Gene Knock-in with CRISPR-Cas9 at the TCR Locus In some alternatives, effect of addition of E4ORF6/E1B55K H354 on homology directed repair (HDR) when using shorter homology arms for gene knock-in with CRISPR-Cas9 was assessed for the TCR locus.

Figure 12A:
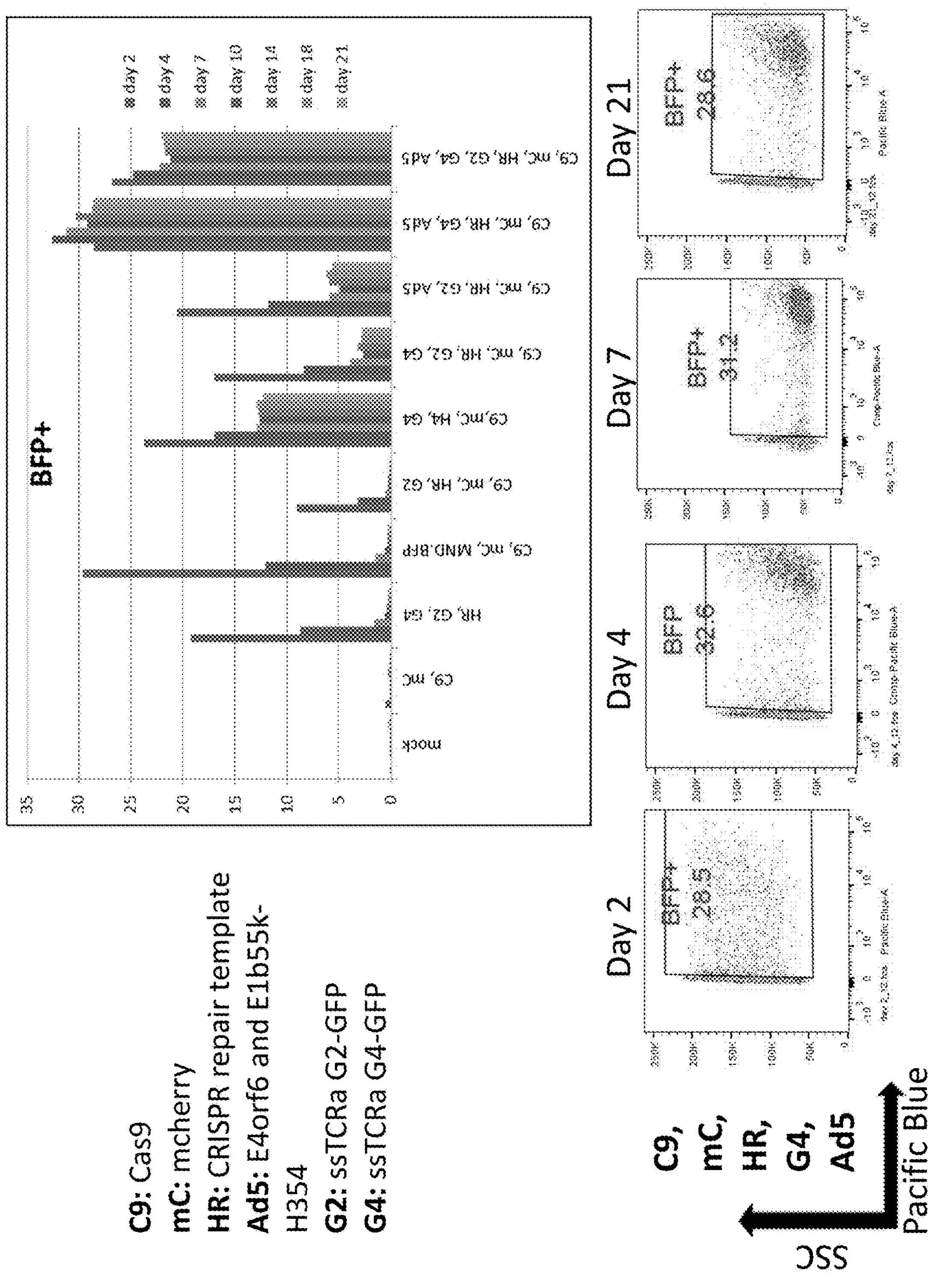
FIG. 12A-FIG. 12C show data related to the effect of addition of E4ORF6/E1B55K H354 on HDR when using shorter homology arms for gene knock-in with CRISPR-Cas9 at the TCR locus.

In some alternatives, $1\times10^6$ T-cells were stimulated with CD3/CD28 beads for 48 hours, and electroporated with the combinations of RNAs encoding the proteins indicated on the legend to the graph (FIG. 12A). Cas9 mRNA was 1.0 μg. Ad5 proteins were 0.1 μg each (0.1 μg of E4ORF6, and 0.1 μg of E1B55K H354 mutant). AAV's encoding the repair templates and guides were iodixanol concentrated viral preps, used at 10% of culture volume.

Figure 12B:
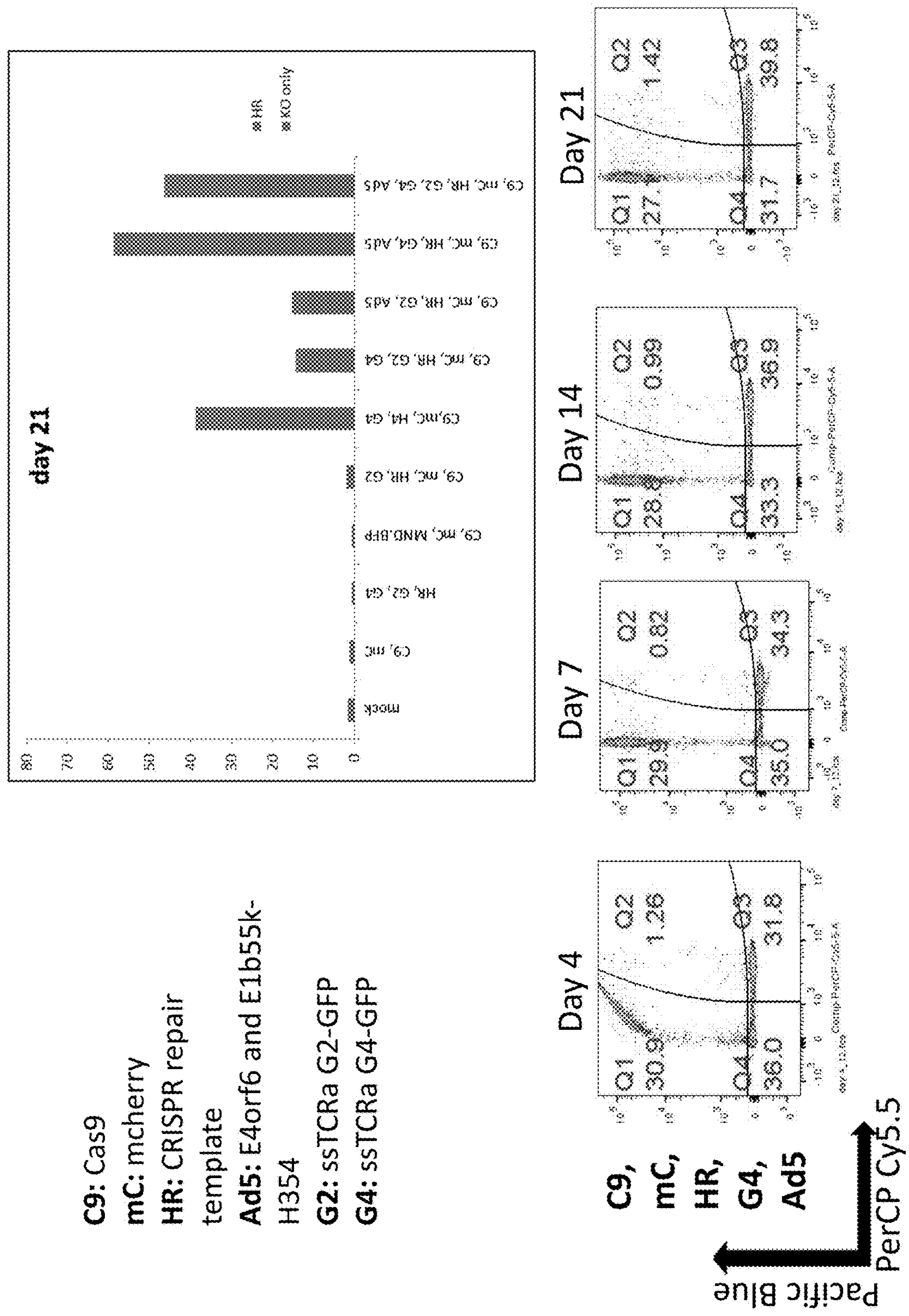

In some alternatives, H354 mutant increased knock-in at the TCR locus (FIG. 12A). In the bar graph of FIG. 12B, NHEJ rates are shown in red, HR rates are shown in blue. In some alternatives, the use of the H354 mutant substantially increased the percentage of breaks resolved through a homology-directed repair assay.

Figure 12C:
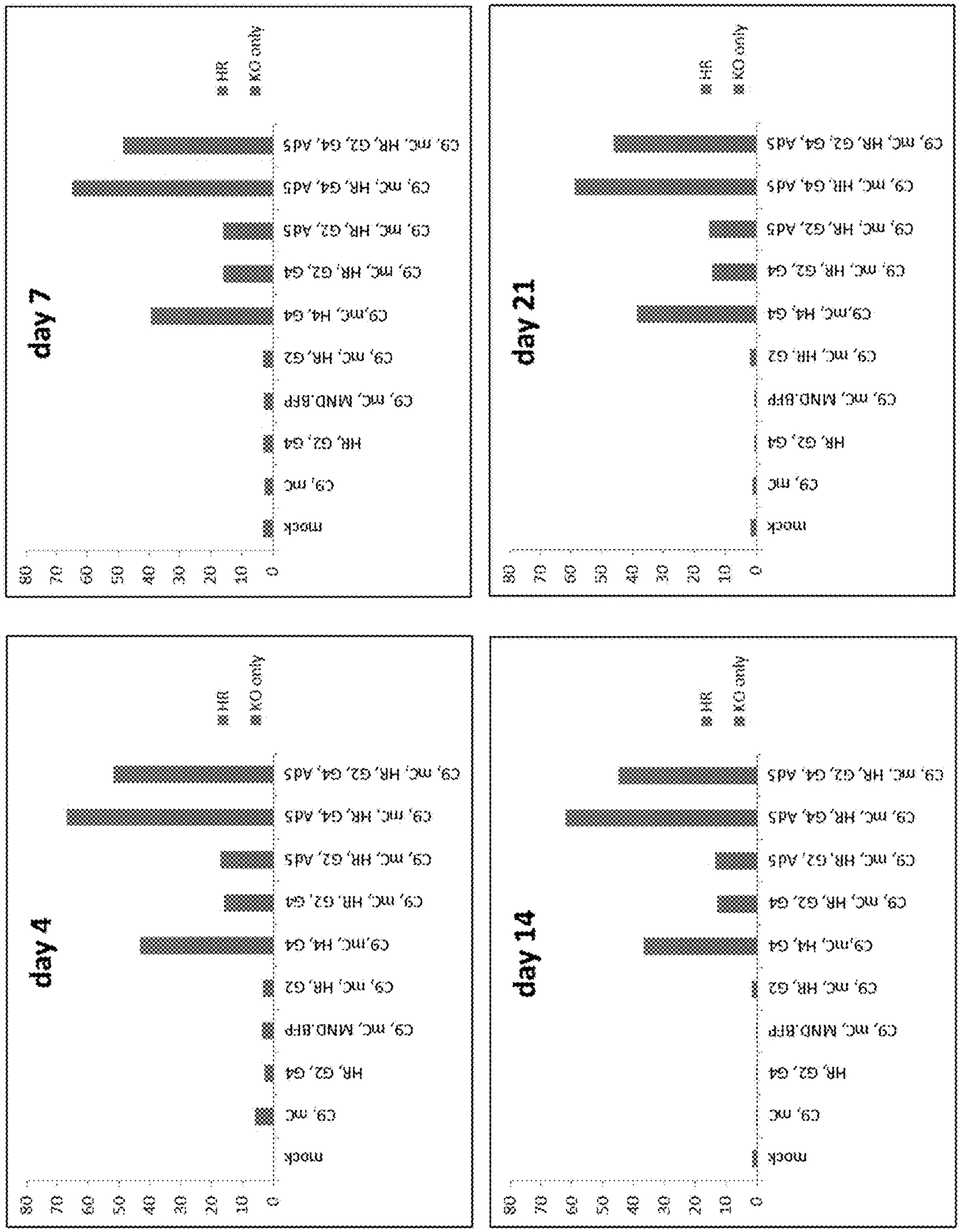

In some alternatives, the observed HDR observed had occurred as early by day 4 post-electroporation (FIG. 12C). In some alternatives, the H354 mutant biases toward increased HDR without significantly increasing NHEJ. In some alternatives, the H354 mutant biases toward increased HDR without significantly increasing NHEJ when a template is present.

EXAMPLE 12

Edited Primary T-cells with E4ORF6/E1B55K H373A Exhibit Normal Surface Marker Phenotype In some alternatives, whether expression of the E4ORF6/E1B55K H373A mutant was detrimentally influencing T-cell phenotype or signaling properties over the course of the editing process was assessed for which expression of a panel of surface markers and measured PHA-induced calcium signaling at two weeks post-editing was evaluated.

Figure 13A:
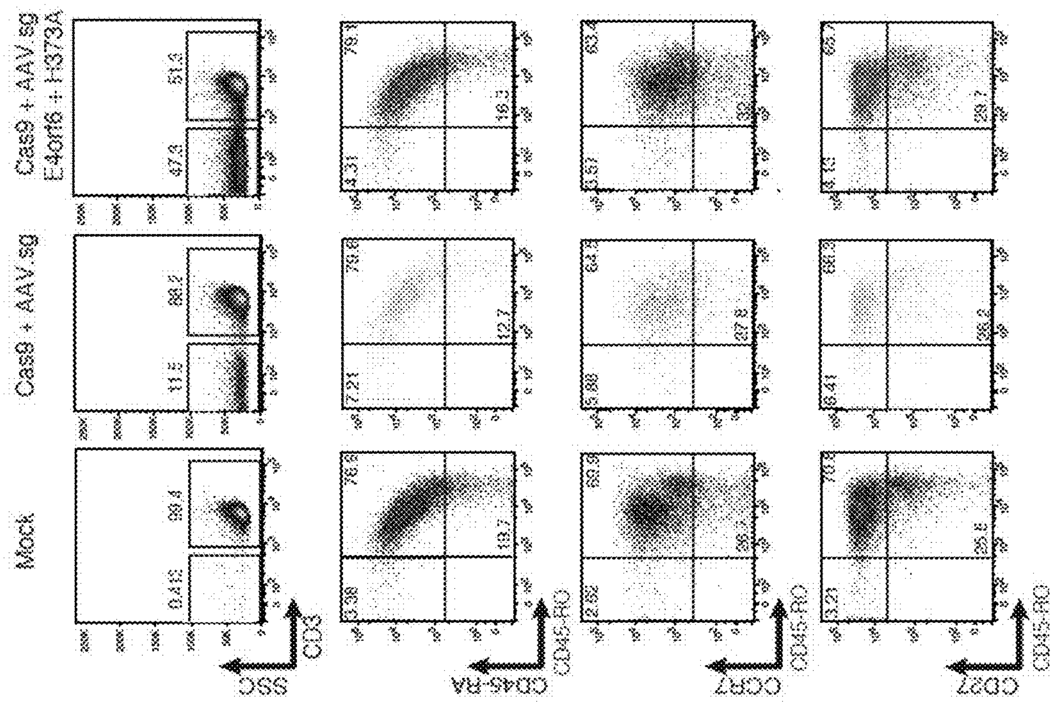
FIG. 13A-FIG. 13B show data related to surface marker phenotype and Ca2+ signaling in edited primary T-cells with E4ORF6/E1B55K H373A.

In some alternatives, representative flow plots (FIG. 13A) of primary CD4+ T-cells that were electroporated with mRNA encoding Cas9-2A-mCherry proteins (1 μg) along with E4ORF6/E1B55K H373A proteins (0.03 μg each) and transduced with AAV driving TCRα guide expression as shown (FIG. 13A). Cells were placed in culture and assessed for surface protein markers 16-20 days following EP/transduction by flow cytometry. n=2 independent experiments (FIG. 13A).

Flow cytometric assessment of cell surface markers that define naïve and memory T-cell populations in T-cells edited using mRNA/AAV co-delivery exhibited normal surface marker phenotype and no differences were between edited versus unedited populations (FIG. 13A).

EXAMPLE 13

T-Cells Rendered TCR-Deficient Via mRNA/AAV Co-Delivery Deficient in TCR Signaling In some alternatives, primary CD4+ T-cells were electroporated with mRNA encoding Cas9-T2A-mCherry proteins (1 μg) along with E4ORF6/E1B55K H373A (0.03 μg each), rested for 2 hours, and transduced with AAV driving TCRα guide expression. Nine days following EP/transduction, CD3− cells were purified using CD3 microbeads (Miltenyi Biotech) and placed back in culture. Cells were allowed to expand for ten days, following which they were collected, re-suspended in Hanks calcium signaling buffer, incubated with 100 μM Indo calcium dye for 30 min, and analyzed for anti-CD3-stimulated calcium signaling by flow cytometry. 200 μg/mL PHA was used to stimulate the cells. Five million cells per condition were used (FIG. 13B).

Figure 13B:
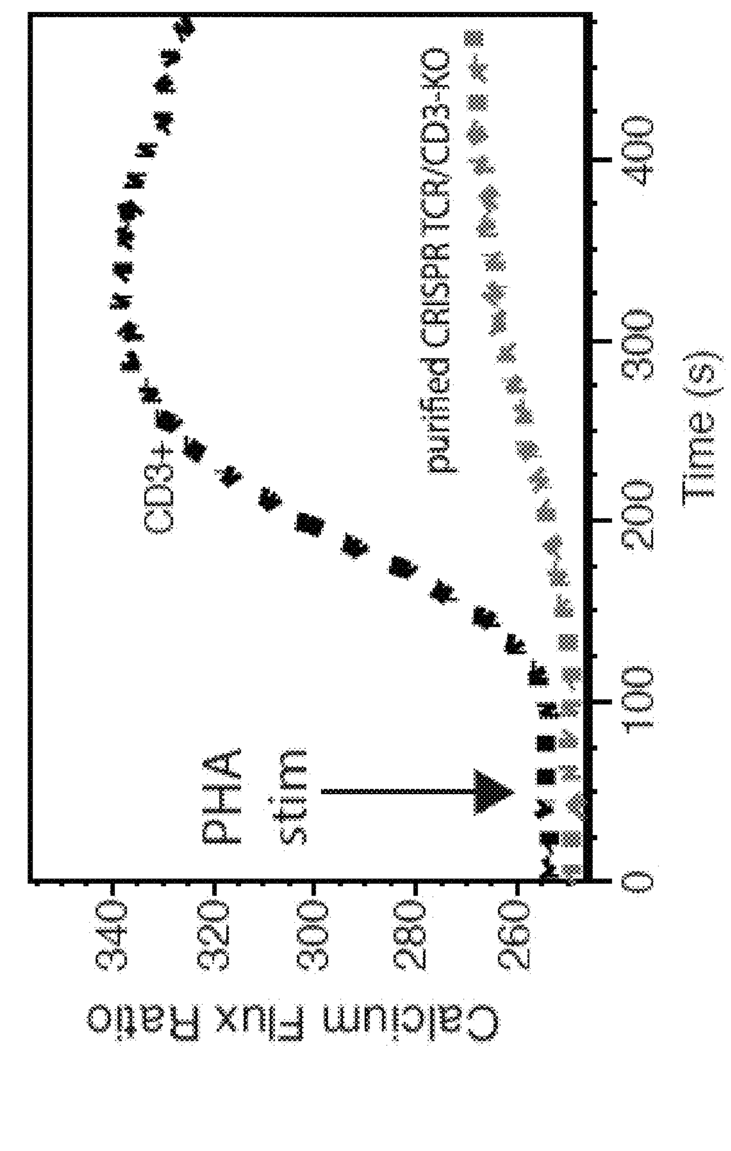

In some alternatives, edited T-cells exhibited a loss of surface TCR following TCRα gene editing showing a loss of capacity to mobilize $Ca^{2+}$ in response to stimulation with PHA relative to cells retaining surface TCR (FIG. 13B). Thus, in some alternatives, TCR knockout T-cells using E4ORF6/E1B55K mutants were deficient in $Ca^{2+}$ signaling.

EXAMPLE 14

Cells Exhibit Normal Karyotype Following Multiplex CRISPR Editing

Figure 14A:
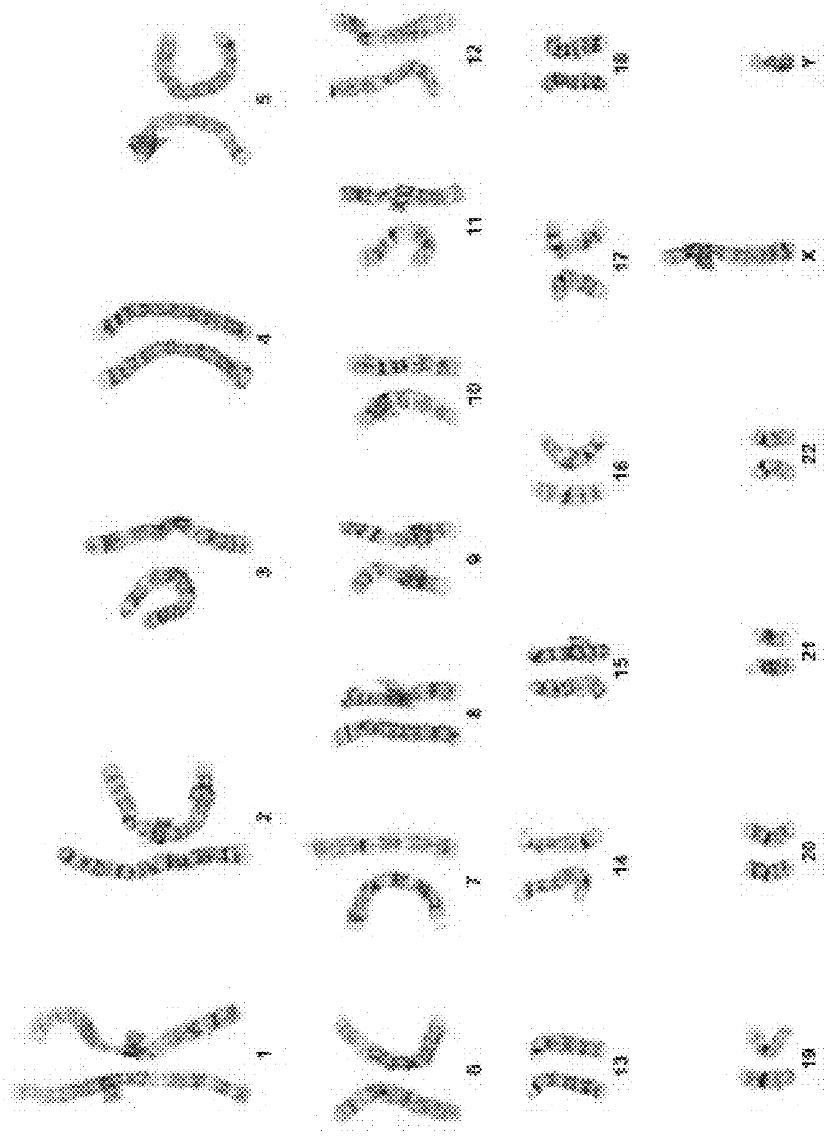
FIG. 14A-FIG. 14B show data related to cell karyotype following multiplex CRISPR editing.
Figure 14B:
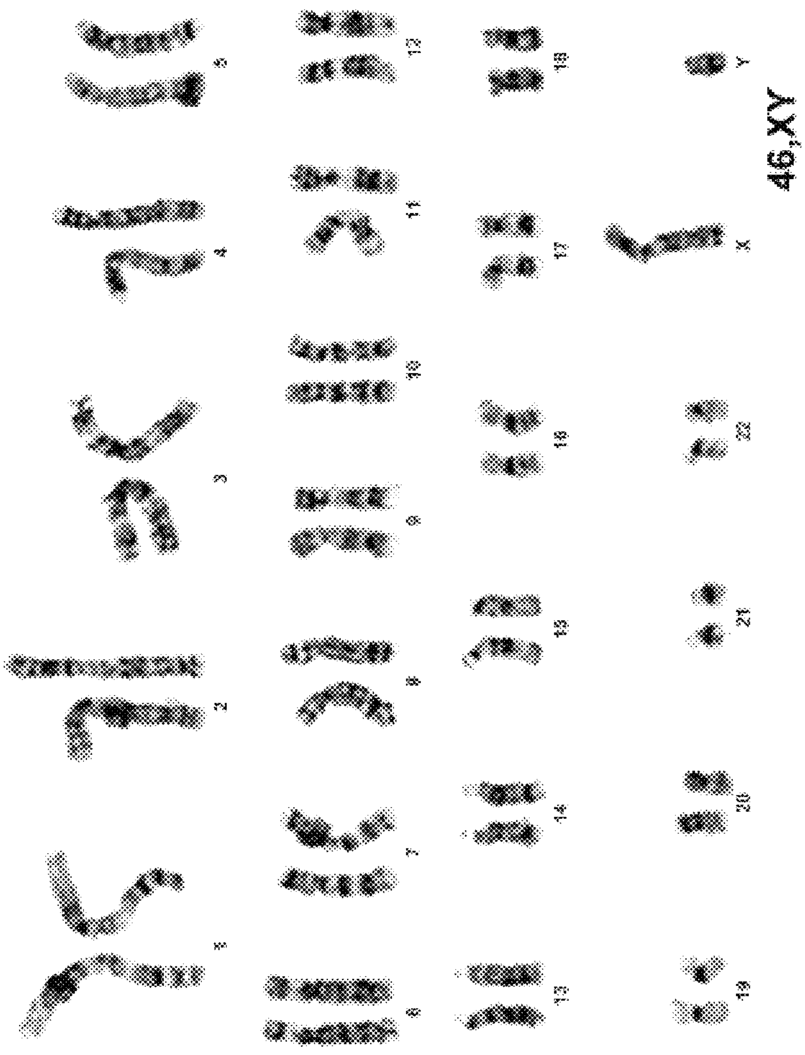

As translocations are a potential consequence of simultaneous induction of multiple double strand breaks, in some alternatives, karyotyping was performed as an unbiased approach to detecting cell engineering-associated translocations, and did not observe any gross abnormalities in any of twenty metaphase spreads from each condition (FIG. 14).

In some alternatives, G-banding analysis following GTW staining indicated normal phenotype in cells that have undergone CRISPR/Cas9 editing with E4ORF6/E1B55K-H373A (FIG. 14). Cells were stimulated using PMA/ionomycin for 3-4 hours, and left to recover for 72 hours. All samples achieved metaphase spreads. Twenty metaphase spreads were created and analyzed using G-banding karyotype analysis per sample. In some alternatives, no abnormalities were detected in any sample (FIG. 14).

In some alternatives, representative image (FIG. 14A) shows normal karyotype in cells treated with Cas9 (1 μg) with AAV expressing guides against Tim3 and TCRa. Knockout frequencies can be seen in FIG. 8B and FIG. 8C.

Representative image (FIG. 14A) shows normal karyotype in cells treated with Cas9 (1 μg) with AAV expressing guides against Tim3 and TCRα, and E4ORF6/E1B55K-H373A (0.03 μg) RNAs. Knockout frequencies can be seen in FIG. 8B and FIG. 8C.

For karyotype analysis, in some alternatives, ~$20\times10^6$ cells per sample were submitted for analysis following PMA/ionomycin stimulation, and metaphase spreads were successfully obtained from each sample. Data from karyotyping results are shown in TABLE 1.

TABLE 1

| Sample | Band Level | Metaphase Cells Analyzed | Abnormalities Detected (Y/N)? |
|---|---|---|---|
| Untreated | 400-450 | 20 | N |
| AAV.sgTim3.GFP | 300-450 | 20 | N |
| AAV.sgTim3.sg.TCRα.GFP | 300-400 | 20 | N |
| Cas9 alone | 300-550 | 20 | N |
| Cas9 + AAV.sgTim3.GFP | 300-450 | 20 | N |
| Cas9 + AAV.sgTim3.sg.TCRα.GFP | 450-650 | 20 | N |
| Cas9 + E4ORF6/ E1B55K-H373A + AAV.sgTim3.GFP | 300-400 | 20 | N |
| Cas9 + E4ORF6/ E1B55K-H373A + AAV.sgTim3.sg.TCRα.GFP | 300-450 | 20 | N |

In some alternatives, no discernable abnormalities were detected in any of the twenty spreads analyzed, at the band resolutions indicated, suggesting a translocation rate of less than 5% indicating that cells with double gene knockout do not commonly have gross rearrangements/karyotypic abnormalities.

EXAMPLE 15

Molecular Confirmation of Precise HDR Events Following CRISPR-Cas9 Breaks with E4ORF6/E1B55K H373A or H354

The molecular nature of the HDR events was assessed by sequencing through the junctions to confirm seamless HDR (FIG. 15). A schematic of donor template, with homology arms and BFP insert. Primer binding sites are indicated, and resulting amplicon (1.3 kb) is shown in FIG. 15A. A representative agarose gel indicating results of PCR from primers is shown in FIG. 15A. Results are from n=3 independent PCR experiments, from cells obtained from data shown in FIG. 10. PCR products from FIG. 15B were purified, cloned into vectors, and sequenced. Representative amplicons are shown indicating precise junctions at both the upstream (1) and downstream (2) regions of the 3' homology arm, as indicated in FIG. 15A. No clones were obtained that had non-precise junctions, nor were any clones obtained that included AAV-based ITR sequence Thus, in some alternatives, targeted integrations are indeed seamless integrations as determined by the precise HDR events following CRISPR-Cas9 breaks with E4ORF6/E1B55K H373A or H354.

EXAMPLE 16

Comparison of Different Guide RNA Alternatives for Generating TCR Knockout

In some alternatives, the CRISPR-Cas9 system was used for generating TCR knockout. Human TCR αδ locus corresponds to chr14 NG_001332.2. Location within the TCRα gene corresponds to 1,071,537-1.071,809.

In some alternatives, guide RNAs guide1 (SEQ ID NO: 15; FIG. 16A), guide2 (SEQ ID NO: 16; FIG. 16A), guide3 (SEQ ID NO: 17; FIG. 16A), and guide4 (SEQ ID NO: 5; FIG. 16A) were used.

In some alternatives, primary T-cells were transfected with Cas9-mCherry mRNA followed by transduction with AAV guides. Data from four different experiments are shown in FIG. 16B-FIG. 16I.

Figure 16B:
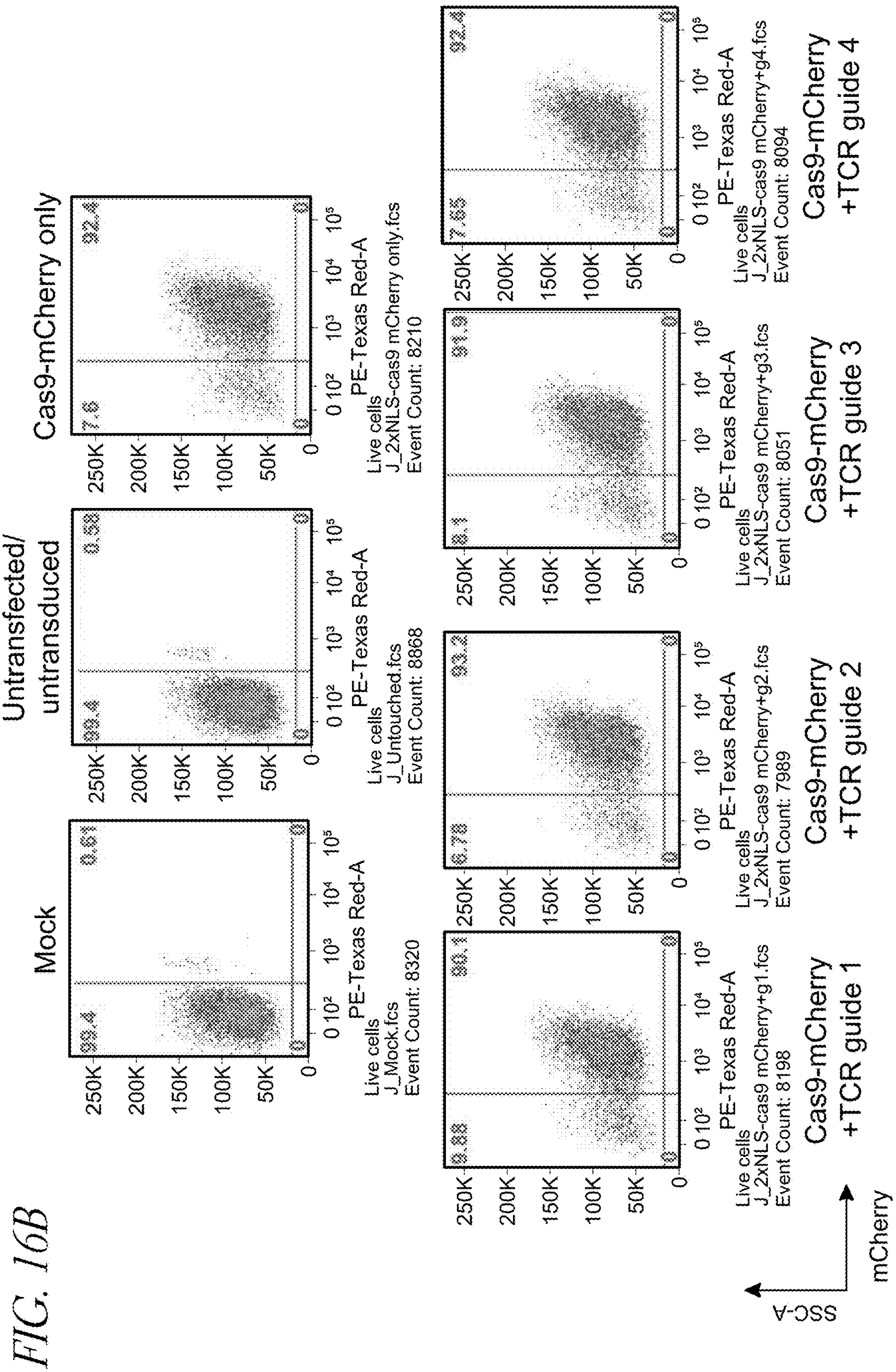
FIG. 16B shows flow cytometry data comparing the efficiency of Cas9-mCherry expression from mRNA in primary T-cells from donor 1 when using guide RNAs guide1-guide4.

In some alternatives, comparison of the efficiency of generation of TCR knockout in primary T-cells from donor 1 when using guide RNAs guide1-guide4. Cas9-mCherry expression at 24 hrs was comparable in primary T-cells from donor 1 irrespective of the guide RNA sequence alternative used (FIG. 16B). Same MOI was used for all AAV guide RNAs. Controls are shown in FIG. 16B, top panel.

Figure 16C:
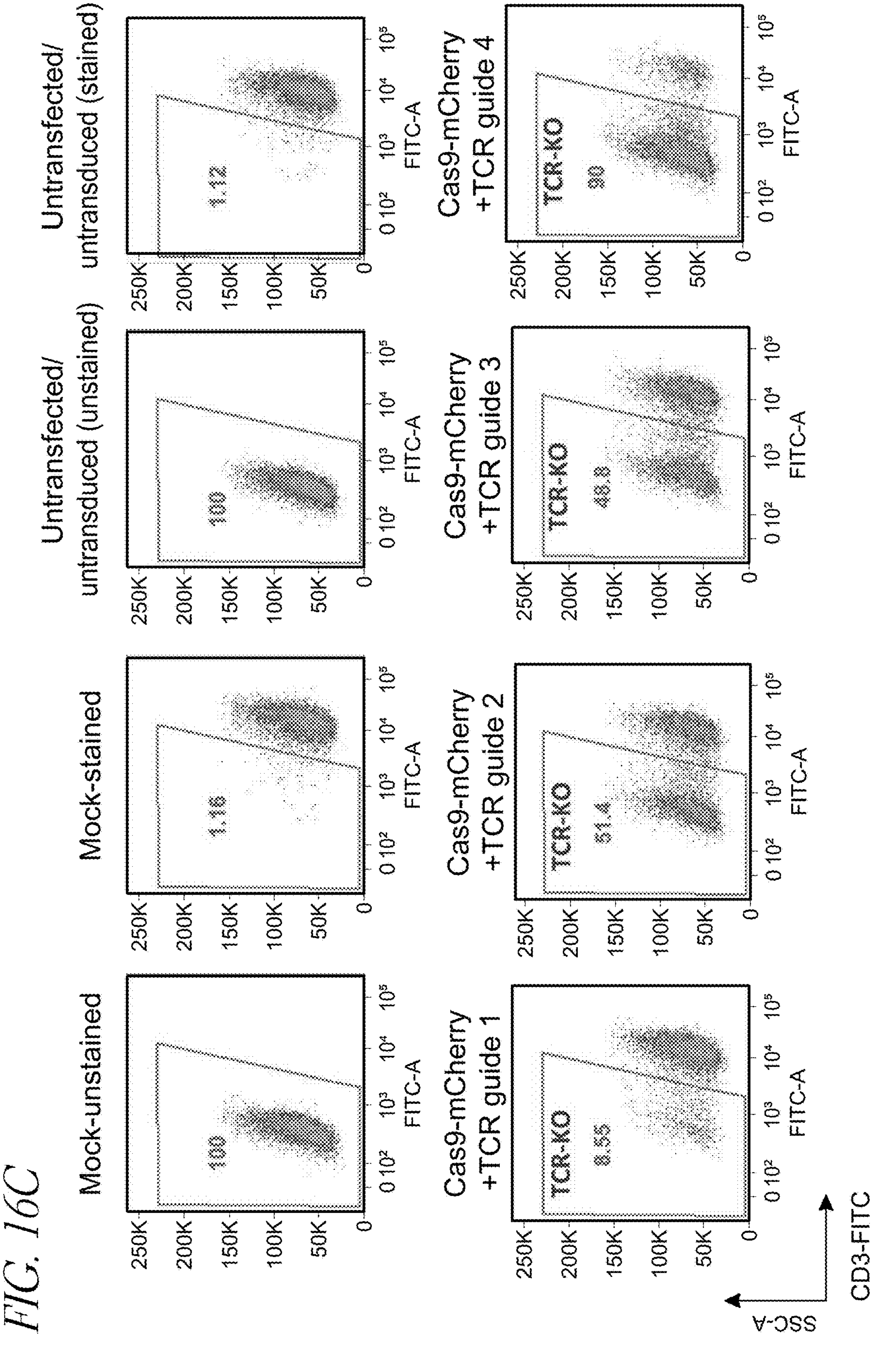
FIG. 16C shows flow cytometry data comparing the efficiency of generation of TCR knockout in primary T-cells from donor 1 when using guide RNAs guide1-guide4.
Figure 21:
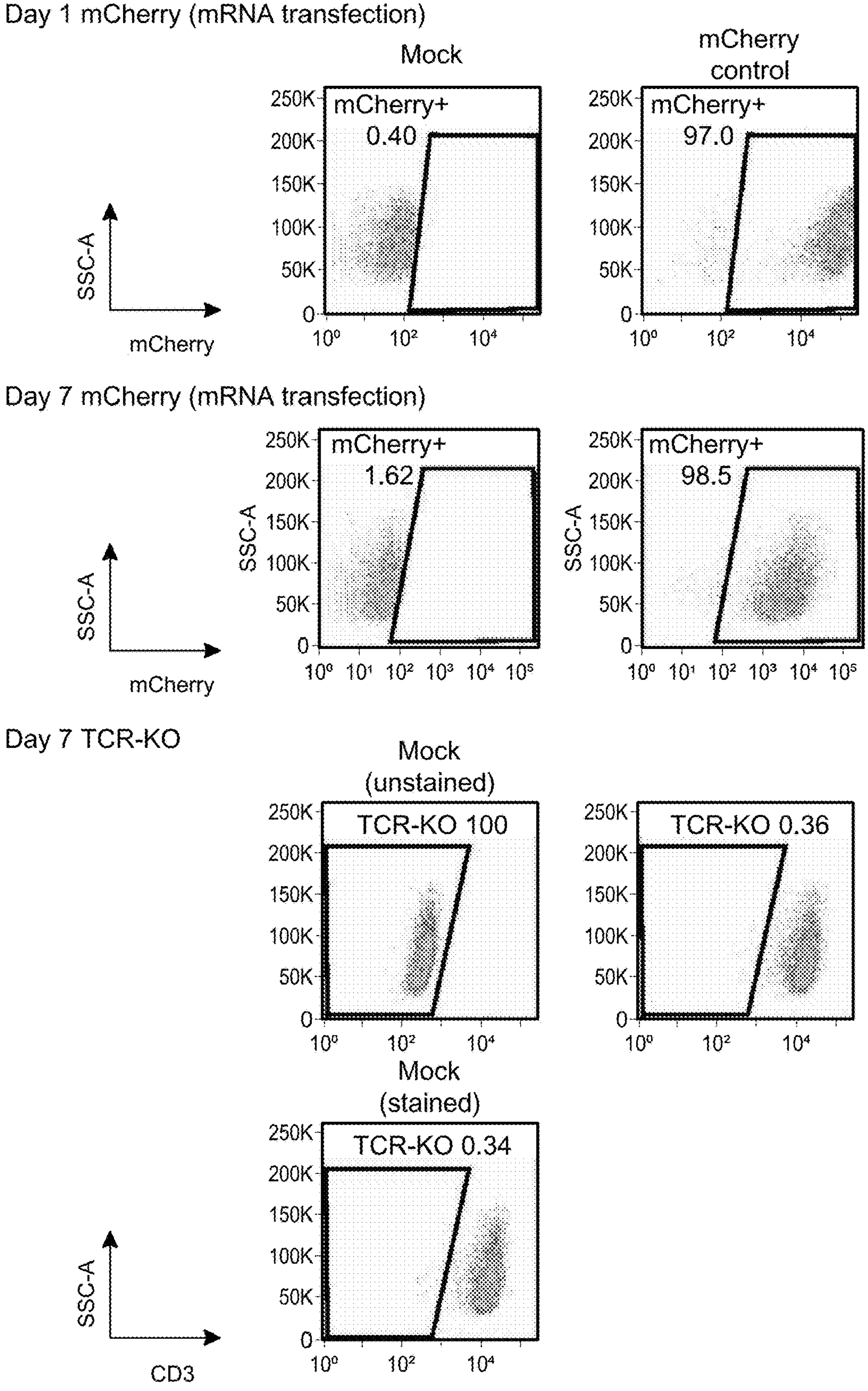
FIG. 21 shows flow cytometry data of generation of TCRα knockout with CRISPR guide RNAs guide1 (G1), guide2 (G2), guide3 (G3) and guide4 (G4).

In some alternatives, comparison of the efficiency of generation of TCR knockout in primary T-cells from donor 1 when using guide RNAs guide1-guide4 showed that guide4 (FIG. 16A) yielded the highest knockout efficiency (90%) (FIG. 16C). Flow cytometry analysis was performed using anti-CD3-Alexa488 antibody at 168 hrs. Controls are shown in FIG. 16C, top panel. FIG. 21 also shows data that guide4 generated the highest TCRα knockout.

Figure 16D:
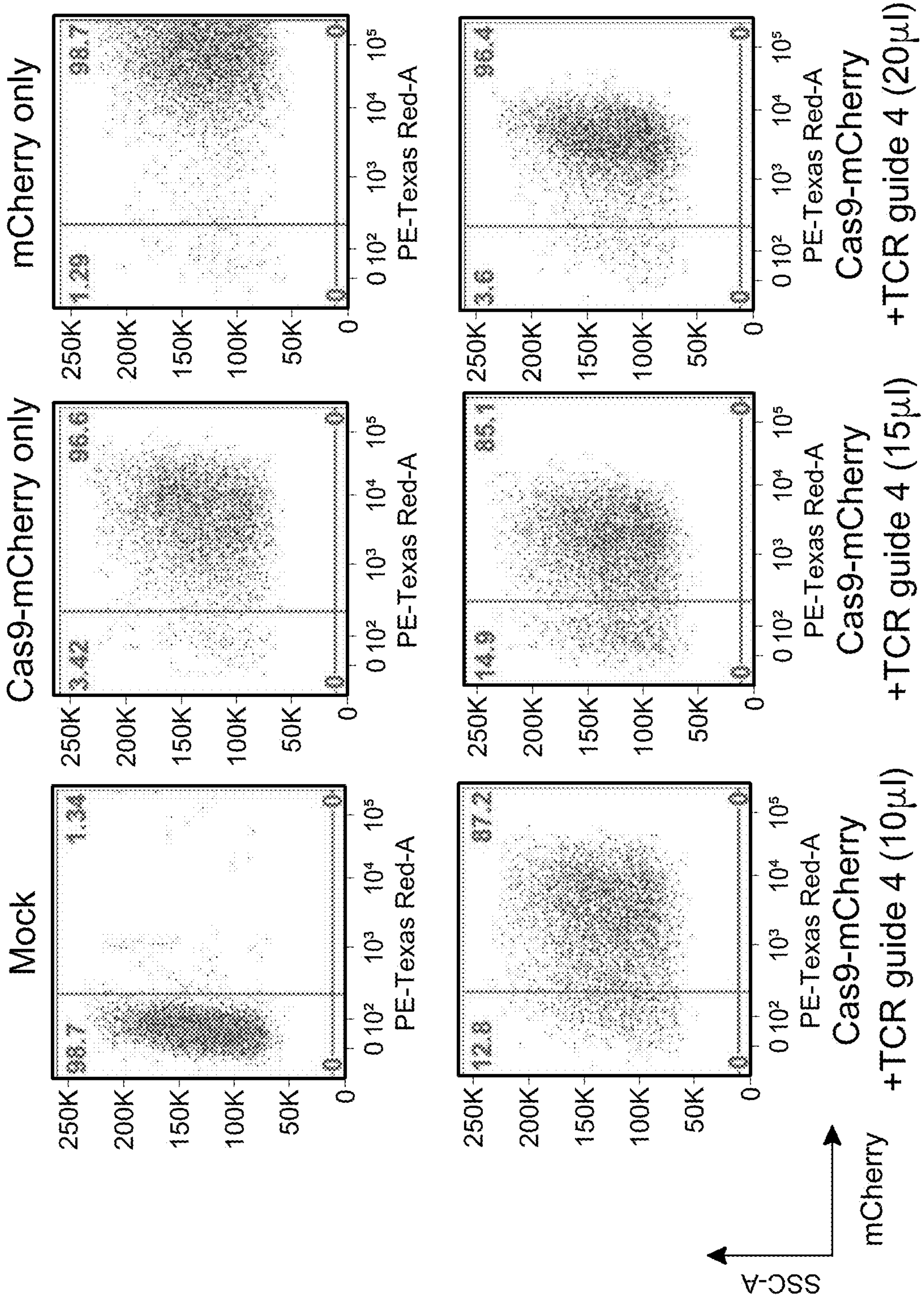
FIG. 16D shows flow cytometry data comparing Cas9-mCherry expression levels in primary T-cells from donor 1 when using different volumes of Cas9/guide sample.

In some alternatives, comparison of Cas9-mCherry expression levels at 24 hrs in primary T-cells from donor 1 when using different volumes of Cas9/guide sample showed a slightly higher percentage of cells expressing Cas9-mCherry at 20 μL volume (96.4%) as compared to 10 μL (87.2%) or 15 μL (85.1%) (FIG. 16D). Controls are shown in FIG. 16D, top panel.

Figure 16E:
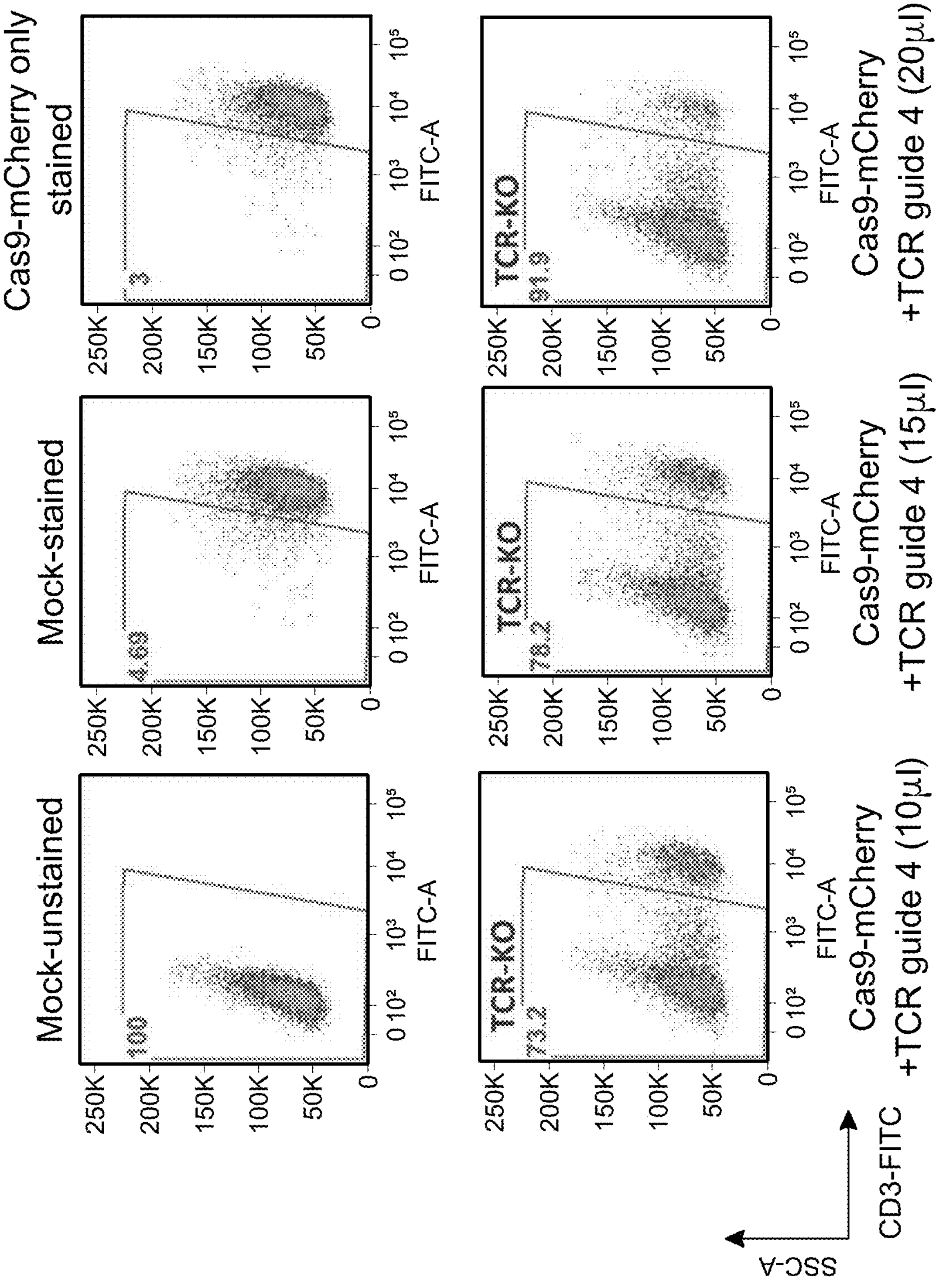
FIG. 16E shows flow cytometry data comparing the efficiency of generation of TCR knockout in primary T-cells from donor 1 when using different volumes of sample containing guide RNA guide4.

In some alternatives, comparison of efficiency of generation of TCR knockout in primary T-cells from donor 1 when using different volumes of sample containing guide4 yielded highest efficiency at 20 μL volume (91.9%). The efficiency was 73.2% at 10 μL and 78.2% at 15 μL (FIG. 16E). Flow cytometry analysis was performed using anti-CD3-Alexa488 antibody at 168 hrs. Controls are shown in FIG. 16E, top panel.

Figure 16F:
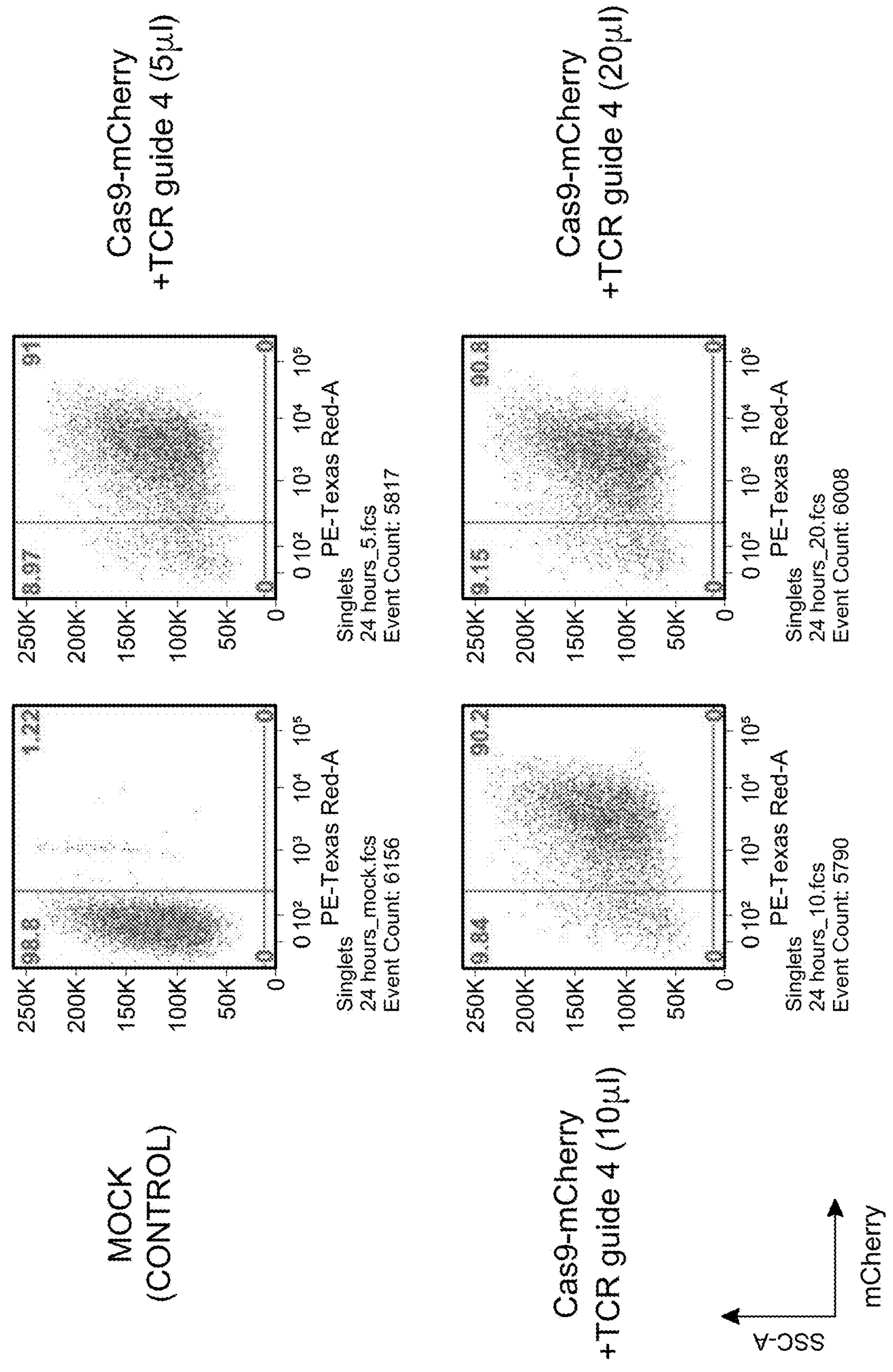
FIG. 16F shows flow cytometry data comparing Cas9-mCherry expression levels in primary T-cells from donor 2 when using different volumes of Cas9/guide sample containing guide RNA guide4.

In some alternatives, comparison of Cas9-mCherry expression levels at 24 hrs in primary T-cells from donor 2 when using different volumes of Cas9/guide sample showed a similar percentage of cells expressing Cas9-mCherry at 5 μL (91%), 10 μL (90.2%) and 20 μL (90.8%) of sample volume (FIG. 16F).

In some alternatives, comparison of efficiency of generation of TCR knockout in primary T-cells from donor 2 when using different volumes of sample containing guide RNA guide4 yielded highest efficiency at 20 μL volume (68.4%). The efficiency was 30.7% at 5 μL and 38.4% at 10 μL (FIG.

Figure 16G:
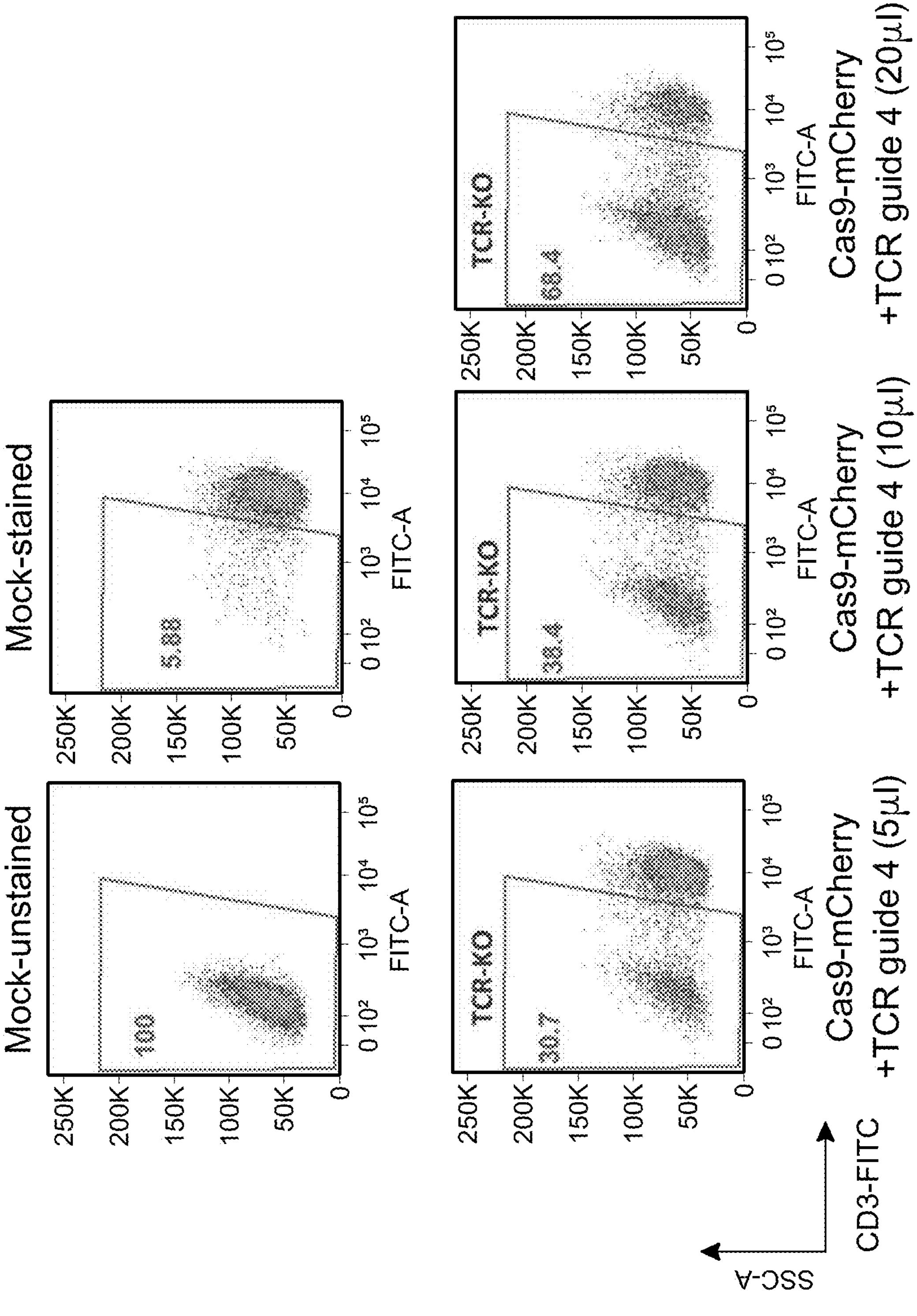
FIG. 16G shows flow cytometry data comparing the efficiency of generation of TCR knockout in primary T-cells from donor 2 when using different volumes of sample containing guide RNA guide4.

16G). Flow cytometry analysis was performed using anti-CD3-Alexa488 antibody at 168 hrs. Controls are shown in FIG. 16G, top panel.

Figure 16H:
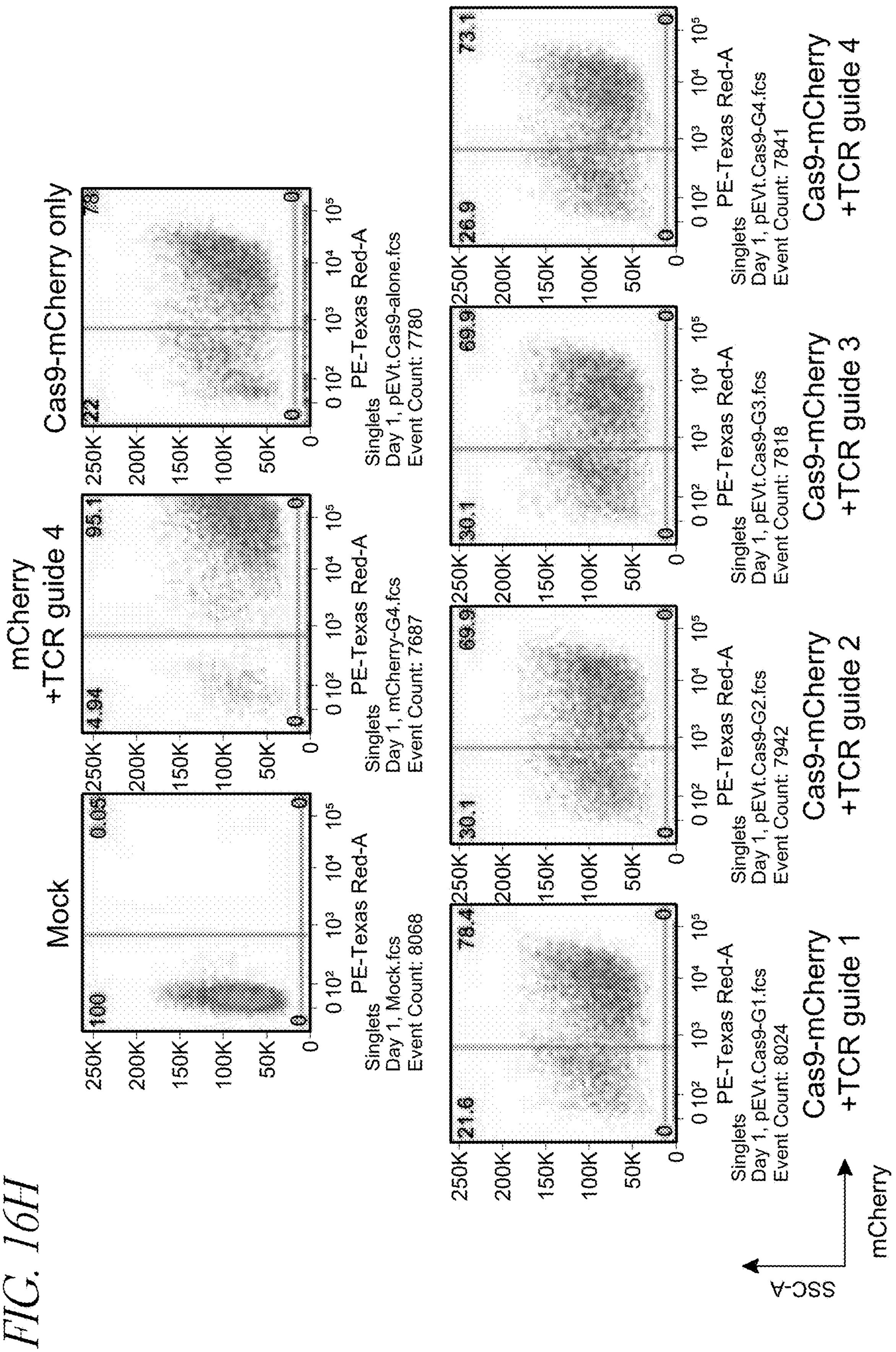
FIG. 16H shows flow cytometry data comparing the efficiency of Cas9-mCherry expression from mRNA in Jurkat T-cells when using guide RNAs guide1-guide4.

In some alternatives, Cas9-mCherry expression at 24 hrs was comparable in Jurkat T-cells irrespective of the guide RNA sequence alternative used (FIG. 16H, bottom panel). Cas9-mCherry expression was lowest for guide1. Same MOI was used for all AAV guide RNAs. Controls are shown in FIG. 16H, top panel.

Figure 16I:
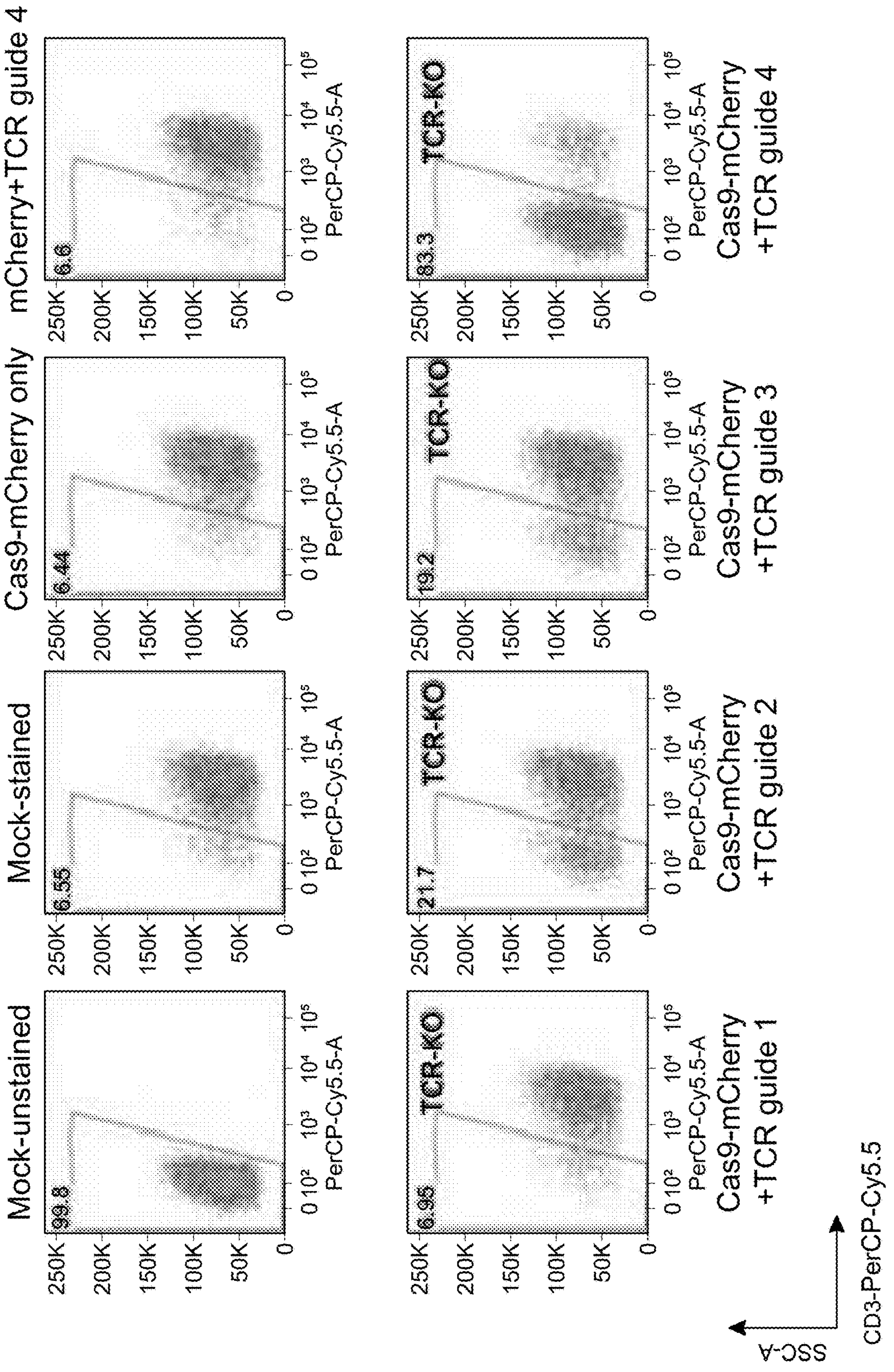
FIG. 16I shows flow cytometry data comparing the efficiency of generation of TCR knockout in Jurkat T-cells when using guide RNAs guide1-guide4.

In some alternatives, comparison of the efficiency of generation of TCR knockout in Jurkat T-cells when using guide RNAs guide 1-guide4 showed that guide4 (FIG. 16A) yielded the highest knockout efficiency (83.3%) (FIG. 16I, bottom panel). Flow cytometry analysis was performed using anti-CD3-Alexa488 antibody at 168 hrs. Controls are shown in FIG. 16I, top panel.

EXAMPLE 17

CRISPR/Cas9 System Using the TCRα CRISPR Guide RNA Guide4

In some alternatives, primary human CD4+ T-cells were thawed from a frozen isolate, stimulated with CD3/CD28 Dynabeads (Life Technologies) in the presence of cytokines (IL-2, IL-7 and IL-15) for 60 hours in antibiotic free media. Next, beads were removed and $4.5\times10^5$ cells per condition were electroporated using a 10 μL Neon tip ($3\times10^5$ cells post electroporation) and AAV was added 3 hours post electroporation. Cas9 RNA was used at 1.5 μg/sample (1 ug post electroporation) and guide-specific AAV's were added at an MOI of $1.33\times10^4$/sample. Post electroporation, cells were plated in a 96 well plate in 200 μl media with cytokines and left in a 30° C. $CO_2$ incubator for 24 hours, after which cells were moved to a 37° C. $CO_2$ incubator.

At 24 hours post electroporation, cells were checked for Cas9-mCherry expression and subsequently at 72, 96 and 168 hours for both mCherry and TCR-knockout with CD3-Alexa488 antibody (Biolegend) using BD LSRII. Voltages were kept same throughout the duration of the experiment.

In some alternatives, data showed that TCRα CRISPR guide RNA guide4 generated the highest TCRα knockout (FIG. 16B-FIG. 16I).

EXAMPLE 18

Enhanced Efficiency of CRISPR-mediated Gene Knockout in Primary Human T-cells Translational application of the CRISPR/Cas9 programmable endonuclease system has been hindered by the need to transiently and simultaneously express Cas9 protein and guide RNA at sufficient levels to achieve high on-target nuclease activity in primary cells. In some alternatives, an mRNA/AAV split vector system that allows for highly efficient CRISPR-mediated gene editing in primary human T-cells is provided. This approach utilizes mRNA to express Cas9 in conjunction with adenoviral serotype 5 E4ORF6 and E1B55K proteins, the latter serving to render the T-cell permissive to AAV transduction for the purpose of guide RNA expression. In some alternatives, this approach is applied to disrupt the T-cell receptor a subunit gene, a translationally relevant target, at efficiencies up to 60%, and demonstrate that the resulting edited T-cell population is otherwise phenotypically indistinguishable from the parental population. In some alternatives, this approach can be coupled to mRNA-based TREX2 exonuclease expression to achieve even higher editing efficiencies, illustrating the flexibility and potency of a split-vector approach. Transient expression of $Ad5^{wt}$ proteins increases AAV transduction in human T-cells. Transient expression of $Ad5^{wt}$ proteins increases AAV transduction for both ssAAV6 and scAAV6. Transient expression of $Ad5^{MRN-}$ proteins increases CRISPR knockout efficiency in primary human T-cells.

EXAMPLE 19

Increased Rate of HDR with TALENs

Figure 32A:
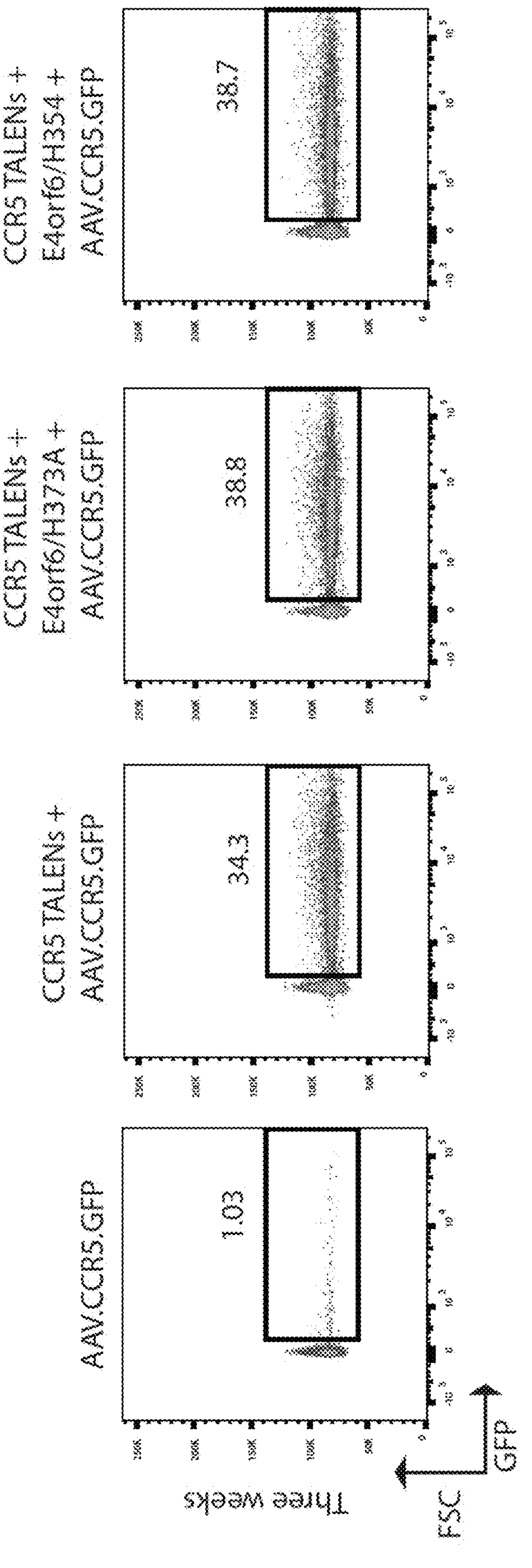
FIG. 32A shows the effect of TALENs on HDR for the CCR5 locus.

In some alternatives, primary human CD4+ T-cells were electroporated with 0.5 μg of each half of CCR5 TALEN mRNA (FIG. 32A) or CD40L TALEN mRNA (FIG. 32B), without or with E4ORF6/E1B55K-H373A or without or with E1B55K-H354 mRNA (0.03 μg each) on a Neon Transfection System (Life Technologies). Immediately following electroporation, cells were placed at 30° C. for 24 hours and returned to 37° C. for the duration of culture. Two hours following electroporation, cells were transduced with AAV6 containing donor template at 10% culture volume. Cells were analyzed for knock-in of the donor template (GFP+) at three weeks following electroporation/transduction on an LSRII flow cytometer (BD Biosciences).

Figure 32B:
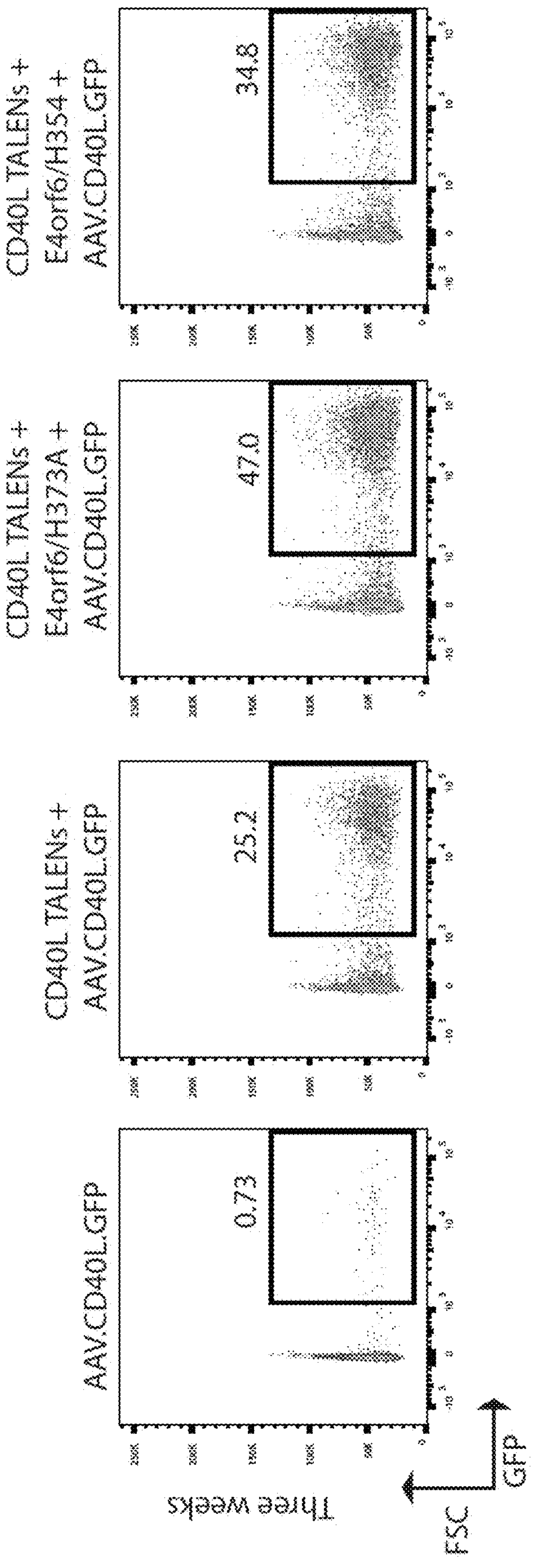
FIG. 32B shows the effect of TALENs on HDR for the CD40L locus.

In some alternatives, TALENs used in combination with the Ad5 mutants, increased gene targeting at two different loci. Thus, in some alternatives, TALENs used in combination with the Ad5 mutants, increased gene targeting at the CCR5 locus (FIG. 32A) and at the CD40L (FIG. 32B).

In some alternatives, the number of genes that can be targeted using TALENs ranges from 1-10. In some alternatives, the number of genes that can be targeted using TALENs is 1, 2, 3, 4, 5, 6, 7, 8, 9 or 10 or within a range defined by any two of the aforementioned numbers.

EXAMPLE 20

Endonuclease-based Genome Editing

A system for editing at least one target gene in a cell and a method of using the system for genome editing are contemplated. The target gene is a gene of interest, which is edited by can be either gene disruption. The cell is a primary T-cell.

The system comprises a first nucleic acid sequence encoding one or more guide RNA and a second nucleic acid sequence encoding an endonuclease protein. The endonuclease can be any of the endonucleases disclosed herein and/or alternative variants and modifications of that are within the scope of the current disclosure. The second nucleic acid is an mRNA and encodes any of the endonuclease protein. The second nucleic acid sequence encoding the endonuclease protein is codon optimized for expression in a eukaryotic cell. The one or more guide RNA is complimentary to the at least one target gene in a cell. The one or more guide RNA is provided in a vector. The vector can be a viral vector. The viral vector is an Adeno-associated virus (AAV) vector. The AAV vector can be a self-complementary vector, or a single stranded vector, or a combination of a self-complementary vector and a single stranded vector.

As many cell types possess a post-entry restriction on AAV vectors that renders AAV-mediated expression of transgenes, including guide RNAs, very inefficient, proteins that suppress the post-entry restriction on AAV vectors are provided on additional nucleic acid sequences. Thus, the system comprises a third nucleic acid sequence encoding a first adenoviral protein and a fourth nucleic acid sequence encoding a second adenoviral protein. The third nucleic acid and the fourth nucleic acid are mRNAs, which are codon optimized for expression in a eukaryotic cell. The nucleic acid sequences can either be introduced into the cell sequentially and in any order or be introduced into the cell simultaneously.

The first and second adenoviral proteins are from an AAV of serotype 5. The first adenoviral protein is a wild type E4ORF6, or an AXA mutant of E4ORF6. The second adenoviral protein is a wild type E1B55K, or an H373A mutant of E1B55K, or an H354 mutant of E1B55K, or an R240A mutant of E1B55K. While the mutant proteins are not as efficient as wild type proteins at suppressing at post-entry restriction on AAV vectors, they are relatively more efficient at enhancing gene targeting.

The first, second, third and fourth nucleic acid sequences are operably linked to regulatory elements that are operable in a eukaryotic cell. The first nucleic acid sequence can encode one or more guide RNA and each guide RNA is operably linked to a separate regulatory element. The first nucleic acid sequence encoding the guide RNA is transiently expressed in the cell. The one or more guide RNA sequences are complementary to the TCRα gene, the PD1 gene, the TIGIT gene, the Lag3 gene, and/or the Tim3 gene. The system also comprises nucleic acid sequences regions that bear homology to the gene of interest.

The system comprising the above-mentioned components is introduced into the primary T cell. These nucleic acid sequence regions that bear homology to the gene of interest direct the endonuclease-based system to be targeted to a specific gene. Targeting to the specific gene can result in a gene knockout, a gene knock-in, or both.

Depending on the nature of gene targeting approach (knockout or knock-in) the result can be determined by flow cytometry, or sequencing or both. For example, if the system is used for knocking out a gene of interest that encodes a cell surface-expressed protein, flow cytometry can be used to check for suppressed and/or lack of cell surface expression of the protein. Or, if the system is used for knocking out a gene of interest that encodes an intracellularly-expressed protein, flow cytometry can be used to check for suppressed and/or lack of intracellular expression of the protein. Or, if the system is used for knock-in, for example, knock-in of a dominant epitope of an antigen into a gene of interest that encodes a cell surface-expressed protein, flow cytometry can be used to check for cell surface expression of the dominant epitope. Or, if the system is used for knock-in, for example, knock-in of a dominant epitope of an antigen into a gene of interest that encodes an intracellularly-expressed protein, flow cytometry can be used to check for intracellular expression of the dominant epitope. In any of the above cases, the DNA sequencing of genomic DNA can also be used to confirm the desired gene targeting event. The number of genes that can be simultaneously targeted for knockout, knock-in or both can be 2-5.

The T-cells in which the gene of interest has been targeted are enriched by cell sorting or other cell enrichments methods. If the enriched cells are intended to be used for treating, ameliorating, and/or inhibiting a disease and/or a condition in a subject, the enriched cells are administered to the subject. For example, the subject may have a disease and/or a condition because the T-cells in the subject are "exhausted," and therefore, are not effective at clearing one or more antigens from the disease and/or condition.

By targeting one or more "exhaustion" markers (e.g., PD1, TIGIT, Lag3 and Tim3), the "exhausted" condition of T-cells can be reversed. The targeted T-cells are administered to the subject (e.g., via the intravenous route). Follow-up testing is performed on the subject to assess the status of the targeted T-cells and their effect on the disease and/or condition. For example, blood is drawn from the subject at various intervals following administration of the targeted T-cells. Testing is performed to determine whether the administered T-cells are activated, for example, by assessing their secretion of the cytokine (e.g., IL-2, TNFα). Testing is also performed to determine the effect of administration of the targeted T-cells on the disease and/or condition.

EXAMPLE 21

Materials and Methods

DNA Constructs—Cas9 was obtained from Addgene (plasmid #41815), PCR amplified and cloned into pWNY backbone (an in-house modified pUC57), pEVL200 and pEVL300 (linear mRNA vector with a 200 or 300 encoded polyA tail) with a T7 promoter and two Nuclear Localization Signals (NLS)—one each at the N-terminus and C-terminus, respectively. Cas9 was modified to remove BsaI sites to clone into the pEVL vector, without changing amino acid sequence. mCherry was linked to Cas9 with a T2A peptide at 3' end of Cas9. An mCherry only control containing a T7 promoter and a single NLS at the 5' end of mCherry was also generated in pWNY and pEVL200. E4ORF6 and E1B55K genes were gene synthesized (Integrated DNA Technologies, IDT) and cloned into pWNY downstream of a T7 promoter. E1B55K mutants were generated using site-directed mutagenesis (QuikChange II XL Site-Directed Mutagenesis Kit, Agilent).

AAV constructs for single guide RNA (sgRNA) design, cloning and expression—Guides targeting the constant region of TCRα, PD-1, TIGIT, Lag3, Tim3, and CCR5 were designed using online CRISPR design tools (http://crispr.mit.edu and the Broad Institute's sgRNA designer—http://www.broadinstitute.org/rnai/public/analysis-tools/sgrna-design). Guides were then generated as gblocks by commercial DNA synthesis (Integrated DNA Technologies). The gblocks were cloned into scAAV6 or ssAAV6-GFP constructs using standard cloning techniques.

The gblocks were cloned into scAAV or ssAAV-GFP constructs with either a "GG" (T7 promoter requirement) or a "G" (U6 promoter) at the beginning of the guide, if a "G" was not already present at the start of the guide. Some guides with a U6 promoter had "GG" but the editing efficiency of the ones with "GG" or "G" was similar. Post ITR check, the constructs were used to generate AAV6.

In some alternatives, the guide targets used correspond to the following guide sequences: TCRα guide target: ACAAAACTGTGCTAGACATG (SEQ ID NO: 16); PD1 guide target: GCCCACGACACCAACCACCA (SEQ ID NO: 18); TIGIT guide target: TCTTCCCTAGGAATGATGAC (SEQ ID NO: 19); Lag3 guide target: GCGGTCCCTGAGGTGCACCG (SEQ ID NO: 20); Tim3 guide target: AGAAGTGGAATACAGAGCGG (SEQ ID NO: 21).

Production of Recombinant AAV6 vectors—AAV stocks were produced by triple transfection of AAV vector, serotype helper and Adenoviral helper (HGT1-Adeno) plasmids in HEK293T cells. Transfected cells were collected 48 hrs later, lysed by freeze-thaw, benzonase treated and purified over iodixanol density gradient. Titers of the viral stocks were determined by qPCR of AAV genomes and ranged from $10^{10}$-$10^{12}$/ml.

mRNA production—DNA template was linearized with unique restriction enzymes and linearized plasmids were purified using the QiaQuick PCR purification kit (Qiagen). mRNA was transcribed in-vitro using commercial kits (mMessage mMachine T7 Ultra; Ambion or T7 mScript Standard RNA production system; CellScript) with slight modifications from the manufacturer's protocol. Briefly, the IVT reaction incubated for 2.5-3 hours, followed by DNase treatment for 1 hour. Poly(A) tailing, if required, was done for 1 hour and mRNA was purified using RNeasy (Qiagen).

Primary human T cell transfection by electroporation and transduction—T-cells were obtained from frozen PBMCs, using CD4+ or CD3+ isolation kits (Miltenyi Biotec). Briefly, PBMCs were thawed using drop-wise addition of cold DNase I Buffer: PBS, 5 mM $MgCl_2$, 20 Kunitz Units/ml DNase I (EMD-Millipore), followed by centrifugation, and left to rest overnight in T cell media (RPMI, 20% FBS, 1% HEPES, 1% L-glutamine) supplemented with low-dose IL-15 (0.1 ng/mL). T-cells were isolated the following day, according to the manufacturer's instructions, and purified T-cells were resuspended at $1\times10^6$ live cells/ml in T cell growth media (culture media supplemented with IL-2 and IL-15; 5 and 1 ng/ml, respectively), and stimulated by using CD3/CD28 beads (Dynal Beads, Life Technologies) for 72 hrs at a 1:1 cell-bead ratio. Beads were then removed and cells were allowed to rest in T cell growth media for 0.5-2 hrs. Next, cells were electroporated with mRNA using either a Neon Transfection System (FIGS. 1, 2, 4) or MaxCyte GT (FIG. 3) as follows: Cells were washed twice with PBS, resuspended in Neon Buffer T or MaxCyte Buffer at a density of $4.5\times10^7$ cells/ml (Neon) or $1.25\times10^8$ cells/ml (MaxCyte). After mixing, cells were electroporated (Neon conditions: 1400 V, 10 ms, 3 pulses, 10 μl tip; MaxCyte conditions determined by the manufacturer for primary T-cells) and immediately dispensed into 200 μL of pre-warmed T cell growth media in a 96-well plate. Cells were immediately incubated at 30° C., and AAV was added to the culture 2-4 hrs post electroporation, followed by continued 30° C. incubation for 20 additional hrs. AAV donor was added as 10% of the final culture volume regardless of titer (~$1\times10^{4-5}$ MOI), unless specified otherwise. Subsequently, edited cells were cultured using standard conditions: 37° C. and expanded in T cell growth media, replenished as needed to maintain a density of ~$1\times10^6$ cells/ml every 2-3 days.

Flow cytometry and antibodies—Analysis of knock-out (TCRα, PD-1, TIGIT, Lag3, and Tim3) and HDR (BFP) was performed using the LSRII flow cytometer (BD Biosciences) and data was analyzed using FlowJo software (Treestar). All antibodies were from Biolegend, unless otherwise indicated. To assess knockout of surface markers, cells were labeled with fluorophore-conjugated antibodies, as follows: CD3-Alexa 488, CD3-PerCPCy5.5, or CD3-APC clone HIT3a; PD1-APC clone eh12.2H7; TIGIT-Alexa 700 clone 741182 (Novus Biologicals); Tim3-APC-Cy7 clone F38-2E2; and Lag3-FITC clone 3DS223H (eBioscience). CD4 or CD8 staining was done using CD4-BFP (clone OKT4) or CD8-BFP (RPA-T8). To upregulate surface expression of T cell exhaustion markers, T-cells were stimulated using CD3/CD28 beads for 48 hrs, 9-12 days following initial stimulation, except in the absence of TCRα, in which case PMA/ionomycin stimulation was used (see below). Cells were washed and acquired on LSRII by gating on live cells based on the forward and side scatter for downstream analysis.

Stimulation with PMA/ionomycin—Cells were plated at a density of $1\times10^6$ in a 48 or 24 well plate. 10 ng/mL PMA (Sigma) and 1 μg/mL of ionomycin (Sigma) was added to the media for 3-4 hours, cells were washed 3-4 times with PBS with 2% FBS, and then re-plated with fresh media. Cells were allowed to recover for 48 hours before flow cytometry, or for 72 hours for karyotype analysis.

Karyotype analysis—Cells were grown in T-25 flasks at a density of $1\times10^6$-$1.5\times10^6$ per sample. Each sample was stimulated with PMA/ionomycin for 3-4 hrs, and then allowed to rest for 72 hrs in full media and cytokines. Karyotype analysis was done by the University of Washington Cytogenetics and Genomics Laboratory as Research Testing. Standard G-banding (GTW stain) chromosome analysis was performed, on 20 cells per sample.

T7 Endonuclease I (T7EI) assay—The cleavage efficiency of Cas9 and sgRNA was estimated using the T7EI assay for both TCRα and CCR5 loci. Targeted genomic loci were amplified using either Accuprime Pfx or Hifi Platinum Taq DNA polymerase (Life Technologies), using the manufacturer's instructions. 400 ng of the purified product (Qiaquick PCR clean-up kit, Qiagen) was denatured, subjected to T7EI (New England Biolabs) digestion for 30 mins at 37° C. and analyzed on a 1-2% agarose gel (FIG. 2B).

Analysis of calcium signaling—$5\times10^6$ cells were used per sample. Cells were washed in HBSS (with $Ca^{2+}$ and $Mg^{2+}$) (Thermofisher), loaded with 30 μM Indo-1 AM (Molecular Probes, Life Technologies) in HBSS and incubated at 37° C. for 30 min, washed twice, and re-suspended in buffer. Baseline flow was obtained for 30 sec, after which cells were stimulated with 200 μg/mL PHA to stimulate T-cells, and data was collected for 5 min.

Statistical analysis—Statistical analyses were performed with Prism 6 (GraphPad Software). Data is shown as mean+/−SEM unless otherwise noted. Tests of statistical significance were performed using an unpaired two-tailed Student's t-test with Welsh's correction for unequal standard deviations when appropriate.

In some alternatives, implementation of CRISPR/Cas9 nuclease technology in primary human T-cells using an mRNA/AAV co-delivery method in which mRNA is used for Cas9 expression and an AAV vector is used for guide RNA expression and/or recombination template delivery is provided.

As AAV transduction manifested as an important limitation on efficacy during initial development of the mRNA/AAV co-delivery method, in some alternatives, mRNA-based co-expression of E4ORF6/E1B55K adenoviral helper proteins and a panel of mutants to determine whether a combination of biochemical activities could be identified that would disable post-entry restrictions on AAV-mediated gene expression while maintaining a cellular DNA repair environment conducive to efficient gene editing is evaluated.

In some alternatives, two of the mutants, E4ORF6/E1B55K H373A and H354, were identified as uniquely capable of supporting substantially enhanced efficiencies of both CRISPR-Cas9-mediated gene disruption and homology-directed gene targeting.

Adenoviral serotype 4 E4ORF6/E1B55K complexes enhance CRISPR-mediated gene targeting (but not gene disruption) in cultured cell models, an effect attributed to inhibition of DNA ligase IV activity and, as a consequence, reduced non-homologous end joining repair activity.

Thus, in some alternatives, the expression of adenoviral serotype 5 E4ORF6/E1B55K complexes with mRNA/AAV co-delivery might produce a synergistic effect on gene targeting efficiency through both inhibition of DNA ligase IV activity and relief of AAV post-entry transduction restrictions was contemplated.

In some alternatives, although transient expression of wild type E4ORF6/E1B55K complexes was highly efficacious at relieving restrictions on AAV-driven gene expression, it produced only modest increases in gene disruption or gene targeting efficiency in the primary human T-cell context. In contrast, in some alternatives, E4ORF6/E1B55K H373A or H354 mutants, which exhibited only a modest capacity to enhance AAV-driven gene expression, were observed to produce substantial enhancements in both gene disruption and gene targeting efficiency.

The H373A and H354 mutants' modest effect on AAV-driven gene expression (e.g. as in FIG. 3), which would be predicted to produce a correspondingly modest increase in both the level and duration of guide RNA expression, may in part explain their capacities to potentiate both gene disruption and gene targeting. Their collective residual biochemical activities may also allow an increased proportion of AAV genomes to remain available to participate in homology-directed repair, thus contributing to increased gene targeting efficiency.

However, two known biochemical activities are contemplated as central to these mutants' capacity to potentiate both gene disruption and gene targeting efficiency relative to the wild type E1B55K: 1) they preserve MRN-dependent DNA damage signaling (which promotes double strand break resolution by various forms of homology-directed DNA repair) while 2) limiting p53-dependent DNA damage signaling (which arrests cells in G1-phase in response to DNA double strand breaks). As a consequence, in some alternatives, T-cells expressing these complexes would be predicted to permit a high fraction of Cas9-induced double strand breaks to transition to S-phase where they would be repaired by mutagenic alternative end joining in the absence of a recombination template, or by homology-directed repair in the case that a recombination template is provided.

In some alternatives, adenoviral serotype 5 E4ORF6/E1B55K H373A and H354 mutant "helper" proteins were identified as possessing the capacity to enhance the efficiency of Cas9-mediated gene editing in primary human T-cells. Collectively, in some alternatives, our results suggest that E4ORF6/E1B55K-H373A might be the best choice for an investigator interested in a general tool to enhance CRISPR/Cas9 gene editing, as it exhibited the most consistent activity across multiple types of gene editing applications.

The biochemical activities of these proteins suggest that their effects on gene editing efficiency are likely attributable to their promotion of S-phase repair of DNA double strand breaks. Thus, in some alternatives, they are likely to be generally applicable approaches to enhance homology-directed genome modification in primary human cells. In some alternatives, they are likely to be generally applicable as approaches to enhance homology-directed genome modification in primary human cells including with alternative nuclease platforms. In some alternatives, they are likely to be generally applicable approaches to enhance homology-directed genome modification in primary human cells including with alternative viral template delivery methods other than AAV.

Further, as accessory proteins from many human viruses can disable or modify various components of cellular DNA damage response and repair mechanisms, such proteins may represent a rich trove of biochemical activities for use as tools in human genome engineering.

Thus, in some alternatives, the use of accessory proteins from other human (and/or mammalian) viruses that disable and/or modify various components of cellular DNA damage response and/or repair mechanisms are contemplated in the CRISPR/Cas9 system provided herein. In some alternatives, such proteins are contemplated to represent a rich trove of biochemical activities for use as tools in human genome engineering.

The foregoing description and Examples detail certain alternatives of the invention. However, no matter how detailed the foregoing may appear in text, it will be appreciated that the invention may be practiced in many ways and the invention should be construed in accordance with the appended claims and any equivalents thereof. While the present teachings have been described in terms of these exemplary alternatives, one of ordinary skill in the art will readily comprehend that numerous variations and modifications of these exemplary alternatives are possible without undue experimentation. All such variations and modifications are within the scope of the current teachings.

The foregoing examples are provided to better illustrate the disclosed teachings and are not intended to limit the scope of the teachings presented herein. All references cited herein, including patents, patent applications, papers, text books, and the like, and the references cited therein, to the extent that they are not already, are hereby incorporated by reference in their entirety.

The foregoing is considered to be sufficient to enable one of ordinary skill in the art to practice the invention. The foregoing description and examples detail certain preferred alternatives of the invention and describe the best mode contemplated by the inventors. In the event that one or more of the incorporated literature and similar materials differs from or contradicts this application, including but not limited to defined terms, term usage, described techniques, or the like, this application controls.

What is claimed is:

1. A system for editing at least one target gene in a cell, the system comprising:

one or more vectors comprising a first nucleic acid sequence, or a set of nucleic acid sequences, encoding one or more CRISPR guide RNAs, wherein the one or more CRISPR guide RNAs is complementary to the at least one target gene in a cell;

a Cas9 protein or a second nucleic acid sequence encoding a Cas9 protein;

a third nucleic acid sequence encoding a first adenoviral protein, wherein the first adenoviral protein is one of a wild type E4ORF6 or an AXA mutant of E4ORF6; and a fourth nucleic acid sequence encoding a second adenoviral protein, wherein the second adenoviral protein is one of an H373A mutant of E1B55K or an H354 mutant of E1B55K.

2. The system of claim 1, wherein the cell is a mammalian cell.

3. The system of claim 1, wherein the cell is one or more of a primary cell, a primary lymphocyte, a CD34+ stem cell, a hepatocyte, a cardiomyocyte, a neuron, a glial cell, a muscle cell or an intestinal cell.

4. The system of claim 1, wherein the vector is an Adeno-associated virus (AAV) vector.

5. The system of claim 4, wherein the AAV vector is a self-complementary vector, single stranded or a combination therefore.

6. The system of claim 1, wherein the second nucleic acid encoding the Cas9 protein is an mRNA, which is codon optimized for expression in a mammalian cell.

7. The system of claim 1, wherein the Cas9 protein is from *S. pyogenes*.

8. The system of claim 1, wherein the third nucleic acid encoding the first adenoviral protein and the fourth nucleic acid encoding the second adenoviral protein are mRNAs, which are codon optimized for expression in a mammalian cell.

9. The system of claim 1, wherein (a) the wild type E4ORF6 comprises the amino acid sequence of SEQ ID NO: 3;

(b) the AXA mutant of E4ORF6 comprises the amino acid sequence of SEQ ID NO: 23;

(c) the H373A mutant of E1B55K comprises the amino acid sequence of SEQ ID NO: 2; and/or (d) the H354 mutant of E1B55K comprises the amino acid sequence of SEQ ID NO: 4.

10. The system of claim 1, wherein the first, second, third and fourth nucleic acid sequences are operably linked to regulatory elements that are operable in a mammalian cell.

11. The system of claim 1, wherein each of the one or more CRISPR guide RNA is operably linked to a separate regulatory element.

12. The system of claim 1, wherein each of the one or more CRISPR guide RNA is transiently expressed.

13. The system of claim 1, wherein the sequence of the one or more CRISPR guide RNA is one of SEQ ID NO: 5, SEQ ID NO: 15, SEQ ID NO: 16, SEQ ID NO: 17, SEQ ID NO: 18, SEQ ID NO: 19, SEQ ID NO: 20, or SEQ ID NO: 21.

14. The system of claim 1, wherein (a) (i) the one or more CRISPR guide RNAs target a coding sequence of the at least one target gene or (ii) the one or more CRISPR guide RNAs target non-coding sequences of the at least one target gene; and/or (b) the system further comprises a nucleic acid template for homology-directed repair (HDR) of the at least one target gene.

* * * * *